US012581852B2

(12) United States Patent
Cho et al.

(10) Patent No.: US 12,581,852 B2
(45) Date of Patent: Mar. 17, 2026

(54) COMPOUND, LUMINESCENT MATERIAL, DELAYED FLUORESCENT MATERIAL, AND ORGANIC OPTICAL DEVICE

(71) Applicant: KYULUX, INC., Fukuoka (JP)

(72) Inventors: Yong Joo Cho, Fukuoka (JP); YuSeok Yang, Fukuoka (JP); Masataka Yamashita, Fukuoka (JP); Yoshitake Suzuki, Fukuoka (JP); Kaori Fujisawa, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 800 days.

(21) Appl. No.: 17/760,077

(22) PCT Filed: Feb. 3, 2021

(86) PCT No.: PCT/JP2021/003846

§ 371 (c)(1),
(2) Date: Sep. 22, 2022

(87) PCT Pub. No.: WO2021/157600

PCT Pub. Date: Aug. 12, 2021

(65) Prior Publication Data

US 2023/0114170 A1 Apr. 13, 2023

(30) Foreign Application Priority Data

Feb. 4, 2020 (JP) ................................ 2020-017486

(51) Int. Cl.

| | |
|---|---|
| ***C07D 401/14*** | (2006.01) |
| ***C07D 491/048*** | (2006.01) |
| ***C07D 519/00*** | (2006.01) |
| ***C09K 11/06*** | (2006.01) |
| ***H01L 51/50*** | (2006.01) |
| ***H10K 85/60*** | (2023.01) |
| *H10K 50/11* | (2023.01) |

(52) U.S. Cl.

CPC ......... *H10K 85/654* (2023.02); *C07D 401/14* (2013.01); *C07D 491/048* (2013.01); *C07D 519/00* (2013.01); *C09K 11/06* (2013.01); *H10K 85/657* (2023.02); *H10K 85/6572* (2023.02); *C09K 2211/1018* (2013.01); *H10K 50/11* (2023.02)

(58) Field of Classification Search

CPC .............................. C07D 401/14; H10K 50/10
USPC ........................................... 544/180; 313/504
See application file for complete search history.

(56) References Cited

U.S. PATENT DOCUMENTS

| | | | |
|---|---|---|---|
| 2018/0182975 A1 | 6/2018 | Yen et al. |
| 2019/0036034 A1 | 1/2019 | Akashi |

FOREIGN PATENT DOCUMENTS

| | | | |
|---|---|---|---|
| CN | 106187861 A | 12/2016 |
| CN | 107759566 A | 3/2018 |
| CN | 110078754 A | 8/2019 |
| CN | 110452239 | 11/2019 |
| EP | 3581632 A1 | 12/2019 |
| JP | 2015-229677 A | 12/2015 |
| KR | 10-2015-0124637 | 11/2015 |
| KR | 10-2019-0027537 A | 3/2019 |
| WO | 2018/237393 A1 | 12/2018 |
| WO | 2019/046734 A1 | 3/2019 |

OTHER PUBLICATIONS

Japanese and English version of International Preliminary Report on Patentability of Chapter I, i.e., International Search Opinion which we received from the WIPO as the International Bureau of the PCT (Jul. 28, 2022).

International Search Report and Search Opinion issued in International Patent Application No. PCT/JP2021/003846, (May 11, 2021).

Chen, D. et al., Bipyridine-containing host materials for high performance yellow thermally activated delayed fluorescence-based organic light emitting diodes with very low efficiency roll-off, Advanced Optical Materials, 2019, vol. 8, pp. 1-10.

Xu, M. et al., Efficient thermally activated delayed fuorescence based on carbonitrile-substituted pyridine and carbazole, Journal of Materials Chemistry C, 2019, vol. 7, pp. 13754-13758.

Choi, S. H. et al., Dyes and Pigments, Elsevier, 2019, vol. 172, pp. 1-7.

Zhang, Q. et al., Manipulating the positions of CH . . . N in acceptors of pyrimidine-pyridine hybrids for highly efficient sky-blue thermally activated delayed fluorescent OLEDs, Materials Chemistry Frontiers, 2018, vol. 2, pp. 2054-2062.

(Continued)

*Primary Examiner* — Charanjit Aulakh

(74) *Attorney, Agent, or Firm* — Troutman Pepper Locke LLP; Nicholas J. DiCeglie, Jr.; James E. Armstrong, IV

(57) ABSTRACT

The compound represented by the following formula is useful as a light-emitting material. $R^1$ or $R^2$ is Het-$L^A$-* or CN-$L^A$-*; one to three of $R^1$ to $R^5$ are diarylamino groups; the rest are a hydrogen atom or an aryl group; Het is a heteroaryl group; and $L^A$ is a single bond or an arylene group.

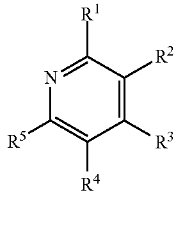

3 Claims, No Drawings

(56) References Cited

OTHER PUBLICATIONS

Wu, Q. et al., Carbazole/alpha-carboline hybrid biopolar compounds as electron acceptors in exciplex or non-exciplex mixed cohosts and exciplex-TADF emitters for high-efficiency OLEDs, Journal of Materials Chemistry C, 2018, vol. 6, pp. 8784-8792.

Office Action dated Jan. 2, 2024 issued in the corresponding Chinese patent application No. 202180020726.X with its English Machine Translation.

Chinese office action dated Sep. 29, 2023, in Chinese application No. 202180020726.X.

Office Action dated Mar. 31, 2025 issued in the corresponding European patent application No. 21750929.8.

Office Action dated May 13, 2025 issued in the corresponding Japanese patent application No. 2021-575824 with its English Machine translation.

Chinese office action dated May 20, 2023, from corresponding Chinese patent application No. 202180020726.

European search report dated Jun. 12, 2023, from corresponding European patent application No. 21750929.8.

Arsenyan, et al., Dual versus normal TADF of pyridines ornamented with multiple donor moieties and their performance in OLEDs, J. Mater. Chem., 9:3928-3938 (2021).

European Office Action dated Dec. 20, 2023, from corresponding European application No. 21 750 929.8.

Liu, et al., Novel Carbazol-Pyridine-Carbonitrile Derivative as Excellent Blue Thermally Activated Delayed Fluorescence Emitter for Highly Efficient Organic Light-Emitting Devices, ACS Appl. Mater Interfaces, 7:18930-18936 (2015).

Vigante, et al., Synthesis of Linear and V-Shaped Carbazolyl-Substituted Pyridine-3,5-dicarbonitriles Exhibiting Efficient Bipolar Charge Transport and E-Type Fluorescence, Chem. Eur. J., 25:3325-3336 (2019).

Office Action dated Dec. 10, 2024 issued in the corresponding Japanese patent application No. 2021-575824 with its English Machine Translation.

Office Action dated Aug. 5, 2024 issued in the corresponding European patent application No. 21750929.8.

Office Action dated Jun. 15, 2025 issued in the corresponding Korean patent application No. 10-2022-7030414 with its English Machine Translation.

COMPOUND, LUMINESCENT MATERIAL, DELAYED FLUORESCENT MATERIAL, AND ORGANIC OPTICAL DEVICE

TECHNICAL FIELD

The present invention relates to a compound having good luminescence characteristics. Further, the present invention also relates to a light-emitting material using the compound, a delayed fluorescence material, and an organic optical device.

BACKGROUND ART

Research has been actively conducted to improve the luminous efficiency of organic optical devices such as organic light emitting diodes (OLEDs). For example, in relation to the material of a light emitting layer, research on the use of compounds in which inverse intersystem crossing can be caused from an excited triplet state to an excited singlet state have been energetically conducted. When a normal fluorescent light-emitting material is current-excited at room temperature, singlet excitons and triplet excitons are generated with a probability of 25:75. Among these, the singlet excitons are radiatively deactivated to a ground singlet state and emit fluorescence. Whereas the triplet excitons have a long lifetime, and thus lose energy due to thermal radiation prior to transition to a ground state and are deactivated without radiation. Therefore, the energy of triplet excitons having a high generation probability cannot be effectively used for light emission. On the other hand, in compounds in which inverse intersystem crossing can be caused from the excited triplet state to the excited singlet state, since singlet excitons generated by inverse intersystem crossing from the excited triplet state to the excited singlet state also emit fluorescence during the transition to the ground singlet state, the energy of triplet excitons having a high generation probability can also be indirectly allowed to contribute to the fluorescence emission. Therefore, a significantly high luminous efficiency can be expected as compared to in the case where the normal fluorescent light-emitting material not causing inverse intersystem crossing is used.

As for an organic optical device using a compound capable of causing such inverse intersystem crossing, many things having a single light emitting layer formed by co-depositing a thermal activation-type delayed fluorophore and a host material have been suggested (see, for example, Patent Document 1). Here, the thermal activation-type delayed fluorophore is a compound in which inverse intersystem crossing occurs from the excited triplet state to the excited singlet state due to absorption of heat energy. After the fluorescence radiation from the singlet excitons directly excited from the ground singlet state is observed, the fluorescence radiation (delayed fluorescence radiation) from the singlet excitons generated via the inverse intersystem crossing is observed with a delay.

CITATION LIST

Patent Literature

Patent Document 1: WO2018/237393

SUMMARY OF INVENTION

Technical Problem

However, in the conventionally suggested light-emitting material, there is room for further improvement in terms of luminous efficiency. Thus, the present inventors, etc. have found a light-emitting material having good luminescence characteristics, and have conducted intensive studies for the purpose of providing an organic optical device having high luminous efficiency.

Solution to Problem

The present inventors, etc. have conducted intensive studies, and as a result, have found that a compound having a specific structure has excellent luminescence characteristics. The present invention is suggested on the basis of such findings, and has the following configurations.

[1] A compound represented by the following formula (1).

Formula (1)

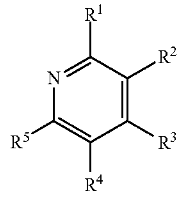

[In the formula (1), among $R^1$ to $R^5$,
one of $R^1$ and $R^2$ is A,
among the rest of $R^1$ to $R^5$, p are D's, and
the remaining 4-p are R's.
Here,
A is a group represented by Het-$L^A$-* or CN-$L^A$-*, in which Het represents a substituted or unsubstituted heteroaryl group bonded via a carbon atom (meanwhile, at least one nitrogen atom is included as a ring skeleton-forming atom of the heteroaryl group), $L^A$ represents a single bond or a substituted or unsubstituted arylene group, and * represents a bond position.
D is a group represented by the following formula (IIa), (IIb), (IIc) or (IId).

Formula (IIa)

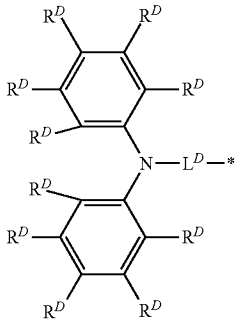

Formula (IIb)

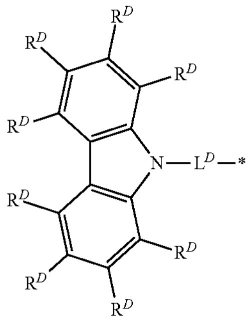

-continued

Formula (IIc)

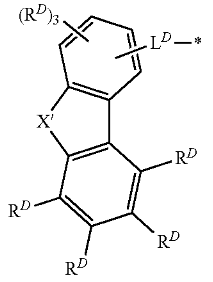

Formula (IId)

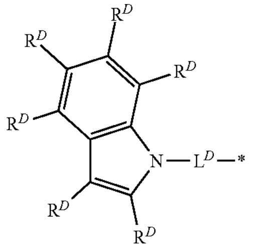

Here, X' represents N—$R^{D'}$, an oxygen atom, or a sulfur atom, each $R^D$ independently represents a hydrogen atom, a deuterium atom, a substituted or unsubstituted alkyl group, a substituted or unsubstituted alkoxy group, a substituted or unsubstituted amino group, a cyano group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $R^{D'}$ represents a hydrogen atom, a deuterium atom, a substituted or unsubstituted alkyl group, a substituted or unsubstituted amino group, a substituted or unsubstituted aryl group, or a substituted or unsubstituted heteroaryl group, and $R^{D'}$ may be bonded to one or more $R^D$'s to form a cyclic structure, each $L^D$ independently represents a single bond, a substituted or unsubstituted arylene group, or a substituted or unsubstituted heteroarylene group, and

* represents a bond position.

R is a hydrogen atom, a deuterium atom, or a substituted or unsubstituted aryl group (but, other than a group that may be A or D).

p is any integer of 1 to 3. When p is 2 or 3. D's present in the molecule may be the same or different. When p is 1 or 2. R's present in the molecule may be the same or different.]

[2] The compound described in [1], in which $R^2$ is A.

[3] The compound described in [1], in which $R^1$ is A.

[4] The compound described in any one of [1] to [3], in which at least one of $R^1$ to $R^5$ is a hydrogen atom or a deuterium atom.

[5] The compound described in [2], in which $R^2$ is A. and moreover, at least one of $R^1$ and $R^3$ is a hydrogen atom or a deuterium atom.

[6] The compound described in [3], in which $R^1$ is A. and moreover, $R^2$ is a hydrogen atom or a deuterium atom.

[7] The compound described in any one of [1] to [6], in which p is 3.

[8] The compound described in [7], in which R is a hydrogen atom or a deuterium atom.

[9] The compound described in any one of [1] to [6], in which p is 2.

[10] The compound described in [9], in which one of two R's is a hydrogen atom or a deuterium atom, and the other is a substituted or unsubstituted aryl group (but, other than a group that may be A or D).

[11] The compound described in [9], in which each of two R's is independently a hydrogen atom or a deuterium atom.

[12] The compound described in any one of [1] to [11], in which each of $R^4$ and $R^5$ is independently D.

[13] The compound described in any one of [1] to [11], in which one of $R^4$ and $R^5$ is D, and the other is a substituted or unsubstituted aryl group (but, other than a group that may be A or D).

[14] The compound described in any one of [1] to [13], in which A is Het-$L^A$-.

[15] The compound described in [14], in which A is represented by any of the following formulas (IIIa) to (IIIe).

Formula (IIIa)

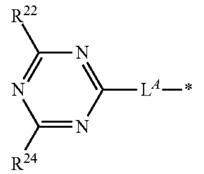

Formula (IIIb)

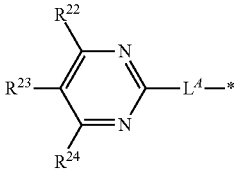

Formula (IIIc)

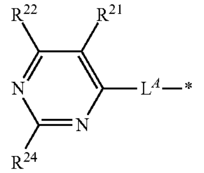

Formula (IIId)

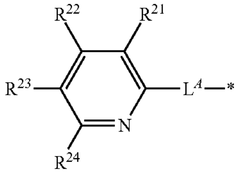

Formula (IIIe)

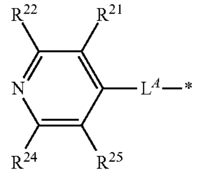

[In the formulas (IIIa) to (IIIe), each of $R^{21}$ to $R^{25}$ independently represents a hydrogen atom or a substituent. $R^{21}$ and $R^{22}$, $R^{22}$ and $R^{23}$, $R^{23}$ and $R^{24}$, and $R^{24}$ and $R^{25}$ may be bonded to each other to form cyclic structures. $L^A$ represents a single bond or a substituted or unsubstituted arylene group.]

[16] The compound described in [14] or [15], in which Het is not a dialkylphenyl-1,3,5-triazinyl group.

[17] The compound described in [16], in which $L^A$ is a single bond.

[18] The compound described in any one of [1] to [17], in which D is a group represented by the formula (IIb).

[19] A light-emitting material including the compound described in any one of [1] to [18].

[20] A delayed fluorescence material including the compound described in any one of [1] to [18].

[21] An organic optical device including the compound described in any one of [1] to [18].

[22] The organic optical device described in [21], in which the device has a layer containing the compound, and the layer also contains a host material.

[23] The organic optical device described in [21], in which the device has a layer containing the compound, and the layer also contains a light-emitting material.

[24] The organic optical device described in any one of [21] to [23], in which among the materials contained in the device, the compound emits the maximum amount of light.

[25] The organic optical device described in [23], in which the amount of light emitted from the light-emitting material is larger than the amount of light emitted from the compound.

[26] The organic optical device described in any one of [21] to [25], which is an organic light emitting diode (OLED).

[27] The organic optical device described in any one of [21] to [26], which emits delayed fluorescence.

[28] A compound represented by the following formula (1').

Formula (1')

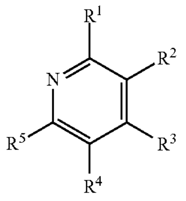

[In the formula (1'), $R^1$ to $R^5$ satisfy the following condition 1 or condition 2.

(Condition 1) Among $R^1$ to $R^5$, one of $R^1$ and $R^2$ is a halogen atom, among the rest of $R^1$ to R, p are D's, and the remaining 4-p are R's.

(Condition 2) Among $R^1$ to $R^5$, one of $R^1$ and $R^2$ is A, among the rest of $R^1$ to $R^5$, p are halogen atoms, and the remaining 4-p are R's.

Here,

A is a group represented by Het-$L^A$-* or CN-$L^A$-*, in which Het represents a substituted or unsubstituted heteroaryl group bonded via a carbon atom (meanwhile, at least one nitrogen atom is included as a ring skeleton-forming atom of the heteroaryl group), $L^A$ represents a single bond or a substituted or unsubstituted arylene group, and * represents a bond position.

D is a group represented by the following formula (IIa), (IIb), (IIc) or (IId).

Formula (IIa)

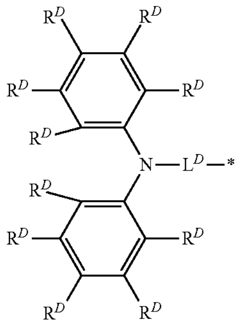

Formula (IIb)

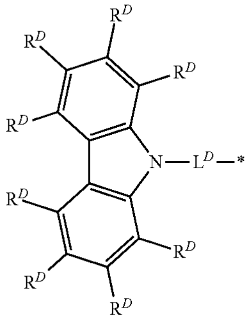

Formula (IIc)

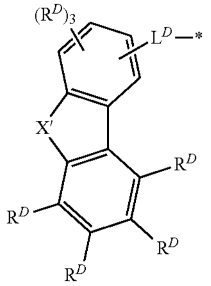

Formula (IId)

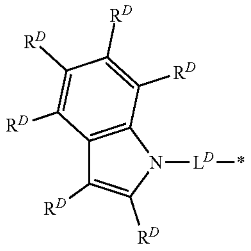

Here, X' represents N—$R^{D'}$, an oxygen atom, or a sulfur atom, each $R^D$ independently represents a hydrogen atom, a deuterium atom, a substituted or unsubstituted alkyl group, a substituted or unsubstituted alkoxy group, a substituted or unsubstituted amino group, a cyano group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $R^{D'}$ represents a hydrogen atom, a deuterium atom, a substituted or unsubstituted alkyl group, a substituted or unsubstituted aryl group, or a substituted or unsubstituted heteroaryl group, and $R^{D'}$ may be bonded to one or more $R^D$'s to form a cyclic structure, each $L^D$ independently represents a single bond, a substituted or unsubstituted arylene group, or a substituted or unsubstituted heteroarylene group, and

* represents a bond position.

R is a hydrogen atom, a deuterium atom, or a substituted or unsubstituted aryl group (but, other than a group that may be A or D).

p is any integer of 1 to 3. When p is 2 or 3, D's present in the molecule may be the same or different. When p is 1 or 2, R's present in the molecule may be the same or different.]

[29] The compound described in [28], which satisfies the condition 1.

[30] The compound described in [29], in which p is 2.

[31] The compound described in [29] or [30], in which D is a group represented by the formula (lib).

[32] The compound described in any one of [29] to [31], in which the halogen atom is a chlorine atom or an iodine atom.

[33] The compound described in any one of [29] to [32], in which R is a substituted or unsubstituted aryl group.

[34] The compound described in [33], in which R is an unsubstituted phenyl group.

[35] The compound described in [28], which satisfies the condition 2.

[36] The compound described in [35], in which p is 2 or 3.

[37] The compound described in [35] or [36], in which A has a substituted or unsubstituted triazinyl group.

[38] The compound described in any one of [35] to [37], in which the halogen atom is a fluorine atom.

Advantageous Effects of Invention

According to the present invention, it is possible to provide a light-emitting material having good luminescence characteristics. Further, according to the present invention, it is possible to provide an organic optical device having high luminous efficiency.

DESCRIPTION OF EMBODIMENTS

Hereinafter, the contents of the present invention will be described in detail. The descriptions on constituent elements to be described below may be made on the basis of representative embodiments or specific examples of the present invention, but the present invention is not limited to such embodiments or specific examples. The numerical value range represented by using "to" in the present specification means a range including numerical values described before and after "to", as the lower limit value and the upper limit value. The entire specification of Japanese Application No. 2020-017486, which is the basis of the priority claim of the present application, is cited herein as a part of the specification of the present application.

The present invention provides a compound represented by the following formula (1).

Formula (1)

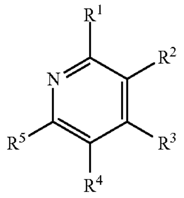

In the formula (1), among $R^1$ to $R^5$, one of $R^1$ and $R^2$ is A, among the rest of $R^1$ to $R^5$, p are D's, and the remaining 4-p are R's. Here, p is any integer of 1 to 3.

In some embodiments, $R^2$ is A. In a preferred embodiment, $R^2$ is A, and moreover, at least one of $R^1$ and $R^3$ is a hydrogen atom or a deuterium atom. For example, $R^2$ is A, $R^1$ is a hydrogen atom or a deuterium atom, and $R^3$ is D or a substituted or unsubstituted aryl group (but, other than a group that may be A or D). For example, $R^2$ is A, $R^3$ is a hydrogen atom or a deuterium atom, and $R^1$ is D or a substituted or unsubstituted aryl group (but, other than a group that may be A or D). For example, $R^2$ is A. and each of $R^1$ and $R^2$ is independently a hydrogen atom or a deuterium atom. In a preferred embodiment of the present invention, $R^2$ is A, and at least one of $R^4$ and $R^5$ is D. For example, $R^2$ is A, $R^4$ is D. and $R^5$ is R [more preferably a substituted or unsubstituted aryl group (but, other than a group that may be A or D)]. For example, $R^2$ is A, $R^5$ is D, and $R^4$ is R [more preferably, a substituted or unsubstituted aryl group (but, other than a group that may be A or D)]. For example, $R^2$ is A, and each of $R^4$ and $R^5$ is independently D. In a preferred embodiment of the present invention, $R^2$ is A, at least one of $R^1$ and $R^3$ is a hydrogen atom or a deuterium atom, and at least one of $R^4$ and $R^5$ is D.

In some embodiments, $R^1$ is A. In a preferred embodiment, $R^1$ is A, and moreover, $R^2$ is a hydrogen atom or a deuterium atom. In another preferred embodiment, $R^1$ is A, and moreover, at least one of $R^4$ and $R^5$ is D. For example, $R^1$ is A, $R^4$ is D, and $R^5$ is R [more preferably a substituted or unsubstituted aryl group (but, other than a group that may be A or D)]. For example, $R^1$ is A, $R^5$ is D, and $R^4$ is R [more preferably, a substituted or unsubstituted aryl group (but, other than a group that may be A or D)]. For example, $R^1$ is A, and each of $R^4$ and $R^5$ is independently D. In a preferred embodiment of the present invention, $R^1$ is A, $R^2$ is a hydrogen atom or a deuterium atom, and at least one of $R^4$ and $R^5$ is D. Further, in some embodiments, $R^1$ is A, and $R^3$ is R. For example, $R^1$ is A, and $R^3$ is a hydrogen atom or a deuterium atom. For example, $R^1$ is A, and $R^3$ is a substituted or unsubstituted aryl group (but, other than a group that may be A or D). Further, in some embodiments, $R^1$ is A, and $R^3$ is D.

In some embodiments, $R^3$ is a hydrogen atom or a deuterium atom. In some embodiments, $R^3$ is a substituted or unsubstituted aryl group (but, other than a group that may be A or D). In some embodiments, $R^3$ is D.

In some embodiments, at least one of $R^4$ and $R^5$ is D. In a preferred embodiment of the present invention, each of $R^4$ and $R^5$ is independently D. For example, $R^4$ and $R^5$ are the same D's. For example, $R^4$ and $R^5$ are different D's. In some embodiments, each of $R^1$, $R^4$ and $R^5$ is independently D. In some embodiments, each of $R^2$, $R^4$ and $R^5$ is independently D. In some embodiments, each of $R^3$, $R^4$ and $R^5$ is independently D.

In some embodiments, at least one of $R^3$ and $R^5$ is D. For example, each of $R^3$ and $R^5$ is independently D. For example, $R^3$ is D. and $R^5$ is R [more preferably, a substituted or unsubstituted aryl group (but, other than a group that may be A or D)]. For example, $R^5$ is D, and $R^3$ is R [more preferably, a substituted or unsubstituted aryl group (but, other than a group that may be A or D)]. For example, $R^3$ is D. and $R^5$ is a hydrogen atom or a deuterium atom. For example, $R^5$ is D, and $R^3$ is a hydrogen atom or a deuterium atom.

In some embodiments, at least one of $R^1$ and $R^5$ is D. For example, each of $R^1$ and $R^5$ is independently D. For example, $R^1$ is D. and $R^5$ is R [more preferably, a substituted or unsubstituted aryl group (but, other than a group that may be A or D)]. For example, $R^5$ is D, and $R^1$ is R [more preferably, a substituted or unsubstituted aryl group (but, other than a group that may be A or D)]. For example, $R^5$ is D, and $R^1$ is a hydrogen atom or a deuterium atom. For example, $R^1$ is D, and $R^5$ is a hydrogen atom or a deuterium atom.

In some embodiments, at least one of $R^1$ and $R^4$ is D. For example, each of $R^1$ and $R^4$ is independently D. For example, $R^1$ is D. and $R^4$ is R [more preferably, a substituted or unsubstituted aryl group (but, other than a group that may be A or D)]. For example, $R^4$ is D. and $R^1$ is R [more preferably, a substituted or unsubstituted aryl group (but, other than a group that may be A or D)]. For example, $R^4$ is D, and $R^1$ is a hydrogen atom or a deuterium atom. For example, $R^1$ is D, and $R^4$ is a hydrogen atom or a deuterium atom.

In some embodiments, at least one of $R^1$, $R^4$ and $R^5$ is a substituted or unsubstituted aryl group (but, other than a group that may be A or D). In some embodiments, only one of $R^1$, $R^4$ and $R^5$ is a substituted or unsubstituted aryl group (but, other than a group that may be A or D). For example, $R^1$ is a substituted or unsubstituted aryl group (but, other than a group that may be A or D). For example, $R^4$ is a substituted or unsubstituted aryl group (but, other than a group that may be A or D). For example, $R^5$ is a substituted or unsubstituted aryl group (but, other than a group that may be A or D).

As a group of combinations of $R^1$ to $R^5$, a group in which ($R^1$, $R^2$, $R^3$, $R^4$, $R^5$) is (H, A, D, D, D), (D, A, H, D, D) or (H, A, H, D, D) may be exemplified. As another group, a group in which ($R^1$, $R^2$, $R^3$, $R^4$, $R^5$) is (H, A, D, D, D), (H, A, Ar, D, D), (H, A, D, Ar, D) or (H, A, D, D, Ar) may be exemplified. As another group, a group in which ($R^1$, $R^2$, $R^3$, $R^4$, $R^5$) is (H, A, D, D, D), (H, A, Ar, Ar, D), (H, A, D, Ar, Ar) or (H, A, Ar, D, Ar) may be exemplified. As another group, a group in which ($R^1$, $R^2$, $R^3$, $R^4$, $R^5$) is (Ar, A, H, D, D), (D, A, H, Ar, D) or (D, A, H, D, Ar) may be exemplified. As another group, a group in which ($R^1$, $R^2$, $R^3$, $R^4$, $R^5$) is (Ar, A, H, Ar, D), (Ar, A, H, D, Ar) or (D, A, H, Ar, Ar) may be exemplified. As another group, a group in which ($R^1$, $R^2$, $R^3$, $R^4$, $R^5$) is (H, A, H, D, D), (H, A, H, Ar, D) or (H, A, H, D, Ar) may be exemplified. As another group, a group of (A, D, D, D, H), (A, D, D, D, Ar), (A, D, D, Ar, D) and (A, D, Ar, D, D) may be exemplified. As another group, a group of (A, D, H, D, Ar) and (A, D, Ar, D, H) may be exemplified. As another group, a group of (A, D, D, H, Ar) and (A, D, D, Ar, H) may be exemplified. As another group, a group of (A, D, Ar, H, D) and (A, D, H, Ar, D) may be exemplified. As another group, a group of (D, A, H, D, D), (D, A, H, H, D), (D, A, H, Ar, D) and (D, A, H, D, Ar) may be exemplified. As another group, (H, A, D, Ar, D) may be exemplified. Here, H represents a hydrogen atom, and Ar represents a substituted or unsubstituted aryl group (but, other than a group that may be A or D). In the present invention, combinations of $R^1$ to $R^5$, which do not belong to the groups exemplified herein, can also be adopted.

In the formula (1), A is a group represented by Het-$L^A$-* or CN-$L^A$-*. Here, Het is a substituted or unsubstituted heteroaryl group bonded via a carbon atom, and the heteroaryl group mentioned herein contains at least one nitrogen atom as a ring skeleton-forming atom. $L^A$ represents a single bond or a substituted or unsubstituted arylene group. * represents a bond position.

As A in the formula (1), Het-$L^A$-* can be preferably selected. Further, as A, CN-$L^A$-* can also be selected.

Het has a heteroaryl ring in which a nitrogen atom is contained as a ring skeleton-forming atom, and it is desirable that a ring skeleton-forming carbon atom of the heteroaryl ring is bonded to $L^A$ (bonded to a ring skeleton-forming carbon atom of a pyridine ring of the formula (1) when $L^A$ mentioned herein is a single bond). Het-$L^A$-* is preferably a group represented by any of the following formulas (IIIa), (IIIb), (IIIc), (IIId) and (IIIe).

Formula (IIIa)

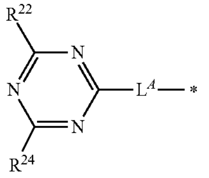

Formula (IIIb)

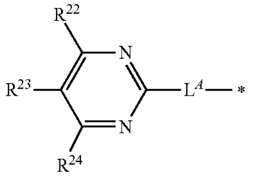

Formula (IIIc)

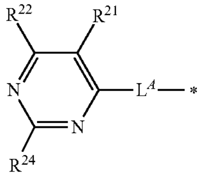

Formula (IIId)

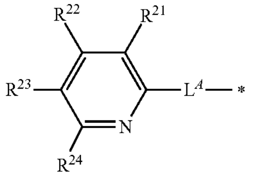

Formula (IIIe)

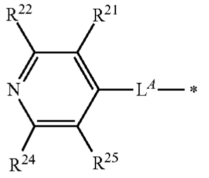

Each of $R^{21}$ to $R^{25}$ independently represents a hydrogen atom or a substituent. $L^A$ represents a single bond or a substituted or unsubstituted arylene group. In some embodiments, each of $R^{21}$ to $R^{25}$ is independently a hydrogen atom, a deuterium atom, a cyano group, a substituted or unsubstituted alkyl group, a substituted or unsubstituted aryl group, or a substituted or unsubstituted heteroaryl group. The alkyl group mentioned herein may be substituted with, for example, one or more substituents selected from a deuterium atom, a substituted or unsubstituted aryl group, and a substituted or unsubstituted heteroaryl group. Each of the aryl group and the heteroaryl group mentioned herein may be independently substituted with, for example, one or more substituents selected from a deuterium atom, a substituted or unsubstituted alkyl group, a substituted or unsubstituted aryl group, and a substituted or unsubstituted heteroaryl group. Two or more of these substituents may be bonded to form a cyclic structure. Further, $R^{21}$ and $R^{22}$, $R^{22}$ and $R^{23}$, $R^{23}$ and $R^{24}$, and $R^{24}$ and $R^{25}$ may be bonded to each other to form cyclic structures. The cyclic structure mentioned herein may be a substituted or unsubstituted aromatic ring, or may be a substituted or unsubstituted aliphatic ring. Further, it may be a carbon ring or a hetero ring. In a preferred embodiment, each of $R^{21}$ to $R^{25}$ is independently a substituted or unsubstituted alkyl group, or a substituted or unsubstituted aryl group. In another preferred embodiment, at least one of $R^{21}$ to $R^{24}$ is an aryl group that may be substituted with an aryl group. In a more preferred embodiment, each of $R^{21}$ to $R^{25}$ is independently a substituted or unsubstituted aryl group. $R^{21}$ to $R^{25}$ may be the same or different, and, for example, can be the same. Further, in a preferred embodiment, a benzene ring is formed through bonding in one of $R^{21}$ and $R^{22}$, $R^{22}$ and $R^{23}$, $R^{23}$ and $R^{24}$, and $R^{24}$ and $R^{25}$. In another preferred embodiment, a benzofuran ring or a benzothiophene ring is formed through bonding in one of $R^{21}$ and $R^{22}$, $R^{22}$ and $R^{23}$, $R^{23}$ and $R^{24}$, and $R^{24}$ and $R^{25}$.

$R^{21}$ and $L^A$, and $R^{25}$ and $L^A$ do not bond to each other and form cyclic structures.

Het-$L^A$-* can be, for example, a group represented by any of the formulas (IIIa), (IIIb) and (IIIc). Further, it can be a group represented by either the formula (IIIb) or (IIIc). Further, it can be a group represented by either the formula (IIId) or (IIIe). Further, in a preferred embodiment, Het-$L^A$-* is a group represented by the formula (IIIa).

In some embodiments, $L^A$ is a single bond.

Further, in other embodiments of the present invention, $L^A$ is a substituted or unsubstituted arylene group. $L^A$ may be a linking group in which two or three substituted or unsubstituted arylene groups are linked. Further. $L^A$ may be composed of only one substituted or unsubstituted arylene group. In some embodiments, $L^A$ is an unsubstituted arylene group. Further, in some embodiments, $L^A$ is a substituted arylene group. Here, the arylene group may be substituted with, for example, one or more substituents selected from a deuterium atom, a substituted or unsubstituted alkyl group, a substituted or unsubstituted aryl group, a substituted or unsubstituted heteroaryl group, and a cyano group, and two or more of these substituents may be combined to form a cyclic structure. The cyclic structure mentioned herein may be a substituted or unsubstituted aromatic ring, or a substituted or unsubstituted aliphatic ring. Further, it may be a carbon ring, or may be a hetero ring. Further, the arylene group represented by $L^A$ may be substituted with a group represented by any of (IIIa) to (IIIe). In some embodiments of the present invention, A is Het-$L^A$-*, and $L^A$ an arylene group that may be substituted with one group selected from the group consisting of an alkyl group, an aryl group, and a cyano group, or a group formed by combining two or more thereof. In some embodiments of the present invention, A is CN-$L^A$-*, and $L^A$ is an arylene group that may be substituted with an alkyl group or a cyano group. In some embodiments, $L^A$ is a single bond, an unsubstituted phenylene group, or a phenylene group substituted with at least one alkyl group. Examples of the phenylene group include a 1,4-phenylene group, a 1,3-phenylene group, and a 1,2-phenylene group, and a 1,4-phenylene group and a 1,3-phenylene group are preferred.

In some embodiments, A is selected from the group consisting of A1 to A21 illustrated below. In some embodiments, A is selected from the group consisting of A1 to A5 and A12 to A21. In some embodiments, A is selected from the group consisting of A6 to A11. * represents a bond position.

A1

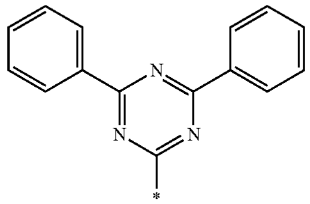

A2

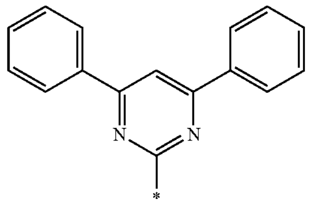

A3

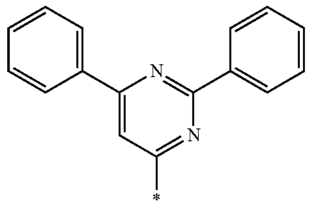

A4

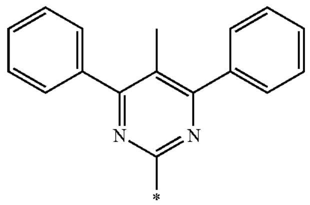

A5

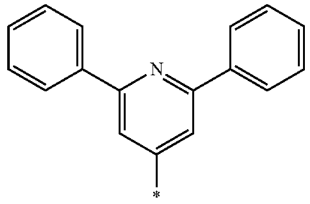

A6

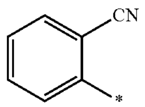

A7

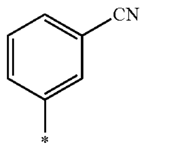

A8

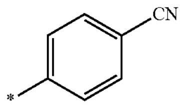

A9

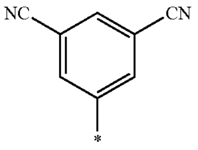

-continued

A10

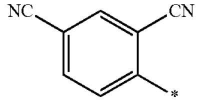

A11

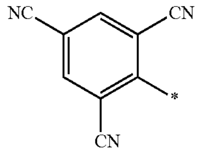

A12

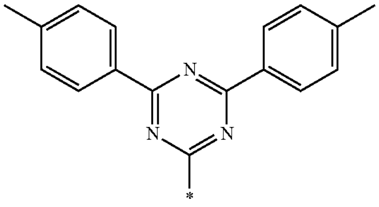

A13

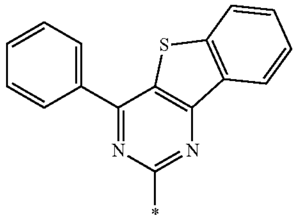

A14

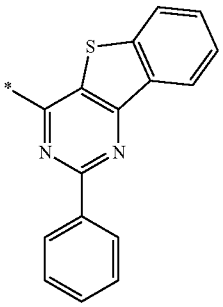

A15

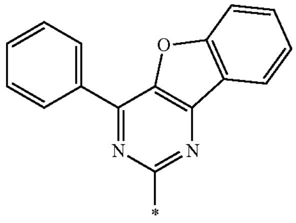

A16

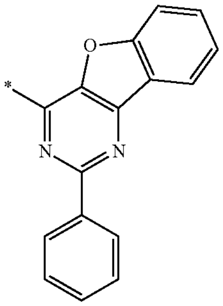

-continued

A17

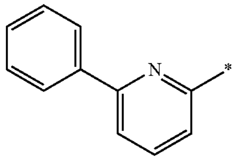

A18

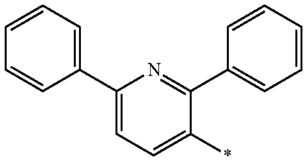

A19

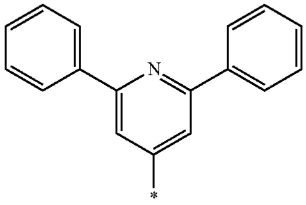

A20

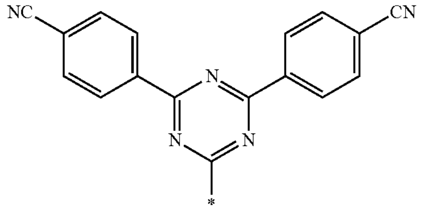

A21

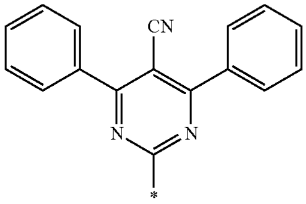

In the formula (1), D is a group represented by the following formula (IIa), (IIb), (IIc) or (IId). In some embodiments, D is a group represented by the formula (IIa), (IIb) or (IId). In some embodiments, D is a group represented by the formula (IIa). In some embodiments. D is a group represented by the formula (IIb). In some embodiments, D is a group represented by the formula (IId).

Formula (IIa)

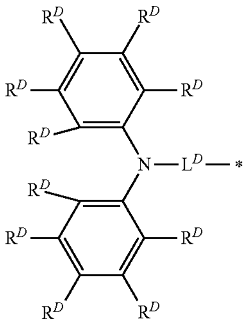

-continued

Formula (IIb)

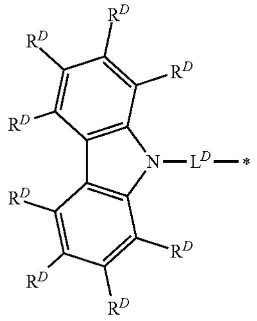

Formula (IIc)

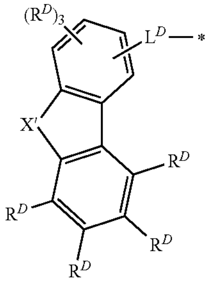

Formula (IId)

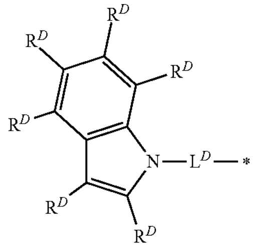

Each $R^D$ independently represents a hydrogen atom, a deuterium atom, a substituted or unsubstituted alkyl group, a substituted or unsubstituted alkoxy group, a substituted or unsubstituted amino group, a cyano group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure. In some embodiments of the present invention, each $R^D$ is independently selected from the group consisting of a hydrogen atom, a deuterium atom, a substituted or unsubstituted alkyl group, a substituted or unsubstituted amino group, a cyano group, and a substituted or unsubstituted aryl group. In some embodiments of the present invention, each $R^D$ is independently selected from the group consisting of a hydrogen atom, a deuterium atom, a substituted or unsubstituted alkyl group, and a substituted or unsubstituted alkoxy group. In some embodiments of the present invention, each $R^D$ is independently selected from the group consisting of a hydrogen atom, a deuterium atom, a substituted or unsubstituted aryl group, and a substituted or unsubstituted aryloxy group. In some embodiments of the present invention, each $R^D$ is independently selected from the group consisting of a hydrogen atom, a deuterium atom, a substituted or unsubstituted heteroaryl group, and a substituted or unsubstituted heteroaryloxy group. In some embodiments of the present invention, each $R^D$ is independently a hydrogen atom or a deuterium atom. Among $R^D$'s present in D, the number of substituents that are neither hydrogen atoms nor deuterium atoms is three or four in some embodiments, two in other embodiments of the present invention, or one in some embodiments.

X' represents N—$R^{D'}$, an oxygen atom, or a sulfur atom. In some embodiments, X' is N—$R^{D'}$. In some embodiments, X' is an oxygen atom. In some embodiments, X' is a sulfur atom.

$R^{D'}$ represents a hydrogen atom, a deuterium atom, a substituted or unsubstituted alkyl group, a substituted or unsubstituted aryl group, or a substituted or unsubstituted heteroaryl group, and $R^{D'}$ may be bonded to one or more $R^D$'s to form a cyclic structure. In some embodiments of the present invention, each $R^{D'}$ is independently a hydrogen atom or a deuterium atom. In some embodiments of the present invention, $R^{D'}$ is a substituted or unsubstituted alkyl group. In some embodiments of the present invention, $R^{D'}$ is a substituted or unsubstituted aryl group.

The cyclic structure formed by combining two or more $R^D$'s, or $R^{D'}$ and one or more $R^D$'s may be a substituted or unsubstituted aromatic ring, or a substituted or unsubstituted aliphatic ring. Further, it may be a carbon ring, or may be a hetero ring.

$R^D$ and $L^D$, and $R^{D'}$ and $L^D$ do not bond to each other to form a cyclic structure.

Each $L^D$ independently represents a single bond, a substituted or unsubstituted arylene group, or a substituted or unsubstituted heteroarylene group. In some embodiments, $L^D$ is a single bond. In some embodiments, $L^D$ is a substituted or unsubstituted arylene group. $L^D$ may be a linking group in which two or three selected from the group consisting of a substituted or unsubstituted arylene group and a substituted or unsubstituted heteroarylene group are linked to each other. In some embodiments, $L^D$ is a linking group in which two or three substituted or unsubstituted arylene groups are linked. In some embodiments, $L^D$ is composed of only one substituted or unsubstituted arylene group. In some embodiments, $L^D$ is an unsubstituted arylene group. Further, in some embodiments, $L^D$ is a substituted arylene group. Here, an arylene group may be substituted with, for example, one or more substituents selected from a deuterium atom, a substituted or unsubstituted alkyl group, a substituted or unsubstituted aryl group, and a substituted or unsubstituted heteroaryl group, and two or more of these substituents may be combined to form a cyclic structure. The cyclic structure mentioned herein may be a substituted or unsubstituted aromatic ring, or a substituted or unsubstituted aliphatic ring. Further, it may be a carbon ring, or may be a hetero ring.

In some embodiments, $L^D$ is a single bond, an unsubstituted phenylene group, or a phenylene group substituted with at least one alkyl group. Examples of the phenylene group include a 1,4-phenylene group, a 1,3-phenylene group, and a 1,2-phenylene group, and the 1,4-phenylene group and the 1,3-phenylene group are preferred.

In some embodiments, D is selected from the group consisting of D1 to D96 illustrated below. In some embodiments, D is selected from the group consisting of D1 to D4, D41 to D43, D84, D86 to D88, and D94 to D96. In some embodiments, D is selected from the group consisting of D1 to D5, D16 to D19, and D21 to D24. In some embodiments, D is selected from the group consisting of D32 to D38, D40 to D43, and D60 to D88. In some embodiments, D is selected from the group consisting of D89 to D91 and D93 to D96. * represents a bond position. Ph represents an unsubstituted phenyl group.

D1
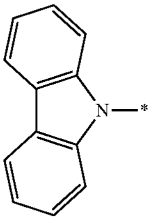
D2
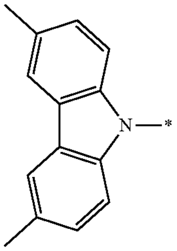
D3
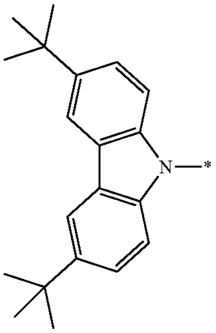
D4
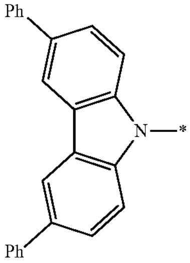
D5
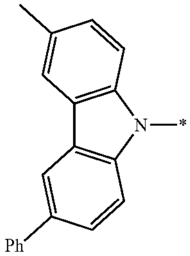
D6
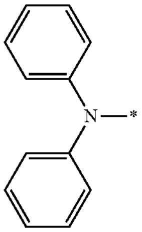
-continued
D7
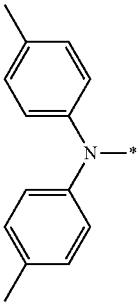
D8
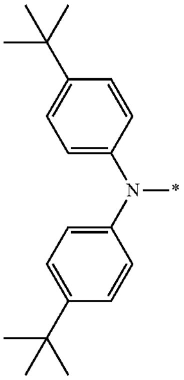
D9
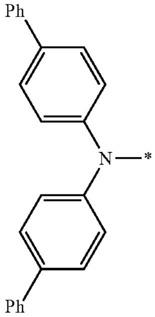
D10
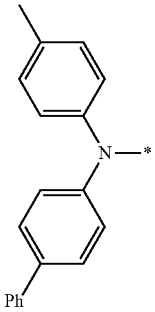
D11
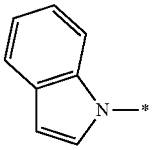

-continued
D12
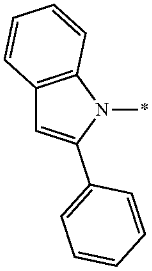
D13
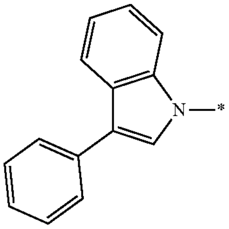
D14
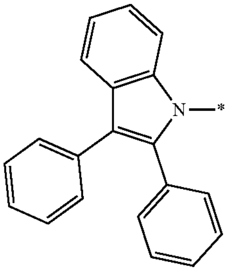
D15
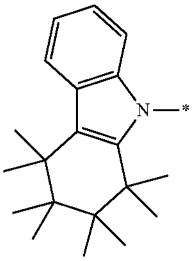
D16
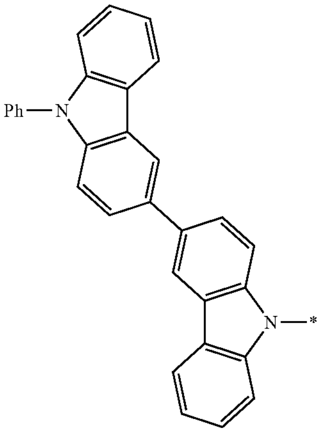
-continued
D17
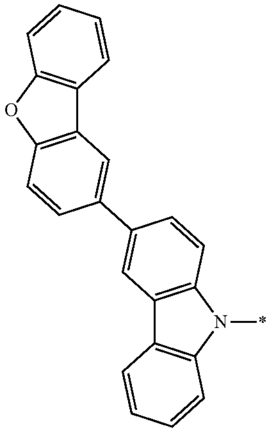
D18
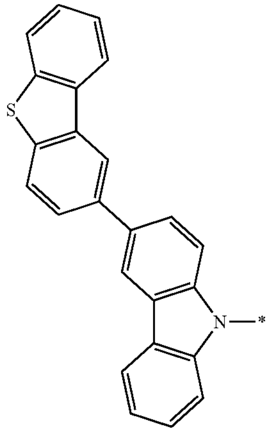
D19
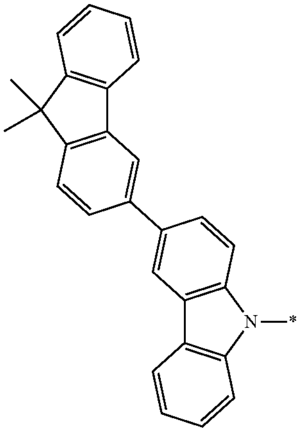

D20
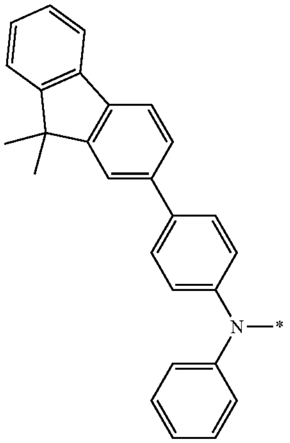
D21
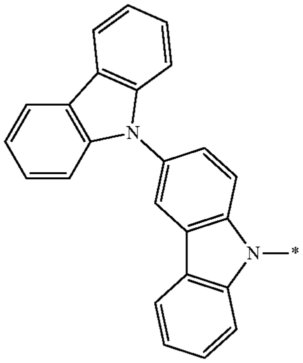
D22
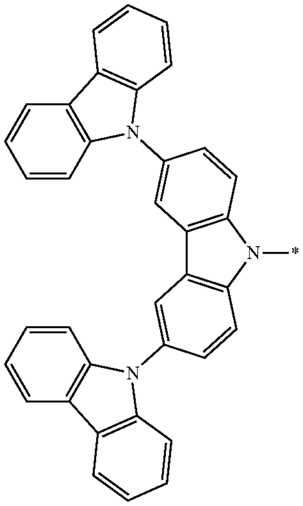
D23
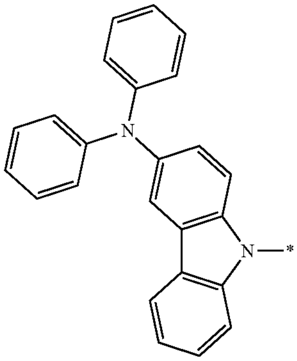
D24
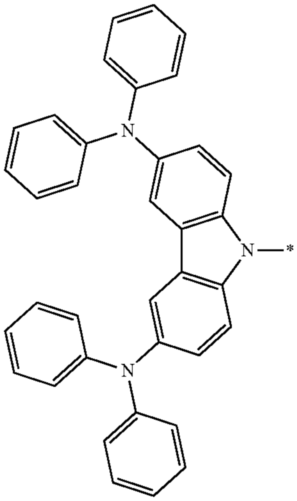
D25
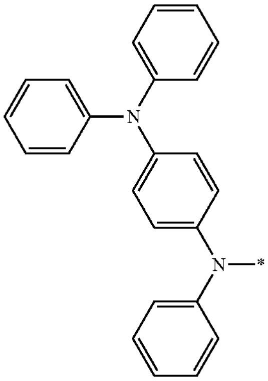

-continued
D26
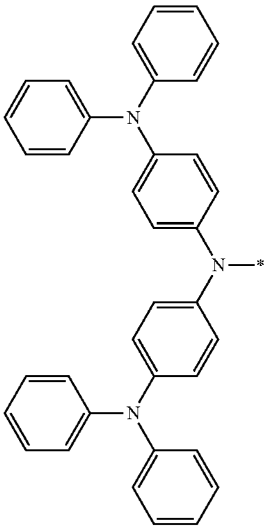
D27
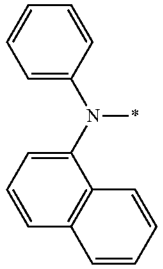
D28
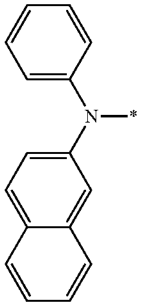
D29
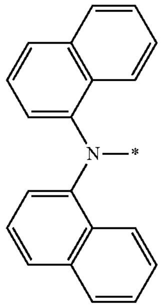
-continued
D30
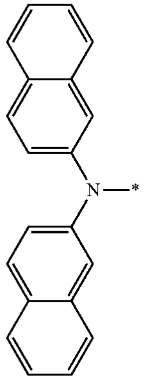
D31
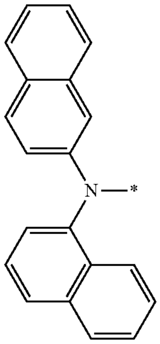
D32
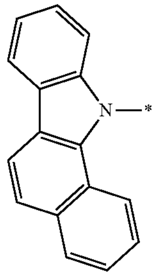
D33
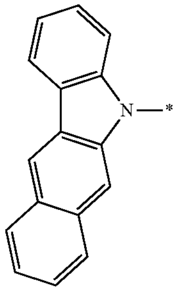
D34
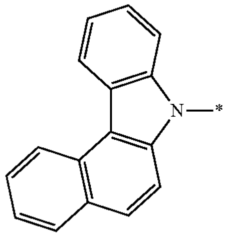

-continued
D35
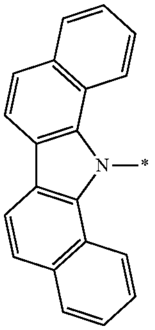
D36
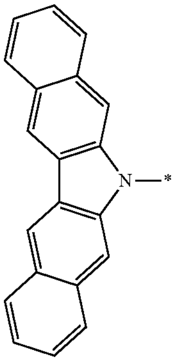
D37
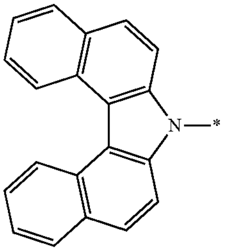
D38
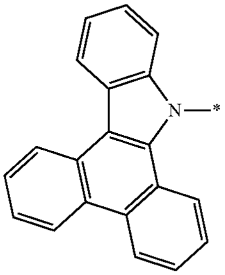
D39
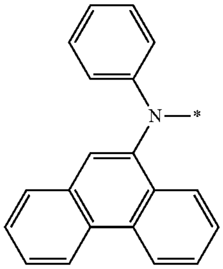
-continued
D40
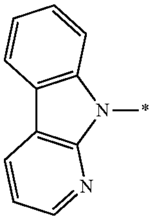
D41
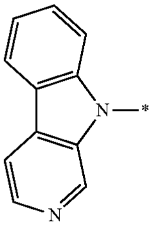
D42
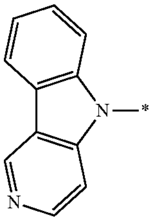
D43
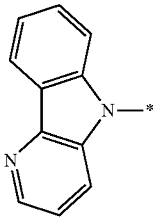
D44
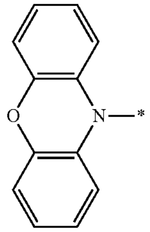
D45
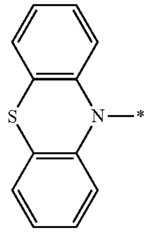
D46
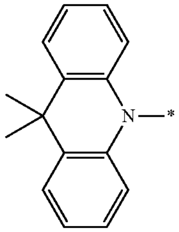

-continued
D47
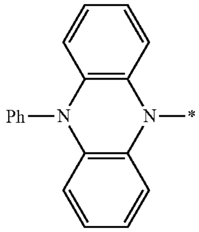
D48
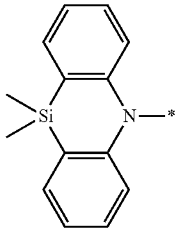
D49
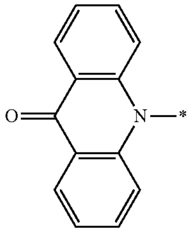
D50
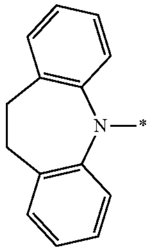
D51
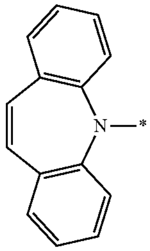
D52
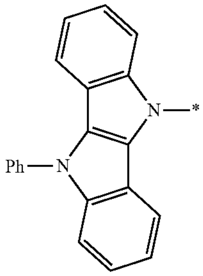
-continued
D53
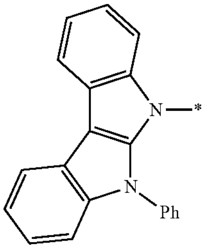
D54
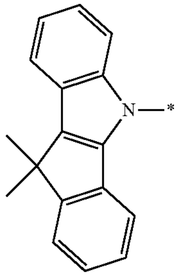
D55
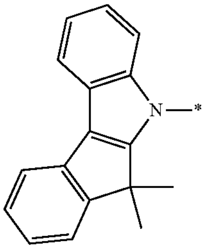
D56
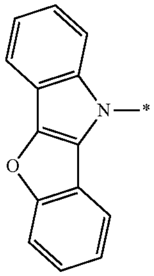
D57
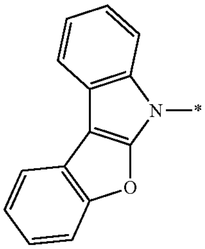
D58
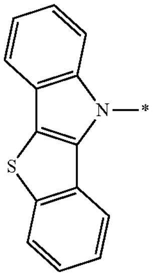

-continued
D59
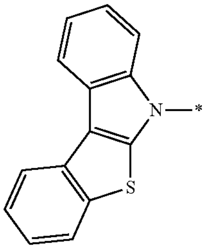
D60
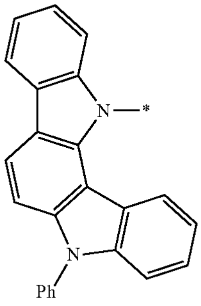
D61
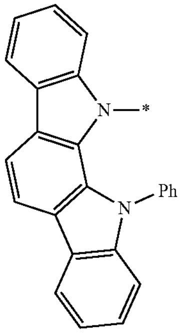
D62
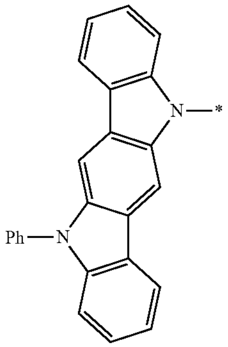
D63
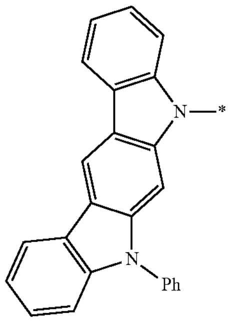
-continued
D64
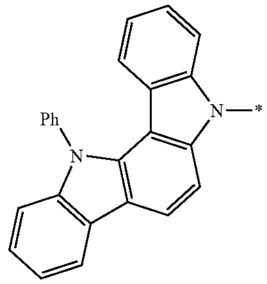
D65
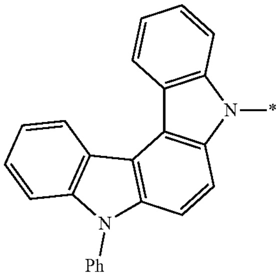
D66
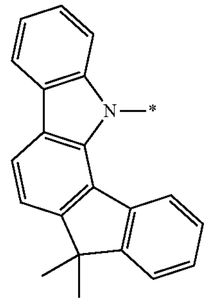
D67
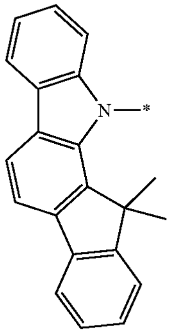
D68
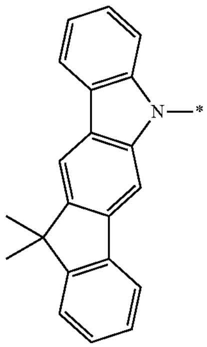

-continued
D69
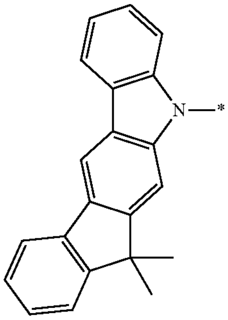
D70
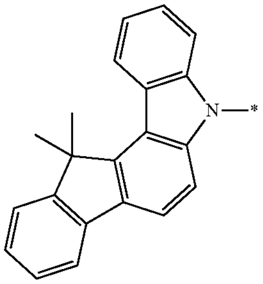
D71
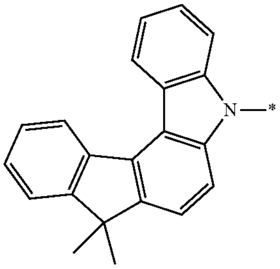
D72
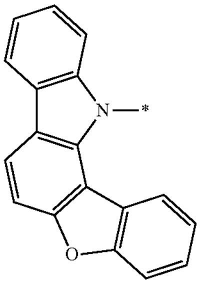
D73
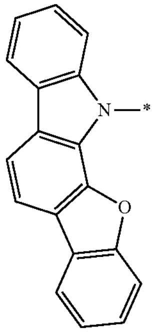
-continued
D74
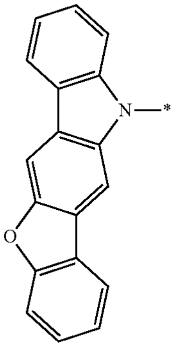
D75
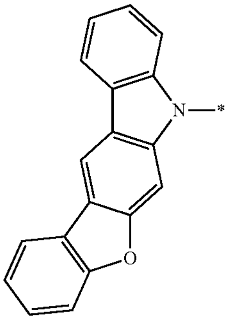
D76
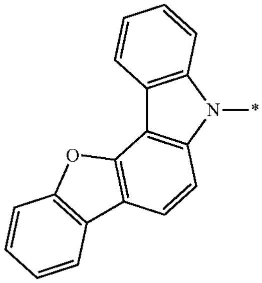
D77
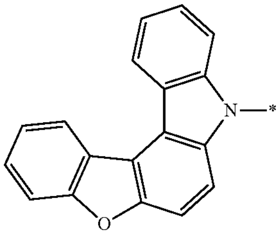
D78
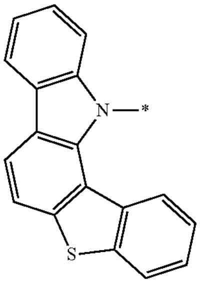

-continued
D79
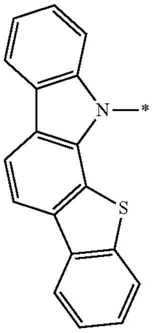
D80
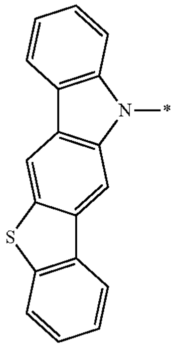
D81
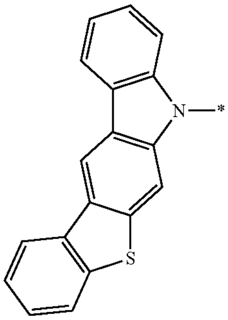
D82
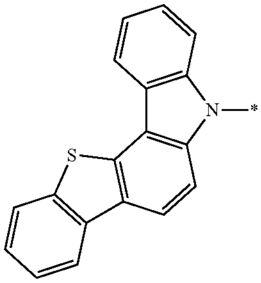
D83
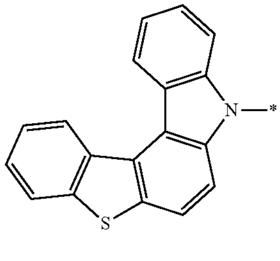
-continued
D84
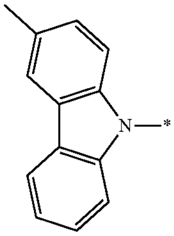
D85
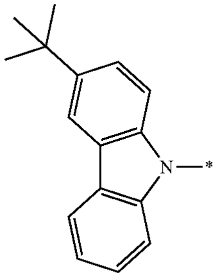
D86
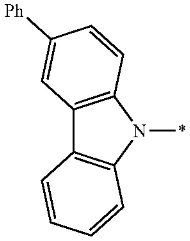
D87
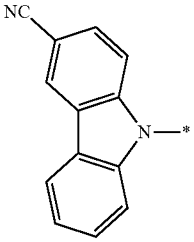
D88
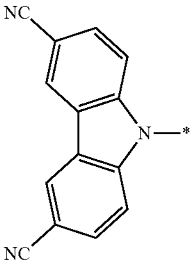
D89
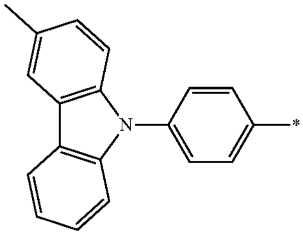

-continued

D90

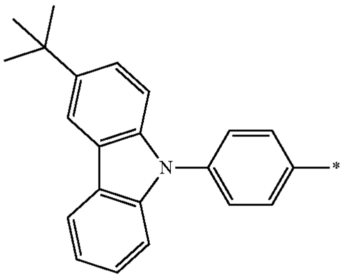

D91

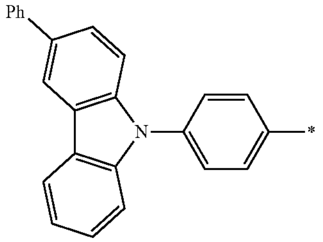

D92

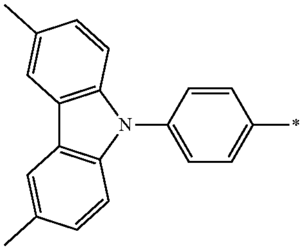

D93

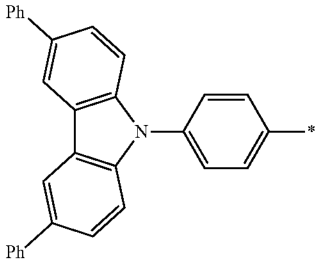

D94

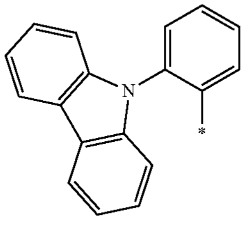

D95

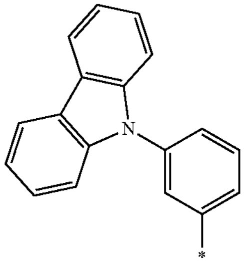

-continued

D96

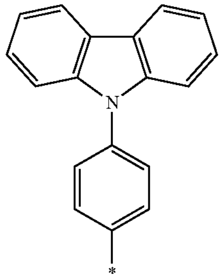

In the formula (1), R is a hydrogen atom, a deuterium atom, or a substituted or unsubstituted aryl group (but, other than a group that may be A or D). In some embodiments, R is a hydrogen atom. In some embodiments, R is a substituted or unsubstituted aryl group (but, other than a group that may be A or D). For example, R is an unsubstituted aryl group. When R is a substituted aryl group, the aryl group may be substituted with, for example, one or more substituents selected from a deuterium atom, a substituted or unsubstituted alkyl group, and a substituted or unsubstituted aryl group. Two or more of these substituents may be bonded to form a cyclic structure. The cyclic structure mentioned herein may be a substituted or unsubstituted aromatic ring, or a substituted or unsubstituted aliphatic ring. Further, it may be a carbon ring, or may be a hetero ring. In a preferred embodiment, each R is independently a hydrogen atom, or a substituted or unsubstituted aryl group. In a more preferred embodiment, each R is independently a hydrogen atom or an unsubstituted aryl group. For example, each R can be independently a hydrogen atom or a phenyl group.

In the formula (1), p is any integer of 1 to 3. When p is 2 or 3, D's present in the molecule may be the same or different. When p is 1 or 2, R's present in the molecule may be the same or different. In some embodiments, p is 3. In some embodiments, p is 2.

In a preferred embodiment, in the formula (1), in $R^1$ and $R^2$, $R^2$ and $R^3$, $R^3$ and $R^4$, and $R^4$ and $R^5$, none of these are bonded to each other to form a cyclic structure.

The molecular weight of the compound represented by the formula (1) is preferably 1500 or less, more preferably 1200 or less, further preferably 1000 or less, still further preferably 900 or less, for example, when there is an intention to form and use a film of an organic layer containing the compound represented by the formula (1), through a deposition method. The lower limit value of the molecular weight is the molecular weight of the smallest compound represented by the formula (1).

The compound represented by the formula (1) may be formed into a film through a coating method regardless of the molecular weight. When the coating method is used, it is possible to form a film even if the compound has a relatively large molecular weight.

Through an application of the present invention, a compound in which a plurality of structures represented by the formula (1) is included in the molecule may be prepared. The use of such a compound as, for example, a charge transport material may be taken into consideration.

For example, it is possible to obtain a polymer by allowing a polymerizable group to exist in the structure represented by the formula (1) in advance, and polymerizing the polymerizable group. Specifically, a monomer including a polymerizable functional group may be prepared in any of $R^1$ to $R^5$ of the formula (1), and this may be polymerized alone or copolymerized with another monomer so as to obtain a polymer having repeating units. Alternatively, a dimer or a trimer may also be obtained by coupling compounds having the structures represented by the formula (1) with each other.

In some embodiments, the compound represented by the formula (1) does not include a metal atom. In some embodiments, the compound represented by the formula (1) is composed of only a hydrogen atom, a carbon atom, and a nitrogen atom. In some embodiments, the compound represented by the formula (1) is composed of only atoms selected from the group consisting of a hydrogen atom, a carbon atom, a nitrogen atom, and an oxygen atom. In some embodiments, the compound represented by the formula (1) is composed of only atoms selected from the group consisting of a hydrogen atom, a carbon atom, a nitrogen atom, and a sulfur atom. In some embodiments, the compound represented by the formula (1) is composed of only atoms selected from the group consisting of a hydrogen atom, a carbon atom, a nitrogen atom, an oxygen atom, a sulfur atom, and a silicon atom. In some embodiments, the compound represented by the formula (1) does not include a cyano group. In some embodiments, the compound represented by the formula (1) does not include a diarylamino group (meanwhile, two aryl groups constituting the diarylamino group do not bond to each other by a single bond or a linking group and form a cyclic structure).

Specific examples of a compound represented by the formula (1) will be mentioned below. Meanwhile, the scope of compounds of the present invention should not be construed as limiting to these specific examples.

TABLE 1

| No. | $R^1$ | $R^2$ | $R^3$ | $R^4$ | $R^5$ |
|---|---|---|---|---|---|
| 1 | A1 | D1 | D1 | D1 | H |
| 2 | A1 | D1 | D1 | H | D1 |
| 3 | A1 | D1 | H | D1 | D1 |
| 4 | A1 | H | D1 | D1 | D1 |
| 5 | A1 | D1 | D1 | D1 | Ph |
| 6 | A1 | D1 | D1 | Ph | D1 |
| 7 | A1 | D1 | Ph | D1 | D1 |
| 8 | A1 | Ph | D1 | D1 | D1 |
| 9 | A1 | D1 | D1 | H | H |
| 10 | A1 | D1 | H | D1 | H |
| 11 | A1 | D1 | H | H | D1 |
| 12 | A1 | H | D1 | D1 | H |
| 13 | A1 | H | D1 | H | D1 |
| 14 | A1 | H | H | D1 | D1 |
| 15 | A1 | D1 | D1 | Ph | H |
| 16 | A1 | D1 | D1 | H | Ph |
| 17 | A1 | D1 | Ph | D1 | H |
| 18 | A1 | D1 | H | D1 | Ph |
| 19 | A1 | D1 | Ph | H | D1 |
| 20 | A1 | D1 | H | Ph | D1 |
| 21 | A1 | Ph | D1 | D1 | H |
| 22 | A1 | H | D1 | D1 | Ph |
| 23 | A1 | Ph | D1 | H | D1 |
| 24 | A1 | H | D1 | Ph | D1 |
| 25 | A1 | Ph | H | D1 | D1 |
| 26 | A1 | H | Ph | D1 | D1 |
| 27 | A1 | D2 | D2 | D2 | H |
| 28 | A1 | D2 | D2 | H | D2 |
| 29 | A1 | D2 | H | D2 | D2 |
| 30 | A1 | H | D2 | D2 | D2 |
| 31 | A1 | D2 | D2 | D2 | Ph |
| 32 | A1 | D2 | D2 | Ph | D2 |
| 33 | A1 | D2 | Ph | D2 | D2 |
| 34 | A1 | Ph | D2 | D2 | D2 |
| 35 | A1 | D2 | D2 | H | H |
| 36 | A1 | D2 | H | D2 | H |
| 37 | A1 | D2 | H | H | D2 |
| 38 | A1 | H | D2 | D2 | H |

TABLE 1-continued

| No. | $R^1$ | $R^2$ | $R^3$ | $R^4$ | $R^5$ |
|---|---|---|---|---|---|
| 39 | A1 | H | D2 | H | D2 |
| 40 | A1 | H | H | D2 | D2 |
| 41 | A1 | D2 | D2 | Ph | H |
| 42 | A1 | D2 | D2 | H | Ph |
| 43 | A1 | D2 | Ph | D2 | H |
| 44 | A1 | D2 | H | D2 | Ph |
| 45 | A1 | D2 | Ph | H | D2 |
| 46 | A1 | D2 | H | Ph | D2 |
| 47 | A1 | Ph | D2 | D2 | H |
| 48 | A1 | H | D2 | D2 | Ph |
| 49 | A1 | Ph | D2 | H | D2 |
| 50 | A1 | H | D2 | Ph | D2 |
| 51 | A1 | Ph | H | D2 | D2 |
| 52 | A1 | H | Ph | D2 | D2 |
| 53 | A1 | D3 | D3 | D3 | H |
| 54 | A1 | D3 | D3 | H | D3 |
| 55 | A1 | D3 | H | D3 | D3 |
| 56 | A1 | H | D3 | D3 | D3 |
| 57 | A1 | D3 | D3 | D3 | Ph |
| 58 | A1 | D3 | D3 | Ph | D3 |
| 59 | A1 | D3 | Ph | D3 | D3 |
| 60 | A1 | Ph | D3 | D3 | D3 |
| 61 | A1 | D3 | D3 | H | H |
| 62 | A1 | D3 | H | D3 | H |
| 63 | A1 | D3 | H | H | D3 |
| 64 | A1 | H | D3 | D3 | H |
| 65 | A1 | H | D3 | H | D3 |
| 66 | A1 | H | H | D3 | D3 |
| 67 | A1 | D3 | D3 | Ph | H |
| 68 | A1 | D3 | D3 | H | Ph |
| 69 | A1 | D3 | Ph | D3 | H |
| 70 | A1 | D3 | H | D3 | Ph |
| 71 | A1 | D3 | Ph | H | D3 |
| 72 | A1 | D3 | H | Ph | D3 |
| 73 | A1 | Ph | D3 | D3 | H |
| 74 | A1 | H | D3 | D3 | Ph |
| 75 | A1 | Ph | D3 | H | D3 |
| 76 | A1 | H | D3 | Ph | D3 |
| 77 | A1 | Ph | H | D3 | D3 |
| 78 | A1 | H | Ph | D3 | D3 |
| 79 | A1 | D4 | D4 | D4 | H |
| 80 | A1 | D4 | D4 | H | D4 |
| 81 | A1 | D4 | H | D4 | D4 |
| 82 | A1 | H | D4 | D4 | D4 |
| 83 | A1 | D4 | D4 | D4 | Ph |
| 84 | A1 | D4 | D4 | Ph | D4 |
| 85 | A1 | D4 | Ph | D4 | D4 |
| 86 | A1 | Ph | D4 | D4 | D4 |
| 87 | A1 | D4 | D4 | H | H |
| 88 | A1 | D4 | H | D4 | H |
| 89 | A1 | D4 | H | H | D4 |
| 90 | A1 | H | D4 | D4 | H |
| 91 | A1 | H | D4 | H | D4 |
| 92 | A1 | H | H | D4 | D4 |
| 93 | A1 | D4 | D4 | Ph | H |
| 94 | A1 | D4 | D4 | H | Ph |
| 95 | A1 | D4 | Ph | D4 | H |
| 96 | A1 | D4 | H | D4 | Ph |
| 97 | A1 | D4 | Ph | H | D4 |
| 98 | A1 | D4 | H | Ph | D4 |
| 99 | A1 | Ph | D4 | D4 | H |
| 100 | A1 | H | D4 | D4 | Ph |
| 101 | A1 | Ph | D4 | H | D4 |
| 102 | A1 | H | D4 | Ph | D4 |
| 103 | A1 | Ph | H | D4 | D4 |
| 104 | A1 | H | Ph | D4 | D4 |
| 105 | A1 | D40 | D40 | D40 | H |
| 106 | A1 | D40 | D40 | H | D40 |
| 107 | A1 | D40 | H | D40 | D40 |
| 108 | A1 | H | D40 | D40 | D40 |
| 109 | A1 | D40 | D40 | D40 | Ph |
| 110 | A1 | D40 | D40 | Ph | D40 |
| 111 | A1 | D40 | Ph | D40 | D40 |
| 112 | A1 | Ph | D40 | D40 | D40 |
| 113 | A1 | D40 | D40 | H | H |
| 114 | A1 | D40 | H | D40 | H |
| 115 | A1 | D40 | H | H | D40 |
| 116 | A1 | H | D40 | D40 | H |

TABLE 1-continued

| No. | $R^1$ | $R^2$ | $R^3$ | $R^4$ | $R^5$ |
|---|---|---|---|---|---|
| 117 | A1 | H | D40 | H | D40 |
| 118 | A1 | H | H | D40 | D40 |
| 119 | A1 | D40 | D40 | Ph | H |
| 120 | A1 | D40 | D40 | H | Ph |
| 121 | A1 | D40 | Ph | D40 | H |
| 122 | A1 | D40 | H | D40 | Ph |
| 123 | A1 | D40 | Ph | H | D40 |
| 124 | A1 | D40 | H | Ph | D40 |
| 125 | A1 | Ph | D40 | D40 | H |
| 126 | A1 | H | D40 | D40 | Ph |
| 127 | A1 | Ph | D40 | H | D40 |
| 128 | A1 | H | D40 | Ph | D40 |
| 129 | A1 | Ph | H | D40 | D40 |
| 130 | A1 | H | Ph | D40 | D40 |
| 131 | A1 | D41 | D41 | D41 | H |
| 132 | A1 | D41 | D41 | H | D41 |
| 133 | A1 | D41 | H | D41 | D41 |
| 134 | A1 | H | D41 | D41 | D41 |
| 135 | A1 | D41 | D41 | D41 | Ph |
| 136 | A1 | D41 | D41 | Ph | D41 |
| 137 | A1 | D41 | Ph | D41 | D41 |
| 138 | A1 | Ph | D41 | D41 | D41 |
| 139 | A1 | D41 | D41 | H | H |
| 140 | A1 | D41 | H | D41 | H |
| 141 | A1 | D41 | H | H | D41 |
| 142 | A1 | H | D41 | D41 | H |
| 143 | A1 | H | D41 | H | D41 |
| 144 | A1 | H | H | D41 | D41 |
| 145 | A1 | D41 | D41 | Ph | H |
| 146 | A1 | D41 | D41 | H | Ph |
| 147 | A1 | D41 | Ph | D41 | H |
| 148 | A1 | D41 | H | D41 | Ph |
| 149 | A1 | D41 | Ph | H | D41 |
| 150 | A1 | D41 | H | Ph | D41 |
| 151 | A1 | Ph | D41 | D41 | H |
| 152 | A1 | H | D41 | D41 | Ph |
| 153 | A1 | Ph | D41 | H | D41 |
| 154 | A1 | H | D41 | Ph | D41 |
| 155 | A1 | Ph | H | D41 | D41 |
| 156 | A1 | H | Ph | D41 | D41 |
| 157 | A1 | D42 | D42 | D42 | H |
| 158 | A1 | D42 | D42 | H | D42 |
| 159 | A1 | D42 | H | D42 | D42 |
| 160 | A1 | H | D42 | D42 | D42 |
| 161 | A1 | D42 | D42 | D42 | Ph |
| 162 | A1 | D42 | D42 | Ph | D42 |
| 163 | A1 | D42 | Ph | D42 | D42 |
| 164 | A1 | Ph | D42 | D42 | D42 |
| 165 | A1 | D42 | D42 | H | H |
| 166 | A1 | D42 | H | D42 | H |
| 167 | A1 | D42 | H | H | D42 |
| 168 | A1 | H | D42 | D42 | H |
| 169 | A1 | H | D42 | H | D42 |
| 170 | A1 | H | H | D42 | D42 |
| 171 | A1 | D42 | D42 | Ph | H |
| 172 | A1 | D42 | D42 | H | Ph |
| 173 | A1 | D42 | Ph | D42 | H |
| 174 | A1 | D42 | H | D42 | Ph |
| 175 | A1 | D42 | Ph | H | D42 |
| 176 | A1 | D42 | H | Ph | D42 |
| 177 | A1 | Ph | D42 | D42 | H |
| 178 | A1 | H | D42 | D42 | Ph |
| 179 | A1 | Ph | D42 | H | D42 |
| 180 | A1 | H | D42 | Ph | D42 |
| 181 | A1 | Ph | H | D42 | D42 |
| 182 | A1 | H | Ph | D42 | D42 |
| 183 | A1 | D43 | D43 | D43 | H |
| 184 | A1 | D43 | D43 | H | D43 |
| 185 | A1 | D43 | H | D43 | D43 |
| 186 | A1 | H | D43 | D43 | D43 |
| 187 | A1 | D43 | D43 | D43 | Ph |
| 188 | A1 | D43 | D43 | Ph | D43 |
| 189 | A1 | D43 | Ph | D43 | D43 |
| 190 | A1 | Ph | D43 | D43 | D43 |
| 191 | A1 | D43 | D43 | H | H |
| 192 | A1 | D43 | H | D43 | H |
| 193 | A1 | D43 | H | H | D43 |
| 194 | A1 | H | D43 | D43 | H |

TABLE 1-continued

| No. | $R^1$ | $R^2$ | $R^3$ | $R^4$ | $R^5$ |
|---|---|---|---|---|---|
| 195 | A1 | H | D43 | H | D43 |
| 196 | A1 | H | H | D43 | D43 |
| 197 | A1 | D43 | D43 | Ph | H |
| 198 | A1 | D43 | D43 | H | Ph |
| 199 | A1 | D43 | Ph | D43 | H |
| 200 | A1 | D43 | H | D43 | Ph |
| 201 | A1 | D43 | Ph | H | D43 |
| 202 | A1 | D43 | H | Ph | D43 |
| 203 | A1 | Ph | D43 | D43 | H |
| 204 | A1 | H | D43 | D43 | Ph |
| 205 | A1 | Ph | D43 | H | D43 |
| 206 | A1 | H | D43 | Ph | D43 |
| 207 | A1 | Ph | H | D43 | D43 |
| 208 | A1 | H | Ph | D43 | D43 |
| 209 | A1 | D84 | D84 | D84 | H |
| 210 | A1 | D84 | D84 | H | D84 |
| 211 | A1 | D84 | H | D84 | D84 |
| 212 | A1 | H | D84 | D84 | D84 |
| 213 | A1 | D84 | D84 | D84 | Ph |
| 214 | A1 | D84 | D84 | Ph | D84 |
| 215 | A1 | D84 | Ph | D84 | D84 |
| 216 | A1 | Ph | D84 | D84 | D84 |
| 217 | A1 | D84 | D84 | H | H |
| 218 | A1 | D84 | H | D84 | H |
| 219 | A1 | D84 | H | H | D84 |
| 220 | A1 | H | D84 | D84 | H |
| 221 | A1 | H | D84 | H | D84 |
| 222 | A1 | H | H | D84 | D84 |
| 223 | A1 | D84 | D84 | Ph | H |
| 224 | A1 | D84 | D84 | H | Ph |
| 225 | A1 | D84 | Ph | D84 | H |
| 226 | A1 | D84 | H | D84 | Ph |
| 227 | A1 | D84 | Ph | H | D84 |
| 228 | A1 | D84 | H | Ph | D84 |
| 229 | A1 | Ph | D84 | D84 | H |
| 230 | A1 | H | D84 | D84 | Ph |
| 231 | A1 | Ph | D84 | H | D84 |
| 232 | A1 | H | D84 | Ph | D84 |
| 233 | A1 | Ph | H | D84 | D84 |
| 234 | A1 | H | Ph | D84 | D84 |
| 235 | A1 | D86 | D86 | D86 | H |
| 236 | A1 | D86 | D86 | H | D86 |
| 237 | A1 | D86 | H | D86 | D86 |
| 238 | A1 | H | D86 | D86 | D86 |
| 239 | A1 | D86 | D86 | D86 | Ph |
| 240 | A1 | D86 | D86 | Ph | D86 |
| 241 | A1 | D86 | Ph | D86 | D86 |
| 242 | A1 | Ph | D86 | D86 | D86 |
| 243 | A1 | D86 | D86 | H | H |
| 244 | A1 | D86 | H | D86 | H |
| 245 | A1 | D86 | H | H | D86 |
| 246 | A1 | H | D86 | D86 | H |
| 247 | A1 | H | D86 | H | D86 |
| 248 | A1 | H | H | D86 | D86 |
| 249 | A1 | D86 | D86 | Ph | H |
| 250 | A1 | D86 | D86 | H | Ph |
| 251 | A1 | D86 | Ph | D86 | H |
| 252 | A1 | D86 | H | D86 | Ph |
| 253 | A1 | D86 | Ph | H | D86 |
| 254 | A1 | D86 | H | Ph | D86 |
| 255 | A1 | Ph | D86 | D86 | H |
| 256 | A1 | H | D86 | D86 | Ph |
| 257 | A1 | Ph | D86 | H | D86 |
| 258 | A1 | H | D86 | Ph | D86 |
| 259 | A1 | Ph | H | D86 | D86 |
| 260 | A1 | H | Ph | D86 | D86 |
| 261 | A1 | D87 | D87 | D87 | H |
| 262 | A1 | D87 | D87 | H | D87 |
| 263 | A1 | D87 | H | D87 | D87 |
| 264 | A1 | H | D87 | D87 | D87 |
| 265 | A1 | D87 | D87 | D87 | Ph |
| 268 | A1 | D87 | D87 | Ph | D87 |
| 267 | A1 | D87 | Ph | D87 | D87 |
| 288 | A1 | Ph | D87 | D87 | D87 |
| 269 | A1 | D87 | D87 | H | H |
| 270 | A1 | D87 | H | D87 | H |
| 271 | A1 | D87 | H | H | D87 |
| 272 | A1 | H | D87 | D87 | H |

TABLE 1-continued

| No. | $R^1$ | $R^2$ | $R^3$ | $R^4$ | $R^5$ |
|---|---|---|---|---|---|
| 273 | A1 | H | D87 | H | D87 |
| 274 | A1 | H | H | D87 | D87 |
| 275 | A1 | D87 | D87 | Ph | H |
| 276 | A1 | D87 | D87 | H | Ph |
| 277 | A1 | D87 | Ph | D87 | H |
| 278 | A1 | D87 | H | D87 | Ph |
| 279 | A1 | D87 | Ph | H | D87 |
| 280 | A1 | D87 | H | Ph | D87 |
| 281 | A1 | Ph | D87 | D87 | H |
| 282 | A1 | H | D87 | D87 | Ph |
| 283 | A1 | Ph | D87 | H | D87 |
| 284 | A1 | H | D87 | Ph | D87 |
| 285 | A1 | Ph | H | D87 | D87 |
| 288 | A1 | H | Ph | D87 | D87 |
| 287 | A1 | D88 | D88 | D88 | H |
| 288 | A1 | D88 | D88 | H | D88 |
| 289 | A1 | D88 | H | D88 | D88 |
| 290 | A1 | H | D88 | D88 | D88 |
| 291 | A1 | D88 | D88 | D88 | Ph |
| 292 | A1 | D88 | D88 | Ph | D88 |
| 293 | A1 | D88 | Ph | D88 | D88 |
| 294 | A1 | Ph | D88 | D88 | D88 |
| 295 | A1 | D88 | D88 | H | H |
| 296 | A1 | D88 | H | D88 | H |
| 297 | A1 | D88 | H | H | D88 |
| 298 | A1 | H | D88 | D88 | H |
| 299 | A1 | H | D88 | H | D88 |
| 300 | A1 | H | H | D88 | D88 |
| 301 | A1 | D88 | D88 | Ph | H |
| 302 | A1 | D88 | D88 | H | Ph |
| 303 | A1 | D88 | Ph | D88 | H |
| 304 | A1 | D88 | H | D88 | Ph |
| 305 | A1 | D88 | Ph | H | D88 |
| 306 | A1 | D88 | H | Ph | D88 |
| 307 | A1 | Ph | D88 | D88 | H |
| 308 | A1 | H | D88 | D88 | Ph |
| 309 | A1 | Ph | D88 | H | D88 |
| 310 | A1 | H | D88 | Ph | D88 |
| 311 | A1 | Ph | H | D88 | D88 |
| 312 | A1 | H | Ph | D88 | D88 |
| 313 | A2 | D1 | D1 | D1 | H |
| 314 | A2 | D1 | D1 | H | D1 |
| 315 | A2 | D1 | H | D1 | D1 |
| 316 | A2 | H | D1 | D1 | D1 |
| 317 | A2 | D1 | D1 | D1 | Ph |
| 318 | A2 | D1 | D1 | Ph | D1 |
| 319 | A2 | D1 | Ph | D1 | D1 |
| 320 | A2 | Ph | D1 | D1 | D1 |
| 321 | A2 | D1 | D1 | H | H |
| 322 | A2 | D1 | H | D1 | H |
| 323 | A2 | D1 | H | H | D1 |
| 324 | A2 | H | D1 | D1 | H |
| 325 | A2 | H | D1 | H | D1 |
| 326 | A2 | H | H | D1 | D1 |
| 327 | A2 | D1 | D1 | Ph | H |
| 328 | A2 | D1 | D1 | H | Ph |
| 329 | A2 | D1 | Ph | D1 | H |
| 330 | A2 | D1 | H | D1 | Ph |
| 331 | A2 | D1 | Ph | H | D1 |
| 332 | A2 | D1 | H | Ph | D1 |
| 333 | A2 | Ph | D1 | D1 | H |
| 334 | A2 | H | D1 | D1 | Ph |
| 335 | A2 | Ph | D1 | H | D1 |
| 336 | A2 | H | D1 | Ph | D1 |
| 337 | A2 | Ph | H | D1 | D1 |
| 338 | A2 | H | Ph | D1 | D1 |
| 339 | A2 | D2 | D2 | D2 | H |
| 340 | A2 | D2 | D2 | H | D2 |
| 341 | A2 | D2 | H | D2 | D2 |
| 342 | A2 | H | D2 | D2 | D2 |
| 343 | A2 | D2 | D2 | D2 | Ph |
| 344 | A2 | D2 | D2 | Ph | D2 |
| 345 | A2 | D2 | Ph | D2 | D2 |
| 346 | A2 | Ph | D2 | D2 | D2 |
| 347 | A2 | D2 | D2 | H | H |
| 348 | A2 | D2 | H | D2 | H |
| 349 | A2 | D2 | H | H | D2 |
| 350 | A2 | H | D2 | D2 | H |

TABLE 1-continued

| No. | $R^1$ | $R^2$ | $R^3$ | $R^4$ | $R^5$ |
|---|---|---|---|---|---|
| 351 | A2 | H | D2 | H | D2 |
| 352 | A2 | H | H | D2 | D2 |
| 353 | A2 | D2 | D2 | Ph | H |
| 354 | A2 | D2 | D2 | H | Ph |
| 355 | A2 | D2 | Ph | D2 | H |
| 356 | A2 | D2 | H | D2 | Ph |
| 357 | A2 | D2 | Ph | H | D2 |
| 358 | A2 | D2 | H | Ph | D2 |
| 359 | A2 | Ph | D2 | D2 | H |
| 360 | A2 | H | D2 | D2 | Ph |
| 361 | A2 | Ph | D2 | H | D2 |
| 362 | A2 | H | D2 | Ph | D2 |
| 363 | A2 | Ph | H | D2 | D2 |
| 364 | A2 | H | Ph | D2 | D2 |
| 365 | A2 | D3 | D3 | D3 | H |
| 366 | A2 | D3 | D3 | H | D3 |
| 367 | A2 | D3 | H | D3 | D3 |
| 368 | A2 | H | D3 | D3 | D3 |
| 369 | A2 | D3 | D3 | D3 | Ph |
| 370 | A2 | D3 | D3 | Ph | D3 |
| 371 | A2 | D3 | Ph | D3 | D3 |
| 372 | A2 | Ph | D3 | D3 | D3 |
| 373 | A2 | D3 | D3 | H | H |
| 374 | A2 | D3 | H | D3 | H |
| 375 | A2 | D3 | H | H | D3 |
| 376 | A2 | H | D3 | D3 | H |
| 377 | A2 | H | D3 | H | D3 |
| 378 | A2 | H | H | D3 | D3 |
| 379 | A2 | D3 | D3 | Ph | H |
| 380 | A2 | D3 | D3 | H | Ph |
| 381 | A2 | D3 | Ph | D3 | H |
| 382 | A2 | D3 | H | D3 | Ph |
| 383 | A2 | D3 | Ph | H | D3 |
| 384 | A2 | D3 | H | Ph | D3 |
| 385 | A2 | Ph | D3 | D3 | H |
| 386 | A2 | H | D3 | D3 | Ph |
| 387 | A2 | Ph | D3 | H | D3 |
| 388 | A2 | H | D3 | Ph | D3 |
| 389 | A2 | Ph | H | D3 | D3 |
| 390 | A2 | H | Ph | D3 | D3 |
| 391 | A2 | D4 | D4 | D4 | H |
| 392 | A2 | D4 | D4 | H | D4 |
| 393 | A2 | D4 | H | D4 | D4 |
| 394 | A2 | H | D4 | D4 | D4 |
| 395 | A2 | D4 | D4 | D4 | Ph |
| 396 | A2 | D4 | D4 | Ph | D4 |
| 397 | A2 | D4 | Ph | D4 | D4 |
| 398 | A2 | Ph | D4 | D4 | D4 |
| 399 | A2 | D4 | D4 | H | H |
| 400 | A2 | D4 | H | D4 | H |
| 401 | A2 | D4 | H | H | D4 |
| 402 | A2 | H | D4 | D4 | H |
| 403 | A2 | H | D4 | H | D4 |
| 404 | A2 | H | H | D4 | D4 |
| 405 | A2 | D4 | D4 | Ph | H |
| 406 | A2 | D4 | D4 | H | Ph |
| 407 | A2 | D4 | Ph | D4 | H |
| 408 | A2 | D4 | H | D4 | Ph |
| 409 | A2 | D4 | Ph | H | D4 |
| 410 | A2 | D4 | H | Ph | D4 |
| 411 | A2 | Ph | D4 | D4 | H |
| 412 | A2 | H | D4 | D4 | Ph |
| 413 | A2 | Ph | D4 | H | D4 |
| 414 | A2 | H | D4 | Ph | D4 |
| 415 | A2 | Ph | H | D4 | D4 |
| 416 | A2 | H | Ph | D4 | D4 |
| 417 | A2 | D40 | D40 | D40 | H |
| 418 | A2 | D40 | D40 | H | D40 |
| 419 | A2 | D40 | H | D40 | D40 |
| 420 | A2 | H | D40 | D40 | D40 |
| 421 | A2 | D40 | D40 | D40 | Ph |
| 422 | A2 | D40 | D40 | Ph | D40 |
| 423 | A2 | D40 | Ph | D40 | D40 |
| 424 | A2 | Ph | D40 | D40 | D40 |
| 425 | A2 | D40 | D40 | H | H |
| 426 | A2 | D40 | H | D40 | H |
| 427 | A2 | D40 | H | H | D40 |
| 428 | A2 | H | D40 | D40 | H |

TABLE 1-continued

| No. | $R^1$ | $R^2$ | $R^3$ | $R^4$ | $R^5$ |
|---|---|---|---|---|---|
| 429 | A2 | H | D40 | H | D40 |
| 430 | A2 | H | H | D40 | D40 |
| 431 | A2 | D40 | D40 | Ph | H |
| 432 | A2 | D40 | D40 | H | Ph |
| 433 | A2 | D40 | Ph | D40 | H |
| 434 | A2 | D40 | H | D40 | Ph |
| 435 | A2 | D40 | Ph | H | D40 |
| 436 | A2 | D40 | H | Ph | D40 |
| 437 | A2 | Ph | D40 | D40 | H |
| 438 | A2 | H | D40 | D40 | Ph |
| 439 | A2 | Ph | D40 | H | D40 |
| 440 | A2 | H | D40 | Ph | D40 |
| 441 | A2 | Ph | H | D40 | D40 |
| 442 | A2 | H | Ph | D40 | D40 |
| 443 | A2 | D41 | D41 | D41 | H |
| 444 | A2 | D41 | D41 | H | D41 |
| 445 | A2 | D41 | H | D41 | D41 |
| 446 | A2 | H | D41 | D41 | D41 |
| 447 | A2 | D41 | D41 | D41 | Ph |
| 448 | A2 | D41 | D41 | Ph | D41 |
| 449 | A2 | D41 | Ph | D41 | D41 |
| 450 | A2 | Ph | D41 | D41 | D41 |
| 451 | A2 | D41 | D41 | H | H |
| 452 | A2 | D41 | H | D41 | H |
| 453 | A2 | D41 | H | H | D41 |
| 454 | A2 | H | D41 | D41 | H |
| 455 | A2 | H | D41 | H | D41 |
| 456 | A2 | H | H | D41 | D41 |
| 457 | A2 | D41 | D41 | Ph | H |
| 458 | A2 | D41 | D41 | H | Ph |
| 459 | A2 | D41 | Ph | D41 | H |
| 460 | A2 | D41 | H | D41 | Ph |
| 461 | A2 | D41 | Ph | H | D41 |
| 462 | A2 | D41 | H | Ph | D41 |
| 463 | A2 | Ph | D41 | D41 | H |
| 464 | A2 | H | D41 | D41 | Ph |
| 465 | A2 | Ph | D41 | H | D41 |
| 466 | A2 | H | D41 | Ph | D41 |
| 467 | A2 | Ph | H | D41 | D41 |
| 468 | A2 | H | Ph | D41 | D41 |
| 469 | A2 | D42 | D42 | D42 | H |
| 470 | A2 | D42 | D42 | H | D42 |
| 471 | A2 | D42 | H | D42 | D42 |
| 472 | A2 | H | D42 | D42 | D42 |
| 473 | A2 | D42 | D42 | D42 | Ph |
| 474 | A2 | D42 | D42 | Ph | D42 |
| 475 | A2 | D42 | Ph | 42 | D42 |
| 476 | A2 | Ph | D42 | D42 | D42 |
| 477 | A2 | D42 | D42 | H | H |
| 478 | A2 | D42 | H | D42 | H |
| 479 | A2 | D42 | H | H | D42 |
| 480 | A2 | H | D42 | D42 | H |
| 481 | A2 | H | D42 | H | D42 |
| 482 | A2 | H | H | D42 | D42 |
| 483 | A2 | D42 | D42 | Ph | H |
| 484 | A2 | D42 | D42 | H | Ph |
| 485 | A2 | D42 | Ph | D42 | H |
| 486 | A2 | D42 | H | D42 | Ph |
| 487 | A2 | D42 | Ph | H | D42 |
| 488 | A2 | D42 | H | Ph | D42 |
| 489 | A2 | Ph | D42 | D42 | H |
| 490 | A2 | H | D42 | D42 | Ph |
| 491 | A2 | Ph | D42 | H | D42 |
| 492 | A2 | H | D42 | Ph | D42 |
| 493 | A2 | Ph | H | D42 | D42 |
| 494 | A2 | H | Ph | D42 | D42 |
| 495 | A2 | D43 | D43 | D43 | H |
| 498 | A2 | D43 | D43 | H | D43 |
| 497 | A2 | D43 | H | D43 | D43 |
| 498 | A2 | H | D43 | D43 | D43 |
| 499 | A2 | D43 | D43 | D43 | Ph |
| 500 | A2 | D43 | D43 | Ph | D43 |
| 501 | A2 | D43 | Ph | D43 | D43 |
| 502 | A2 | Ph | D43 | D43 | D43 |
| 503 | A2 | D43 | D43 | H | H |
| 504 | A2 | D43 | H | D43 | H |
| 505 | A2 | D43 | H | H | D43 |
| 506 | A2 | H | D43 | D43 | H |

TABLE 1-continued

| No. | $R^1$ | $R^2$ | $R^3$ | $R^4$ | $R^5$ |
|---|---|---|---|---|---|
| 507 | A2 | H | D43 | H | D43 |
| 508 | A2 | H | H | D43 | D43 |
| 509 | A2 | D43 | D43 | Ph | H |
| 510 | A2 | D43 | D43 | H | Ph |
| 511 | A2 | D43 | Ph | D43 | H |
| 512 | A2 | D43 | H | D43 | Ph |
| 513 | A2 | D43 | Ph | H | D43 |
| 514 | A2 | D43 | H | Ph | D43 |
| 515 | A2 | Ph | D43 | D43 | H |
| 516 | A2 | H | D43 | D43 | Ph |
| 517 | A2 | Ph | D43 | H | D43 |
| 518 | A2 | H | D43 | Ph | D43 |
| 519 | A2 | Ph | H | D43 | D43 |
| 520 | A2 | H | Ph | D43 | D43 |
| 521 | A2 | D84 | D84 | D84 | H |
| 522 | A2 | D84 | D84 | H | D84 |
| 523 | A2 | D84 | H | D84 | D84 |
| 524 | A2 | H | D84 | D84 | D84 |
| 525 | A2 | D84 | D84 | D84 | Ph |
| 526 | A2 | D84 | D84 | Ph | D84 |
| 527 | A2 | D84 | Ph | D84 | D84 |
| 528 | A2 | Ph | D84 | D84 | D84 |
| 529 | A2 | D84 | D84 | H | H |
| 530 | A2 | D84 | H | D84 | H |
| 531 | A2 | D84 | H | H | D84 |
| 532 | A2 | H | D84 | D84 | H |
| 533 | A2 | H | D84 | H | D84 |
| 534 | A2 | H | H | 84 | D84 |
| 535 | A2 | D84 | D84 | Ph | H |
| 536 | A2 | D84 | D84 | H | Ph |
| 537 | A2 | D84 | Ph | D84 | H |
| 538 | A2 | D84 | H | D84 | Ph |
| 539 | A2 | D84 | Ph | H | D84 |
| 540 | A2 | D84 | H | Ph | D84 |
| 541 | A2 | Ph | D84 | D84 | H |
| 542 | A2 | H | D84 | D84 | Ph |
| 543 | A2 | Ph | D84 | H | D84 |
| 544 | A2 | H | D84 | Ph | D84 |
| 545 | A2 | Ph | H | D84 | D84 |
| 546 | A2 | H | Ph | D84 | D84 |
| 547 | A2 | D86 | D86 | D86 | H |
| 548 | A2 | D86 | D86 | H | D86 |
| 549 | A2 | D86 | H | D86 | D86 |
| 550 | A2 | H | D86 | D86 | D86 |
| 551 | A2 | D86 | D86 | D86 | Ph |
| 552 | A2 | D86 | D86 | Ph | D86 |
| 553 | A2 | D86 | Ph | D86 | D86 |
| 554 | A2 | Ph | D86 | D86 | D86 |
| 555 | A2 | D86 | D86 | H | H |
| 556 | A2 | D86 | H | D86 | H |
| 557 | A2 | D86 | H | H | D86 |
| 558 | A2 | H | D86 | D86 | H |
| 559 | A2 | H | D86 | H | D86 |
| 560 | A2 | H | H | D86 | D86 |
| 561 | A2 | D86 | D86 | Ph | H |
| 562 | A2 | D86 | D86 | H | Ph |
| 563 | A2 | D86 | Ph | D86 | H |
| 564 | A2 | D86 | H | D86 | Ph |
| 565 | A2 | D86 | Ph | H | D86 |
| 566 | A2 | D86 | H | Ph | D86 |
| 567 | A2 | Ph | D86 | D86 | H |
| 568 | A2 | H | D86 | D86 | Ph |
| 569 | A2 | Ph | D86 | H | D86 |
| 570 | A2 | H | D86 | Ph | D86 |
| 571 | A2 | Ph | H | D86 | D86 |
| 572 | A2 | H | Ph | D86 | D86 |
| 573 | A2 | D87 | D87 | D87 | H |
| 574 | A2 | D87 | D87 | H | D87 |
| 575 | A2 | D87 | H | D87 | D87 |
| 576 | A2 | H | D87 | D87 | D87 |
| 577 | A2 | D87 | D87 | D87 | Ph |
| 578 | A2 | D87 | D87 | Ph | D87 |
| 579 | A2 | D87 | Ph | D87 | D87 |
| 580 | A2 | Ph | D87 | D87 | D87 |
| 581 | A2 | D87 | D87 | H | H |
| 582 | A2 | D87 | H | D87 | H |
| 583 | A2 | D87 | H | H | D87 |
| 584 | A2 | H | D87 | D87 | H |

TABLE 1-continued

| No. | $R^1$ | $R^2$ | $R^3$ | $R^4$ | $R^5$ |
|---|---|---|---|---|---|
| 585 | A2 | H | D87 | H | D87 |
| 586 | A2 | H | H | D87 | D87 |
| 587 | A2 | D87 | D87 | Ph | H |
| 588 | A2 | D87 | D87 | H | Ph |
| 589 | A2 | D87 | Ph | D87 | H |
| 590 | A2 | D87 | H | D87 | Ph |
| 591 | A2 | D87 | Ph | H | D87 |
| 592 | A2 | D87 | H | Ph | D87 |
| 593 | A2 | Ph | D87 | D87 | H |
| 594 | A2 | H | D87 | D87 | Ph |
| 595 | A2 | Ph | D87 | H | D87 |
| 596 | A2 | H | D87 | Ph | D87 |
| 597 | A2 | Ph | H | D87 | D87 |
| 598 | A2 | H | Ph | D87 | D87 |
| 599 | A2 | D88 | D88 | D88 | H |
| 600 | A2 | D88 | D88 | H | D88 |
| 601 | A2 | D88 | H | D88 | D88 |
| 602 | A2 | H | D88 | D88 | D88 |
| 603 | A2 | D88 | D88 | D88 | Ph |
| 604 | A2 | D88 | D88 | Ph | D88 |
| 605 | A2 | D88 | Ph | D88 | D88 |
| 606 | A2 | Ph | D88 | D88 | D88 |
| 607 | A2 | D88 | D88 | H | H |
| 608 | A2 | D88 | H | D88 | H |
| 609 | A2 | D88 | H | H | D88 |
| 610 | A2 | H | D88 | D88 | H |
| 611 | A2 | H | D88 | H | D88 |
| 612 | A2 | H | H | D88 | D88 |
| 613 | A2 | D88 | D88 | Ph | H |
| 614 | A2 | D88 | D88 | H | Ph |
| 615 | A2 | D88 | Ph | D88 | H |
| 616 | A2 | D88 | H | D88 | Ph |
| 617 | A2 | D88 | Ph | H | D88 |
| 618 | A2 | D88 | H | Ph | D88 |
| 619 | A2 | Ph | D88 | D88 | H |
| 620 | A2 | H | D88 | D88 | Ph |
| 621 | A2 | Ph | D88 | H | D88 |
| 622 | A2 | H | D88 | Ph | D88 |
| 623 | A2 | Ph | H | D88 | D88 |
| 624 | A2 | H | Ph | D88 | D88 |
| 625 | A3 | D1 | D1 | D1 | H |
| 626 | A3 | D1 | D1 | H | D1 |
| 627 | A3 | D1 | H | D1 | D1 |
| 628 | A3 | H | D1 | D1 | D1 |
| 629 | A3 | D1 | D1 | D1 | Ph |
| 630 | A3 | D1 | D1 | Ph | D1 |
| 631 | A3 | D1 | Ph | D1 | D1 |
| 632 | A3 | Ph | D1 | D1 | D1 |
| 633 | A3 | D1 | D1 | H | H |
| 634 | A3 | D1 | H | D1 | H |
| 635 | A3 | D1 | H | H | D1 |
| 636 | A3 | H | D1 | D1 | H |
| 637 | A3 | H | D1 | H | D1 |
| 638 | A3 | H | H | D1 | D1 |
| 639 | A3 | D1 | D1 | Ph | H |
| 640 | A3 | D1 | D1 | H | Ph |
| 641 | A3 | D1 | Ph | D1 | H |
| 642 | A3 | D1 | H | D1 | Ph |
| 643 | A3 | D1 | Ph | H | D1 |
| 644 | A3 | D1 | H | Ph | D1 |
| 645 | A3 | Ph | D1 | D1 | H |
| 646 | A3 | H | D1 | D1 | Ph |
| 647 | A3 | Ph | D1 | H | D1 |
| 648 | A3 | H | D1 | Ph | D1 |
| 649 | A3 | Ph | H | D1 | D1 |
| 650 | A3 | H | Ph | D1 | D1 |
| 651 | A3 | D2 | D2 | D2 | H |
| 652 | A3 | D2 | D2 | H | D2 |
| 653 | A3 | D2 | H | D2 | D2 |
| 654 | A3 | H | D2 | D2 | D2 |
| 655 | A3 | D2 | D2 | D2 | Ph |
| 656 | A3 | D2 | D2 | Ph | D2 |
| 657 | A3 | D2 | Ph | D2 | D2 |
| 658 | A3 | Ph | D2 | D2 | D2 |
| 659 | A3 | D2 | D2 | H | H |
| 660 | A3 | D2 | H | D2 | H |
| 661 | A3 | D2 | H | H | D2 |
| 662 | A3 | H | D2 | D2 | H |
| 663 | A3 | H | D2 | H | D2 |
| 664 | A3 | H | H | D2 | D2 |
| 665 | A3 | D2 | D2 | Ph | H |
| 666 | A3 | D2 | D2 | H | Ph |
| 667 | A3 | D2 | Ph | D2 | H |
| 688 | A3 | D2 | H | D2 | Ph |
| 669 | A3 | D2 | Ph | H | D2 |
| 670 | A3 | D2 | H | Ph | D2 |
| 671 | A3 | Ph | D2 | D2 | H |
| 672 | A3 | H | D2 | D2 | Ph |
| 673 | A3 | Ph | D2 | H | D2 |
| 674 | A3 | H | D2 | Ph | D2 |
| 675 | A3 | Ph | H | D2 | D2 |
| 676 | A3 | H | Ph | D2 | D2 |
| 677 | A3 | D3 | D3 | D3 | H |
| 678 | A3 | D3 | D3 | H | D3 |
| 679 | A3 | D3 | H | D3 | D3 |
| 680 | A3 | H | D3 | D3 | D3 |
| 681 | A3 | D3 | D3 | D3 | Ph |
| 682 | A3 | D3 | D3 | Ph | D3 |
| 683 | A3 | D3 | Ph | D3 | D3 |
| 684 | A3 | Ph | D3 | D3 | D3 |
| 685 | A3 | D3 | D3 | H | H |
| 686 | A3 | D3 | H | D3 | H |
| 687 | A3 | D3 | H | H | D3 |
| 688 | A3 | H | D3 | D3 | H |
| 689 | A3 | H | D3 | H | D3 |
| 690 | A3 | H | H | D3 | D3 |
| 691 | A3 | D3 | D3 | Ph | H |
| 692 | A3 | D3 | D3 | H | Ph |
| 693 | A3 | D3 | Ph | D3 | H |
| 694 | A3 | D3 | H | D3 | Ph |
| 695 | A3 | D3 | Ph | H | D3 |
| 696 | A3 | D3 | H | Ph | D3 |
| 697 | A3 | Ph | D3 | D3 | H |
| 698 | A3 | H | D3 | D3 | Ph |
| 699 | A3 | Ph | D3 | H | D3 |
| 700 | A3 | H | D3 | Ph | D3 |
| 701 | A3 | Ph | H | D3 | D3 |
| 702 | A3 | H | Ph | D3 | D3 |
| 703 | A3 | D4 | D4 | D4 | H |
| 704 | A3 | D4 | D4 | H | D4 |
| 705 | A3 | D4 | H | D4 | D4 |
| 706 | A3 | H | D4 | D4 | D4 |
| 707 | A3 | D4 | D4 | D4 | Ph |
| 708 | A3 | D4 | D4 | Ph | D4 |
| 709 | A3 | D4 | Ph | D4 | D4 |
| 710 | A3 | Ph | D4 | D4 | D4 |
| 711 | A3 | D4 | D4 | H | H |
| 712 | A3 | D4 | H | D4 | H |
| 713 | A3 | D4 | H | H | D4 |
| 714 | A3 | H | D4 | D4 | H |
| 715 | A3 | H | D4 | H | D4 |
| 716 | A3 | H | H | D4 | D4 |
| 717 | A3 | D4 | D4 | Ph | H |
| 718 | A3 | D4 | D4 | H | Ph |
| 719 | A3 | D4 | Ph | D4 | H |
| 720 | A3 | D4 | H | D4 | Ph |
| 721 | A3 | D4 | Ph | H | D4 |
| 722 | A3 | D4 | H | Ph | D4 |
| 723 | A3 | Ph | D4 | D4 | H |
| 724 | A3 | H | D4 | D4 | Ph |
| 725 | A3 | Ph | D4 | H | D4 |
| 726 | A3 | H | D4 | Ph | D4 |
| 727 | A3 | Ph | H | D4 | D4 |
| 728 | A3 | H | Ph | D4 | D4 |
| 729 | A3 | D40 | D40 | D40 | H |
| 730 | A3 | D40 | D40 | H | D40 |
| 731 | A3 | D40 | H | D40 | D40 |
| 732 | A3 | H | D40 | D40 | D40 |
| 733 | A3 | D40 | D40 | D40 | Ph |
| 734 | A3 | D40 | D40 | Ph | D40 |
| 735 | A3 | D40 | Ph | D40 | D40 |
| 736 | A3 | Ph | D40 | D40 | D40 |
| 737 | A3 | D40 | D40 | H | H |
| 738 | A3 | D40 | H | D40 | H |
| 739 | A3 | D40 | H | H | D40 |
| 740 | A3 | H | D40 | D40 | H |

TABLE 1-continued

| No. | $R^1$ | $R^2$ | $R^3$ | $R^4$ | $R^5$ |
|---|---|---|---|---|---|
| 741 | A3 | H | D40 | H | D40 |
| 742 | A3 | H | H | D40 | D40 |
| 743 | A3 | D40 | D40 | Ph | H |
| 744 | A3 | D40 | D40 | H | Ph |
| 745 | A3 | D40 | Ph | D40 | H |
| 746 | A3 | D40 | H | D40 | Ph |
| 747 | A3 | D40 | Ph | H | D40 |
| 748 | A3 | D40 | H | Ph | D40 |
| 749 | A3 | Ph | D40 | D40 | H |
| 750 | A3 | H | D40 | D40 | Ph |
| 751 | A3 | Ph | D40 | H | D40 |
| 752 | A3 | H | D40 | Ph | D40 |
| 753 | A3 | Ph | H | D40 | D40 |
| 754 | A3 | H | Ph | D40 | D40 |
| 755 | A3 | D41 | D41 | D41 | H |
| 756 | A3 | D41 | D41 | H | D41 |
| 757 | A3 | D41 | H | D41 | D41 |
| 758 | A3 | H | D41 | D41 | D41 |
| 759 | A3 | D41 | D41 | D41 | Ph |
| 760 | A3 | D41 | D41 | Ph | D41 |
| 761 | A3 | D41 | Ph | D41 | D41 |
| 762 | A3 | Ph | D41 | D41 | D41 |
| 763 | A3 | D41 | D41 | H | H |
| 764 | A3 | D41 | H | D41 | H |
| 765 | A3 | D41 | H | H | D41 |
| 766 | A3 | H | D41 | D41 | H |
| 767 | A3 | H | D41 | H | D41 |
| 768 | A3 | H | H | D41 | D41 |
| 769 | A3 | D41 | D41 | Ph | H |
| 770 | A3 | D41 | D41 | H | Ph |
| 771 | A3 | D41 | Ph | D41 | H |
| 772 | A3 | D41 | H | D41 | Ph |
| 773 | A3 | D41 | Ph | H | D41 |
| 774 | A3 | D41 | H | Ph | D41 |
| 775 | A3 | Ph | D41 | D41 | H |
| 776 | A3 | H | D41 | D41 | Ph |
| 777 | A3 | Ph | D41 | H | D41 |
| 778 | A3 | H | D41 | Ph | D41 |
| 779 | A3 | Ph | H | D41 | D41 |
| 780 | A3 | H | Ph | D41 | D41 |
| 781 | A3 | D42 | D42 | D42 | H |
| 782 | A3 | D42 | D42 | H | D42 |
| 783 | A3 | D42 | H | D42 | D42 |
| 784 | A3 | H | D42 | D42 | D42 |
| 785 | A3 | D42 | D42 | D42 | Ph |
| 786 | A3 | D42 | D42 | Ph | D42 |
| 787 | A3 | D42 | Ph | D42 | D42 |
| 788 | A3 | Ph | D42 | D42 | D42 |
| 789 | A3 | D42 | D42 | H | H |
| 790 | A3 | D42 | H | D42 | H |
| 791 | A3 | D42 | H | H | D42 |
| 792 | A3 | H | D42 | D42 | H |
| 793 | A3 | H | D42 | H | D42 |
| 794 | A3 | H | H | D42 | D42 |
| 795 | A3 | D42 | D42 | Ph | H |
| 798 | A3 | D42 | D42 | H | Ph |
| 797 | A3 | D42 | Ph | D42 | H |
| 798 | A3 | D42 | H | D42 | Ph |
| 799 | A3 | D42 | Ph | H | D42 |
| 800 | A3 | D42 | H | Ph | D42 |
| 801 | A3 | Ph | D42 | D42 | H |
| 802 | A3 | H | H | D42 | Ph |
| 803 | A3 | Ph | D42 | H | D42 |
| 804 | A3 | H | D42 | Ph | D42 |
| 805 | A3 | Ph | H | D42 | D42 |
| 806 | A3 | H | Ph | D42 | D42 |
| 807 | A3 | D43 | D43 | D43 | H |
| 808 | A3 | D43 | D43 | H | D43 |
| 809 | A3 | D43 | H | D43 | D43 |
| 810 | A3 | H | D43 | D43 | D43 |
| 811 | A3 | D43 | D43 | D43 | Ph |
| 812 | A3 | D43 | D43 | Ph | D43 |
| 813 | A3 | D43 | Ph | D43 | D43 |
| 814 | A3 | Ph | D43 | D43 | D43 |
| 815 | A3 | D43 | D43 | H | H |
| 816 | A3 | D43 | H | D43 | H |
| 817 | A3 | D43 | H | H | D43 |
| 818 | A3 | H | D43 | D43 | H |

TABLE 1-continued

| No. | $R^1$ | $R^2$ | $R^3$ | $R^4$ | $R^5$ |
|---|---|---|---|---|---|
| 819 | A3 | H | D43 | H | D43 |
| 820 | A3 | H | H | D43 | D43 |
| 821 | A3 | D43 | D43 | Ph | H |
| 822 | A3 | D43 | D43 | H | Ph |
| 823 | A3 | D43 | Ph | D43 | H |
| 824 | A3 | D43 | H | D43 | Ph |
| 825 | A3 | D43 | Ph | H | D43 |
| 826 | A3 | D43 | H | Ph | D43 |
| 827 | A3 | Ph | D43 | D43 | H |
| 828 | A3 | H | D43 | D43 | Ph |
| 828 | A3 | Ph | D43 | H | D43 |
| 830 | A3 | H | D43 | Ph | D43 |
| 831 | A3 | Ph | H | D43 | D43 |
| 832 | A3 | H | Ph | D43 | D43 |
| 833 | A3 | D84 | D84 | D84 | H |
| 834 | A3 | D84 | D84 | H | D84 |
| 835 | A3 | D84 | H | D84 | D84 |
| 836 | A3 | H | D84 | D84 | D84 |
| 837 | A3 | D84 | D84 | D84 | Ph |
| 838 | A3 | D84 | D84 | Ph | D84 |
| 839 | A3 | D84 | Ph | D84 | D84 |
| 840 | A3 | Ph | D84 | D84 | D84 |
| 841 | A3 | D84 | D84 | H | H |
| 842 | A3 | D84 | H | D84 | H |
| 843 | A3 | D84 | H | H | D84 |
| 844 | A3 | H | D84 | D84 | H |
| 845 | A3 | H | D84 | H | D84 |
| 846 | A3 | H | H | D84 | D84 |
| 847 | A3 | D84 | D84 | Ph | H |
| 848 | A3 | D84 | D84 | H | Ph |
| 849 | A3 | D84 | Ph | D84 | H |
| 850 | A3 | D84 | H | D84 | Ph |
| 851 | A3 | D84 | Ph | H | D84 |
| 852 | A3 | D84 | H | Ph | D84 |
| 853 | A3 | Ph | D84 | D84 | H |
| 854 | A3 | H | D84 | D84 | Ph |
| 855 | A3 | Ph | D84 | H | D84 |
| 856 | A3 | H | D84 | Ph | D84 |
| 857 | A3 | Ph | H | D84 | D84 |
| 858 | A3 | H | Ph | D84 | D84 |
| 859 | A3 | D86 | D86 | D86 | H |
| 860 | A3 | D86 | D86 | H | D86 |
| 861 | A3 | D86 | H | D86 | D86 |
| 862 | A3 | H | D86 | D86 | D86 |
| 863 | A3 | D86 | D86 | D86 | Ph |
| 864 | A3 | D86 | D86 | Ph | D86 |
| 865 | A3 | D86 | Ph | D86 | D86 |
| 866 | A3 | Ph | D86 | D86 | D86 |
| 867 | A3 | D86 | D86 | H | H |
| 868 | A3 | D86 | H | D86 | H |
| 869 | A3 | D86 | H | H | D86 |
| 870 | A3 | H | D86 | D86 | H |
| 871 | A3 | H | D86 | H | D86 |
| 872 | A3 | H | H | D86 | D86 |
| 873 | A3 | D86 | D86 | Ph | H |
| 874 | A3 | D86 | D86 | H | Ph |
| 875 | A3 | D86 | Ph | D86 | H |
| 876 | A3 | D86 | H | D86 | Ph |
| 877 | A3 | D86 | Ph | H | D86 |
| 878 | A3 | D86 | H | Ph | D86 |
| 879 | A3 | Ph | D86 | D86 | H |
| 880 | A3 | H | D86 | D86 | Ph |
| 881 | A3 | Ph | D86 | H | D86 |
| 882 | A3 | H | D86 | Ph | D86 |
| 883 | A3 | Ph | H | D86 | D86 |
| 884 | A3 | H | Ph | D86 | D86 |
| 885 | A3 | D87 | D87 | D87 | H |
| 886 | A3 | D87 | D87 | H | D87 |
| 887 | A3 | D87 | H | D87 | D87 |
| 888 | A3 | H | D87 | D87 | D87 |
| 889 | A3 | D87 | D87 | D87 | Ph |
| 890 | A3 | D87 | D87 | Ph | D87 |
| 891 | A3 | D87 | Ph | D87 | D87 |
| 892 | A3 | Ph | D87 | D87 | D87 |
| 893 | A3 | D87 | D87 | H | H |
| 894 | A3 | D87 | H | D87 | H |
| 895 | A3 | D87 | H | H | D87 |
| 896 | A3 | H | D87 | D87 | H |

TABLE 1-continued

| No. | $R^1$ | $R^2$ | $R^3$ | $R^4$ | $R^5$ |
|---|---|---|---|---|---|
| 897 | A3 | H | D87 | H | D87 |
| 898 | A3 | H | H | D87 | D87 |
| 899 | A3 | D87 | D87 | Ph | H |
| 900 | A3 | D87 | D87 | H | Ph |
| 901 | A3 | D87 | Ph | D87 | H |
| 902 | A3 | D87 | H | D87 | Ph |
| 903 | A3 | D87 | Ph | H | D87 |
| 904 | A3 | D87 | H | Ph | D87 |
| 905 | A3 | Ph | D87 | D87 | H |
| 908 | A3 | H | D87 | D87 | Ph |
| 907 | A3 | Ph | D87 | H | D87 |
| 908 | A3 | H | D87 | Ph | D87 |
| 909 | A3 | Ph | H | D87 | D87 |
| 910 | A3 | H | Ph | D87 | D87 |
| 911 | A3 | D88 | D88 | D88 | H |
| 912 | A3 | D88 | D88 | H | D88 |
| 913 | A3 | D88 | H | D88 | D88 |
| 914 | A3 | H | D88 | D88 | D88 |
| 915 | A3 | D88 | D88 | D88 | Ph |
| 916 | A3 | D88 | D88 | Ph | D88 |
| 917 | A3 | D88 | Ph | D88 | D88 |
| 918 | A3 | Ph | D88 | D88 | D88 |
| 919 | A3 | D88 | D88 | H | H |
| 920 | A3 | D88 | H | D88 | H |
| 921 | A3 | D88 | H | H | D88 |
| 922 | A3 | H | D88 | D88 | H |
| 923 | A3 | H | D88 | H | D88 |
| 924 | A3 | H | H | D88 | D88 |
| 925 | A3 | D88 | D88 | Ph | H |
| 926 | A3 | D88 | D88 | H | Ph |
| 927 | A3 | D88 | Ph | D88 | H |
| 928 | A3 | D88 | H | D88 | Ph |
| 929 | A3 | D88 | Ph | H | D88 |
| 930 | A3 | D88 | H | Ph | D88 |
| 931 | A3 | Ph | D88 | D88 | H |
| 932 | A3 | H | D88 | D88 | Ph |
| 933 | A3 | Ph | D88 | H | D88 |
| 934 | A3 | H | D88 | Ph | D88 |
| 935 | A3 | Ph | H | D88 | D88 |
| 936 | A3 | H | Ph | D88 | D88 |
| 937 | D1 | A1 | D1 | D1 | H |
| 938 | D1 | A1 | D1 | H | D1 |
| 939 | D1 | A1 | H | D1 | D1 |
| 940 | H | A1 | D1 | D1 | D1 |
| 941 | D1 | A1 | D1 | D1 | Ph |
| 942 | D1 | A1 | D1 | Ph | D1 |
| 943 | D1 | A1 | Ph | D1 | D1 |
| 944 | Ph | A1 | D1 | D1 | D1 |
| 945 | D1 | A1 | D1 | H | H |
| 946 | D1 | A1 | H | D1 | H |
| 947 | D1 | A1 | H | H | D1 |
| 948 | H | A1 | D1 | D1 | H |
| 949 | H | A1 | D1 | H | D1 |
| 950 | H | A1 | H | D1 | D1 |
| 951 | D1 | A1 | D1 | Ph | H |
| 952 | D1 | A1 | D1 | H | Ph |
| 953 | D1 | A1 | Ph | D1 | H |
| 954 | D1 | A1 | H | D1 | Ph |
| 955 | D1 | A1 | Ph | H | D1 |
| 956 | D1 | A1 | H | Ph | D1 |
| 957 | Ph | A1 | D1 | D1 | H |
| 958 | H | A1 | D1 | D1 | Ph |
| 959 | Ph | A1 | D1 | H | D1 |
| 960 | H | A1 | D1 | Ph | D1 |
| 961 | Ph | A1 | H | H | D1 |
| 962 | H | A1 | Ph | D1 | D1 |
| 963 | D2 | A1 | D2 | D2 | H |
| 964 | D2 | A1 | D2 | H | D2 |
| 965 | D2 | A1 | H | D2 | D2 |
| 966 | H | A1 | D2 | D2 | D2 |
| 967 | D2 | A1 | D2 | D2 | Ph |
| 968 | D2 | A1 | D2 | Ph | D2 |
| 969 | D2 | A1 | Ph | D2 | D2 |
| 970 | Ph | A1 | D2 | D2 | D2 |
| 971 | D2 | A1 | D2 | H | H |
| 972 | D2 | A1 | H | D2 | H |
| 973 | D2 | A1 | H | H | D2 |
| 974 | H | A1 | D2 | D2 | H |

TABLE 1-continued

| No. | $R^1$ | $R^2$ | $R^3$ | $R^4$ | $R^5$ |
|---|---|---|---|---|---|
| 975 | H | A1 | D2 | H | D2 |
| 976 | H | A1 | H | D2 | D2 |
| 977 | D2 | A1 | D2 | Ph | H |
| 978 | D2 | A1 | D2 | H | Ph |
| 979 | D2 | A1 | Ph | D2 | H |
| 980 | D2 | A1 | H | D2 | Ph |
| 981 | D2 | A1 | Ph | H | D2 |
| 982 | D2 | A1 | H | Ph | D2 |
| 983 | Ph | A1 | D2 | D2 | H |
| 984 | H | A1 | D2 | D2 | Ph |
| 985 | Ph | A1 | D2 | H | D2 |
| 986 | H | A1 | D2 | Ph | D2 |
| 987 | Ph | A1 | H | D2 | D2 |
| 988 | H | A1 | Ph | D2 | D2 |
| 989 | D3 | A1 | D3 | D3 | H |
| 990 | D3 | A1 | D3 | H | D3 |
| 991 | D3 | A1 | H | D3 | D3 |
| 992 | H | A1 | D3 | D3 | D3 |
| 993 | D3 | A1 | D3 | D3 | Ph |
| 994 | D3 | A1 | D3 | Ph | D3 |
| 995 | D3 | A1 | Ph | D3 | D3 |
| 996 | Ph | A1 | D3 | D3 | D3 |
| 997 | D3 | A1 | D3 | H | H |
| 998 | D3 | A1 | H | D3 | H |
| 999 | D3 | A1 | H | H | D3 |
| 1000 | H | A1 | D3 | D3 | H |
| 1001 | H | A1 | D3 | H | D3 |
| 1002 | H | A1 | H | D3 | D3 |
| 1003 | D3 | A1 | D3 | Ph | H |
| 1004 | D3 | A1 | D3 | H | Ph |
| 1005 | D3 | A1 | Ph | D3 | H |
| 1006 | D3 | A1 | H | D3 | Ph |
| 1007 | D3 | A1 | Ph | H | D3 |
| 1008 | D3 | A1 | H | Ph | D3 |
| 1009 | Ph | A1 | D3 | D3 | H |
| 1010 | H | A1 | D3 | D3 | Ph |
| 1011 | Ph | A1 | D3 | H | D3 |
| 1012 | H | A1 | D3 | Ph | D3 |
| 1013 | Ph | A1 | H | D3 | D3 |
| 1014 | H | A1 | Ph | D3 | D3 |
| 1015 | D4 | A1 | D4 | D4 | H |
| 1016 | D4 | A1 | D4 | H | D4 |
| 1017 | D4 | A1 | H | D4 | D4 |
| 1018 | H | A1 | D4 | D4 | D4 |
| 1019 | D4 | A1 | D4 | D4 | Ph |
| 1020 | D4 | A1 | D4 | Ph | D4 |
| 1021 | D4 | A1 | Ph | D4 | D4 |
| 1022 | Ph | A1 | D4 | D4 | D4 |
| 1023 | D4 | A1 | D4 | H | H |
| 1024 | D4 | A1 | H | D4 | H |
| 1025 | D4 | A1 | H | H | D4 |
| 1026 | H | A1 | D4 | D4 | H |
| 1027 | H | A1 | D4 | H | D4 |
| 1028 | H | A1 | H | D4 | D4 |
| 1029 | D4 | A1 | D4 | Ph | H |
| 1030 | D4 | A1 | D4 | H | Ph |
| 1031 | D4 | A1 | Ph | D4 | H |
| 1032 | D4 | A1 | H | D4 | Ph |
| 1033 | D4 | A1 | Ph | H | D4 |
| 1034 | D4 | A1 | H | Ph | D4 |
| 1035 | Ph | A1 | D4 | D4 | H |
| 1036 | H | A1 | D4 | D4 | Ph |
| 1037 | Ph | A1 | D4 | H | D4 |
| 1038 | H | A1 | D4 | Ph | D4 |
| 1039 | Ph | A1 | H | D4 | D4 |
| 1040 | H | A1 | Ph | D4 | D4 |
| 1041 | D40 | A1 | D40 | D40 | H |
| 1042 | D40 | A1 | D40 | H | D40 |
| 1043 | D40 | A1 | H | D40 | D40 |
| 1044 | H | A1 | D40 | D40 | D40 |
| 1045 | D40 | A1 | D40 | D40 | Ph |
| 1046 | D40 | A1 | D40 | Ph | D40 |
| 1047 | D40 | A1 | Ph | D40 | D40 |
| 1048 | Ph | A1 | D40 | D40 | D40 |
| 1049 | D40 | A1 | D40 | H | H |
| 1050 | D40 | A1 | H | D40 | H |
| 1051 | D40 | A1 | H | H | D40 |
| 1052 | H | A1 | D40 | D40 | H |

TABLE 1-continued

| No. | $R^1$ | $R^2$ | $R^3$ | $R^4$ | $R^5$ |
|---|---|---|---|---|---|
| 1053 | H | A1 | D40 | H | D40 |
| 1054 | H | A1 | H | D40 | D40 |
| 1055 | D40 | A1 | D40 | Ph | H |
| 1056 | D40 | A1 | D40 | H | Ph |
| 1057 | D40 | A1 | Ph | D40 | H |
| 1058 | D40 | A1 | H | D40 | Ph |
| 1059 | D40 | A1 | Ph | H | D40 |
| 1060 | D40 | A1 | H | Ph | D40 |
| 1061 | Ph | A1 | D40 | D40 | H |
| 1062 | H | A1 | D40 | D40 | Ph |
| 1063 | Ph | A1 | D40 | H | D40 |
| 1064 | H | A1 | D40 | Ph | D40 |
| 1065 | Ph | A1 | H | D40 | D40 |
| 1066 | H | A1 | Ph | D40 | D40 |
| 1067 | D86 | A1 | D86 | D86 | H |
| 1068 | D86 | A1 | D86 | H | D86 |
| 1069 | D86 | A1 | H | D86 | D86 |
| 1070 | H | A1 | D86 | D86 | D86 |
| 1071 | D86 | A1 | D86 | D86 | Ph |
| 1072 | D86 | A1 | D86 | Ph | D86 |
| 1073 | D86 | A1 | Ph | D86 | D86 |
| 1074 | Ph | A1 | D86 | D86 | D86 |
| 1075 | D86 | A1 | D86 | H | H |
| 1076 | D86 | A1 | H | D86 | H |
| 1077 | D86 | A1 | H | H | D86 |
| 1078 | H | A1 | D86 | D86 | H |
| 1079 | H | A1 | D86 | H | D86 |
| 1080 | H | A1 | H | D86 | D86 |
| 1081 | D86 | A1 | D86 | Ph | H |
| 1082 | D86 | A1 | D86 | H | Ph |
| 1083 | D86 | A1 | Ph | D86 | H |
| 1084 | D86 | A1 | H | D86 | Ph |
| 1085 | D86 | A1 | Ph | H | D86 |
| 1086 | D86 | A1 | H | Ph | D86 |
| 1087 | Ph | A1 | D86 | D86 | H |
| 1088 | H | A1 | D86 | D86 | Ph |
| 1089 | Ph | A1 | D86 | H | D86 |
| 1090 | H | A1 | D86 | Ph | D86 |
| 1091 | Ph | A1 | H | D86 | D86 |
| 1092 | H | A1 | Ph | D86 | D86 |
| 1093 | D42 | A1 | D42 | D42 | H |
| 1094 | D42 | A1 | D42 | H | D42 |
| 1095 | D42 | A1 | H | D42 | D42 |
| 1096 | H | A1 | D42 | D42 | D42 |
| 1097 | D42 | A1 | D42 | D42 | Ph |
| 1098 | D42 | A1 | D42 | Ph | D42 |
| 1099 | D42 | A1 | Ph | D42 | D42 |
| 1100 | Ph | A1 | D42 | D42 | D42 |
| 1101 | D42 | A1 | D42 | H | H |
| 1102 | D42 | A1 | H | D42 | H |
| 1103 | D42 | A1 | H | H | D42 |
| 1104 | H | A1 | D42 | D42 | H |
| 1105 | H | A1 | D42 | H | D42 |
| 1106 | H | A1 | H | D42 | D42 |
| 1107 | D42 | A1 | D42 | Ph | H |
| 1108 | D42 | A1 | D42 | H | Ph |
| 1109 | D42 | A1 | Ph | D42 | H |
| 1110 | D42 | A1 | H | D42 | Ph |
| 1111 | D42 | A1 | Ph | H | D42 |
| 1112 | D42 | A1 | H | Ph | D42 |
| 1113 | Ph | A1 | D42 | D42 | H |
| 1114 | H | A1 | D42 | D42 | Ph |
| 1115 | Ph | A1 | D42 | H | D42 |
| 1116 | H | A1 | D42 | Ph | D42 |
| 1117 | Ph | A1 | H | D42 | D42 |
| 1118 | H | A1 | Ph | D42 | D42 |
| 1119 | D43 | A1 | D43 | D43 | H |
| 1120 | D43 | A1 | D43 | H | D43 |
| 1121 | D43 | A1 | H | D43 | D43 |
| 1122 | H | A1 | D43 | D43 | D43 |
| 1123 | D43 | A1 | D43 | D43 | Ph |
| 1124 | D43 | A1 | D43 | Ph | D43 |
| 1125 | D43 | A1 | Ph | D43 | D43 |
| 1126 | Ph | A1 | D43 | D43 | D43 |
| 1127 | D43 | A1 | D43 | H | H |
| 1128 | D43 | A1 | H | D43 | H |
| 1129 | D43 | A1 | H | H | D43 |
| 1130 | H | A1 | D43 | D43 | H |

TABLE 1-continued

| No. | $R^1$ | $R^2$ | $R^3$ | $R^4$ | $R^5$ |
|---|---|---|---|---|---|
| 1131 | H | A1 | D43 | H | D43 |
| 1132 | H | A1 | H | D43 | D43 |
| 1133 | D43 | A1 | D43 | Ph | H |
| 1134 | D43 | A1 | D43 | H | Ph |
| 1135 | D43 | A1 | Ph | D43 | H |
| 1136 | D43 | A1 | H | D43 | Ph |
| 1137 | D43 | A1 | Ph | H | D43 |
| 1138 | D43 | A1 | H | Ph | D43 |
| 1139 | Ph | A1 | D43 | D43 | H |
| 1140 | H | A1 | D43 | D43 | Ph |
| 1141 | Ph | A1 | D43 | H | D43 |
| 1142 | H | A1 | D43 | Ph | D43 |
| 1143 | Ph | A1 | H | D43 | D43 |
| 1144 | H | A1 | Ph | D43 | D43 |
| 1145 | D84 | A1 | D84 | D84 | H |
| 1146 | D84 | A1 | D84 | H | D84 |
| 1147 | D84 | A1 | H | D84 | D84 |
| 1148 | H | A1 | D84 | D84 | D84 |
| 1149 | D84 | A1 | D84 | D84 | Ph |
| 1150 | D84 | A1 | D84 | Ph | D84 |
| 1151 | D84 | A1 | Ph | D84 | D84 |
| 1152 | Ph | A1 | D84 | D84 | D84 |
| 1153 | D84 | A1 | D84 | H | H |
| 1154 | D84 | A1 | H | D84 | H |
| 1155 | D84 | A1 | H | H | D84 |
| 1156 | H | A1 | D84 | D84 | H |
| 1157 | H | A1 | D84 | H | D84 |
| 1158 | H | A1 | H | D84 | D84 |
| 1159 | D84 | A1 | D84 | Ph | H |
| 1160 | D84 | A1 | D84 | H | Ph |
| 1161 | D84 | A1 | Ph | D84 | H |
| 1162 | D84 | A1 | H | D84 | Ph |
| 1163 | D84 | A1 | Ph | H | D84 |
| 1164 | D84 | A1 | H | Ph | D84 |
| 1165 | Ph | A1 | D84 | D84 | H |
| 1166 | H | A1 | D84 | D84 | Ph |
| 1167 | Ph | A1 | D84 | H | D84 |
| 1168 | H | A1 | D84 | Ph | D84 |
| 1169 | Ph | A1 | H | D84 | D84 |
| 1170 | H | A1 | Ph | D84 | D84 |
| 1171 | D86 | A1 | D86 | D86 | H |
| 1172 | D86 | A1 | D86 | H | D86 |
| 1173 | D86 | A1 | H | D86 | D86 |
| 1174 | H | A1 | D86 | D86 | D86 |
| 1175 | D86 | A1 | D86 | D86 | Ph |
| 1176 | D86 | A1 | D86 | Ph | D86 |
| 1177 | D86 | A1 | Ph | D86 | D86 |
| 1178 | Ph | A1 | D86 | D86 | D86 |
| 1179 | D86 | A1 | D86 | H | H |
| 1180 | D86 | A1 | H | D86 | H |
| 1181 | D86 | A1 | H | H | D86 |
| 1182 | H | A1 | D86 | D86 | H |
| 1183 | H | A1 | D86 | H | D86 |
| 1184 | H | A1 | H | D86 | D86 |
| 1185 | D86 | A1 | D86 | Ph | H |
| 1186 | D86 | A1 | D86 | H | Ph |
| 1187 | D86 | A1 | Ph | D86 | H |
| 1188 | D86 | A1 | H | D86 | Ph |
| 1189 | D86 | A1 | Ph | H | D86 |
| 1190 | D86 | A1 | H | Ph | D86 |
| 1191 | Ph | A1 | D86 | D86 | H |
| 1192 | H | A1 | D86 | D86 | Ph |
| 1193 | Ph | A1 | D86 | H | D86 |
| 1194 | H | A1 | D86 | Ph | D86 |
| 1195 | Ph | A1 | H | D86 | D86 |
| 1196 | H | A1 | Ph | D86 | D86 |
| 1197 | D87 | A1 | D87 | D87 | H |
| 1198 | D87 | A1 | D87 | H | D87 |
| 1199 | D87 | A1 | H | D87 | D87 |
| 1200 | H | A1 | D87 | D87 | D87 |
| 1201 | D87 | A1 | D87 | D87 | Ph |
| 1202 | D87 | A1 | D87 | Ph | D87 |
| 1203 | D87 | A1 | Ph | D87 | D87 |
| 1204 | Ph | A1 | D87 | D87 | D87 |
| 1205 | D87 | A1 | D87 | H | H |
| 1206 | D87 | A1 | H | D87 | H |
| 1207 | D87 | A1 | H | H | D87 |
| 1208 | H | A1 | D87 | D87 | H |

TABLE 1-continued

| No. | $R^1$ | $R^2$ | $R^3$ | $R^4$ | $R^5$ |
|---|---|---|---|---|---|
| 1209 | H | A1 | D87 | H | D87 |
| 1210 | H | A1 | H | D87 | D87 |
| 1211 | D87 | A1 | D87 | Ph | H |
| 1212 | D87 | A1 | D87 | H | Ph |
| 1213 | D87 | A1 | Ph | D87 | H |
| 1214 | D87 | A1 | H | D87 | Ph |
| 1215 | D87 | A1 | Ph | H | D87 |
| 1216 | D87 | A1 | H | Ph | D87 |
| 1217 | Ph | A1 | D87 | D87 | H |
| 1218 | H | A1 | D87 | D87 | Ph |
| 1219 | Ph | A1 | D87 | H | D87 |
| 1220 | H | A1 | D87 | Ph | D87 |
| 1221 | Ph | A1 | H | D87 | D87 |
| 1222 | H | A1 | Ph | D87 | D87 |
| 1223 | D88 | A1 | D88 | D88 | H |
| 1224 | D88 | A1 | D88 | H | D88 |
| 1225 | D88 | A1 | H | D88 | D88 |
| 1226 | H | A1 | D88 | D88 | D88 |
| 1227 | D88 | A1 | D88 | D88 | Ph |
| 1228 | D88 | A1 | D88 | Ph | D88 |
| 1229 | D88 | A1 | Ph | D88 | D88 |
| 1230 | Ph | A1 | D88 | D88 | D88 |
| 1231 | D88 | A1 | D88 | H | H |
| 1232 | D88 | A1 | H | D88 | H |
| 1233 | D88 | A1 | H | H | D88 |
| 1234 | H | A1 | D88 | D88 | H |
| 1235 | H | A1 | D88 | H | D88 |
| 1236 | H | A1 | H | D88 | D88 |
| 1237 | D88 | A1 | D88 | Ph | H |
| 1238 | D88 | A1 | D88 | H | Ph |
| 1239 | D88 | A1 | Ph | D88 | H |
| 1240 | D88 | A1 | H | D88 | Ph |
| 1241 | D88 | A1 | Ph | H | D88 |
| 1242 | D88 | A1 | H | Ph | D88 |
| 1243 | Ph | A1 | D88 | D88 | H |
| 1244 | H | A1 | D88 | D88 | Ph |
| 1245 | Ph | A1 | D88 | H | D88 |
| 1246 | H | A1 | D88 | Ph | D88 |
| 1247 | Ph | A1 | H | D88 | D88 |
| 1248 | H | A1 | Ph | D88 | D88 |
| 1249 | D1 | A2 | D1 | D1 | H |
| 1250 | D1 | A2 | D1 | H | D1 |
| 1251 | D1 | A2 | H | D1 | D1 |
| 1252 | H | A2 | D1 | D1 | D1 |
| 1253 | D1 | A2 | D1 | D1 | Ph |
| 1254 | D1 | A2 | D1 | Ph | D1 |
| 1255 | D1 | A2 | Ph | D1 | D1 |
| 1256 | Ph | A2 | D1 | D1 | D1 |
| 1257 | D1 | A2 | D1 | H | H |
| 1258 | D1 | A2 | H | D1 | H |
| 1259 | D1 | A2 | H | H | D1 |
| 1260 | H | A2 | D1 | D1 | H |
| 1261 | H | A2 | D1 | H | D1 |
| 1262 | H | A2 | H | D1 | D1 |
| 1263 | D1 | A2 | D1 | Ph | H |
| 1264 | D1 | A2 | D1 | H | Ph |
| 1265 | D1 | A2 | Ph | D1 | H |
| 1266 | D1 | A2 | H | D1 | Ph |
| 1267 | D1 | A2 | Ph | H | D1 |
| 1268 | D1 | A2 | H | Ph | D1 |
| 1269 | Ph | A2 | D1 | D1 | H |
| 1270 | H | A2 | D1 | D1 | Ph |
| 1271 | Ph | A2 | D1 | H | D1 |
| 1272 | H | A2 | D1 | Ph | D1 |
| 1273 | Ph | A2 | H | D1 | D1 |
| 1274 | H | A2 | Ph | D1 | D1 |
| 1275 | D2 | A2 | D2 | D2 | H |
| 1276 | D2 | A2 | D2 | H | D2 |
| 1277 | D2 | A2 | H | D2 | D2 |
| 1278 | H | A2 | D2 | D2 | D2 |
| 1279 | D2 | A2 | D2 | D2 | Ph |
| 1280 | D2 | A2 | D2 | Ph | D2 |
| 1281 | D2 | A2 | Ph | D2 | D2 |
| 1282 | Ph | A2 | D2 | D2 | D2 |
| 1283 | D2 | A2 | D2 | H | H |
| 1284 | D2 | A2 | H | D2 | H |
| 1285 | D2 | A2 | H | H | D2 |
| 1286 | H | A2 | D2 | D2 | H |

TABLE 1-continued

| No. | $R^1$ | $R^2$ | $R^3$ | $R^4$ | $R^5$ |
|---|---|---|---|---|---|
| 1287 | H | A2 | D2 | H | D2 |
| 1288 | H | A2 | H | D2 | D2 |
| 1289 | D2 | A2 | D2 | Ph | H |
| 1290 | D2 | A2 | D2 | H | Ph |
| 1291 | D2 | A2 | Ph | D2 | H |
| 1292 | D2 | A2 | H | D2 | Ph |
| 1293 | D2 | A2 | Ph | H | D2 |
| 1294 | D2 | A2 | H | Ph | D2 |
| 1295 | Ph | A2 | D2 | D2 | H |
| 1296 | H | A2 | D2 | D2 | Ph |
| 1297 | Ph | A2 | D2 | H | D2 |
| 1298 | H | A2 | D2 | Ph | D2 |
| 1299 | Ph | A2 | H | D2 | D2 |
| 1300 | H | A2 | Ph | D2 | D2 |
| 1301 | D3 | A2 | D3 | D3 | H |
| 1302 | D3 | A2 | D3 | H | D3 |
| 1303 | D3 | A2 | H | D3 | D3 |
| 1304 | H | A2 | D3 | D3 | D3 |
| 1305 | D3 | A2 | D3 | D3 | Ph |
| 1306 | D3 | A2 | D3 | Ph | D3 |
| 1307 | D3 | A2 | Ph | D3 | D3 |
| 1308 | Ph | A2 | D3 | D3 | D3 |
| 1309 | D3 | A2 | D3 | H | H |
| 1310 | D3 | A2 | H | D3 | H |
| 1311 | D3 | A2 | H | H | D3 |
| 1312 | H | A2 | D3 | D3 | H |
| 1313 | H | A2 | D3 | H | D3 |
| 1314 | H | A2 | H | D3 | D3 |
| 1315 | D3 | A2 | D3 | Ph | H |
| 1316 | D3 | A2 | D3 | H | Ph |
| 1317 | D3 | A2 | Ph | D3 | H |
| 1318 | D3 | A2 | H | D3 | Ph |
| 1319 | D3 | A2 | Ph | H | D3 |
| 1320 | D3 | A2 | H | Ph | D3 |
| 1321 | Ph | A2 | D3 | D3 | H |
| 1322 | H | A2 | D3 | D3 | Ph |
| 1323 | Ph | A2 | D3 | H | D3 |
| 1324 | H | A2 | D3 | Ph | D3 |
| 1325 | Ph | A2 | H | D3 | D3 |
| 1326 | H | A2 | Ph | D3 | D3 |
| 1327 | D4 | A2 | D4 | D4 | H |
| 1328 | D4 | A2 | D4 | H | D4 |
| 1329 | D4 | A2 | H | D4 | D4 |
| 1330 | H | A2 | D4 | D4 | D4 |
| 1331 | D4 | A2 | D4 | D4 | Ph |
| 1332 | D4 | A2 | D4 | Ph | D4 |
| 1333 | D4 | A2 | Ph | D4 | D4 |
| 1334 | Ph | A2 | D4 | D4 | D4 |
| 1335 | D4 | A2 | D4 | H | H |
| 1336 | D4 | A2 | H | D4 | H |
| 1337 | D4 | A2 | H | H | D4 |
| 1338 | H | A2 | D4 | D4 | H |
| 1339 | H | A2 | D4 | H | D4 |
| 1340 | H | A2 | H | D4 | D4 |
| 1341 | D4 | A2 | D4 | Ph | H |
| 1342 | D4 | A2 | D4 | H | Ph |
| 1343 | D4 | A2 | Ph | D4 | H |
| 1344 | D4 | A2 | H | D4 | Ph |
| 1345 | D4 | A2 | Ph | H | D4 |
| 1346 | D4 | A2 | H | Ph | D4 |
| 1347 | Ph | A2 | D4 | D4 | H |
| 1348 | H | A2 | D4 | D4 | Ph |
| 1349 | Ph | A2 | D4 | H | D4 |
| 1350 | H | A2 | D4 | Ph | D4 |
| 1351 | Ph | A2 | H | D4 | D4 |
| 1352 | H | A2 | Ph | D4 | D4 |
| 1353 | D40 | A2 | D40 | D40 | H |
| 1354 | D40 | A2 | D40 | H | D40 |
| 1355 | D40 | A2 | H | D40 | D40 |
| 1356 | H | A2 | D40 | D40 | D40 |
| 1357 | D40 | A2 | D40 | D40 | Ph |
| 1358 | D40 | A2 | D40 | Ph | D40 |
| 1359 | D40 | A2 | Ph | D40 | D40 |
| 1360 | Ph | A2 | D40 | D40 | D40 |
| 1361 | D40 | A2 | D40 | H | H |
| 1362 | D40 | A2 | H | D40 | H |
| 1363 | D40 | A2 | H | H | D40 |
| 1364 | H | A2 | D40 | D40 | H |

TABLE 1-continued

| No. | $R^1$ | $R^2$ | $R^3$ | $R^4$ | $R^5$ |
|---|---|---|---|---|---|
| 1365 | H | A2 | D40 | H | D40 |
| 1366 | H | A2 | H | D40 | D40 |
| 1367 | D40 | A2 | D40 | Ph | H |
| 1368 | D40 | A2 | D40 | H | Ph |
| 1369 | D40 | A2 | Ph | D40 | H |
| 1370 | D40 | A2 | H | D40 | Ph |
| 1371 | D40 | A2 | Ph | H | D40 |
| 1372 | D40 | A2 | H | Ph | D40 |
| 1373 | Ph | A2 | D40 | D40 | H |
| 1374 | H | A2 | D40 | D40 | Ph |
| 1375 | Ph | A2 | D40 | H | D40 |
| 1376 | H | A2 | D40 | Ph | D40 |
| 1377 | Ph | A2 | H | D40 | D40 |
| 1378 | H | A2 | Ph | D40 | D40 |
| 1379 | D86 | A2 | D86 | D86 | H |
| 1380 | D86 | A2 | D86 | H | D86 |
| 1381 | D86 | A2 | H | D86 | D86 |
| 1382 | H | A2 | D86 | D86 | D86 |
| 1383 | D86 | A2 | D86 | D86 | Ph |
| 1384 | D86 | A2 | D86 | Ph | D86 |
| 1385 | D86 | A2 | Ph | D86 | D86 |
| 1386 | Ph | A2 | D86 | D86 | D86 |
| 1387 | D86 | A2 | D86 | H | H |
| 1388 | D86 | A2 | H | D86 | H |
| 1389 | D86 | A2 | H | H | D86 |
| 1390 | H | A2 | D86 | D86 | H |
| 1391 | H | A2 | D86 | H | D86 |
| 1392 | H | A2 | H | D86 | D86 |
| 1393 | D86 | A2 | D86 | Ph | H |
| 1394 | D86 | A2 | D86 | H | Ph |
| 1395 | D86 | A2 | Ph | D86 | H |
| 1396 | D86 | A2 | H | D86 | Ph |
| 1397 | D86 | A2 | Ph | H | D86 |
| 1398 | D86 | A2 | H | Ph | D86 |
| 1399 | Ph | A2 | D86 | D86 | H |
| 1400 | H | A2 | D86 | D86 | Ph |
| 1401 | Ph | A2 | D86 | H | D86 |
| 1402 | H | A2 | D86 | Ph | D86 |
| 1403 | Ph | A2 | H | D86 | D86 |
| 1404 | H | A2 | Ph | D86 | D86 |
| 1405 | D42 | A2 | D42 | D42 | H |
| 1406 | D42 | A2 | D42 | H | D42 |
| 1407 | D42 | A2 | H | D42 | D42 |
| 1408 | H | A2 | D42 | D42 | D42 |
| 1409 | D42 | A2 | D42 | D42 | Ph |
| 1410 | D42 | A2 | D42 | Ph | D42 |
| 1411 | D42 | A2 | Ph | D42 | D42 |
| 1412 | Ph | A2 | D42 | D42 | D42 |
| 1413 | D42 | A2 | D42 | H | H |
| 1414 | D42 | A2 | H | D42 | H |
| 1415 | D42 | A2 | H | H | D42 |
| 1416 | H | A2 | D42 | D42 | H |
| 1417 | H | A2 | D42 | H | D42 |
| 1418 | H | A2 | H | D42 | D42 |
| 1419 | D42 | A2 | D42 | Ph | H |
| 1420 | D42 | A2 | D42 | H | Ph |
| 1421 | D42 | A2 | Ph | D42 | H |
| 1422 | D42 | A2 | H | D42 | Ph |
| 1423 | D42 | A2 | Ph | H | D42 |
| 1424 | D42 | A2 | H | Ph | D42 |
| 1425 | Ph | A2 | D42 | D42 | H |
| 1426 | H | A2 | D42 | D42 | Ph |
| 1427 | Ph | A2 | D42 | H | D42 |
| 1428 | H | A2 | D42 | Ph | D42 |
| 1429 | Ph | A2 | H | D42 | D42 |
| 1430 | H | A2 | Ph | D42 | D42 |
| 1431 | D43 | A2 | D43 | D43 | H |
| 1432 | D43 | A2 | D43 | H | D43 |
| 1433 | D43 | A2 | H | D43 | D43 |
| 1434 | H | A2 | D43 | D43 | D43 |
| 1435 | D43 | A2 | D43 | D43 | Ph |
| 1436 | D43 | A2 | D43 | Ph | D43 |
| 1437 | D43 | A2 | Ph | D43 | D43 |
| 1438 | Ph | A2 | D43 | D43 | D43 |
| 1439 | D43 | A2 | D43 | H | H |
| 1440 | D43 | A2 | H | D43 | H |
| 1441 | D43 | A2 | H | H | D43 |
| 1442 | H | A2 | D43 | D43 | H |

TABLE 1-continued

| No. | $R^1$ | $R^2$ | $R^3$ | $R^4$ | $R^5$ |
|---|---|---|---|---|---|
| 1443 | H | A2 | D43 | H | D43 |
| 1444 | H | A2 | H | D43 | D43 |
| 1445 | D43 | A2 | D43 | Ph | H |
| 1446 | D43 | A2 | D43 | H | Ph |
| 1447 | D43 | A2 | Ph | D43 | H |
| 1448 | D43 | A2 | H | D43 | Ph |
| 1449 | D43 | A2 | Ph | H | D43 |
| 1450 | D43 | A2 | H | Ph | D43 |
| 1451 | Ph | A2 | D43 | D43 | H |
| 1452 | H | A2 | D43 | D43 | Ph |
| 1453 | Ph | A2 | D43 | H | D43 |
| 1454 | H | A2 | D43 | Ph | D43 |
| 1455 | Ph | A2 | H | D43 | D43 |
| 1456 | H | A2 | Ph | D43 | D43 |
| 1457 | D84 | A2 | D84 | D84 | H |
| 1458 | D84 | A2 | D84 | H | D84 |
| 1459 | D84 | A2 | H | D84 | D84 |
| 1460 | H | A2 | D84 | D84 | D84 |
| 1461 | D84 | A2 | D84 | D84 | Ph |
| 1462 | D84 | A2 | D84 | Ph | D84 |
| 1463 | D84 | A2 | Ph | D84 | D84 |
| 1464 | Ph | A2 | D84 | D84 | D84 |
| 1465 | D84 | A2 | D84 | H | H |
| 1466 | D84 | A2 | H | D84 | H |
| 1467 | D84 | A2 | H | H | D84 |
| 1468 | H | A2 | D84 | D84 | H |
| 1469 | H | A2 | D84 | H | D84 |
| 1470 | H | A2 | H | D84 | D84 |
| 1471 | D84 | A2 | D84 | Ph | H |
| 1472 | D84 | A2 | D84 | H | Ph |
| 1473 | D84 | A2 | Ph | D84 | H |
| 1474 | D84 | A2 | H | D84 | Ph |
| 1475 | D84 | A2 | Ph | H | D84 |
| 1476 | D84 | A2 | H | Ph | D84 |
| 1477 | Ph | A2 | D84 | D84 | H |
| 1478 | H | A2 | D84 | D84 | Ph |
| 1479 | Ph | A2 | D84 | H | D84 |
| 1480 | H | A2 | D84 | Ph | D84 |
| 1481 | Ph | A2 | H | D84 | D84 |
| 1482 | H | A2 | Ph | D84 | D84 |
| 1483 | D86 | A2 | D86 | D86 | H |
| 1484 | D86 | A2 | D86 | H | D86 |
| 1485 | D86 | A2 | H | D86 | D86 |
| 1486 | H | A2 | D86 | D86 | D86 |
| 1487 | D86 | A2 | D86 | D86 | Ph |
| 1488 | D86 | A2 | D86 | Ph | D86 |
| 1489 | D86 | A2 | Ph | D86 | D86 |
| 1490 | Ph | A2 | D86 | D86 | D86 |
| 1491 | D86 | A2 | D86 | H | H |
| 1492 | D86 | A2 | H | D86 | H |
| 1493 | D86 | A2 | H | H | D86 |
| 1494 | H | A2 | D86 | D86 | H |
| 1495 | H | A2 | D86 | H | D86 |
| 1496 | H | A2 | H | D86 | D86 |
| 1497 | D86 | A2 | D86 | Ph | H |
| 1498 | D86 | A2 | D86 | H | Ph |
| 1499 | D86 | A2 | Ph | D86 | H |
| 1500 | D86 | A2 | H | D86 | Ph |
| 1501 | D86 | A2 | Ph | H | D86 |
| 1502 | D86 | A2 | H | Ph | D86 |
| 1503 | Ph | A2 | D86 | D86 | H |
| 1504 | H | A2 | D86 | D86 | Ph |
| 1505 | Ph | A2 | D86 | H | D86 |
| 1506 | H | A2 | D86 | Ph | D86 |
| 1507 | Ph | A2 | H | D86 | D86 |
| 1508 | H | A2 | Ph | D86 | D86 |
| 1509 | D87 | A2 | D87 | D87 | H |
| 1510 | D87 | A2 | D87 | H | D87 |
| 1511 | D87 | A2 | H | D87 | D87 |
| 1512 | H | A2 | D87 | D87 | D87 |
| 1513 | D87 | A2 | D87 | D87 | Ph |
| 1514 | D87 | A2 | D87 | Ph | D87 |
| 1515 | D87 | A2 | Ph | D87 | D87 |
| 1516 | Ph | A2 | D87 | D87 | D87 |
| 1517 | D87 | A2 | D87 | H | H |
| 1518 | D87 | A2 | H | D87 | H |
| 1519 | D87 | A2 | H | H | D87 |
| 1520 | H | A2 | D87 | D87 | H |

TABLE 1-continued

| No. | $R^1$ | $R^2$ | $R^3$ | $R^4$ | $R^5$ |
|---|---|---|---|---|---|
| 1521 | H | A2 | D87 | H | D87 |
| 1522 | H | A2 | H | D87 | D87 |
| 1523 | D87 | A2 | D87 | Ph | H |
| 1524 | D87 | A2 | D87 | H | Ph |
| 1525 | D87 | A2 | Ph | D87 | H |
| 1526 | D87 | A2 | H | D87 | Ph |
| 1527 | D87 | A2 | Ph | H | D87 |
| 1528 | D87 | A2 | H | Ph | D87 |
| 1529 | Ph | A2 | D87 | D87 | H |
| 1530 | H | A2 | D87 | D87 | Ph |
| 1531 | Ph | A2 | D87 | H | D87 |
| 1532 | H | A2 | D87 | Ph | D87 |
| 1533 | Ph | A2 | H | D87 | D87 |
| 1534 | H | A2 | Ph | D87 | D87 |
| 1535 | D88 | A2 | D88 | D88 | H |
| 1536 | D88 | A2 | D88 | H | D88 |
| 1537 | D88 | A2 | H | D88 | D88 |
| 1538 | H | A2 | D88 | D88 | D88 |
| 1539 | D88 | A2 | D88 | D88 | Ph |
| 1540 | D88 | A2 | D88 | Ph | D88 |
| 1541 | D88 | A2 | Ph | D88 | D88 |
| 1542 | Ph | A2 | D88 | D88 | D88 |
| 1543 | D88 | A2 | D88 | H | H |
| 1544 | D88 | A2 | H | D88 | H |
| 1545 | D88 | A2 | H | H | D88 |
| 1546 | H | A2 | D88 | D88 | H |
| 1547 | H | A2 | D88 | H | D88 |
| 1548 | H | A2 | H | D88 | D88 |
| 1549 | D88 | A2 | D88 | Ph | H |
| 1550 | D88 | A2 | D88 | H | Ph |
| 1551 | D88 | A2 | Ph | D88 | H |
| 1552 | D88 | A2 | H | D88 | Ph |
| 1553 | D88 | A2 | Ph | H | D88 |
| 1554 | D88 | A2 | H | Ph | D88 |
| 1555 | Ph | A2 | D88 | D88 | H |
| 1556 | H | A2 | D88 | D88 | Ph |
| 1557 | Ph | A2 | D88 | H | D88 |
| 1558 | H | A2 | D88 | Ph | D88 |
| 1559 | Ph | A2 | H | D88 | D88 |
| 1560 | H | A2 | Ph | D88 | D88 |
| 1561 | D1 | A3 | D1 | D1 | H |
| 1562 | D1 | A3 | D1 | H | D1 |
| 1563 | D1 | A3 | H | D1 | D1 |
| 1564 | H | A3 | D1 | D1 | D1 |
| 1565 | D1 | A3 | D1 | D1 | Ph |
| 1566 | D1 | A3 | D1 | Ph | D1 |
| 1567 | D1 | A3 | Ph | D1 | D1 |
| 1588 | Ph | A3 | D1 | D1 | D1 |
| 1569 | D1 | A3 | D1 | H | H |
| 1570 | D1 | A3 | H | D1 | H |
| 1571 | D1 | A3 | H | H | D1 |
| 1572 | H | A3 | D1 | D1 | H |
| 1573 | H | A3 | D1 | H | D1 |
| 1574 | H | A3 | H | D1 | D1 |
| 1575 | D1 | A3 | D1 | Ph | H |
| 1576 | D1 | A3 | D1 | H | Ph |
| 1577 | D1 | A3 | Ph | D1 | H |
| 1578 | D1 | A3 | H | D1 | Ph |
| 1579 | D1 | A3 | Ph | H | D1 |
| 1580 | D1 | A3 | H | Ph | D1 |
| 1581 | Ph | A3 | D1 | D1 | H |
| 1582 | H | A3 | D1 | D1 | Ph |
| 1583 | Ph | A3 | D1 | H | D1 |
| 1584 | H | A3 | D1 | Ph | D1 |
| 1585 | Ph | A3 | H | D1 | D1 |
| 1586 | H | A3 | Ph | D1 | D1 |
| 1587 | D2 | A3 | D2 | D2 | H |
| 1588 | D2 | A3 | D2 | H | D2 |
| 1589 | D2 | A3 | H | D2 | D2 |
| 1590 | H | A3 | D2 | D2 | D2 |
| 1591 | D2 | A3 | D2 | D2 | Ph |
| 1592 | D2 | A3 | D2 | Ph | D2 |
| 1593 | D2 | A3 | Ph | D2 | D2 |
| 1594 | Ph | A3 | D2 | D2 | D2 |
| 1595 | D2 | A3 | D2 | H | H |
| 1596 | D2 | A3 | H | D2 | H |
| 1597 | D2 | A3 | H | H | D2 |
| 1598 | H | A3 | D2 | D2 | H |

TABLE 1-continued

| No. | $R^1$ | $R^2$ | $R^3$ | $R^4$ | $R^5$ |
|---|---|---|---|---|---|
| 1599 | H | A3 | D2 | H | D2 |
| 1600 | H | A3 | H | D2 | D2 |
| 1601 | D2 | A3 | D2 | Ph | H |
| 1602 | D2 | A3 | D2 | H | Ph |
| 1603 | D2 | A3 | Ph | D2 | H |
| 1604 | D2 | A3 | H | D2 | Ph |
| 1605 | D2 | A3 | Ph | H | D2 |
| 1606 | D2 | A3 | H | Ph | D2 |
| 1607 | Ph | A3 | D2 | D2 | H |
| 1608 | H | A3 | D2 | D2 | Ph |
| 1609 | Ph | A3 | D2 | H | D2 |
| 1610 | H | A3 | D2 | Ph | D2 |
| 1611 | Ph | A3 | H | D2 | D2 |
| 1612 | H | A3 | Ph | D2 | D2 |
| 1613 | D3 | A3 | D3 | D3 | H |
| 1614 | D3 | A3 | D3 | H | D3 |
| 1615 | D3 | A3 | H | D3 | D3 |
| 1616 | H | A3 | D3 | D3 | D3 |
| 1617 | D3 | A3 | D3 | D3 | Ph |
| 1618 | D3 | A3 | D3 | Ph | D3 |
| 1619 | D3 | A3 | Ph | D3 | D3 |
| 1620 | Ph | A3 | D3 | D3 | D3 |
| 1621 | D3 | A3 | D3 | H | H |
| 1622 | D3 | A3 | H | D3 | H |
| 1623 | D3 | A3 | H | H | D3 |
| 1624 | H | A3 | D3 | D3 | H |
| 1625 | H | A3 | D3 | H | D3 |
| 1626 | H | A3 | H | D3 | D3 |
| 1627 | D3 | A3 | D3 | Ph | H |
| 1628 | D3 | A3 | D3 | H | Ph |
| 1629 | D3 | A3 | Ph | D3 | H |
| 1630 | D3 | A3 | H | D3 | Ph |
| 1631 | D3 | A3 | Ph | H | D3 |
| 1632 | D3 | A3 | H | Ph | D3 |
| 1633 | Ph | A3 | D3 | D3 | H |
| 1634 | H | A3 | D3 | D3 | Ph |
| 1635 | Ph | A3 | D3 | H | D3 |
| 1636 | H | A3 | D3 | Ph | D3 |
| 1637 | Ph | A3 | H | D3 | D3 |
| 1638 | H | A3 | Ph | D3 | D3 |
| 1639 | D4 | A3 | D4 | D4 | H |
| 1640 | D4 | A3 | D4 | H | D4 |
| 1641 | D4 | A3 | H | D4 | D4 |
| 1642 | H | A3 | D4 | D4 | D4 |
| 1643 | D4 | A3 | D4 | D4 | Ph |
| 1644 | D4 | A3 | D4 | Ph | D4 |
| 1645 | D4 | A3 | Ph | D4 | D4 |
| 1646 | Ph | A3 | D4 | D4 | D4 |
| 1647 | D4 | A3 | D4 | H | H |
| 1648 | D4 | A3 | H | D4 | H |
| 1649 | D4 | A3 | H | H | D4 |
| 1650 | H | A3 | D4 | D4 | H |
| 1651 | H | A3 | D4 | H | D4 |
| 1652 | H | A3 | H | D4 | D4 |
| 1653 | D4 | A3 | D4 | Ph | H |
| 1654 | D4 | A3 | D4 | H | Ph |
| 1655 | D4 | A3 | Ph | D4 | H |
| 1656 | D4 | A3 | H | D4 | Ph |
| 1657 | D4 | A3 | Ph | H | D4 |
| 1658 | D4 | A3 | H | Ph | D4 |
| 1659 | Ph | A3 | D4 | D4 | H |
| 1660 | H | A3 | D4 | D4 | Ph |
| 1661 | Ph | A3 | D4 | H | D4 |
| 1662 | H | A3 | D4 | Ph | D4 |
| 1663 | Ph | A3 | H | D4 | D4 |
| 1664 | H | A3 | Ph | D4 | D4 |
| 1665 | D40 | A3 | D40 | D40 | H |
| 1666 | D40 | A3 | D40 | H | D40 |
| 1667 | D40 | A3 | H | D40 | D40 |
| 1668 | H | A3 | D40 | D40 | D40 |
| 1669 | D40 | A3 | D40 | D40 | Ph |
| 1670 | D40 | A3 | D40 | Ph | D40 |
| 1671 | D40 | A3 | Ph | D40 | D40 |
| 1672 | Ph | A3 | D40 | D40 | D40 |
| 1673 | D40 | A3 | D40 | H | H |
| 1674 | D40 | A3 | H | D40 | H |
| 1675 | D40 | A3 | H | H | D40 |
| 1676 | H | A3 | D40 | D40 | D |

TABLE 1-continued

| No. | $R^1$ | $R^2$ | $R^3$ | $R^4$ | $R^5$ |
|---|---|---|---|---|---|
| 1677 | H | A3 | D40 | H | D40 |
| 1678 | H | A3 | H | D40 | D40 |
| 1679 | D40 | A3 | D40 | Ph | H |
| 1680 | D40 | A3 | D40 | H | Ph |
| 1681 | D40 | A3 | Ph | D40 | H |
| 1682 | D40 | A3 | H | D40 | Ph |
| 1683 | D40 | A3 | Ph | H | D40 |
| 1684 | D40 | A3 | H | Ph | D40 |
| 1685 | Ph | A3 | D40 | D40 | H |
| 1686 | H | A3 | D40 | D40 | Ph |
| 1687 | Ph | A3 | D40 | H | D40 |
| 1688 | H | A3 | D40 | Ph | D40 |
| 1689 | Ph | A3 | H | D40 | D40 |
| 1690 | H | A3 | Ph | D40 | D40 |
| 1691 | D86 | A3 | D86 | D86 | H |
| 1692 | D86 | A3 | D86 | H | D86 |
| 1693 | D86 | A3 | H | D86 | D86 |
| 1694 | H | A3 | D86 | D86 | D86 |
| 1695 | D86 | A3 | D86 | D86 | Ph |
| 1696 | D86 | A3 | D86 | Ph | D86 |
| 1897 | D86 | A3 | Ph | D86 | D86 |
| 1698 | Ph | A3 | D86 | 86 | D86 |
| 1699 | D86 | A3 | D86 | H | H |
| 1700 | D86 | A3 | H | D86 | H |
| 1701 | D86 | A3 | H | H | D86 |
| 1702 | H | A3 | D86 | D86 | H |
| 1703 | H | A3 | D86 | H | D86 |
| 1704 | H | A3 | H | D86 | D86 |
| 1705 | D86 | A3 | D86 | Ph | H |
| 1706 | D86 | A3 | D86 | H | Ph |
| 1707 | D86 | A3 | Ph | D86 | H |
| 1708 | D86 | A3 | H | D86 | Ph |
| 1709 | D86 | A3 | Ph | H | D86 |
| 1710 | D86 | A3 | H | Ph | D86 |
| 1711 | Ph | A3 | D86 | D86 | H |
| 1712 | H | A3 | D86 | D86 | Ph |
| 1713 | Ph | A3 | D86 | H | D86 |
| 1714 | H | A3 | D86 | Ph | D86 |
| 1715 | Ph | A3 | H | D86 | D86 |
| 1716 | H | A3 | Ph | D86 | D86 |
| 1717 | D42 | A3 | D42 | D42 | H |
| 1718 | D42 | A3 | D42 | H | D42 |
| 1719 | D42 | A3 | H | D42 | D42 |
| 1720 | H | A3 | D42 | D42 | D42 |
| 1721 | D42 | A3 | D42 | D42 | Ph |
| 1722 | D42 | A3 | D42 | Ph | D42 |
| 1723 | D42 | A3 | Ph | D42 | D42 |
| 1724 | Ph | A3 | D42 | D42 | D42 |
| 1725 | D42 | A3 | D42 | H | H |
| 1726 | D42 | A3 | H | D42 | H |
| 1727 | D42 | A3 | H | H | D42 |
| 1728 | H | A3 | D42 | D42 | H |
| 1729 | H | A3 | D42 | H | D42 |
| 1730 | H | A3 | H | D42 | D42 |
| 1731 | D42 | A3 | D42 | Ph | H |
| 1732 | D42 | A3 | D42 | H | Ph |
| 1733 | D42 | A3 | Ph | D42 | H |
| 1734 | D42 | A3 | H | D42 | Ph |
| 1735 | D42 | A3 | Ph | H | D42 |
| 1736 | D42 | A3 | H | Ph | D42 |
| 1737 | Ph | A3 | D42 | D42 | H |
| 1738 | H | A3 | D42 | D42 | Ph |
| 1739 | Ph | A3 | D42 | H | D42 |
| 1740 | H | A3 | D42 | Ph | D42 |
| 1741 | Ph | A3 | H | D42 | D42 |
| 1742 | H | A3 | Ph | D42 | D42 |
| 1743 | D43 | A3 | D43 | D43 | H |
| 1744 | D43 | A3 | D43 | H | D43 |
| 1745 | D43 | A3 | H | D43 | D43 |
| 1746 | H | A3 | D43 | D43 | D43 |
| 1747 | D43 | A3 | D43 | D43 | Ph |
| 1748 | D43 | A3 | D43 | Ph | D43 |
| 1749 | D43 | A3 | Ph | D43 | D43 |
| 1750 | Ph | A3 | D43 | D43 | D43 |
| 1751 | D43 | A3 | D43 | H | H |
| 1752 | D43 | A3 | H | D43 | H |
| 1753 | D43 | A3 | H | H | D43 |
| 1754 | H | A3 | D43 | D43 | H |

TABLE 1-continued

| No. | $R^1$ | $R^2$ | $R^3$ | $R^4$ | $R^5$ |
|---|---|---|---|---|---|
| 1755 | H | A3 | D43 | H | D43 |
| 1756 | H | A3 | H | D43 | D43 |
| 1757 | D43 | A3 | D43 | Ph | H |
| 1758 | D43 | A3 | D43 | H | Ph |
| 1759 | D43 | A3 | Ph | D43 | H |
| 1760 | D43 | A3 | H | D43 | Ph |
| 1761 | D43 | A3 | Ph | H | D43 |
| 1762 | D43 | A3 | H | Ph | D43 |
| 1763 | Ph | A3 | D43 | D43 | H |
| 1764 | H | A3 | D43 | D43 | Ph |
| 1765 | Ph | A3 | D43 | H | D43 |
| 1766 | H | A3 | D43 | Ph | D43 |
| 1767 | Ph | A3 | H | D43 | D43 |
| 1768 | H | A3 | Ph | D43 | D43 |
| 1769 | D84 | A3 | D84 | D84 | H |
| 1770 | D84 | A3 | D84 | H | D84 |
| 1771 | D84 | A3 | H | D84 | D84 |
| 1772 | H | A3 | D84 | D84 | D84 |
| 1773 | D84 | A3 | D84 | D84 | Ph |
| 1774 | D84 | A3 | D84 | Ph | D84 |
| 1775 | D84 | A3 | Ph | D84 | D84 |
| 1776 | Ph | A3 | H | D84 | D84 |
| 1777 | D84 | A3 | D84 | H | H |
| 1778 | D84 | A3 | H | D84 | H |
| 1779 | D84 | A3 | H | H | D84 |
| 1780 | H | A3 | D84 | D84 | H |
| 1781 | H | A3 | D84 | H | D84 |
| 1782 | H | A3 | H | D84 | D84 |
| 1783 | D84 | A3 | D84 | Ph | H |
| 1784 | D84 | A3 | D84 | H | Ph |
| 1785 | D84 | A3 | Ph | D84 | H |
| 1786 | D84 | A3 | H | D84 | Ph |
| 1787 | D84 | A3 | Ph | H | D84 |
| 1788 | D84 | A3 | H | Ph | D84 |
| 1789 | Ph | A3 | D84 | D84 | H |
| 1790 | H | A3 | D84 | D84 | Ph |
| 1791 | Ph | A3 | D84 | H | D84 |
| 1792 | H | A3 | D84 | Ph | D84 |
| 1793 | Ph | A3 | H | D84 | D84 |
| 1794 | H | A3 | Ph | D84 | D84 |
| 1795 | D86 | A3 | D86 | D86 | H |
| 1796 | D86 | A3 | D86 | H | D86 |
| 1797 | D86 | A3 | H | D86 | D86 |
| 1798 | H | A3 | D86 | D86 | D86 |
| 1799 | D86 | A3 | D86 | D86 | Ph |
| 1800 | D86 | A3 | D86 | Ph | D86 |
| 1801 | D86 | A3 | Ph | D86 | D86 |
| 1802 | Ph | A3 | D86 | D86 | D86 |
| 1803 | D86 | A3 | D86 | H | H |
| 1804 | D86 | A3 | H | D86 | H |
| 1805 | D86 | A3 | H | H | D86 |
| 1806 | H | A3 | D86 | D86 | H |
| 1807 | H | A3 | D86 | H | D86 |
| 1808 | H | A3 | H | D86 | D86 |
| 1809 | D86 | A3 | D86 | Ph | H |
| 1810 | D86 | A3 | D86 | H | Ph |
| 1811 | D86 | A3 | Ph | D86 | H |
| 1812 | D86 | A3 | H | D86 | Ph |
| 1813 | D86 | A3 | Ph | H | D86 |
| 1814 | D86 | A3 | H | Ph | D86 |
| 1815 | Ph | A3 | D86 | D86 | H |
| 1816 | H | A3 | D86 | D86 | Ph |
| 1817 | Ph | A3 | D86 | H | D86 |
| 1818 | H | A3 | D86 | Ph | D86 |
| 1819 | Ph | A3 | H | D86 | D86 |
| 1820 | H | A3 | Ph | D86 | D86 |
| 1821 | D87 | A3 | D87 | D87 | H |
| 1822 | D87 | A3 | D87 | H | D87 |
| 1823 | D87 | A3 | H | D87 | D87 |
| 1824 | H | A3 | D87 | D87 | D87 |
| 1825 | D87 | A3 | D87 | D87 | Ph |
| 1826 | D87 | A3 | D87 | Ph | D87 |
| 1827 | D87 | A3 | Ph | D87 | D87 |
| 1828 | Ph | A3 | D87 | D87 | D87 |
| 1829 | D87 | A3 | D87 | H | H |
| 1830 | D87 | A3 | H | D87 | H |
| 1831 | D87 | A3 | H | H | D87 |
| 1832 | H | A3 | D87 | D87 | H |

TABLE 1-continued

| No. | $R^1$ | $R^2$ | $R^3$ | $R^4$ | $R^5$ |
|---|---|---|---|---|---|
| 1833 | H | A3 | D87 | H | D87 |
| 1834 | H | A3 | H | D87 | D87 |
| 1835 | D87 | A3 | D87 | Ph | H |
| 1836 | D87 | A3 | D87 | H | Ph |
| 1837 | D87 | A3 | Ph | D87 | H |
| 1838 | D87 | A3 | H | D87 | Ph |
| 1839 | D87 | A3 | Ph | H | D87 |
| 1840 | D87 | A3 | H | Ph | D87 |
| 1841 | Ph | A3 | D87 | D87 | H |
| 1842 | H | A3 | D87 | D87 | Ph |
| 1843 | Ph | A3 | D87 | H | D87 |
| 1844 | H | A3 | D87 | Ph | D87 |
| 1845 | Ph | A3 | H | D87 | D87 |
| 1846 | H | A3 | Ph | D87 | D87 |
| 1847 | D88 | A3 | D88 | D88 | H |
| 1848 | D88 | A3 | D88 | H | D88 |
| 1849 | D88 | A3 | H | D88 | D88 |
| 1850 | H | A3 | D88 | D88 | D88 |
| 1851 | D88 | A3 | D88 | D88 | Ph |
| 1852 | D88 | A3 | D88 | Ph | D88 |
| 1853 | D88 | A3 | Ph | D88 | D88 |
| 1854 | Ph | A3 | D88 | D88 | D88 |
| 1855 | D88 | A3 | D88 | H | H |
| 1856 | D88 | A3 | H | D88 | H |
| 1857 | D88 | A3 | H | H | D88 |
| 1858 | H | A3 | D88 | D88 | H |
| 1859 | H | A3 | D88 | H | D88 |
| 1860 | H | A3 | H | D88 | D88 |
| 1861 | D88 | A3 | D88 | Ph | H |
| 1862 | D88 | A3 | D88 | H | Ph |
| 1863 | D88 | A3 | Ph | D88 | H |
| 1864 | D88 | A3 | H | D88 | Ph |
| 1865 | D88 | A3 | Ph | H | D88 |
| 1866 | D88 | A3 | H | Ph | D88 |
| 1867 | Ph | A3 | D88 | D88 | H |
| 1868 | H | A3 | D88 | D88 | Ph |
| 1869 | Ph | A3 | D88 | H | D88 |
| 1870 | H | A3 | H | Ph | D88 |
| 1871 | Ph | A3 | H | D88 | D88 |
| 1872 | H | A3 | Ph | D88 | D88 |
| 1873 | A1 | D94 | D1 | D1 | D1 |
| 1874 | A1 | D95 | D1 | D1 | D1 |
| 1875 | A1 | D96 | D1 | D1 | D1 |
| 1876 | A1 | D94 | D86 | D86 | D86 |
| 1877 | A1 | D95 | D86 | D86 | D86 |
| 1878 | A1 | D96 | D86 | D86 | D86 |
| 1879 | A1 | H | D94 | D1 | D1 |
| 1880 | A1 | H | D95 | D1 | D1 |
| 1881 | A1 | H | D96 | D1 | D1 |
| 1882 | A1 | H | D94 | D86 | D86 |
| 1883 | A1 | H | D95 | D86 | D86 |
| 1884 | A1 | H | D96 | D86 | D86 |
| 1885 | A13 | H | D1 | D1 | D1 |
| 1886 | A13 | D1 | H | D1 | D1 |
| 1887 | A13 | D1 | D1 | H | D1 |
| 1888 | A13 | D1 | D1 | D1 | H |
| 1889 | A14 | H | D1 | D1 | D1 |
| 1890 | A14 | D1 | H | D1 | D1 |
| 1891 | A14 | D1 | D1 | H | D1 |
| 1892 | A14 | D1 | D1 | D1 | H |
| 1893 | A13 | H | D1 | D1 | D84 |
| 1894 | A13 | D1 | H | D84 | D1 |
| 1895 | A13 | D1 | D84 | H | D1 |
| 1896 | A13 | D84 | D1 | D1 | H |
| 1897 | A14 | H | D1 | D1 | D84 |
| 1898 | A14 | D1 | H | D84 | D1 |
| 1899 | A14 | D1 | D84 | H | D1 |
| 1900 | A14 | D84 | D1 | D1 | H |
| 1901 | A13 | H | D84 | D84 | D84 |
| 1902 | A13 | D84 | H | D84 | D84 |
| 1903 | A13 | D84 | D84 | H | D84 |
| 1904 | A13 | D84 | D84 | D84 | H |
| 1905 | A14 | H | D84 | D84 | D84 |
| 1906 | A14 | D84 | H | D84 | D84 |
| 1907 | A14 | D84 | D84 | H | D84 |
| 1908 | A14 | D84 | D84 | D84 | H |
| 1909 | A13 | Ph | D1 | D1 | H |
| 1910 | A13 | D1 | Ph | D1 | H |

TABLE 1-continued

| No. | $R^1$ | $R^2$ | $R^3$ | $R^4$ | $R^5$ |
|---|---|---|---|---|---|
| 1911 | A13 | D1 | D1 | Ph | H |
| 1912 | A13 | Ph | D1 | H | D1 |
| 1913 | A13 | D1 | Ph | H | D1 |
| 1914 | A13 | D1 | D1 | H | Ph |
| 1915 | A13 | Ph | H | D1 | D1 |
| 1916 | A13 | D1 | H | Ph | D1 |
| 1917 | A13 | D1 | H | D1 | Ph |
| 1918 | A13 | H | Ph | D1 | D1 |
| 1919 | A13 | H | D1 | Ph | D1 |
| 1920 | A13 | H | D1 | D1 | Ph |
| 1921 | A14 | Ph | D1 | D1 | H |
| 1922 | A14 | D1 | Ph | D1 | H |
| 1923 | A14 | D1 | D1 | Ph | H |
| 1924 | A14 | Ph | D1 | H | D1 |
| 1925 | A14 | D1 | Ph | H | D1 |
| 1926 | A14 | D1 | D1 | H | Ph |
| 1927 | A14 | Ph | H | D1 | D1 |
| 1928 | A14 | D1 | H | Ph | D1 |
| 1929 | A14 | D1 | H | D1 | Ph |
| 1930 | A14 | H | Ph | D1 | D1 |
| 1931 | A14 | H | D1 | Ph | D1 |
| 1932 | A14 | H | D1 | D1 | Ph |
| 1933 | A13 | Ph | D84 | D84 | H |
| 1934 | A13 | D84 | Ph | D84 | H |
| 1935 | A13 | D84 | D84 | Ph | H |
| 1936 | A13 | Ph | D84 | H | D84 |
| 1937 | A13 | D84 | Ph | H | D84 |
| 1938 | A13 | D84 | D84 | H | Ph |
| 1939 | A13 | Ph | H | D84 | D84 |
| 1940 | A13 | D84 | H | Ph | D84 |
| 1941 | A13 | D84 | H | D84 | Ph |
| 1942 | A13 | H | Ph | D84 | D84 |
| 1943 | A13 | H | D84 | Ph | D84 |
| 1944 | A13 | H | D84 | D84 | Ph |
| 1945 | A14 | Ph | D84 | D84 | H |
| 1946 | A14 | D84 | Ph | D84 | H |
| 1947 | A14 | D84 | D84 | Ph | H |
| 1948 | A14 | Ph | D84 | H | D84 |
| 1949 | A14 | D84 | Ph | H | D84 |
| 1950 | A14 | D84 | D84 | H | Ph |
| 1951 | A14 | Ph | H | D84 | D84 |
| 1952 | A14 | D84 | H | Ph | D84 |
| 1953 | A14 | D84 | H | D84 | Ph |
| 1954 | A14 | H | Ph | D84 | D84 |
| 1955 | A14 | H | D84 | Ph | D84 |
| 1956 | A14 | H | D84 | D84 | Ph |
| 1957 | A13 | Ph | D1 | D1 | D1 |
| 1958 | A13 | D1 | Ph | D1 | D1 |
| 1959 | A13 | D1 | D1 | Ph | D1 |
| 1960 | A13 | D1 | D1 | D1 | Ph |
| 1961 | A14 | Ph | D1 | D1 | D1 |
| 1962 | A14 | D1 | Ph | D1 | D1 |
| 1963 | A14 | D1 | D1 | Ph | D1 |
| 1964 | A14 | D1 | D1 | D1 | Ph |
| 1965 | A13 | Ph | D1 | D1 | D84 |
| 1966 | A13 | D1 | Ph | D84 | D1 |
| 1967 | A13 | D1 | D84 | Ph | D1 |
| 1968 | A13 | D84 | H | D1 | Ph |
| 1969 | A14 | Ph | D1 | D1 | D84 |
| 1970 | A14 | D1 | Ph | D84 | D1 |
| 1971 | A14 | D1 | D84 | Ph | D1 |
| 1972 | A14 | D84 | D1 | D1 | Ph |
| 1973 | A13 | Ph | D84 | D84 | D84 |
| 1974 | A13 | D84 | Ph | D84 | D84 |
| 1975 | A13 | D84 | D84 | Ph | D84 |
| 1976 | A13 | D84 | D84 | D84 | Ph |
| 1977 | A14 | Ph | D84 | D84 | D84 |
| 1978 | A14 | D84 | Ph | D84 | D84 |
| 1979 | A14 | D84 | D84 | Ph | D84 |
| 1980 | A14 | D84 | D84 | D84 | Ph |
| 1981 | D1 | A1 | H | D1 | D95 |
| 1982 | D1 | A1 | H | D95 | D1 |
| 1983 | H | A1 | D95 | D1 | D1 |
| 1984 | D95 | A1 | H | D1 | D1 |
| 1985 | D1 | A1 | H | D1 | D94 |
| 1986 | D1 | A1 | H | D94 | D1 |
| 1987 | H | A1 | D94 | D1 | D1 |
| 1988 | D94 | A1 | H | D1 | D1 |

TABLE 1-continued

| No. | $R^1$ | $R^2$ | $R^3$ | $R^4$ | $R^5$ |
|---|---|---|---|---|---|
| 1989 | D1 | A1 | H | D1 | D96 |
| 1990 | D1 | A1 | H | D96 | D1 |
| 1991 | H | A1 | D96 | D1 | D1 |
| 1992 | D96 | A1 | H | D1 | D1 |
| 1993 | D86 | A1 | H | D86 | D95 |
| 1994 | D86 | A1 | H | D95 | D86 |
| 1995 | H | A1 | D95 | D86 | D86 |
| 1996 | D95 | A1 | H | D86 | D86 |
| 1997 | D86 | A1 | H | D86 | D94 |
| 1998 | D86 | A1 | H | D94 | D86 |
| 1999 | H | A1 | D94 | D86 | D86 |
| 2000 | D94 | A1 | H | D86 | D86 |
| 2001 | D86 | A1 | H | D86 | D96 |
| 2002 | D86 | A1 | H | D96 | D86 |
| 2003 | H | A1 | D96 | D86 | D86 |
| 2004 | D96 | A1 | H | D86 | D86 |
| 2005 | H | A14 | H | D1 | D1 |
| 2006 | H | A13 | D1 | D1 | D1 |
| 2007 | D1 | A13 | H | D1 | D1 |
| 2008 | D1 | A13 | D1 | H | D1 |
| 2009 | D1 | A13 | D1 | D1 | H |
| 2010 | H | A14 | D1 | D1 | D1 |
| 2011 | D1 | A14 | H | D1 | D1 |
| 2012 | D1 | A14 | D1 | H | D1 |
| 2013 | D1 | A14 | D1 | D1 | H |
| 2014 | H | A13 | D1 | D1 | D84 |
| 2015 | D1 | A13 | H | D84 | D1 |
| 2016 | D1 | A13 | D84 | H | D1 |
| 2017 | D84 | A13 | D1 | D1 | H |
| 2018 | H | A14 | D1 | D1 | D84 |
| 2019 | D1 | A14 | H | D84 | D1 |
| 2020 | D1 | A14 | D84 | H | D1 |
| 2021 | D84 | A14 | D1 | D1 | H |
| 2022 | H | A13 | D84 | D84 | D84 |
| 2023 | D84 | A13 | H | D84 | D84 |
| 2024 | D84 | A13 | D84 | H | D84 |
| 2025 | D84 | A13 | D84 | D84 | H |
| 2026 | H | A14 | D84 | D84 | D84 |
| 2027 | D84 | A14 | H | D84 | D84 |
| 2028 | D84 | A14 | D84 | H | D84 |
| 2029 | D84 | A14 | D84 | D84 | H |
| 2030 | Ph | A13 | D1 | D1 | H |
| 2031 | D1 | A13 | Ph | D1 | H |
| 2032 | D1 | A13 | D1 | Ph | H |
| 2033 | Ph | A13 | D1 | H | D1 |
| 2034 | D1 | A13 | Ph | H | D1 |
| 2035 | D1 | A13 | D1 | H | Ph |
| 2036 | Ph | A13 | H | D1 | D1 |
| 2037 | D1 | A13 | H | Ph | D1 |
| 2038 | D1 | A13 | H | D1 | Ph |
| 2039 | H | A13 | Ph | D1 | D1 |
| 2040 | H | A13 | D1 | Ph | H |
| 2041 | H | A13 | D1 | D1 | Ph |
| 2042 | Ph | A14 | D1 | D1 | H |
| 2043 | D1 | A14 | Ph | D1 | H |
| 2044 | D1 | A14 | D1 | Ph | H |
| 2045 | Ph | A14 | D1 | H | D1 |
| 2046 | D1 | A14 | Ph | H | D1 |
| 2047 | D1 | A14 | D1 | H | Ph |
| 2048 | Ph | A14 | H | D1 | D1 |
| 2049 | D1 | A14 | H | Ph | D1 |
| 2050 | D1 | A14 | H | D1 | Ph |
| 2051 | H | A14 | Ph | D1 | D1 |
| 2052 | H | A14 | D1 | Ph | D1 |
| 2053 | H | A14 | D1 | D1 | Ph |
| 2054 | Ph | A13 | D84 | D84 | H |
| 2055 | D84 | A13 | Ph | D84 | H |
| 2056 | D84 | A13 | D84 | Ph | H |
| 2057 | Ph | A13 | D84 | H | D84 |
| 2058 | D84 | A13 | Ph | H | D84 |
| 2059 | D84 | A13 | D84 | H | Ph |
| 2060 | Ph | A13 | H | D84 | D84 |
| 2061 | D84 | A13 | H | Ph | D84 |
| 2062 | D84 | A13 | H | D84 | Ph |
| 2063 | H | A13 | Ph | D84 | D84 |
| 2064 | H | A13 | D84 | Ph | D84 |
| 2065 | H | A13 | D84 | D84 | Ph |
| 2066 | Ph | A14 | D84 | D84 | H |
| 2067 | D84 | A14 | Ph | D84 | H |
| 2068 | D84 | A14 | D84 | Ph | H |
| 2069 | Ph | A14 | D84 | H | D84 |
| 2070 | D84 | A14 | Ph | H | D84 |
| 2071 | D84 | A14 | D84 | H | Ph |
| 2072 | Ph | A14 | H | D84 | D84 |
| 2073 | D84 | A14 | H | Ph | D84 |
| 2074 | D84 | A14 | H | D84 | Ph |
| 2075 | H | A14 | Ph | D84 | D84 |
| 2076 | H | A14 | D84 | Ph | D84 |
| 2077 | H | A14 | D84 | D84 | Ph |
| 2078 | Ph | A13 | D1 | D1 | D1 |
| 2079 | D1 | A13 | Ph | D1 | D1 |
| 2080 | D1 | A13 | D1 | Ph | D1 |
| 2081 | D1 | A13 | D1 | D1 | Ph |
| 2082 | Ph | A14 | D1 | D1 | D1 |
| 2083 | D1 | A14 | Ph | D1 | D1 |
| 2084 | D1 | A14 | D1 | Ph | D1 |
| 2085 | D1 | A14 | D1 | D1 | Ph |
| 2086 | Ph | A13 | D1 | D1 | D84 |
| 2087 | D1 | A13 | Ph | D84 | D1 |
| 2088 | D1 | A13 | D84 | Ph | D1 |
| 2089 | D84 | A13 | D1 | D1 | Ph |
| 2090 | Ph | A14 | D1 | D1 | D84 |
| 2091 | D1 | A14 | Ph | D84 | D1 |
| 2092 | D1 | A14 | D84 | Ph | D1 |
| 2093 | D84 | A14 | D1 | D1 | Ph |
| 2094 | Ph | A13 | D84 | D84 | D84 |
| 2095 | D84 | A13 | Ph | D84 | D84 |
| 2096 | D84 | A13 | D84 | Ph | D84 |
| 2097 | D84 | A13 | D84 | D84 | Ph |
| 2098 | Ph | A14 | D84 | D84 | D84 |
| 2099 | D84 | A14 | Ph | D84 | D84 |
| 2100 | D84 | A14 | D84 | Ph | D84 |
| 2101 | D84 | A14 | D84 | D84 | Ph |
| 2102 | A4 | D1 | D1 | D1 | H |
| 2103 | A4 | D1 | D1 | H | D1 |
| 2104 | A4 | D1 | H | D1 | D1 |
| 2105 | A4 | H | D1 | D1 | D1 |
| 2106 | A4 | D1 | D1 | D1 | Ph |
| 2107 | A4 | D1 | D1 | Ph | D1 |
| 2108 | A4 | D1 | Ph | D1 | D1 |
| 2109 | A4 | Ph | D1 | D1 | D1 |
| 2110 | A4 | D1 | D1 | H | H |
| 2111 | A4 | D1 | H | D1 | H |
| 2112 | A4 | D1 | H | H | D1 |
| 2113 | A4 | H | D1 | D1 | H |
| 2114 | A4 | H | D1 | H | D1 |
| 2115 | A4 | H | H | D1 | D1 |
| 2116 | A4 | D1 | D1 | Ph | H |
| 2117 | A4 | D1 | D1 | H | Ph |
| 2118 | A4 | D1 | Ph | D1 | H |
| 2119 | A4 | D1 | H | D1 | Ph |
| 2120 | A4 | D1 | Ph | H | D1 |
| 2121 | A4 | D1 | H | Ph | D1 |
| 2122 | A4 | Ph | D1 | D1 | H |
| 2123 | A4 | H | D1 | D1 | Ph |
| 2124 | A4 | Ph | D1 | H | D1 |
| 2125 | A4 | H | D1 | Ph | D1 |
| 2126 | A4 | Ph | H | D1 | D1 |
| 2127 | A4 | H | Ph | D1 | D1 |
| 2128 | A4 | D2 | D2 | D2 | H |
| 2129 | A4 | D2 | D2 | H | D2 |
| 2130 | A4 | D2 | H | D2 | D2 |
| 2131 | A4 | H | D2 | D2 | D2 |
| 2132 | A4 | D2 | D2 | D2 | Ph |
| 2133 | A4 | D2 | D2 | Ph | D2 |
| 2134 | A4 | D2 | Ph | D2 | D2 |
| 2135 | A4 | Ph | D2 | D2 | D2 |
| 2136 | A4 | D2 | D2 | H | H |
| 2137 | A4 | D2 | H | D2 | H |
| 2138 | A4 | D2 | H | H | D2 |
| 2139 | A4 | H | D2 | D2 | H |
| 2140 | A4 | H | D2 | H | D2 |
| 2141 | A4 | H | H | D2 | D2 |
| 2142 | A4 | D2 | D2 | Ph | H |
| 2143 | A4 | D2 | D2 | H | Ph |
| 2144 | A4 | D2 | Ph | D2 | H |

TABLE 1-continued

| No. | $R^1$ | $R^2$ | $R^3$ | $R^4$ | $R^5$ |
|---|---|---|---|---|---|
| 2145 | A4 | D2 | H | D2 | Ph |
| 2146 | A4 | D2 | Ph | H | D2 |
| 2147 | A4 | D2 | H | Ph | D2 |
| 2148 | A4 | Ph | D2 | D2 | H |
| 2149 | A4 | H | D2 | D2 | Ph |
| 2150 | A4 | Ph | D2 | H | D2 |
| 2151 | A4 | H | D2 | Ph | D2 |
| 2152 | A4 | Ph | H | D2 | D2 |
| 2153 | A4 | H | Ph | D2 | D2 |
| 2154 | A4 | D3 | D3 | D3 | H |
| 2155 | A4 | D3 | D3 | H | D3 |
| 2156 | A4 | D3 | H | D3 | D3 |
| 2157 | A4 | H | D3 | D3 | D3 |
| 2158 | A4 | D3 | D3 | D3 | Ph |
| 2159 | A4 | D3 | D3 | Ph | D3 |
| 2160 | A4 | D3 | Ph | D3 | D3 |
| 2161 | A4 | Ph | D3 | D3 | D3 |
| 2162 | A4 | D3 | D3 | H | H |
| 2163 | A4 | D3 | H | D3 | H |
| 2164 | A4 | D3 | H | H | D3 |
| 2165 | A4 | H | D3 | D3 | H |
| 2166 | A4 | H | D3 | H | D3 |
| 2167 | A4 | H | H | D3 | D3 |
| 2168 | A4 | D3 | D3 | Ph | H |
| 2169 | A4 | D3 | D3 | H | Ph |
| 2170 | A4 | D3 | Ph | D3 | H |
| 2171 | A4 | D3 | H | D3 | Ph |
| 2172 | A4 | D3 | Ph | H | D3 |
| 2173 | A4 | D3 | H | Ph | D3 |
| 2174 | A4 | Ph | D3 | D3 | H |
| 2175 | A4 | H | D3 | D3 | Ph |
| 2176 | A4 | Ph | D3 | H | D3 |
| 2177 | A4 | H | D3 | Ph | D3 |
| 2178 | A4 | Ph | H | D3 | D3 |
| 2179 | A4 | H | Ph | D3 | D3 |
| 2180 | A4 | D4 | D4 | D4 | H |
| 2181 | A4 | D4 | D4 | H | D4 |
| 2182 | A4 | D4 | H | D4 | D4 |
| 2183 | A4 | H | D4 | D4 | D4 |
| 2184 | A4 | D4 | D4 | D4 | Ph |
| 2185 | A4 | D4 | D4 | Ph | D4 |
| 2186 | A4 | D4 | Ph | D4 | D4 |
| 2187 | A4 | Ph | D4 | D4 | D4 |
| 2188 | A4 | D4 | D4 | H | H |
| 2189 | A4 | D4 | H | D4 | H |
| 2190 | A4 | D4 | H | H | D4 |
| 2191 | A4 | H | D4 | D4 | H |
| 2192 | A4 | H | D4 | H | D4 |
| 2193 | A4 | H | H | D4 | D4 |
| 2194 | A4 | D4 | D4 | Ph | H |
| 2195 | A4 | D4 | D4 | H | Ph |
| 2196 | A4 | D4 | Ph | D4 | H |
| 2197 | A4 | D4 | H | D4 | Ph |
| 2198 | A4 | D4 | Ph | H | D4 |
| 2199 | A4 | D4 | H | Ph | D4 |
| 2200 | A4 | Ph | D4 | D4 | H |
| 2201 | A4 | H | D4 | D4 | Ph |
| 2202 | A4 | Ph | D4 | H | D4 |
| 2203 | A4 | H | D4 | Ph | D4 |
| 2204 | A4 | Ph | H | D4 | D4 |
| 2205 | A4 | H | Ph | D4 | D4 |
| 2206 | A4 | D40 | D40 | D40 | H |
| 2207 | A4 | D40 | D40 | H | D40 |
| 2208 | A4 | D40 | H | D40 | D40 |
| 2209 | A4 | H | D40 | D40 | D40 |
| 2210 | A4 | D40 | D40 | D40 | Ph |
| 2211 | A4 | D40 | D40 | Ph | D40 |
| 2212 | A4 | D40 | Ph | D40 | D40 |
| 2213 | A4 | Ph | D40 | D40 | D40 |
| 2214 | A4 | D40 | D40 | H | H |
| 2215 | A4 | D40 | H | D40 | H |
| 2216 | A4 | D40 | H | H | D40 |
| 2217 | A4 | H | D40 | D40 | H |
| 2218 | A4 | H | D40 | H | D40 |
| 2219 | A4 | H | H | D40 | D40 |
| 2220 | A4 | D40 | D40 | Ph | H |
| 2221 | A4 | D40 | D40 | H | Ph |
| 2222 | A4 | D40 | Ph | D40 | H |

TABLE 1-continued

| No. | $R^1$ | $R^2$ | $R^3$ | $R^4$ | $R^5$ |
|---|---|---|---|---|---|
| 2223 | A4 | D40 | H | D40 | Ph |
| 2224 | A4 | D40 | Ph | H | D40 |
| 2225 | A4 | D40 | H | Ph | D40 |
| 2226 | A4 | Ph | D40 | D40 | H |
| 2227 | A4 | H | D40 | D40 | Ph |
| 2228 | A4 | Ph | D40 | H | D40 |
| 2229 | A4 | H | D40 | Ph | D40 |
| 2230 | A4 | Ph | H | D40 | D40 |
| 2231 | A4 | H | Ph | D40 | D40 |
| 2232 | A4 | D41 | D41 | D41 | H |
| 2233 | A4 | D41 | D41 | H | D41 |
| 2234 | A4 | D41 | H | D41 | D41 |
| 2235 | A4 | D41 | D41 | D41 | D41 |
| 2236 | A4 | D41 | D41 | D41 | Ph |
| 2237 | A4 | D41 | D41 | Ph | D41 |
| 2238 | A4 | D41 | Ph | D41 | D41 |
| 2239 | A4 | Ph | D41 | D41 | D41 |
| 2240 | A4 | D41 | D41 | H | H |
| 2241 | A4 | D41 | H | D41 | H |
| 2242 | A4 | D41 | H | H | D41 |
| 2243 | A4 | H | D41 | D41 | H |
| 2244 | A4 | H | D41 | H | D41 |
| 2245 | A4 | H | H | D41 | D41 |
| 2246 | A4 | D41 | D41 | Ph | H |
| 2247 | A4 | D41 | D41 | H | Ph |
| 2248 | A4 | D41 | Ph | D41 | H |
| 2249 | A4 | D41 | H | D41 | Ph |
| 2250 | A4 | D41 | Ph | H | D41 |
| 2251 | A4 | D41 | H | Ph | D41 |
| 2252 | A4 | Ph | D41 | D41 | H |
| 2253 | A4 | H | D41 | D41 | Ph |
| 2254 | A4 | Ph | D41 | H | D41 |
| 2255 | A4 | H | D41 | Ph | D41 |
| 2256 | A4 | Ph | H | D41 | D41 |
| 2257 | A4 | H | Ph | D41 | D41 |
| 2258 | A4 | D42 | D42 | D42 | H |
| 2259 | A4 | D42 | D42 | H | D42 |
| 2260 | A4 | D42 | H | D42 | D42 |
| 2261 | A4 | H | D42 | D42 | D42 |
| 2262 | A4 | D42 | D42 | D42 | Ph |
| 2263 | A4 | D42 | D42 | Ph | D42 |
| 2264 | A4 | D42 | Ph | D42 | D42 |
| 2265 | A4 | Ph | D42 | D42 | D42 |
| 2266 | A4 | D42 | D42 | H | H |
| 2267 | A4 | D42 | H | D42 | H |
| 2268 | A4 | D42 | H | H | D42 |
| 2269 | A4 | H | D42 | D42 | H |
| 2270 | A4 | H | D42 | H | D42 |
| 2271 | A4 | H | H | D42 | D42 |
| 2272 | A4 | D42 | D42 | Ph | H |
| 2273 | A4 | D42 | D42 | H | Ph |
| 2274 | A4 | D42 | H | D42 | H |
| 2275 | A4 | D42 | H | D42 | Ph |
| 2276 | A4 | D42 | Ph | H | D42 |
| 2277 | A4 | D42 | H | Ph | D42 |
| 2278 | A4 | Ph | D42 | D42 | H |
| 2279 | A4 | H | D42 | D42 | Ph |
| 2280 | A4 | Ph | D42 | H | D42 |
| 2281 | A4 | H | D42 | Ph | D42 |
| 2282 | A4 | Ph | H | D42 | D42 |
| 2283 | A4 | H | Ph | D42 | D42 |
| 2284 | A4 | D43 | D43 | D43 | H |
| 2285 | A4 | D43 | D43 | H | D43 |
| 2286 | A4 | D43 | H | D43 | D43 |
| 2287 | A4 | H | D43 | D43 | D43 |
| 2288 | A4 | D43 | D43 | D43 | Ph |
| 2289 | A4 | D43 | D43 | Ph | D43 |
| 2290 | A4 | D43 | Ph | D43 | D43 |
| 2291 | A4 | Ph | D43 | D43 | D43 |
| 2292 | A4 | D43 | D43 | H | H |
| 2293 | A4 | D43 | H | D43 | H |
| 2294 | A4 | D43 | H | H | D43 |
| 2295 | A4 | H | D43 | D43 | H |
| 2296 | A4 | H | D43 | H | D43 |
| 2297 | A4 | H | H | D43 | D43 |
| 2298 | A4 | D43 | D43 | Ph | H |
| 2299 | A4 | D43 | D43 | H | Ph |
| 2300 | A4 | D43 | Ph | D43 | H |

TABLE 1-continued

| No. | $R^1$ | $R^2$ | $R^3$ | $R^4$ | $R^5$ |
|---|---|---|---|---|---|
| 2301 | A4 | D43 | H | D43 | Ph |
| 2302 | A4 | D43 | Ph | H | D43 |
| 2303 | A4 | D43 | H | Ph | D43 |
| 2304 | A4 | Ph | D43 | D43 | H |
| 2305 | A4 | H | D43 | D43 | Ph |
| 2306 | A4 | Ph | D43 | H | D43 |
| 2307 | A4 | H | D43 | Ph | D43 |
| 2308 | A4 | Ph | H | D43 | D43 |
| 2309 | A4 | H | Ph | D43 | D43 |
| 2310 | A4 | D84 | D84 | D84 | H |
| 2311 | A4 | D84 | D84 | H | D84 |
| 2312 | A4 | D84 | H | D84 | D84 |
| 2313 | A4 | H | D84 | D84 | D84 |
| 2314 | A4 | D84 | D84 | D84 | Ph |
| 2315 | A4 | D84 | D84 | Ph | D84 |
| 2316 | A4 | D84 | Ph | D84 | D84 |
| 2317 | A4 | Ph | D84 | D84 | D84 |
| 2318 | A4 | D84 | D84 | H | H |
| 2319 | A4 | D84 | H | D84 | H |
| 2320 | A4 | D84 | H | H | D84 |
| 2321 | A4 | H | D84 | D84 | H |
| 2322 | A4 | H | D84 | H | D84 |
| 2323 | A4 | H | H | D84 | D84 |
| 2324 | A4 | D84 | D84 | Ph | H |
| 2325 | A4 | D84 | D84 | H | Ph |
| 2326 | A4 | D84 | Ph | D84 | H |
| 2327 | A4 | D84 | H | D84 | Ph |
| 2328 | A4 | D84 | Ph | H | D84 |
| 2329 | A4 | D84 | H | Ph | D84 |
| 2330 | A4 | Ph | D84 | D84 | H |
| 2331 | A4 | H | D84 | D84 | Ph |
| 2332 | A4 | Ph | D84 | H | D84 |
| 2333 | A4 | H | D84 | Ph | D84 |
| 2334 | A4 | Ph | H | D84 | D84 |
| 2335 | A4 | H | Ph | D841 | D84 |
| 2336 | A4 | D86 | D86 | D86 | H |
| 2337 | A4 | D86 | D86 | H | D86 |
| 2338 | A4 | D86 | H | D86 | D86 |
| 2339 | A4 | H | D86 | D86 | D86 |
| 2340 | A4 | D86 | D86 | D86 | Ph |
| 2341 | A4 | D86 | D86 | Ph | D86 |
| 2342 | A4 | D86 | Ph | D86 | D86 |
| 2343 | A4 | Ph | D86 | D86 | D86 |
| 2344 | A4 | D86 | D86 | H | H |
| 2345 | A4 | D86 | H | D86 | H |
| 2346 | A4 | D86 | H | H | D86 |
| 2347 | A4 | H | D86 | D86 | H |
| 2348 | A4 | H | D86 | H | D86 |
| 2349 | A4 | H | H | D86 | D86 |
| 2350 | A4 | D86 | D86 | Ph | H |
| 2351 | A4 | D86 | D86 | H | Ph |
| 2352 | A4 | D86 | Ph | D86 | H |
| 2353 | A4 | D86 | H | D86 | Ph |
| 2354 | A4 | D86 | Ph | H | D86 |
| 2355 | A4 | D86 | H | Ph | D86 |
| 2356 | A4 | Ph | D86 | D86 | H |
| 2357 | A4 | H | D86 | D86 | Ph |
| 2358 | A4 | Ph | D86 | H | D86 |
| 2359 | A4 | H | D86 | Ph | D86 |
| 2360 | A4 | Ph | H | D86 | D86 |
| 2361 | A4 | H | Ph | D86 | D86 |
| 2362 | A4 | D87 | D87 | D87 | H |
| 2363 | A4 | D87 | D87 | H | D87 |
| 2364 | A4 | D87 | H | D87 | D87 |
| 2365 | A4 | H | D87 | D87 | D87 |
| 2366 | A4 | D87 | D87 | D87 | Ph |
| 2367 | A4 | D87 | D87 | Ph | D87 |
| 2368 | A4 | D87 | Ph | D87 | D87 |
| 2369 | A4 | Ph | D87 | D87 | D87 |
| 2370 | A4 | D87 | D87 | H | H |
| 2371 | A4 | D87 | H | D87 | H |
| 2372 | A4 | D87 | H | H | D87 |
| 2373 | A4 | H | D87 | D87 | H |
| 2374 | A4 | H | D87 | H | D87 |
| 2375 | A4 | H | H | D87 | D87 |
| 2376 | A4 | D87 | D87 | Ph | H |
| 2377 | A4 | D87 | D87 | H | Ph |
| 2378 | A4 | D87 | Ph | D87 | H |

TABLE 1-continued

| No. | $R^1$ | $R^2$ | $R^3$ | $R^4$ | $R^5$ |
|---|---|---|---|---|---|
| 2379 | A4 | D87 | H | D87 | Ph |
| 2380 | A4 | D87 | Ph | H | D87 |
| 2381 | A4 | D87 | H | Ph | D87 |
| 2382 | A4 | Ph | D87 | D87 | H |
| 2383 | A4 | H | D87 | D87 | Ph |
| 2384 | A4 | Ph | D87 | H | D87 |
| 2385 | A4 | H | D87 | Ph | D87 |
| 2386 | A4 | Ph | H | D87 | D87 |
| 2387 | A4 | H | Ph | D87 | D87 |
| 2388 | A4 | D88 | D88 | D88 | H |
| 2389 | A4 | D88 | D88 | H | D88 |
| 2390 | A4 | D88 | H | D88 | D88 |
| 2391 | A4 | H | D88 | D88 | D88 |
| 2392 | A4 | D88 | D88 | D88 | Ph |
| 2393 | A4 | D88 | D88 | Ph | D88 |
| 2394 | A4 | D88 | Ph | D88 | D88 |
| 2395 | A4 | Ph | D88 | D88 | D88 |
| 2396 | A4 | D88 | D88 | H | H |
| 2397 | A4 | D88 | H | D88 | H |
| 2398 | A4 | D88 | H | H | D88 |
| 2399 | A4 | H | D88 | D88 | H |
| 2400 | A4 | H | D88 | H | D88 |
| 2401 | A4 | H | H | D88 | D88 |
| 2402 | A4 | D88 | D88 | Ph | H |
| 2403 | A4 | D88 | D88 | H | Ph |
| 2404 | A4 | D88 | Ph | D88 | H |
| 2405 | A4 | D88 | H | D88 | Ph |
| 2406 | A4 | D88 | Ph | H | D88 |
| 2407 | A4 | D88 | H | Ph | D88 |
| 2408 | A4 | Ph | D88 | D88 | H |
| 2409 | A4 | H | D88 | D88 | Ph |
| 2410 | A4 | Ph | D88 | H | D88 |
| 2411 | A4 | H | D88 | Ph | D88 |
| 2412 | A4 | Ph | H | D88 | D88 |
| 2413 | A4 | H | Ph | D88 | D88 |
| 2414 | A12 | D1 | D1 | D1 | H |
| 2415 | A12 | D1 | D1 | H | D1 |
| 2416 | A12 | D1 | H | D1 | D1 |
| 2417 | A12 | H | D1 | D1 | D1 |
| 2418 | A12 | D1 | D1 | D1 | Ph |
| 2419 | A12 | D1 | D1 | Ph | D1 |
| 2420 | A12 | D1 | Ph | D1 | D1 |
| 2421 | A12 | Ph | D1 | D1 | D1 |
| 2422 | A12 | D1 | D1 | H | H |
| 2423 | A12 | D1 | H | D1 | H |
| 2424 | A12 | D1 | H | H | D1 |
| 2425 | A12 | H | D1 | D1 | H |
| 2426 | A12 | H | D1 | H | D1 |
| 2427 | A12 | H | H | D1 | D1 |
| 2428 | A12 | D1 | D1 | Ph | H |
| 2429 | A12 | D1 | D1 | H | Ph |
| 2430 | A12 | D1 | Ph | D1 | H |
| 2431 | A12 | D1 | H | D1 | Ph |
| 2432 | A12 | D1 | Ph | H | D1 |
| 2433 | A12 | D1 | H | Ph | D1 |
| 2434 | A12 | Ph | D1 | D1 | H |
| 2435 | A12 | H | D1 | D1 | Ph |
| 2436 | A12 | Ph | D1 | H | D1 |
| 2437 | A12 | H | D1 | Ph | D1 |
| 2438 | A12 | Ph | H | D1 | D1 |
| 2439 | A12 | H | Ph | D1 | D1 |
| 2440 | A12 | D2 | D2 | D2 | H |
| 2441 | A12 | D2 | D2 | H | D2 |
| 2442 | A12 | D2 | H | D2 | D2 |
| 2443 | A12 | H | D2 | D2 | D2 |
| 2444 | A12 | D2 | D2 | D2 | Ph |
| 2445 | A12 | D2 | D2 | Ph | D2 |
| 2446 | A12 | D2 | Ph | D2 | D2 |
| 2447 | A12 | Ph | D2 | D2 | D2 |
| 2448 | A12 | D2 | D2 | H | H |
| 2449 | A12 | D2 | H | D2 | H |
| 2450 | A12 | D2 | H | H | D2 |
| 2451 | A12 | H | D2 | D2 | H |
| 2452 | A12 | H | D2 | H | D2 |
| 2453 | A12 | H | H | D2 | D2 |
| 2454 | A12 | D2 | D2 | Ph | H |
| 2455 | A12 | D2 | D2 | H | Ph |
| 2458 | A12 | D2 | Ph | D2 | H |

TABLE 1-continued

| No. | $R^1$ | $R^2$ | $R^3$ | $R^4$ | $R^5$ |
|---|---|---|---|---|---|
| 2457 | A12 | D2 | H | D2 | Ph |
| 2458 | A12 | D2 | Ph | H | D2 |
| 2459 | A12 | D2 | H | Ph | D2 |
| 2460 | A12 | Ph | D2 | D2 | H |
| 2461 | A12 | H | D2 | D2 | Ph |
| 2462 | A12 | Ph | D2 | H | D2 |
| 2463 | A12 | H | D2 | Ph | D2 |
| 2464 | A12 | Ph | H | D2 | D2 |
| 2465 | A12 | H | Ph | D2 | D2 |
| 2466 | A12 | D3 | D3 | D3 | H |
| 2467 | A12 | D3 | D3 | H | D3 |
| 2468 | A12 | D3 | H | D3 | D3 |
| 2469 | A12 | H | D3 | D3 | D3 |
| 2470 | A12 | D3 | D3 | D3 | Ph |
| 2471 | A12 | D3 | D3 | Ph | D3 |
| 2472 | A12 | D3 | Ph | D3 | D3 |
| 2473 | A12 | Ph | D3 | D3 | D3 |
| 2474 | A12 | D3 | D3 | H | H |
| 2475 | A12 | D3 | H | D3 | H |
| 2476 | A12 | D3 | H | H | D3 |
| 2477 | A12 | H | D3 | D3 | H |
| 2478 | A12 | H | D3 | H | D3 |
| 2479 | A12 | H | H | D3 | D3 |
| 2480 | A12 | D3 | D3 | Ph | H |
| 2481 | A12 | D3 | D3 | H | Ph |
| 2482 | A12 | D3 | Ph | D3 | H |
| 2483 | A12 | D3 | H | D3 | Ph |
| 2484 | A12 | D3 | Ph | H | D3 |
| 2485 | A12 | D3 | H | Ph | D3 |
| 2486 | A12 | Ph | D3 | D3 | H |
| 2487 | A12 | H | D3 | D3 | Ph |
| 2488 | A12 | Ph | D3 | H | D3 |
| 2489 | A12 | H | D3 | Ph | D3 |
| 2490 | A12 | Ph | H | D3 | D3 |
| 2491 | A12 | H | Ph | D3 | D3 |
| 2492 | A12 | D4 | D4 | D4 | H |
| 2493 | A12 | D4 | D4 | H | D4 |
| 2494 | A12 | D4 | H | D4 | D4 |
| 2495 | A12 | H | D4 | D4 | D4 |
| 2496 | A12 | D4 | D4 | D4 | Ph |
| 2497 | A12 | D4 | D4 | Ph | D4 |
| 2498 | A12 | D4 | Ph | D4 | D4 |
| 2499 | A12 | Ph | D4 | D4 | D4 |
| 2500 | A12 | D4 | D4 | H | H |
| 2501 | A12 | D4 | H | D4 | H |
| 2502 | A12 | D4 | H | H | D4 |
| 2503 | A12 | H | D4 | D4 | H |
| 2504 | A12 | H | D4 | H | D4 |
| 2505 | A12 | H | H | D4 | D4 |
| 2506 | A12 | D4 | D4 | Ph | H |
| 2507 | A12 | D4 | D4 | H | Ph |
| 2508 | A12 | D4 | Ph | D4 | H |
| 2509 | A12 | D4 | H | D4 | Ph |
| 2510 | A12 | D4 | Ph | H | D4 |
| 2511 | A12 | D4 | H | Ph | D4 |
| 2512 | A12 | Ph | D4 | D4 | H |
| 2513 | A12 | H | D4 | D4 | Ph |
| 2514 | A12 | Ph | D4 | H | D4 |
| 2515 | A12 | H | D4 | Ph | D4 |
| 2516 | A12 | Ph | H | D4 | D4 |
| 2517 | A12 | H | Ph | D4 | D4 |
| 2518 | A12 | D40 | D40 | D40 | H |
| 2519 | A12 | D40 | D40 | H | D40 |
| 2520 | A12 | D40 | H | D40 | D40 |
| 2521 | A12 | H | D40 | D40 | D40 |
| 2522 | A12 | D40 | D40 | D40 | Ph |
| 2523 | A12 | D40 | D40 | Ph | D40 |
| 2524 | A12 | D40 | Ph | D40 | D40 |
| 2525 | A12 | Ph | D40 | D40 | D40 |
| 2526 | A12 | D40 | D40 | H | H |
| 2527 | A12 | D40 | H | D40 | H |
| 2528 | A12 | D40 | H | H | D40 |
| 2529 | A12 | H | D40 | D40 | H |
| 2530 | A12 | H | D40 | H | D40 |
| 2531 | A12 | H | H | D40 | D40 |
| 2532 | A12 | D40 | D40 | Ph | H |
| 2533 | A12 | D40 | D40 | H | Ph |
| 2534 | A12 | D40 | Ph | D40 | H |
| 2535 | A12 | D40 | H | D40 | Ph |
| 2536 | A12 | D40 | Ph | H | D40 |
| 2537 | A12 | D40 | H | Ph | D40 |
| 2538 | A12 | Ph | D40 | D40 | H |
| 2539 | A12 | H | D40 | D40 | Ph |
| 2540 | A12 | Ph | D40 | H | D40 |
| 2541 | A12 | H | D40 | Ph | D40 |
| 2542 | A12 | Ph | H | D40 | D40 |
| 2543 | A12 | H | Ph | D40 | D40 |
| 2544 | A12 | D41 | D41 | D41 | H |
| 2545 | A12 | D41 | D41 | H | D41 |
| 2546 | A12 | D41 | H | D41 | D41 |
| 2547 | A12 | H | D41 | D41 | D41 |
| 2548 | A12 | D41 | D41 | D41 | Ph |
| 2549 | A12 | D41 | D41 | Ph | D41 |
| 2550 | A12 | D41 | Ph | D41 | D41 |
| 2551 | A12 | Ph | D41 | D41 | D41 |
| 2552 | A12 | D41 | D41 | H | H |
| 2553 | A12 | D41 | H | D41 | H |
| 2554 | A12 | D41 | H | H | D41 |
| 2555 | A12 | H | D41 | D41 | H |
| 2556 | A12 | H | D41 | H | D41 |
| 2557 | A12 | H | H | D41 | D41 |
| 2558 | A12 | D41 | D41 | Ph | H |
| 2559 | A12 | D41 | D41 | H | Ph |
| 2560 | A12 | D41 | Ph | D41 | H |
| 2561 | A12 | D41 | H | D41 | Ph |
| 2562 | A12 | D41 | Ph | H | D41 |
| 2563 | A12 | D41 | H | Ph | D41 |
| 2564 | A12 | Ph | D41 | D41 | H |
| 2565 | A12 | H | D41 | D41 | Ph |
| 2566 | A12 | Ph | D41 | H | D41 |
| 2567 | A12 | H | D41 | Ph | D41 |
| 2568 | A12 | Ph | H | D41 | D41 |
| 2569 | A12 | H | Ph | D41 | D41 |
| 2570 | A12 | D42 | D42 | D42 | H |
| 2571 | A12 | D42 | D42 | H | D42 |
| 2572 | A12 | D42 | H | D42 | D42 |
| 2573 | A12 | H | D42 | D42 | D42 |
| 2574 | A12 | D42 | D42 | D42 | Ph |
| 2575 | A12 | D42 | D42 | Ph | D42 |
| 2576 | A12 | D42 | Ph | D42 | D42 |
| 2577 | A12 | Ph | D42 | D42 | D42 |
| 2578 | A12 | D42 | D42 | H | H |
| 2579 | A12 | D42 | H | D42 | H |
| 2580 | A12 | D42 | H | H | D42 |
| 2581 | A12 | H | D42 | D42 | H |
| 2582 | A12 | H | D42 | H | D42 |
| 2583 | A12 | H | H | D42 | D42 |
| 2584 | A12 | D42 | D42 | Ph | H |
| 2585 | A12 | D42 | D42 | H | Ph |
| 2586 | A12 | D42 | Ph | D42 | H |
| 2587 | A12 | D42 | H | D42 | Ph |
| 2588 | A12 | D42 | Ph | H | D42 |
| 2589 | A12 | D42 | H | Ph | D42 |
| 2590 | A12 | Ph | D42 | D42 | H |
| 2591 | A12 | H | D42 | D42 | Ph |
| 2592 | A12 | Ph | D42 | H | 042 |
| 2593 | A12 | H | D42 | Ph | D42 |
| 2594 | A12 | Ph | H | D42 | D42 |
| 2595 | A12 | H | Ph | D42 | D42 |
| 2596 | A12 | D43 | D43 | D43 | H |
| 2597 | A12 | D43 | D43 | H | D43 |
| 2598 | A12 | D43 | H | D43 | D43 |
| 2599 | A12 | H | D43 | D43 | D43 |
| 2600 | A12 | D43 | D43 | D43 | Ph |
| 2601 | A12 | D43 | D43 | Ph | D43 |
| 2602 | A12 | D43 | Ph | D43 | D43 |
| 2603 | A12 | Ph | D43 | D43 | D43 |
| 2604 | A12 | D43 | D43 | H | H |
| 2605 | A12 | D43 | H | D43 | H |
| 2606 | A12 | D43 | H | H | D43 |
| 2607 | A12 | H | D43 | D43 | H |
| 2608 | A12 | H | D43 | H | D43 |
| 2609 | A12 | H | H | D43 | D43 |
| 2610 | A12 | D43 | D43 | Ph | H |
| 2611 | A12 | D43 | D43 | H | Ph |
| 2612 | A12 | D43 | Ph | D43 | H |

TABLE 1-continued

| No. | $R^1$ | $R^2$ | $R^3$ | $R^4$ | $R^5$ |
|---|---|---|---|---|---|
| 2613 | A12 | D43 | H | D43 | Ph |
| 2614 | A12 | D43 | Ph | H | D43 |
| 2615 | A12 | D43 | H | Ph | D43 |
| 2616 | A12 | Ph | D43 | D43 | H |
| 2617 | A12 | H | D43 | D43 | Ph |
| 2618 | A12 | Ph | D43 | H | D43 |
| 2619 | A12 | H | D43 | Ph | D43 |
| 2620 | A12 | Ph | H | D43 | D43 |
| 2621 | A12 | H | Ph | D43 | D43 |
| 2622 | A12 | D84 | D84 | D84 | H |
| 2623 | A12 | D84 | D84 | H | D84 |
| 2624 | A12 | D84 | H | D84 | D84 |
| 2625 | A12 | H | D84 | D84 | D84 |
| 2626 | A12 | D84 | D84 | D84 | Ph |
| 2627 | A12 | D84 | D84 | Ph | D84 |
| 2628 | A12 | D84 | Ph | D84 | D84 |
| 2629 | A12 | Ph | D84 | D84 | D84 |
| 2630 | A12 | D84 | D84 | H | H |
| 2631 | A12 | D84 | H | D84 | H |
| 2632 | A12 | D84 | H | H | D84 |
| 2633 | A12 | H | D84 | D84 | H |
| 2634 | A12 | H | D84 | H | D84 |
| 2635 | A12 | H | H | D84 | D84 |
| 2636 | A12 | D84 | D84 | Ph | H |
| 2637 | A12 | D84 | D84 | H | Ph |
| 2638 | A12 | D84 | Ph | D84 | H |
| 2639 | A12 | D84 | H | D84 | Ph |
| 2640 | A12 | D84 | Ph | H | D84 |
| 2641 | A12 | D84 | H | Ph | D84 |
| 2642 | A12 | Ph | D84 | D84 | H |
| 2643 | A12 | H | D84 | D84 | Ph |
| 2644 | A12 | Ph | D84 | H | D84 |
| 2645 | A12 | H | D84 | Ph | D84 |
| 2648 | A12 | Ph | H | D84 | D84 |
| 2647 | A12 | H | Ph | D84 | D84 |
| 2648 | A12 | D86 | D86 | D86 | H |
| 2649 | A12 | D86 | D86 | H | D86 |
| 2650 | A12 | D86 | H | D86 | D86 |
| 2651 | A12 | H | D86 | D86 | D86 |
| 2652 | A12 | D86 | D86 | D86 | Ph |
| 2653 | A12 | D86 | D86 | Ph | D86 |
| 2654 | A12 | D86 | Ph | D86 | D86 |
| 2655 | A12 | Ph | D86 | D86 | D86 |
| 2656 | A12 | D86 | D86 | H | H |
| 2657 | A12 | D86 | H | D86 | H |
| 2658 | A12 | D86 | H | H | D86 |
| 2659 | A12 | H | D86 | D86 | H |
| 2660 | A12 | H | D86 | H | D86 |
| 2661 | A12 | H | H | D86 | D86 |
| 2662 | A12 | D86 | D86 | Ph | H |
| 2663 | A12 | D86 | D86 | H | Ph |
| 2664 | A12 | D86 | Ph | D86 | H |
| 2665 | A12 | D86 | H | D86 | Ph |
| 2666 | A12 | D86 | Ph | H | D86 |
| 2667 | A12 | D86 | H | Ph | D86 |
| 2668 | A12 | Ph | D86 | D86 | H |
| 2669 | A12 | H | D86 | D86 | Ph |
| 2670 | A12 | Ph | D86 | H | D86 |
| 2671 | A12 | H | D86 | Ph | D86 |
| 2672 | A12 | Ph | H | D86 | D86 |
| 2673 | A12 | H | Ph | D86 | D86 |
| 2674 | A12 | D87 | D87 | D87 | H |
| 2675 | A12 | D87 | D87 | H | D87 |
| 2876 | A12 | D87 | H | D87 | D87 |
| 2677 | A12 | H | D87 | D87 | D87 |
| 2678 | A12 | D87 | D87 | D87 | Ph |
| 2679 | A12 | D87 | D87 | Ph | D87 |
| 2680 | A12 | D87 | Ph | D87 | D87 |
| 2681 | A12 | Ph | D87 | D87 | D87 |
| 2682 | A12 | D87 | D87 | H | H |
| 2683 | A12 | D87 | H | D87 | H |
| 2684 | A12 | D87 | H | H | D87 |
| 2685 | A12 | H | D87 | D87 | H |
| 2686 | A12 | H | D87 | H | D87 |
| 2687 | A12 | H | H | D87 | D87 |
| 2688 | A12 | D87 | D87 | Ph | H |
| 2889 | A12 | D87 | D87 | H | Ph |
| 2690 | A12 | D87 | Ph | D87 | H |

TABLE 1-continued

| No. | $R^1$ | $R^2$ | $R^3$ | $R^4$ | $R^5$ |
|---|---|---|---|---|---|
| 2691 | A12 | D87 | H | D87 | Ph |
| 2692 | A12 | D87 | Ph | H | D87 |
| 2693 | A12 | D87 | H | Ph | D87 |
| 2694 | A12 | Ph | D87 | D87 | H |
| 2695 | A12 | H | D87 | D87 | Ph |
| 2696 | A12 | Ph | D87 | H | D87 |
| 2897 | A12 | H | D87 | Ph | D87 |
| 2698 | A12 | Ph | H | D87 | D87 |
| 2699 | A12 | H | Ph | D87 | D87 |
| 2700 | A12 | D88 | D88 | D88 | H |
| 2701 | A12 | D88 | D88 | H | D88 |
| 2702 | A12 | D88 | H | D88 | D88 |
| 2703 | A12 | H | D88 | D88 | D88 |
| 2704 | A12 | D88 | D88 | D88 | Ph |
| 2705 | A12 | D88 | D88 | Ph | D88 |
| 2706 | A12 | D88 | Ph | D88 | D88 |
| 2707 | A12 | Ph | D88 | D88 | D88 |
| 2708 | A12 | D88 | D88 | H | H |
| 2709 | A12 | D88 | H | D88 | H |
| 2710 | A12 | D88 | H | H | D88 |
| 2711 | A12 | H | D88 | D88 | H |
| 2712 | A12 | H | D88 | H | D88 |
| 2713 | A12 | H | H | D88 | D88 |
| 2714 | A12 | D88 | D88 | Ph | H |
| 2715 | A12 | D88 | D88 | H | Ph |
| 2716 | A12 | D88 | Ph | D88 | H |
| 2717 | A12 | D88 | H | D88 | Ph |
| 2718 | A12 | D88 | Ph | H | D88 |
| 2719 | A12 | D88 | H | Ph | D88 |
| 2720 | A12 | Ph | D88 | D88 | H |
| 2721 | A12 | H | D88 | D88 | Ph |
| 2722 | A12 | Ph | D88 | H | D88 |
| 2723 | A12 | H | D88 | Ph | D88 |
| 2724 | A12 | Ph | H | D88 | D88 |
| 2725 | A12 | H | Ph | D88 | D88 |
| 2726 | D1 | A4 | D1 | D1 | H |
| 2727 | D1 | A4 | D1 | H | D1 |
| 2728 | D1 | A4 | H | D1 | D1 |
| 2729 | H | A4 | D1 | D1 | D1 |
| 2730 | D1 | A4 | D1 | D1 | Ph |
| 2731 | D1 | A4 | D1 | Ph | D1 |
| 2732 | D1 | A4 | Ph | D1 | D1 |
| 2733 | Ph | A4 | D1 | D1 | D1 |
| 2734 | D1 | A4 | D1 | H | H |
| 2735 | D1 | A4 | H | D1 | H |
| 2736 | D1 | A4 | H | H | D1 |
| 2737 | H | A4 | D1 | D1 | H |
| 2738 | H | A4 | D1 | H | D1 |
| 2739 | H | A4 | H | D1 | D1 |
| 2740 | D1 | A4 | D1 | Ph | H |
| 2741 | D1 | A4 | D1 | H | Ph |
| 2742 | D1 | A4 | Ph | D1 | H |
| 2743 | D1 | A4 | H | D1 | Ph |
| 2744 | D1 | A4 | Ph | H | D1 |
| 2745 | D1 | A4 | H | Ph | D1 |
| 2746 | Ph | A4 | D1 | D1 | H |
| 2747 | H | A4 | D1 | D1 | Ph |
| 2748 | Ph | A4 | D1 | H | D1 |
| 2749 | H | A4 | D1 | Ph | D1 |
| 2750 | Ph | A4 | H | D1 | D1 |
| 2751 | H | A4 | Ph | D1 | D1 |
| 2752 | D2 | A4 | D2 | D2 | H |
| 2753 | D2 | A4 | D2 | H | D2 |
| 2754 | D2 | A4 | H | D2 | D2 |
| 2755 | H | A4 | D2 | D2 | D2 |
| 2756 | D2 | A4 | D2 | D2 | Ph |
| 2757 | D2 | A4 | D2 | Ph | D2 |
| 2758 | D2 | A4 | Ph | D2 | D2 |
| 2759 | Ph | A4 | D2 | D2 | D2 |
| 2760 | D2 | A4 | D2 | H | H |
| 2761 | D2 | A4 | H | D2 | H |
| 2762 | D2 | A4 | H | H | D2 |
| 2763 | H | A4 | D2 | D2 | H |
| 2764 | H | A4 | D2 | H | D2 |
| 2765 | H | A4 | H | D2 | D2 |
| 2766 | D2 | A4 | D2 | Ph | H |
| 2767 | D2 | A4 | D2 | H | Ph |
| 2768 | D2 | A4 | Ph | D2 | H |

TABLE 1-continued

| No. | $R^1$ | $R^2$ | $R^3$ | $R^4$ | $R^5$ |
|---|---|---|---|---|---|
| 2769 | D2 | A4 | H | D2 | Ph |
| 2770 | D2 | A4 | Ph | H | D2 |
| 2771 | D2 | A4 | H | Ph | D2 |
| 2772 | Ph | A4 | D2 | D2 | H |
| 2773 | H | A4 | D2 | D2 | Ph |
| 2774 | Ph | A4 | D2 | H | D2 |
| 2775 | H | A4 | D2 | Ph | D2 |
| 2776 | Ph | A4 | H | D2 | D2 |
| 2777 | H | A4 | Ph | D2 | D2 |
| 2778 | D3 | A4 | D3 | D3 | H |
| 2779 | D3 | A4 | D3 | H | D3 |
| 2780 | D3 | A4 | H | D3 | D3 |
| 2781 | H | A4 | D3 | D3 | D3 |
| 2782 | D3 | A4 | D3 | D3 | Ph |
| 2783 | D3 | A4 | D3 | Ph | D3 |
| 2784 | D3 | A4 | Ph | D3 | D3 |
| 2785 | Ph | A4 | D3 | D3 | D3 |
| 2786 | D3 | A4 | D3 | H | H |
| 2787 | D3 | A4 | H | D3 | H |
| 2788 | D3 | A4 | H | H | D3 |
| 2789 | H | A4 | D3 | D3 | H |
| 2790 | H | A4 | D3 | H | D3 |
| 2791 | H | A4 | H | D3 | D3 |
| 2792 | D3 | A4 | D3 | Ph | H |
| 2793 | D3 | A4 | D3 | H | Ph |
| 2794 | D3 | A4 | Ph | D3 | H |
| 2795 | D3 | A4 | H | D3 | Ph |
| 2796 | D3 | A4 | Ph | H | D3 |
| 2797 | D3 | A4 | H | Ph | D3 |
| 2798 | Ph | A4 | D3 | D3 | H |
| 2799 | H | A4 | D3 | D3 | Ph |
| 2800 | Ph | A4 | D3 | H | D3 |
| 2801 | H | A4 | D3 | Ph | D3 |
| 2802 | Ph | A4 | H | D3 | D3 |
| 2803 | H | A4 | Ph | D3 | D3 |
| 2804 | D4 | A4 | D4 | D4 | H |
| 2805 | D4 | A4 | D4 | H | D4 |
| 2806 | D4 | A4 | H | D4 | D4 |
| 2807 | H | A4 | D4 | D4 | D4 |
| 2808 | D4 | A4 | D4 | D4 | Ph |
| 2809 | D4 | A4 | D4 | Ph | D4 |
| 2810 | D4 | A4 | Ph | D4 | D4 |
| 2811 | Ph | A4 | D4 | D4 | D4 |
| 2812 | D4 | A4 | D4 | H | H |
| 2813 | D4 | A4 | H | D4 | H |
| 2814 | D4 | A4 | H | H | D4 |
| 2815 | H | A4 | D4 | D4 | H |
| 2816 | H | A4 | D4 | H | D4 |
| 2817 | H | A4 | H | D4 | D4 |
| 2818 | D4 | A4 | D4 | Ph | H |
| 2819 | D4 | A4 | D4 | H | Ph |
| 2820 | D4 | A4 | Ph | D4 | H |
| 2821 | D4 | A4 | H | D4 | Ph |
| 2822 | D4 | A4 | Ph | H | D4 |
| 2823 | D4 | A4 | H | Ph | D4 |
| 2824 | Ph | A4 | D4 | D4 | H |
| 2825 | H | A4 | D4 | D4 | Ph |
| 2826 | Ph | A4 | D4 | H | D4 |
| 2827 | H | A4 | D4 | Ph | D4 |
| 2828 | Ph | A4 | H | D4 | D4 |
| 2829 | H | A4 | Ph | D4 | D4 |
| 2830 | D40 | A4 | D40 | D40 | H |
| 2831 | D40 | A4 | D40 | H | D40 |
| 2832 | D40 | A4 | H | D40 | D40 |
| 2833 | H | A4 | D40 | D40 | D40 |
| 2834 | D40 | A4 | D40 | D40 | Ph |
| 2835 | D40 | A4 | D40 | Ph | D40 |
| 2836 | D40 | A4 | Ph | D40 | D40 |
| 2837 | Ph | A4 | D40 | D40 | D40 |
| 2838 | D40 | A4 | D40 | H | H |
| 2839 | D40 | A4 | H | D40 | H |
| 2840 | D40 | A4 | H | H | D40 |
| 2841 | H | A4 | D40 | D40 | H |
| 2842 | H | A4 | D40 | H | D40 |
| 2843 | H | A4 | H | D40 | D40 |
| 2844 | D40 | A4 | D40 | Ph | H |
| 2845 | D40 | A4 | D40 | H | Ph |
| 2846 | D40 | A4 | Ph | D40 | H |

TABLE 1-continued

| No. | $R^1$ | $R^2$ | $R^3$ | $R^4$ | $R^5$ |
|---|---|---|---|---|---|
| 2847 | D40 | A4 | H | D40 | Ph |
| 2848 | D40 | A4 | Ph | H | D40 |
| 2849 | D40 | A4 | H | Ph | D40 |
| 2850 | Ph | A4 | D40 | D40 | H |
| 2851 | H | A4 | D40 | D40 | Ph |
| 2852 | Ph | A4 | D40 | H | D40 |
| 2853 | H | A4 | D40 | Ph | D40 |
| 2854 | Ph | A4 | H | D40 | D40 |
| 2855 | H | A4 | Ph | D40 | D40 |
| 2856 | D86 | A4 | D86 | D86 | H |
| 2857 | D86 | A4 | D86 | H | D86 |
| 2858 | D86 | A4 | H | D86 | D86 |
| 2859 | H | A4 | D86 | D86 | D86 |
| 2860 | D86 | A4 | D86 | D86 | Ph |
| 2861 | D86 | A4 | D86 | Ph | D86 |
| 2862 | D86 | A4 | Ph | D86 | D86 |
| 2863 | Ph | A4 | D86 | D86 | D86 |
| 2864 | D86 | A4 | D86 | H | H |
| 2865 | D86 | A4 | H | D86 | H |
| 2866 | D86 | A4 | H | H | D86 |
| 2867 | H | A4 | D86 | D86 | H |
| 2868 | H | A4 | D86 | H | D86 |
| 2869 | H | A4 | H | D86 | D86 |
| 2870 | D86 | A4 | D86 | Ph | H |
| 2871 | D86 | A4 | D86 | H | Ph |
| 2872 | D86 | A4 | Ph | D86 | H |
| 2873 | D86 | A4 | H | D86 | Ph |
| 2874 | D86 | A4 | Ph | H | D86 |
| 2875 | D86 | A4 | H | Ph | D86 |
| 2876 | Ph | A4 | D86 | D86 | H |
| 2877 | H | A4 | D86 | D86 | Ph |
| 2878 | Ph | A4 | D86 | H | D86 |
| 2879 | H | A4 | D86 | Ph | D86 |
| 2880 | Ph | A4 | H | D86 | 86 |
| 2881 | H | A4 | Ph | D86 | D86 |
| 2882 | D42 | A4 | D42 | D42 | H |
| 2883 | D42 | A4 | D42 | H | D42 |
| 2884 | D42 | A4 | H | D42 | D42 |
| 2885 | H | A4 | D42 | D42 | D42 |
| 2886 | D42 | A4 | D42 | D42 | Ph |
| 2887 | D42 | A4 | D42 | Ph | D42 |
| 2888 | D42 | A4 | Ph | D42 | D42 |
| 2889 | Ph | A4 | D42 | D42 | D42 |
| 2890 | D42 | A4 | D42 | H | H |
| 2891 | D42 | A4 | H | D42 | H |
| 2892 | D42 | A4 | H | H | D42 |
| 2893 | H | A4 | D42 | D42 | H |
| 2894 | H | A4 | D42 | H | D42 |
| 2895 | H | A4 | H | D42 | D42 |
| 2896 | D42 | A4 | D42 | Ph | H |
| 2897 | D42 | A4 | D42 | H | Ph |
| 2898 | D42 | A4 | Ph | D42 | H |
| 2899 | D42 | A4 | H | D42 | Ph |
| 2900 | D42 | A4 | Ph | H | D42 |
| 2901 | D42 | A4 | H | Ph | D42 |
| 2902 | Ph | A4 | D42 | D42 | H |
| 2903 | H | A4 | D42 | D42 | Ph |
| 2904 | Ph | A4 | D42 | H | D42 |
| 2905 | H | A4 | D42 | Ph | D42 |
| 2906 | Ph | A4 | H | D42 | D42 |
| 2907 | H | A4 | Ph | D42 | D42 |
| 2908 | D43 | A4 | D43 | D43 | H |
| 2909 | D43 | A4 | D43 | H | D43 |
| 2910 | D43 | A4 | H | D43 | D43 |
| 2911 | H | A4 | D43 | D43 | D43 |
| 2912 | D43 | A4 | D43 | D43 | Ph |
| 2913 | D43 | A4 | D43 | Ph | D43 |
| 2914 | D43 | A4 | Ph | D43 | D43 |
| 2915 | Ph | A4 | D43 | D43 | D43 |
| 2916 | D43 | A4 | D43 | H | H |
| 2917 | D43 | A4 | H | D43 | H |
| 2918 | D43 | A4 | H | H | D43 |
| 2919 | H | A4 | D43 | D43 | H |
| 2920 | H | A4 | D43 | H | D43 |
| 2921 | H | A4 | H | D43 | D43 |
| 2922 | D43 | A4 | D43 | Ph | H |
| 2923 | D43 | A4 | D43 | H | Ph |
| 2924 | D43 | A4 | Ph | D43 | H |

TABLE 1-continued

| No. | $R^1$ | $R^2$ | $R^3$ | $R^4$ | $R^5$ |
|---|---|---|---|---|---|
| 2925 | D43 | A4 | H | D43 | Ph |
| 2926 | D43 | A4 | Ph | H | D43 |
| 2927 | D43 | A4 | H | Ph | D43 |
| 2928 | Ph | A4 | D43 | D43 | H |
| 2929 | H | A4 | D43 | D43 | Ph |
| 2930 | Ph | A4 | D43 | H | D43 |
| 2931 | H | A4 | D43 | Ph | D43 |
| 2932 | Ph | A4 | H | D43 | D43 |
| 2933 | H | A4 | Ph | D43 | D43 |
| 2934 | D84 | A4 | D84 | D84 | H |
| 2935 | D84 | A4 | D84 | H | D84 |
| 2936 | D84 | A4 | H | D84 | D84 |
| 2937 | H | A4 | D84 | D84 | D84 |
| 2938 | D84 | A4 | D84 | D84 | Ph |
| 2939 | D84 | A4 | D84 | Ph | D84 |
| 2940 | D84 | A4 | Ph | D84 | D84 |
| 2941 | Ph | A4 | D84 | D84 | D84 |
| 2942 | D84 | A4 | D84 | H | H |
| 2943 | D84 | A4 | H | D84 | H |
| 2944 | D84 | A4 | H | H | D84 |
| 2945 | H | A4 | D84 | D84 | H |
| 2946 | H | A4 | D84 | H | D84 |
| 2947 | H | A4 | H | D84 | D84 |
| 2948 | D84 | A4 | D84 | Ph | H |
| 2949 | D84 | A4 | D84 | H | Ph |
| 2950 | D84 | A4 | Ph | D84 | H |
| 2951 | D84 | A4 | H | D84 | Ph |
| 2952 | D84 | A4 | Ph | H | D84 |
| 2953 | D84 | A4 | H | Ph | D84 |
| 2954 | Ph | A4 | D84 | D84 | H |
| 2955 | H | A4 | D84 | D84 | Ph |
| 2956 | Ph | A4 | D84 | H | D84 |
| 2957 | H | A4 | D84 | Ph | D84 |
| 2958 | Ph | A4 | H | D84 | D84 |
| 2959 | H | A4 | Ph | D84 | D84 |
| 2960 | D86 | A4 | D86 | D86 | H |
| 2961 | D86 | A4 | D86 | H | D86 |
| 2962 | D86 | A4 | H | D86 | D86 |
| 2963 | H | A4 | D86 | D86 | D86 |
| 2964 | D86 | A4 | D86 | D86 | Ph |
| 2965 | D86 | A4 | D86 | Ph | D86 |
| 2966 | D86 | A4 | Ph | D86 | D86 |
| 2967 | Ph | A4 | D86 | D86 | D86 |
| 2968 | D86 | A4 | D86 | H | H |
| 2969 | D86 | A4 | H | D86 | H |
| 2970 | D86 | A4 | H | H | D86 |
| 2971 | H | A4 | D86 | D86 | H |
| 2972 | H | A4 | D86 | H | D86 |
| 2973 | H | A4 | H | D86 | D86 |
| 2974 | D86 | A4 | D86 | Ph | H |
| 2975 | D86 | A4 | D86 | H | Ph |
| 2976 | D86 | A4 | Ph | D86 | H |
| 2977 | D86 | A4 | H | D86 | Ph |
| 2978 | D86 | A4 | Ph | H | D86 |
| 2979 | D86 | A4 | H | Ph | D86 |
| 2980 | Ph | A4 | D86 | D86 | H |
| 2981 | H | A4 | D86 | D86 | Ph |
| 2982 | Ph | A4 | D86 | H | D86 |
| 2983 | H | A4 | D86 | Ph | D86 |
| 2984 | Ph | A4 | H | D86 | D86 |
| 2985 | H | A4 | Ph | D86 | D86 |
| 2986 | D87 | A4 | D87 | D87 | H |
| 2987 | D87 | A4 | D87 | H | D87 |
| 2988 | D87 | A4 | H | D87 | D87 |
| 2989 | H | A4 | D87 | D87 | D87 |
| 2990 | D87 | A4 | D87 | D87 | Ph |
| 2991 | D87 | A4 | D87 | Ph | D87 |
| 2992 | D87 | A4 | Ph | D87 | D87 |
| 2993 | Ph | A4 | D87 | D87 | D87 |
| 2994 | D87 | A4 | D87 | H | H |
| 2995 | D87 | A4 | H | D87 | H |
| 2996 | D87 | A4 | H | H | D87 |
| 2997 | H | A4 | D87 | D87 | H |
| 2998 | H | A4 | D87 | H | D87 |
| 2999 | H | A4 | H | D87 | D87 |
| 3000 | D87 | A4 | D87 | Ph | H |
| 3001 | D87 | A4 | D87 | H | Ph |
| 3002 | D87 | A4 | Ph | D87 | H |

TABLE 1-continued

| No. | $R^1$ | $R^2$ | $R^3$ | $R^4$ | $R^5$ |
|---|---|---|---|---|---|
| 3003 | D87 | A4 | H | D87 | Ph |
| 3004 | D87 | A4 | Ph | H | D87 |
| 3005 | D87 | A4 | H | Ph | D87 |
| 3006 | Ph | A4 | D87 | D87 | H |
| 3007 | H | A4 | D87 | D87 | Ph |
| 3008 | Ph | A4 | D87 | H | D87 |
| 3009 | H | A4 | D87 | Ph | D87 |
| 3010 | Ph | A4 | H | D87 | D87 |
| 3011 | H | A4 | Ph | D87 | D87 |
| 3012 | D88 | A4 | D88 | D88 | H |
| 3013 | D88 | A4 | D88 | H | D88 |
| 3014 | D88 | A4 | H | D88 | D88 |
| 3015 | H | A4 | D88 | D88 | D88 |
| 3016 | D88 | A4 | D88 | D88 | Ph |
| 3017 | D88 | A4 | D88 | Ph | D88 |
| 3018 | D88 | A4 | Ph | D88 | D88 |
| 3019 | Ph | A4 | D88 | D88 | D88 |
| 3020 | D88 | A4 | D88 | H | H |
| 3021 | D88 | A4 | H | D88 | H |
| 3022 | D88 | A4 | H | H | D88 |
| 3023 | H | A4 | D88 | D88 | H |
| 3024 | H | A4 | D88 | H | D88 |
| 3025 | H | A4 | H | D88 | D88 |
| 3026 | D88 | A4 | D88 | Ph | H |
| 3027 | D88 | A4 | D88 | H | Ph |
| 3028 | D88 | A4 | Ph | D88 | H |
| 3029 | D88 | A4 | H | D88 | Ph |
| 3030 | D88 | A4 | Ph | H | D88 |
| 3031 | D88 | A4 | H | Ph | D88 |
| 3032 | Ph | A4 | D88 | D88 | H |
| 3033 | H | A4 | D88 | D88 | Ph |
| 3034 | Ph | A4 | D88 | H | D88 |
| 3035 | H | A4 | D88 | Ph | D88 |
| 3036 | Ph | A4 | H | D88 | D88 |
| 3037 | H | A4 | Ph | D88 | D88 |
| 3038 | D1 | A12 | D1 | D1 | H |
| 3039 | D1 | A12 | D1 | H | D1 |
| 3040 | D1 | A12 | H | D1 | D1 |
| 3041 | H | A12 | D1 | D1 | D1 |
| 3042 | D1 | A12 | D1 | D1 | Ph |
| 3043 | D1 | A12 | D1 | Ph | D1 |
| 3044 | D1 | A12 | Ph | D1 | D1 |
| 3045 | Ph | A12 | D1 | D1 | D1 |
| 3046 | D1 | A12 | D1 | H | H |
| 3047 | D1 | A12 | H | D1 | H |
| 3048 | D1 | A12 | H | H | D1 |
| 3049 | H | A12 | D1 | D1 | H |
| 3050 | H | A12 | D1 | H | D1 |
| 3051 | H | A12 | H | D1 | D2 |
| 3052 | D1 | A12 | D1 | Ph | H |
| 3053 | D1 | A12 | D1 | H | Ph |
| 3054 | D1 | A12 | Ph | D1 | H |
| 3055 | D1 | A12 | H | D1 | Ph |
| 3056 | D1 | A12 | Ph | H | D1 |
| 3057 | D1 | A12 | H | Ph | D1 |
| 3058 | Ph | A12 | D1 | D1 | H |
| 3059 | H | A12 | D1 | D1 | Ph |
| 3060 | Ph | A12 | D1 | H | D1 |
| 3061 | H | A12 | D1 | Ph | D1 |
| 3062 | Ph | A12 | H | D1 | D1 |
| 3063 | H | A12 | Ph | D1 | D1 |
| 3064 | D2 | A12 | D2 | D2 | H |
| 3065 | D2 | A12 | D2 | H | D2 |
| 3066 | D2 | A12 | H | D2 | D2 |
| 3067 | H | A12 | D2 | D2 | D2 |
| 3068 | D2 | A12 | D2 | D2 | Ph |
| 3069 | D2 | A12 | D2 | Ph | D2 |
| 3070 | D2 | A12 | Ph | D2 | D2 |
| 3071 | Ph | A12 | D2 | D2 | D2 |
| 3072 | D2 | A12 | D2 | H | H |
| 3073 | D2 | A12 | H | D2 | H |
| 3074 | D2 | A12 | H | H | D2 |
| 3075 | H | A12 | D2 | D2 | H |
| 3076 | H | A12 | D2 | H | D2 |
| 3077 | H | A12 | H | D2 | D2 |
| 3078 | D2 | A12 | D2 | Ph | H |
| 3079 | D2 | A12 | D2 | H | Ph |
| 3080 | D2 | A12 | Ph | D2 | H |

TABLE 1-continued

| No. | $R^1$ | $R^2$ | $R^3$ | $R^4$ | $R^5$ |
|---|---|---|---|---|---|
| 3081 | D2 | A12 | H | D2 | Ph |
| 3082 | D2 | A12 | Ph | H | D2 |
| 3083 | D2 | A12 | H | Ph | D2 |
| 3084 | Ph | A12 | D2 | D2 | H |
| 3085 | H | A12 | D2 | D2 | Ph |
| 3086 | Ph | A12 | D2 | H | D2 |
| 3087 | H | A12 | D2 | Ph | D2 |
| 3088 | Ph | A12 | H | D2 | D2 |
| 3089 | H | A12 | Ph | D2 | D2 |
| 3090 | D3 | A12 | D3 | D3 | H |
| 3091 | D3 | A12 | D3 | H | D3 |
| 3092 | D3 | A12 | H | D3 | D3 |
| 3093 | H | A12 | D3 | D3 | D3 |
| 3094 | D3 | A12 | D3 | D3 | Ph |
| 3095 | D3 | A12 | D3 | Ph | D3 |
| 3096 | D3 | A12 | Ph | D3 | D3 |
| 3097 | Ph | A12 | D3 | D3 | D3 |
| 3098 | D3 | A12 | D3 | H | H |
| 3099 | D3 | A12 | H | D3 | H |
| 3100 | D3 | A12 | H | H | D3 |
| 3101 | H | A12 | D3 | D3 | H |
| 3102 | H | A12 | D3 | H | D3 |
| 3103 | H | A12 | H | D3 | D3 |
| 3104 | D3 | A12 | D3 | Ph | H |
| 3105 | D3 | A12 | D3 | H | Ph |
| 3106 | D3 | A12 | Ph | D3 | H |
| 3107 | D3 | A12 | H | D3 | Ph |
| 3108 | D3 | A12 | Ph | H | D3 |
| 3109 | D3 | A12 | H | Ph | D3 |
| 3110 | Ph | A12 | D3 | D3 | H |
| 3111 | H | A12 | D3 | D3 | Ph |
| 3112 | Ph | A12 | D3 | H | D3 |
| 3113 | H | A12 | D3 | Ph | D3 |
| 3114 | Ph | A12 | H | D3 | D3 |
| 3115 | H | A12 | Ph | D3 | D3 |
| 3116 | D4 | A12 | D4 | D4 | H |
| 3117 | D4 | A12 | D4 | H | D4 |
| 3118 | D4 | A12 | H | D4 | D4 |
| 3119 | H | A12 | D4 | D4 | D4 |
| 3120 | D4 | A12 | D4 | D4 | Ph |
| 3121 | D4 | A12 | D4 | Ph | D4 |
| 3122 | D4 | A12 | Ph | D4 | D4 |
| 3123 | Ph | A12 | D4 | D4 | D4 |
| 3124 | D4 | A12 | D4 | H | H |
| 3125 | D4 | A12 | H | D4 | H |
| 3126 | D4 | A12 | H | H | D4 |
| 3127 | H | A12 | D4 | D4 | H |
| 3128 | H | A12 | D4 | H | D4 |
| 3129 | H | A12 | H | D4 | D4 |
| 3130 | D4 | A12 | D4 | Ph | H |
| 3131 | D4 | A12 | D4 | H | Ph |
| 3132 | D4 | A12 | Ph | D4 | H |
| 3133 | D4 | A12 | H | D4 | Ph |
| 3134 | D4 | A12 | Ph | H | D4 |
| 3135 | D4 | A12 | H | Ph | D4 |
| 3136 | Ph | A12 | D4 | D4 | H |
| 3137 | H | A12 | D4 | D4 | Ph |
| 3138 | Ph | A12 | D4 | H | D4 |
| 3139 | H | A12 | D4 | Ph | D4 |
| 3140 | Ph | A12 | H | D4 | D4 |
| 3141 | H | A12 | Ph | D4 | D4 |
| 3142 | D40 | A12 | D40 | D40 | H |
| 3143 | D40 | A12 | D40 | H | D40 |
| 3144 | D40 | A12 | H | D40 | D40 |
| 3145 | H | A12 | D40 | D40 | D40 |
| 3146 | D40 | A12 | D40 | D40 | Ph |
| 3147 | D40 | A12 | D40 | Ph | D40 |
| 3148 | D40 | A12 | Ph | D40 | D40 |
| 3149 | Ph | A12 | D40 | D40 | D40 |
| 3150 | D40 | A12 | D40 | H | H |
| 3151 | D40 | A12 | H | D40 | H |
| 3152 | D40 | A12 | H | H | D40 |
| 3153 | H | A12 | D40 | D40 | H |
| 3154 | H | A12 | D40 | H | D40 |
| 3155 | H | A12 | H | D40 | D40 |
| 3156 | D40 | A12 | D40 | Ph | H |
| 3157 | D40 | A12 | D40 | H | Ph |
| 3158 | D40 | A12 | Ph | D40 | H |

TABLE 1-continued

| No. | $R^1$ | $R^2$ | $R^3$ | $R^4$ | $R^5$ |
|---|---|---|---|---|---|
| 3159 | D40 | A12 | H | D40 | Ph |
| 3160 | D40 | A12 | Ph | H | D40 |
| 3161 | D40 | A12 | H | Ph | D40 |
| 3162 | Ph | A12 | D40 | D40 | H |
| 3163 | H | A12 | D40 | D40 | Ph |
| 3164 | Ph | A12 | D40 | H | D40 |
| 3165 | H | A12 | D40 | Ph | D40 |
| 3166 | Ph | A12 | H | D40 | D40 |
| 3167 | H | A12 | Ph | D40 | D40 |
| 3168 | D86 | A12 | D86 | D86 | H |
| 3169 | D86 | A12 | D86 | H | D86 |
| 3170 | D86 | A12 | H | D86 | D86 |
| 3171 | H | A12 | D86 | D86 | D86 |
| 3172 | D86 | A12 | D86 | D86 | Ph |
| 3173 | D86 | A12 | D86 | Ph | D86 |
| 3174 | D86 | A12 | Ph | D86 | D86 |
| 3175 | Ph | A12 | D86 | D86 | D86 |
| 3176 | D86 | A12 | D86 | H | H |
| 3177 | D86 | A12 | H | D86 | H |
| 3178 | D86 | A12 | H | H | D86 |
| 3179 | H | A12 | D86 | D86 | H |
| 3180 | H | A12 | D86 | H | D86 |
| 3181 | H | A12 | H | D86 | D86 |
| 3182 | D86 | A12 | D86 | Ph | H |
| 3183 | D86 | A12 | D86 | H | Ph |
| 3184 | D86 | A12 | Ph | D86 | H |
| 3185 | D86 | A12 | H | D86 | Ph |
| 3186 | D86 | A12 | Ph | H | D86 |
| 3187 | D86 | A12 | H | Ph | D86 |
| 3188 | Ph | A12 | D86 | D86 | H |
| 3189 | H | A12 | D86 | D86 | Ph |
| 3190 | Ph | A12 | D86 | H | D86 |
| 3191 | H | A12 | D86 | Ph | D86 |
| 3192 | Ph | A12 | H | D86 | D86 |
| 3193 | H | A12 | Ph | D86 | D86 |
| 3194 | D42 | A12 | D42 | D42 | H |
| 3195 | D42 | A12 | D42 | H | D42 |
| 3196 | D42 | A12 | H | D42 | D42 |
| 3197 | H | A12 | D42 | D42 | D42 |
| 3198 | D42 | A12 | D42 | D42 | Ph |
| 3199 | D42 | A12 | D42 | Ph | D42 |
| 3200 | D42 | A12 | Ph | D42 | D42 |
| 3201 | Ph | A12 | D42 | D42 | D42 |
| 3202 | D42 | A12 | D42 | H | H |
| 3203 | D42 | A12 | H | D42 | H |
| 3204 | D42 | A12 | H | H | D42 |
| 3205 | H | A12 | D42 | D42 | H |
| 3206 | H | A12 | D42 | H | D42 |
| 3207 | H | A12 | H | D42 | D42 |
| 3208 | D42 | A12 | D42 | Ph | H |
| 3209 | D42 | A12 | D42 | H | Ph |
| 3210 | D42 | A12 | Ph | D42 | H |
| 3211 | D42 | A12 | H | D42 | Ph |
| 3212 | D42 | A12 | Ph | H | D42 |
| 3213 | D42 | A12 | H | Ph | D42 |
| 3214 | Ph | A12 | D42 | D42 | H |
| 3215 | H | A12 | D42 | D42 | Ph |
| 3216 | Ph | A12 | D42 | H | D42 |
| 3217 | H | A12 | D42 | Ph | D42 |
| 3218 | Ph | A12 | H | D42 | D42 |
| 3219 | H | A12 | Ph | D42 | D42 |
| 3220 | D43 | A12 | D43 | D43 | H |
| 3221 | D43 | A12 | D43 | H | D43 |
| 3222 | D43 | A12 | H | D43 | D43 |
| 3223 | H | A12 | D43 | D43 | D43 |
| 3224 | D43 | A12 | D43 | D43 | Ph |
| 3225 | D43 | A12 | D43 | Ph | D43 |
| 3226 | D43 | A12 | Ph | D43 | D43 |
| 3227 | Ph | A12 | D43 | D43 | D43 |
| 3228 | D43 | A12 | D43 | H | H |
| 3229 | D43 | A12 | H | D43 | H |
| 3230 | D43 | A12 | H | H | D43 |
| 3231 | H | A12 | D43 | D43 | H |
| 3232 | H | A12 | D43 | H | D43 |
| 3233 | H | A12 | H | D43 | D43 |
| 3234 | D43 | A12 | D43 | Ph | H |
| 3235 | D43 | A12 | D43 | H | Ph |
| 3236 | D43 | A12 | Ph | D43 | H |

TABLE 1-continued

| No. | $R^1$ | $R^2$ | $R^3$ | $R^4$ | $R^5$ |
|---|---|---|---|---|---|
| 3237 | D43 | A12 | H | D43 | Ph |
| 3238 | D43 | A12 | Ph | H | D43 |
| 3239 | D43 | A12 | H | Ph | D43 |
| 3240 | Ph | A12 | D43 | D43 | H |
| 3241 | H | A12 | D43 | D43 | Ph |
| 3242 | Ph | A12 | D43 | H | D43 |
| 3243 | H | A12 | D43 | Ph | D43 |
| 3244 | Ph | A12 | H | D43 | D43 |
| 3245 | H | A12 | Ph | D43 | D43 |
| 3246 | D84 | A12 | D84 | D84 | H |
| 3247 | D84 | A12 | D84 | H | D84 |
| 3248 | D84 | A12 | H | D84 | D84 |
| 3249 | H | A12 | D84 | 84 | D84 |
| 3250 | D84 | A12 | D84 | D84 | Ph |
| 3251 | D84 | A12 | D84 | Ph | D84 |
| 3252 | D84 | A12 | Ph | D84 | D84 |
| 3253 | Ph | A12 | D84 | D84 | D84 |
| 3254 | D84 | A12 | D84 | H | H |
| 3255 | D84 | A12 | H | D84 | H |
| 3256 | D84 | A12 | H | H | D84 |
| 3257 | H | A12 | D84 | D84 | H |
| 3258 | H | A12 | D84 | H | D84 |
| 3259 | H | A12 | H | D84 | D84 |
| 3260 | D84 | A12 | D84 | Ph | H |
| 3261 | D84 | A12 | D84 | H | Ph |
| 3262 | D84 | A12 | Ph | D84 | H |
| 3263 | D84 | A12 | H | D84 | Ph |
| 3264 | D84 | A12 | Ph | H | D84 |
| 3265 | D84 | A12 | H | Ph | D84 |
| 3266 | Ph | A12 | D84 | D84 | H |
| 3267 | H | A12 | D84 | D84 | Ph |
| 3268 | Ph | A12 | D84 | H | D84 |
| 3269 | H | A12 | D84 | Ph | D84 |
| 3270 | Ph | A12 | H | D84 | D84 |
| 3271 | H | A12 | Ph | D84 | D84 |
| 3272 | D86 | A12 | D86] | D86 | H |
| 3273 | D86 | A12 | D86 | H | D86 |
| 3274 | D86 | A12 | H | D86 | D86 |
| 3275 | H | A12 | D86 | D86 | D86 |
| 3276 | D86 | A12 | D86 | D86 | Ph |
| 3277 | D86 | A12 | D86 | Ph | D86 |
| 3278 | D86 | A12 | Ph | D86 | D86 |
| 3279 | Ph | A12 | D86 | D86 | D86 |
| 3280 | D86 | A12 | D86 | H | H |
| 3281 | D86 | A12 | H | D86 | H |
| 3282 | D86 | A12 | H | H | D86 |
| 3283 | H | A12 | D86 | D86 | H |
| 3284 | H | A12 | D86 | H | D86 |
| 3285 | H | A12 | H | D86 | D86 |
| 3286 | D86 | A12 | D86 | Ph | H |
| 3287 | D86 | A12 | D86 | H | Ph |
| 3288 | D86 | A12 | Ph | D86 | H |
| 3289 | D86 | A12 | H | D86 | Ph |
| 3290 | D86 | A12 | Ph | H | D86 |
| 3291 | D86 | A12 | H | Ph | D86 |
| 3292 | Ph | A12 | D86 | D86 | H |
| 3293 | H | A12 | D86 | D86 | Ph |
| 3294 | Ph | A12 | D86 | H | D86 |
| 3295 | H | A12 | D86 | Ph | D86 |
| 3296 | Ph | A12 | H | D86 | D86 |
| 3297 | H | A12 | Ph | D86 | D86 |
| 3298 | D87 | A12 | D87 | D87 | H |
| 3299 | D87 | A12 | D87 | H | D87 |
| 3300 | D87 | A12 | H | D87 | D87 |
| 3301 | H | A12 | D87 | D87 | D87 |
| 3302 | D87 | A12 | D87 | D87 | Ph |
| 3303 | D87 | A12 | D87 | Ph | D87 |
| 3304 | D87 | A12 | Ph | D87 | D87 |
| 3305 | Ph | A12 | D87 | D87 | D87 |
| 3306 | D87 | A12 | D87 | H | H |
| 3307 | D87 | A12 | H | D87 | H |
| 3308 | D87 | A12 | H | H | D87 |
| 3309 | H | A12 | D87 | D87 | H |
| 3310 | H | A12 | D87 | H | D87 |
| 3311 | H | A12 | H | D87 | D87 |
| 3312 | D87 | A12 | D87 | Ph | H |
| 3313 | D87 | A12 | D87 | H | Ph |
| 3314 | D87 | A12 | Ph | D87 | H |

TABLE 1-continued

| No. | $R^1$ | $R^2$ | $R^3$ | $R^4$ | $R^5$ |
|---|---|---|---|---|---|
| 3315 | D87 | A12 | H | D87 | Ph |
| 3316 | D87 | A12 | Ph | H | D87 |
| 3317 | D87 | A12 | H | Ph | D87 |
| 3318 | Ph | A12 | D87 | D87 | H |
| 3319 | H | A12 | D87 | D87 | Ph |
| 3320 | Ph | A12 | D87 | H | D87 |
| 3321 | H | A12 | D87 | Ph | D87 |
| 3322 | Ph | A12 | H | D87 | D87 |
| 3323 | H | A12 | Ph | D87 | D87 |
| 3324 | D88 | A12 | D88 | D88 | H |
| 3325 | D88 | A12 | D88 | H | D88 |
| 3326 | D88 | A12 | H | D88 | D88 |
| 3327 | H | A12 | D88 | D88 | D88 |
| 3328 | D88 | A12 | D88 | D88 | Ph |
| 3329 | D88 | A12 | D88 | Ph | D88 |
| 3330 | D88 | A12 | Ph | D88 | D88 |
| 3331 | Ph | A12 | D88 | D88 | D88 |
| 3332 | D88 | A12 | D88 | H | H |
| 3333 | D88 | A12 | H | D88 | H |
| 3334 | D88 | A12 | H | H | D88 |
| 3335 | H | A12 | D88 | D88 | H |
| 3336 | H | A12 | D88 | H | D88 |
| 3337 | H | A12 | H | D88 | D88 |
| 3338 | D88 | A12 | D88 | Ph | H |
| 3339 | D88 | A12 | D88 | H | Ph |
| 3340 | D88 | A12 | Ph | D88 | H |
| 3341 | D88 | A12 | H | D88 | Ph |
| 3342 | D88 | A12 | Ph | H | D88 |
| 3343 | D88 | A12 | H | Ph | D88 |
| 3344 | Ph | A12 | D88 | D88 | H |
| 3345 | H | A12 | D88 | D88 | Ph |
| 3346 | Ph | A12 | D88 | H | D88 |
| 3347 | H | A12 | D88 | Ph | D88 |
| 3348 | Ph | A12 | H | D88 | D88 |
| 3349 | H | A12 | Ph | D88 | D88 |
| 3350 | A13 | H | D86 | D86 | D86 |
| 3351 | A13 | D86 | H | D86 | D86 |
| 3352 | A13 | D86 | D86 | H | D86 |
| 3353 | A13 | D86 | D86 | D86 | H |
| 3354 | A14 | H | D86 | D86 | D86 |
| 3355 | A14 | D86 | H | D86 | D86 |
| 3356 | A14 | D86 | D86 | H | D86 |
| 3357 | A14 | D86 | D86 | D86 | H |
| 3358 | A13 | Ph | D86 | D86 | H |
| 3359 | A13 | D86 | Ph | D86 | H |
| 3360 | A13 | D86 | D86 | Ph | H |
| 3361 | A13 | Ph | D86 | H | D86 |
| 3362 | A13 | D86 | Ph | H | D86 |
| 3363 | A13 | D86 | D86 | H | Ph |
| 3364 | A13 | Ph | H | D86 | D86 |
| 3365 | A13 | D86 | H | Ph | D86 |
| 3366 | A13 | D86 | H | D86 | Ph |
| 3367 | A13 | H | Ph | D86 | D86 |
| 3368 | A13 | H | D86 | Ph | D86 |
| 3369 | A13 | H | D86 | D86 | Ph |
| 3370 | A14 | Ph | D86 | D86 | H |
| 3371 | A14 | D86 | Ph | D86 | H |
| 3372 | A14 | D86 | D86 | Ph | H |
| 3373 | A14 | Ph | D86 | H | D86 |
| 3374 | A14 | D86 | Ph | H | D86 |
| 3375 | A14 | D86 | D86 | H | Ph |
| 3376 | A14 | Ph | H | D86 | D86 |
| 3377 | A14 | D86 | H | Ph | D86 |
| 3378 | A14 | D86 | H | D86 | Ph |
| 3379 | A14 | H | Ph | D86 | D86 |
| 3380 | A14 | H | D86 | Ph | D86 |
| 3381 | A14 | H | D86 | D86 | Ph |
| 3382 | A13 | Ph | D86 | D86 | D86 |
| 3383 | A13 | D86 | Ph | D86 | D86 |
| 3384 | A13 | D86 | D86 | Ph | D86 |
| 3385 | A13 | D86 | D86 | D86 | Ph |
| 3386 | A14 | Ph | D86 | D86 | D86 |
| 3387 | A14 | D86 | Ph | D86 | D86 |
| 3388 | A14 | D86 | D86 | Ph | D86 |
| 3389 | A14 | D86 | D86 | D86 | Ph |
| 3390 | A13 | H | D1 | D1 | D86 |
| 3391 | A13 | D1 | H | D86 | D1 |
| 3392 | A13 | D1 | D86 | H | D1 |

TABLE 1-continued

| No. | $R^1$ | $R^2$ | $R^3$ | $R^4$ | $R^5$ |
|---|---|---|---|---|---|
| 3393 | A13 | D86 | D1 | D1 | H |
| 3394 | A14 | H | D1 | D1 | D86 |
| 3395 | A14 | D1 | H | D86 | D1 |
| 3396 | A14 | D1 | D86 | H | D1 |
| 3397 | A14 | D86 | D1 | D1 | H |
| 3398 | A13 | Ph | D1 | D1 | D86 |
| 3399 | A13 | D1 | Ph | D86 | D1 |
| 3400 | A13 | D1 | D86 | Ph | D1 |
| 3401 | A13 | D86 | D1 | D1 | Ph |
| 3402 | A14 | Ph | D1 | D1 | D86 |
| 3403 | A14 | D1 | Ph | D86 | D1 |
| 3404 | A14 | D1 | D86 | Ph | D1 |
| 3405 | A14 | D86 | D1 | D1 | Ph |
| 3406 | A13 | H | D84 | D84 | D86 |
| 3407 | A13 | D84 | H | D86 | D84 |
| 3408 | A13 | D84 | D86 | H | D84 |
| 3409 | A13 | D86 | D84 | D84 | H |
| 3410 | A14 | H | D84 | D84 | D86 |
| 3411 | A14 | D84 | H | D86 | D84 |
| 3412 | A14 | D84 | D86 | H | D84 |
| 3413 | A14 | D86 | D84 | D84 | H |
| 3414 | A13 | Ph | D84 | D84 | D86 |
| 3415 | A13 | D84 | Ph | D86 | D84 |
| 3416 | A13 | D84 | D86 | Ph | D84 |
| 3417 | A13 | D86 | D84 | D84 | Ph |
| 3418 | A14 | Ph | D84 | D84 | D86 |
| 3419 | A14 | D84 | Ph | D86 | D84 |
| 3420 | A14 | D84 | | Ph | D84 |
| 3421 | A14 | D86 | D84 | D84 | Ph |
| 3422 | H | A13 | D86 | D86 | D86 |
| 3423 | D86 | A13 | H | D86 | D86 |
| 3424 | D86 | A13 | D86 | H | D86 |
| 3425 | D86 | A13 | D86 | D86 | H |
| 3426 | H | A14 | D86 | D86 | D86 |
| 3427 | D86 | A14 | H | D86 | D86 |
| 3428 | D86 | A14 | D86 | H | D86 |
| 3429 | D86 | A14 | D86 | D86 | H |
| 3430 | Ph | A13 | D86 | D86 | H |
| 3431 | D86 | A13 | Ph | D86 | |
| 3432 | D86 | A13 | D86 | Ph | H |
| 3433 | Ph | A13 | D86 | H | D86 |
| 3434 | D86 | A13 | Ph | H | D86 |
| 3435 | D86 | A13 | D86 | H | Ph |
| 3438 | Ph | A13 | H | D86 | D86 |
| 3437 | D86 | A13 | H | Ph | D86 |
| 3438 | D86 | A13 | H | D86 | Ph |
| 3439 | H | A13 | Ph | D86 | D86 |
| 3440 | H | A13 | D86 | Ph | D86 |
| 3441 | H | A13 | D86 | D86 | Ph |
| 3442 | Ph | A14 | D86 | D86 | H |
| 3443 | D86 | A14 | Ph | D86 | H |
| 3444 | D86 | A14 | D86 | Ph | H |
| 3445 | Ph | A14 | D86 | H | D86 |
| 3446 | D86 | A14 | Ph | H | D86 |
| 3447 | D86 | A14 | D86 | H | Ph |
| 3448 | Ph | A14 | H | D86 | D86 |
| 3449 | D86 | A14 | H | Ph | D86 |
| 3450 | D86 | A14 | H | D86 | Ph |
| 3451 | H | A14 | Ph | D86 | D86 |
| 3452 | H | A14 | D86 | Ph | D86 |
| 3453 | H | A14 | D86 | D86 | Ph |
| 3454 | Ph | A13 | D86 | D86 | D86 |
| 3455 | D86 | A13 | Ph | D86 | D86 |
| 3456 | D86 | A13 | D86 | Ph | D86 |
| 3457 | D86 | A13 | D86 | D86 | Ph |
| 3458 | Ph | A14 | D86 | D86 | D86 |
| 3459 | D86 | A14 | Ph | D86 | D86 |
| 3460 | D86 | A14 | D86 | Ph | D86 |
| 3461 | D86 | A14 | D86 | D86 | Ph |
| 3462 | H | A13 | D1 | D1 | D86 |
| 3463 | D1 | A13 | H | D86 | D1 |
| 3464 | D1 | A13 | D86 | H | D1 |
| 3465 | D86 | A13 | D1 | D1 | H |
| 3466 | H | A14 | D1 | D1 | D86 |
| 3467 | D1 | A14 | H | D86 | D1 |
| 3468 | D1 | A14 | D86 | H | D1 |
| 3469 | D86 | A14 | D1 | D1 | H |
| 3470 | Ph | A13 | D1 | D1 | D86 |

TABLE 1-continued

| No. | $R^1$ | $R^2$ | $R^3$ | $R^4$ | $R^5$ |
|---|---|---|---|---|---|
| 3471 | D1 | A13 | Ph | D86 | D1 |
| 3472 | D1 | A13 | D86 | Ph | D1 |
| 3473 | D86 | A13 | D1 | D1 | Ph |
| 3474 | Ph | A14 | D1 | D1 | D86 |
| 3475 | D1 | A14 | Ph | D86 | D1 |
| 3476 | D1 | A14 | D86 | Ph | D1 |
| 3477 | D86 | A14 | D1 | D1 | Ph |
| 3478 | H | A13 | D84 | D84 | D86 |
| 3479 | D84 | A13 | H | D86 | D84 |
| 3480 | D84 | A13 | D86 | H | D84 |
| 3481 | D86 | A13 | D84 | D84 | H |
| 3482 | H | A14 | D84 | D84 | D86 |
| 3483 | D84 | A14 | H | D86 | D84 |
| 3484 | D84 | A14 | D86 | H | D84 |
| 3485 | D86 | A14 | D84 | D84 | H |
| 3486 | Ph | A13 | D84 | D84 | D86 |
| 3487 | D84 | A13 | Ph | D86 | D84 |
| 3488 | D84 | A13 | D86 | Ph | D84 |
| 3489 | D86 | A13 | D84 | D84 | Ph |
| 3490 | Ph | A14 | D84 | D84 | D86 |
| 3491 | D84 | A14 | Ph | D86 | D84 |
| 3492 | D84 | A14 | D86 | Ph | D84 |
| 3493 | D86 | A14 | D84 | D84 | Ph |
| 3494 | A1 | D56 | D56 | D56 | H |
| 3495 | A1 | D57 | D57 | D57 | H |
| 3496 | A1 | D60 | D60 | D60 | H |
| 3497 | A1 | D64 | D64 | D64 | H |
| 3498 | A1 | D65 | D65 | D65 | H |
| 3499 | A1 | D76 | D76 | D76 | H |
| 3500 | A1 | D56 | D56 | D56 | Ph |
| 3501 | A1 | D57 | D57 | D57 | Ph |
| 3502 | A1 | D60 | D60 | D60 | Ph |
| 3503 | A1 | D64 | D64 | D64 | Ph |
| 3504 | A1 | D65 | D65 | D65 | Ph |
| 3505 | A1 | D76 | D76 | D76 | Ph |
| 3506 | A20 | D56 | D56 | D56 | H |
| 3507 | A20 | D57 | D57 | D57 | H |
| 3508 | A20 | D60 | D60 | D60 | H |
| 3509 | A20 | D64 | D64 | D64 | H |
| 3510 | A20 | D65 | D65 | D65 | H |
| 3511 | A20 | D76 | D76 | D76 | H |
| 3512 | A20 | D56 | D56 | D56 | Ph |
| 3513 | A20 | D57 | D57 | D57 | Ph |
| 3514 | A20 | D60 | D60 | D60 | Ph |
| 3515 | A20 | D64 | D64 | D64 | Ph |
| 3516 | A20 | D65 | D65 | D65 | Ph |
| 3517 | A20 | D76 | D76 | D76 | Ph |
| 3518 | A21 | D56 | D56 | D56 | H |
| 3519 | A21 | D57 | D57 | D57 | H |
| 3520 | A21 | D60 | D60 | D60 | H |
| 3521 | A21 | D64 | D64 | D64 | H |
| 3522 | A21 | D65 | D65 | D65 | H |
| 3523 | A21 | D76 | D76 | D76 | H |
| 3524 | A21 | D56 | D56 | D56 | Ph |
| 3525 | A21 | D57 | D57 | D57 | Ph |
| 3526 | A21 | D60 | D60 | D60 | Ph |
| 3527 | A21 | D64 | D64 | D64 | Ph |
| 3528 | A21 | D65 | D65 | D65 | Ph |
| 3529 | A21 | D76 | D76 | D76 | Ph |
| 3530 | A1 | D1 | D56 | D56 | Ph |
| 3531 | A1 | D1 | D57 | D57 | Ph |
| 3532 | A1 | D1 | D60 | D60 | Ph |
| 3533 | A1 | D1 | D64 | D64 | Ph |
| 3534 | A1 | D1 | D65 | D65 | Ph |
| 3535 | A1 | D1 | D76 | D76 | Ph |
| 3536 | A1 | D56 | D1 | D56 | Ph |
| 3537 | A1 | D57 | D1 | D57 | Ph |
| 3538 | A1 | D60 | D1 | D60 | Ph |
| 3539 | A1 | D64 | D1 | D64 | Ph |
| 3540 | A1 | D65 | D1 | D65 | Ph |
| 3541 | A1 | D76 | D1 | D76 | Ph |
| 3542 | A1 | D56 | D56 | D1 | Ph |
| 3543 | A1 | D57 | D57 | D1 | Ph |
| 3544 | A1 | D60 | D60 | D1 | Ph |
| 3545 | A1 | D64 | D64 | D1 | Ph |
| 3546 | A1 | D65 | D65 | D1 | Ph |
| 3547 | A1 | D76 | D76 | D1 | Ph |
| 3548 | A1 | D1 | D56 | D56 | Ph |

TABLE 1-continued

| No. | $R^1$ | $R^2$ | $R^3$ | $R^4$ | $R^5$ |
|---|---|---|---|---|---|
| 3549 | A1 | D1 | D57 | D57 | Ph |
| 3550 | A1 | D1 | D60 | D60 | Ph |
| 3551 | A1 | D1 | D64 | D64 | Ph |
| 3552 | A1 | D1 | D65 | D65 | Ph |
| 3553 | A1 | D1 | D76 | D76 | Ph |
| 3554 | A1 | D56 | D1 | D56 | Ph |
| 3555 | A1 | D57 | D1 | D57 | Ph |
| 3556 | A1 | D60 | D1 | D60 | Ph |
| 3557 | A1 | D64 | D1 | D64 | Ph |
| 3558 | A1 | D65 | D1 | D65 | Ph |
| 3559 | A1 | D76 | D1 | D76 | Ph |
| 3560 | A1 | D56 | D56 | D1 | Ph |
| 3561 | A1 | D57 | D57 | D1 | Ph |
| 3562 | A1 | D60 | D60 | D1 | Ph |
| 3563 | A1 | D64 | D64 | D1 | Ph |
| 3564 | A1 | D65 | D65 | D1 | Ph |
| 3565 | A1 | D76 | D76 | D1 | Ph |
| 3566 | A20 | D1 | D56 | D56 | Ph |
| 3567 | A20 | D1 | D57 | D57 | Ph |
| 3568 | A20 | D1 | D60 | D60 | Ph |
| 3569 | A20 | D1 | D64 | D64 | Ph |
| 3570 | A20 | D1 | D65 | D65 | Ph |
| 3571 | A20 | D1 | D76 | D76 | Ph |
| 3572 | A20 | D56 | D1 | D56 | Ph |
| 3573 | A20 | D57 | D1 | D57 | Ph |
| 3574 | A20 | D60 | D1 | D60 | Ph |
| 3575 | A20 | D64 | D1 | D64 | Ph |
| 3576 | A20 | D65 | D1 | D65 | Ph |
| 3577 | A20 | D76 | D1 | D76 | Ph |
| 3578 | A20 | D56 | D56 | D1 | Ph |
| 3579 | A20 | D57 | D57 | D1 | Ph |
| 3580 | A20 | D60 | D60 | D1 | Ph |
| 3581 | A20 | D64 | D64 | D1 | Ph |
| 3582 | A20 | D65 | D65 | D1 | Ph |
| 3583 | A20 | D76 | D76 | D1 | Ph |
| 3584 | A20 | D1 | D56 | D56 | Ph |
| 3585 | A20 | D1 | D57 | D57 | Ph |
| 3586 | A20 | D1 | D60 | D60 | Ph |
| 3587 | A20 | D1 | D64 | D64 | Ph |
| 3588 | A20 | D1 | D65 | D65 | Ph |
| 3589 | A20 | D1 | D76 | D76 | Ph |
| 3590 | A20 | D56 | D1 | D56 | Ph |
| 3591 | A20 | D57 | D1 | D57 | Ph |
| 3592 | A20 | D60 | D1 | D60 | Ph |
| 3593 | A20 | D64 | D1 | D64 | Ph |
| 3594 | A20 | D65 | D1 | D65 | Ph |
| 3595 | A20 | D76 | D1 | D76 | Ph |
| 3596 | A20 | D56 | D56 | D1 | Ph |
| 3597 | A20 | D57 | D57 | D1 | Ph |
| 3598 | A20 | D60 | D60 | D1 | Ph |
| 3599 | A20 | D64 | D64 | D1 | Ph |
| 3600 | A20 | D65 | D65 | D1 | Ph |
| 3601 | A20 | D76 | D76 | D1 | Ph |
| 3602 | A1 | D56 | H | D56 | H |
| 3603 | A1 | D57 | H | D57 | H |
| 3604 | A1 | D60 | H | D60 | H |
| 3605 | A1 | D64 | H | D64 | H |
| 3606 | A1 | D65 | H | D65 | H |
| 3607 | A1 | D76 | H | D76 | H |
| 3608 | A1 | D56 | Ph | D56 | H |
| 3609 | A1 | D57 | Ph | D57 | H |
| 3610 | A1 | D60 | Ph | D60 | H |
| 3611 | A1 | D64 | Ph | D64 | H |
| 3612 | A1 | D65 | Ph | D65 | H |
| 3613 | A1 | D76 | Ph | D76 | H |
| 3614 | A1 | D56 | H | D56 | Ph |
| 3615 | A1 | D57 | H | D57 | Ph |
| 3616 | A1 | D60 | H | D60 | Ph |
| 3617 | A1 | D64 | H | D64 | Ph |
| 3618 | A1 | D65 | H | D65 | Ph |
| 3619 | A1 | D76 | H | D76 | Ph |
| 3620 | A1 | D56 | Ph | D56 | Ph |
| 3621 | A1 | D57 | Ph | D57 | Ph |
| 3622 | A1 | D60 | Ph | D60 | Ph |
| 3623 | A1 | D64 | Ph | D64 | Ph |
| 3624 | A1 | D65 | Ph | D65 | Ph |
| 3625 | A1 | D76 | Ph | D76 | Ph |
| 3626 | A20 | D56 | H | D56 | H |

TABLE 1-continued

| No. | $R^1$ | $R^2$ | $R^3$ | $R^4$ | $R^5$ |
|---|---|---|---|---|---|
| 3627 | A20 | D57 | H | D57 | H |
| 3628 | A20 | D60 | H | D60 | H |
| 3629 | A20 | D64 | H | D64 | H |
| 3630 | A20 | D65 | H | D65 | H |
| 3631 | A20 | D76 | H | D76 | H |
| 3632 | A20 | D56 | Ph | D56 | H |
| 3633 | A20 | D57 | Ph | D57 | H |
| 3634 | A20 | D60 | Ph | D60 | H |
| 3635 | A20 | D64 | Ph | D64 | H |
| 3636 | A20 | D65 | Ph | D65 | H |
| 3637 | A20 | D76 | Ph | D76 | H |
| 3638 | A20 | D56 | H | D56 | Ph |
| 3639 | A20 | D57 | H | D57 | Ph |
| 3640 | A20 | D60 | H | D60 | Ph |
| 3641 | A20 | D64 | H | D64 | Ph |
| 3642 | A20 | D65 | H | D65 | Ph |
| 3643 | A20 | D76 | H | D76 | Ph |
| 3644 | A20 | D56 | Ph | D56 | Ph |
| 3645 | A20 | D57 | Ph | D57 | Ph |
| 3646 | A20 | D60 | Ph | D60 | Ph |
| 3647 | A20 | D64 | Ph | D64 | Ph |
| 3648 | A20 | D65 | Ph | D65 | Ph |
| 3649 | A20 | D76 | Ph | D76 | Ph |
| 3650 | A21 | D56 | H | D56 | H |
| 3651 | A21 | D57 | H | D57 | H |
| 3652 | A21 | D60 | H | D60 | H |
| 3653 | A21 | D64 | H | D64 | H |
| 3654 | A21 | D65 | H | D65 | H |
| 3655 | A21 | D76 | H | D76 | H |
| 3656 | A21 | D56 | Ph | D56 | H |
| 3657 | A21 | D57 | Ph | D57 | H |
| 3658 | A21 | D60 | Ph | D60 | H |
| 3659 | A21 | D64 | Ph | D64 | H |
| 3660 | A21 | D65 | Ph | D65 | H |
| 3661 | A21 | D76 | Ph | D76 | H |
| 3662 | A21 | D56 | H | D56 | Ph |
| 3663 | A21 | D57 | H | D57 | Ph |
| 3664 | A21 | D60 | H | D60 | Ph |
| 3665 | A21 | D64 | H | D64 | Ph |
| 3666 | A21 | D65 | H | D65 | Ph |
| 3667 | A21 | D76 | H | D76 | Ph |
| 3668 | A21 | D56 | Ph | D56 | Ph |
| 3669 | A21 | D57 | Ph | D57 | Ph |
| 3670 | A21 | D60 | Ph | D60 | Ph |
| 3671 | A21 | D64 | Ph | D64 | Ph |
| 3672 | A21 | D65 | Ph | D65 | Ph |
| 3673 | A21 | D76 | Ph | D76 | Ph |
| 3674 | A1 | D1 | H | D56 | H |
| 3675 | A1 | D1 | H | D57 | H |
| 3676 | A1 | D1 | H | D60 | H |
| 3677 | A1 | D1 | H | D64 | H |
| 3678 | A1 | D1 | H | D65 | H |
| 3679 | A1 | D1 | H | D76 | H |
| 3680 | A1 | D1 | Ph | D56 | H |
| 3681 | A1 | D1 | Ph | D57 | H |
| 3682 | A1 | D1 | Ph | D60 | H |
| 3683 | A1 | D1 | Ph | D64 | H |
| 3684 | A1 | D1 | Ph | D65 | H |
| 3685 | A1 | D1 | Ph | D76 | H |
| 3688 | A1 | D1 | H | D56 | Ph |
| 3687 | A1 | D1 | H | D57 | Ph |
| 3688 | A1 | D1 | H | D60 | Ph |
| 3689 | A1 | D1 | H | D64 | Ph |
| 3690 | A1 | D1 | H | D65 | Ph |
| 3691 | A1 | D1 | H | D76 | Ph |
| 3692 | A1 | D1 | Ph | D56 | Ph |
| 3693 | A1 | D1 | Ph | D57 | Ph |
| 3694 | A1 | D1 | Ph | D60 | Ph |
| 3695 | A1 | D1 | Ph | D64 | Ph |
| 3696 | A1 | D1 | Ph | D65 | Ph |
| 3697 | A1 | D1 | Ph | D76 | Ph |
| 3698 | A1 | D56 | H | D1 | H |
| 3699 | A1 | D57 | H | D1 | H |
| 3700 | A1 | D60 | H | D1 | H |
| 3701 | A1 | D64 | H | D1 | H |
| 3702 | A1 | D65 | H | D1 | H |
| 3703 | A1 | D76 | H | D1 | H |
| 3704 | A1 | D56 | Ph | D1 | H |

TABLE 1-continued

| No. | $R^1$ | $R^2$ | $R^3$ | $R^4$ | $R^5$ |
|---|---|---|---|---|---|
| 3705 | A1 | D57 | Ph | D1 | H |
| 3706 | A1 | D60 | Ph | D1 | H |
| 3707 | A1 | D64 | Ph | D1 | H |
| 3708 | A1 | D65 | Ph | D1 | H |
| 3709 | A1 | D76 | Ph | D1 | H |
| 3710 | A1 | D56 | H | D1 | Ph |
| 3711 | A1 | D57 | H | D1 | Ph |
| 3712 | A1 | D60 | H | D1 | Ph |
| 3713 | A1 | D64 | H | D1 | Ph |
| 3714 | A1 | D65 | H | D1 | Ph |
| 3715 | A1 | D76 | H | D1 | Ph |
| 3716 | A1 | D56 | Ph | D1 | Ph |
| 3717 | A1 | D57 | Ph | D1 | Ph |
| 3718 | A1 | D60 | Ph | D1 | Ph |
| 3719 | A1 | D64 | Ph | D1 | Ph |
| 3720 | A1 | D65 | Ph | D1 | Ph |
| 3721 | A1 | D76 | Ph | D1 | Ph |
| 3722 | A20 | D1 | H | D56 | H |
| 3723 | A20 | D1 | H | D57 | H |
| 3724 | A20 | D1 | H | D60 | H |
| 3725 | A20 | D1 | H | D64 | H |
| 3726 | A20 | D1 | H | D65 | H |
| 3727 | A20 | D1 | H | D76 | H |
| 3728 | A20 | D1 | Ph | D56 | H |
| 3729 | A20 | D1 | Ph | D57 | H |
| 3730 | A20 | D1 | Ph | D60 | H |
| 3731 | A20 | D1 | Ph | D64 | H |
| 3732 | A20 | D1 | Ph | D65 | H |
| 3733 | A20 | D1 | Ph | D76 | H |
| 3734 | A20 | D1 | H | D56 | Ph |
| 3735 | A20 | D1 | H | D57 | Ph |
| 3736 | A20 | D1 | H | D60 | Ph |
| 3737 | A20 | D1 | H | D64 | Ph |
| 3738 | A20 | D1 | H | D65 | Ph |
| 3739 | A20 | D1 | H | D76 | Ph |
| 3740 | A20 | D1 | Ph | D56 | Ph |
| 3741 | A20 | D1 | Ph | D57 | Ph |
| 3742 | A20 | D1 | Ph | D60 | Ph |
| 3743 | A20 | D1 | Ph | D64 | Ph |
| 3744 | A20 | D1 | Ph | D65 | Ph |
| 3745 | A20 | D1 | Ph | D76 | Ph |
| 3746 | A20 | D56 | H | D1 | H |
| 3747 | A20 | D57 | H | D1 | H |
| 3748 | A20 | D60 | H | D1 | H |
| 3749 | A20 | D64 | H | D1 | H |
| 3750 | A20 | D65 | H | D1 | H |
| 3751 | A20 | D76 | H | D1 | H |
| 3752 | A20 | D56 | Ph | D1 | H |
| 3753 | A20 | D57 | Ph | D1 | H |
| 3754 | A20 | D60 | Ph | D1 | H |
| 3755 | A20 | D64 | Ph | D1 | H |
| 3756 | A20 | D65 | Ph | D1 | H |
| 3757 | A20 | D76 | Ph | H | H |
| 3758 | A20 | D56 | H | D1 | Ph |
| 3759 | A20 | D57 | H | D1 | Ph |
| 3760 | A20 | D60 | H | D1 | Ph |
| 3761 | A20 | D64 | H | D1 | Ph |
| 3762 | A20 | D65 | H | D1 | Ph |
| 3763 | A20 | D76 | H | D1 | Ph |
| 3764 | A20 | D56 | Ph | D1 | Ph |
| 3765 | A20 | D57 | Ph | D1 | Ph |
| 3766 | A20 | D60 | Ph | D1 | Ph |
| 3767 | A20 | D64 | Ph | D1 | Ph |
| 3768 | A20 | D65 | Ph | D1 | Ph |
| 3769 | A20 | D76 | Ph | D1 | Ph |
| 3770 | A21 | D1 | H | D56 | H |
| 3771 | A21 | D1 | H | D57 | H |
| 3772 | A21 | D1 | H | D60 | H |
| 3773 | A21 | D1 | H | D64 | H |
| 3774 | A21 | D1 | H | D65 | H |
| 3775 | A21 | D1 | H | D76 | H |
| 3776 | A21 | D1 | Ph | D56 | H |
| 3777 | A21 | D1 | Ph | D57 | H |
| 3778 | A21 | D1 | Ph | D60 | H |
| 3779 | A21 | D1 | Ph | D64 | H |
| 3780 | A21 | D1 | Ph | D65 | H |
| 3781 | A21 | D1 | Ph | D76 | H |
| 3782 | A21 | D1 | H | D56 | Ph |

TABLE 1-continued

| No. | $R^1$ | $R^2$ | $R^3$ | $R^4$ | $R^5$ |
|---|---|---|---|---|---|
| 3783 | A21 | D1 | H | D57 | Ph |
| 3784 | A21 | D1 | H | D60 | Ph |
| 3785 | A21 | D1 | H | D64 | Ph |
| 3786 | A21 | D1 | H | D65 | Ph |
| 3787 | A21 | D1 | H | D76 | Ph |
| 3788 | A21 | D1 | Ph | D56 | Ph |
| 3789 | A21 | D1 | Ph | D57 | Ph |
| 3790 | A21 | D1 | Ph | D60 | Ph |
| 3791 | A21 | D1 | Ph | D64 | Ph |
| 3792 | A21 | D1 | Ph | D65 | Ph |
| 3793 | A21 | D1 | Ph | D76 | Ph |
| 3794 | A21 | D56 | H | D1 | H |
| 3795 | A21 | D57 | H | D1 | H |
| 3796 | A21 | D60 | H | D1 | H |
| 3797 | A21 | D64 | H | D1 | H |
| 3798 | A21 | D65 | H | D1 | H |
| 3799 | A21 | D76 | H | D1 | H |
| 3800 | A21 | D56 | Ph | D1 | H |
| 3801 | A21 | D57 | Ph | D1 | H |
| 3802 | A21 | D60 | Ph | D1 | H |
| 3803 | A21 | D64 | Ph | D1 | H |
| 3804 | A21 | D65 | Ph | D1 | H |
| 3805 | A21 | D76 | Ph | D1 | H |
| 3806 | A21 | D56 | H | D1 | Ph |
| 3807 | A21 | D57 | H | D1 | Ph |
| 3808 | A21 | D60 | H | D1 | Ph |
| 3809 | A21 | D64 | H | D1 | Ph |
| 3810 | A21 | D65 | H | D1 | Ph |
| 3811 | A21 | D76 | H | D1 | Ph |
| 3812 | A21 | D56 | Ph | D1 | Ph |
| 3813 | A21 | D57 | Ph | D1 | Ph |
| 3814 | A21 | D60 | Ph | D1 | Ph |
| 3815 | A21 | D64 | Ph | D1 | Ph |
| 3816 | A21 | D65 | Ph | D1 | Ph |
| 3817 | A21 | D76 | Ph | D1 | Ph |
| 3818 | A1 | D56 | D56 | H | H |
| 3819 | A1 | D57 | D57 | H | H |
| 3820 | A1 | D60 | D60 | H | H |
| 3821 | A1 | D64 | D64 | H | H |
| 3822 | A1 | D65 | D65 | H | H |
| 3823 | A1 | D76 | D76 | H | H |
| 3824 | A1 | D56 | D56 | Ph | H |
| 3825 | A1 | D57 | D57 | Ph | H |
| 3826 | A1 | D60 | D60 | Ph | H |
| 3827 | A1 | D64 | D64 | Ph | H |
| 3828 | A1 | D65 | D65 | Ph | H |
| 3829 | A1 | D76 | D76 | Ph | H |
| 3830 | A1 | D56 | D56 | H | Ph |
| 3831 | A1 | D57 | D57 | H | Ph |
| 3832 | A1 | D60 | D60 | H | Ph |
| 3833 | A1 | D64 | D64 | H | Ph |
| 3834 | A1 | D65 | D65 | H | Ph |
| 3835 | A1 | D76 | D76 | H | Ph |
| 3836 | A1 | D56 | D56 | Ph | Ph |
| 3837 | A1 | D57 | D57 | Ph | Ph |
| 3838 | A1 | D60 | D60 | Ph | Ph |
| 3839 | A1 | D64 | D64 | Ph | Ph |
| 3840 | A1 | D65 | D65 | Ph | Ph |
| 3841 | A1 | D76 | D76 | Ph | Ph |
| 3842 | A20 | D56 | D56 | H | H |
| 3843 | A20 | D57 | D57 | H | H |
| 3844 | A20 | D60 | D60 | H | H |
| 3845 | A20 | D64 | D64 | H | H |
| 3846 | A20 | D65 | D65 | H | H |
| 3847 | A20 | D76 | D76 | H | H |
| 3848 | A20 | D56 | D56 | Ph | H |
| 3849 | A20 | D57 | D57 | Ph | H |
| 3850 | A20 | D60 | D60 | Ph | H |
| 3851 | A20 | D64 | D64 | Ph | H |
| 3852 | A20 | D65 | D65 | Ph | H |
| 3853 | A20 | D76 | D76 | Ph | H |
| 3854 | A20 | D56 | D56 | H | Ph |
| 3855 | A20 | D57 | D57 | H | Ph |
| 3856 | A20 | D60 | D60 | H | Ph |
| 3857 | A20 | D64 | D64 | H | Ph |
| 3858 | A20 | D65 | D65 | H | Ph |
| 3859 | A20 | D76 | D76 | H | Ph |
| 3860 | A20 | D56 | D56 | Ph | Ph |

TABLE 1-continued

| No. | $R^1$ | $R^2$ | $R^3$ | $R^4$ | $R^5$ |
|---|---|---|---|---|---|
| 3861 | A20 | D57 | D57 | Ph | Ph |
| 3862 | A20 | D60 | D60 | Ph | Ph |
| 3863 | A20 | D64 | D64 | Ph | Ph |
| 3864 | A20 | D65 | D65 | Ph | Ph |
| 3865 | A20 | D76 | D76 | Ph | Ph |
| 3866 | A21 | D56 | D56 | H | H |
| 3867 | A21 | D57 | D57 | H | H |
| 3868 | A21 | D60 | D60 | H | H |
| 3869 | A21 | D64 | D64 | H | H |
| 3870 | A21 | D65 | D65 | H | H |
| 3871 | A21 | D76 | D76 | H | H |
| 3872 | A21 | D56 | D56 | Ph | H |
| 3873 | A21 | D57 | D57 | Ph | H |
| 3874 | A21 | D60 | D60 | Ph | H |
| 3875 | A21 | D64 | D64 | Ph | H |
| 3876 | A21 | D65 | D65 | Ph | H |
| 3877 | A21 | D76 | D76 | Ph | H |
| 3878 | A21 | D56 | D56 | H | Ph |
| 3879 | A21 | D57 | D57 | H | Ph |
| 3880 | A21 | D60 | D60 | H | Ph |
| 3881 | A21 | D64 | D64 | H | Ph |
| 3882 | A21 | D65 | D65 | H | Ph |
| 3883 | A21 | D76 | D76 | H | Ph |
| 3884 | A21 | D56 | D56 | Ph | Ph |
| 3885 | A21 | D57 | D57 | Ph | Ph |
| 3886 | A21 | D60 | D60 | Ph | Ph |
| 3887 | A21 | D64 | D64 | Ph | Ph |
| 3888 | A21 | D65 | D65 | Ph | Ph |
| 3889 | A21 | D76 | D76 | Ph | Ph |
| 3890 | A1 | D1 | D56 | H | H |
| 3891 | A1 | D1 | D57 | H | H |
| 3892 | A1 | D1 | D60 | H | H |
| 3893 | A1 | D1 | D64 | H | H |
| 3894 | A1 | D1 | D65 | H | H |
| 3895 | A1 | D1 | D76 | H | H |
| 3896 | A1 | D1 | D56 | Ph | H |
| 3897 | A1 | D1 | D57 | Ph | H |
| 3898 | A1 | D1 | D60 | Ph | H |
| 3899 | A1 | D1 | D64 | Ph | H |
| 3900 | A1 | D1 | D65 | Ph | H |
| 3901 | A1 | D1 | D76 | Ph | H |
| 3902 | A1 | D1 | D56 | H | Ph |
| 3903 | A1 | D1 | D57 | H | Ph |
| 3904 | A1 | D1 | D60 | H | Ph |
| 3905 | A1 | D1 | D64 | H | Ph |
| 3906 | A1 | D1 | D65 | H | Ph |
| 3907 | A1 | D1 | D76 | H | Ph |
| 3908 | A1 | D1 | D76 | Ph | Ph |
| 3909 | A1 | D56 | D1 | H | H |
| 3910 | A1 | D57 | D1 | H | H |
| 3911 | A1 | D60 | D1 | H | H |
| 3912 | A1 | D64 | D1 | H | H |
| 3913 | A1 | D65 | D1 | H | H |
| 3914 | A1 | D76 | D1 | H | H |
| 3915 | A1 | D56 | D1 | Ph | H |
| 3916 | A1 | D57 | D1 | Ph | H |
| 3917 | A1 | D60 | D1 | Ph | H |
| 3918 | A1 | D64 | D1 | Ph | H |
| 3919 | A1 | D65 | D1 | Ph | H |
| 3920 | A1 | D76 | D1 | Ph | H |
| 3921 | A1 | D56 | D1 | H | Ph |
| 3922 | A1 | D57 | D1 | H | Ph |
| 3923 | A1 | D60 | D1 | H | Ph |
| 3924 | A1 | D64 | D1 | H | Ph |
| 3925 | A1 | D65 | D1 | H | Ph |
| 3926 | A1 | D76 | D1 | H | Ph |
| 3927 | A20 | D1 | D56 | H | H |
| 3928 | A20 | D1 | D57 | H | H |
| 3929 | A20 | D1 | D60 | H | H |
| 3930 | A20 | D1 | D64 | H | H |
| 3931 | A20 | D1 | D65 | H | H |
| 3932 | A20 | D1 | D76 | H | H |
| 3933 | A20 | D1 | D56 | Ph | H |
| 3934 | A20 | D1 | D57 | Ph | H |
| 3935 | A20 | D1 | D60 | Ph | H |
| 3936 | A20 | D1 | D64 | Ph | H |
| 3937 | A20 | D1 | D65 | Ph | H |
| 3938 | A20 | D1 | D76 | Ph | H |

TABLE 1-continued

| No. | $R^1$ | $R^2$ | $R^3$ | $R^4$ | $R^5$ |
|---|---|---|---|---|---|
| 3939 | A20 | D1 | D56 | H | Ph |
| 3940 | A20 | D1 | D57 | H | Ph |
| 3941 | A20 | D1 | D60 | H | Ph |
| 3942 | A20 | D1 | D64 | H | Ph |
| 3943 | A20 | D1 | D65 | H | Ph |
| 3944 | A20 | D1 | D76 | H | Ph |
| 3945 | A20 | D56 | D1 | H | H |
| 3946 | A20 | D57 | D1 | H | H |
| 3947 | A20 | D60 | D1 | H | H |
| 3948 | A20 | D64 | D1 | H | H |
| 3949 | A20 | D65 | D1 | H | H |
| 3950 | A20 | D76 | D1 | H | H |
| 3951 | A20 | D56 | D1 | Ph | H |
| 3952 | A20 | D57 | D1 | Ph | H |
| 3953 | A20 | D60 | D1 | Ph | H |
| 3954 | A20 | D64 | D1 | Ph | H |
| 3955 | A20 | D65 | D1 | Ph | H |
| 3956 | A20 | D76 | D1 | Ph | H |
| 3951 | A20 | D56 | D1 | H | Ph |
| 3958 | A20 | D57 | D1 | H | Ph |
| 3959 | A20 | D60 | D1 | H | Ph |
| 3960 | A20 | D64 | D1 | H | Ph |
| 3961 | A20 | D65 | D1 | H | Ph |
| 3962 | A20 | D76 | D1 | H | Ph |
| 3963 | A21 | D1 | D56 | H | H |
| 3964 | A21 | D1 | D57 | H | H |
| 3965 | A21 | D1 | D60 | H | H |
| 3966 | A21 | D1 | D64 | H | H |
| 3967 | A21 | D1 | D65 | H | H |
| 3968 | A21 | D1 | D76 | H | H |
| 3969 | A21 | D1 | D56 | Ph | H |
| 3970 | A21 | D1 | D57 | Ph | H |
| 3971 | A21 | D1 | D60 | Ph | H |
| 3972 | A21 | D1 | D64 | Ph | H |
| 3973 | A21 | D1 | D65 | Ph | H |
| 3974 | A21 | D1 | D76 | Ph | H |
| 3975 | A21 | D1 | D56 | H | Ph |
| 3976 | A21 | D1 | D57 | H | Ph |
| 3977 | A21 | D1 | D60 | H | Ph |
| 3978 | A21 | D1 | D64 | H | Ph |
| 3979 | A21 | D1 | D65 | H | Ph |
| 3980 | A21 | D1 | D76 | H | Ph |
| 3981 | A21 | D56 | D1 | H | H |
| 3982 | A21 | D57 | D1 | H | H |
| 3983 | A21 | D60 | D1 | H | H |
| 3984 | A21 | D64 | D1 | H | H |
| 3985 | A21 | D65 | D1 | H | H |
| 3988 | A21 | D76 | D1 | H | H |
| 3987 | A21 | D56 | D1 | Ph | H |
| 3988 | A21 | D57 | D1 | Ph | H |
| 3989 | A21 | D60 | D1 | Ph | H |
| 3990 | A21 | D64 | D1 | Ph | H |
| 3991 | A21 | D65 | D1 | Ph | H |
| 3992 | A21 | D76 | D1 | Ph | H |
| 3993 | A21 | D56 | D1 | H | Ph |
| 3994 | A21 | D57 | D1 | H | Ph |
| 3995 | A21 | D60 | D1 | H | Ph |
| 3996 | A21 | D64 | D1 | H | Ph |
| 3997 | A21 | D65 | D1 | H | Ph |
| 3998 | A21 | D76 | D1 | H | Ph |
| 3999 | A1 | D56 | H | H | D56 |
| 4000 | A1 | D57 | H | H | D57 |
| 4001 | A1 | D60 | H | H | D60 |
| 4002 | A1 | D64 | H | H | D64 |
| 4003 | A1 | D65 | H | H | D65 |
| 4004 | A1 | D76 | H | H | D76 |
| 4005 | A1 | D56 | Ph | H | D56 |
| 4006 | A1 | D57 | Ph | H | D57 |
| 4007 | A1 | D60 | Ph | H | D60 |
| 4008 | A1 | D64 | Ph | H | D64 |
| 4009 | A1 | D65 | Ph | H | D65 |
| 4010 | A1 | D76 | Ph | H | D76 |
| 4011 | A1 | D56 | H | Ph | D56 |
| 4012 | A1 | D57 | H | Ph | D57 |
| 4013 | A1 | D60 | H | Ph | D60 |
| 4014 | A1 | D64 | H | Ph | D64 |
| 4015 | A1 | D65 | H | Ph | D65 |
| 4016 | A1 | D76 | H | Ph | D76 |

TABLE 1-continued

| No. | $R^1$ | $R^2$ | $R^3$ | $R^4$ | $R^5$ |
|---|---|---|---|---|---|
| 4017 | A1 | D56 | Ph | Ph | D56 |
| 4018 | A1 | D57 | Ph | Ph | D57 |
| 4019 | A1 | D60 | Ph | Ph | D60 |
| 4020 | A1 | D64 | Ph | Ph | D64 |
| 4021 | A1 | D65 | Ph | Ph | D65 |
| 4022 | A1 | D76 | Ph | Ph | D76 |
| 4023 | A20 | D56 | H | H | D56 |
| 4024 | A20 | D57 | H | H | D57 |
| 4025 | A20 | D60 | H | H | D60 |
| 4026 | A20 | D64 | H | H | D64 |
| 4027 | A20 | D65 | H | H | D65 |
| 4028 | A20 | D76 | H | H | D76 |
| 4029 | A20 | D56 | Ph | H | D56 |
| 4030 | A20 | D57 | Ph | H | D57 |
| 4031 | A20 | D60 | Ph | H | D60 |
| 4032 | A20 | D64 | Ph | H | D64 |
| 4033 | A20 | D65 | Ph | H | D65 |
| 4034 | A20 | D76 | Ph | H | D76 |
| 4035 | A20 | D56 | H | Ph | D56 |
| 4036 | A20 | D57 | H | Ph | D57 |
| 4037 | A20 | D60 | H | Ph | D60 |
| 4038 | A20 | D64 | H | Ph | D64 |
| 4039 | A20 | D65 | H | Ph | D65 |
| 4040 | A20 | D76 | H | Ph | D76 |
| 4041 | A20 | D56 | Ph | Ph | D56 |
| 4042 | A20 | D57 | Ph | Ph | D57 |
| 4043 | A20 | D60 | Ph | Ph | D60 |
| 4044 | A20 | D64 | Ph | Ph | D64 |
| 4045 | A20 | D65 | Ph | Ph | D65 |
| 4046 | A20 | D76 | Ph | Ph | D76 |
| 4047 | A21 | D56 | H | H | D56 |
| 4048 | A21 | D57 | H | H | D57 |
| 4049 | A21 | D60 | H | H | D60 |
| 4050 | A21 | D64 | H | H | D64 |
| 4051 | A21 | D65 | H | H | D65 |
| 4052 | A21 | D76 | H | H | D76 |
| 4053 | A21 | D56 | Ph | H | D56 |
| 4054 | A21 | D57 | Ph | H | D57 |
| 4055 | A21 | D60 | Ph | H | D60 |
| 4056 | A21 | D64 | Ph | H | D64 |
| 4057 | A21 | D65 | Ph | H | D65 |
| 4058 | A21 | D76 | Ph | H | D76 |
| 4059 | A21 | D56 | H | Ph | D56 |
| 4060 | A21 | D57 | H | Ph | D57 |
| 4061 | A21 | D60 | H | Ph | D60 |
| 4062 | A21 | D64 | H | Ph | D64 |
| 4063 | A21 | D65 | H | Ph | D65 |
| 4064 | A21 | D76 | H | Ph | D76 |
| 4065 | A21 | D56 | Ph | Ph | D56 |
| 4066 | A21 | D57 | Ph | Ph | D57 |
| 4067 | A21 | D60 | Ph | Ph | D60 |
| 4068 | A21 | D64 | Ph | Ph | D64 |
| 4089 | A21 | D65 | Ph | Ph | D65 |
| 4070 | A21 | D76 | Ph | Ph | D76 |
| 4071 | A1 | D1 | H | H | D56 |
| 4072 | A1 | D1 | H | H | D57 |
| 4073 | A1 | D1 | H | H | D60 |
| 4074 | A1 | D1 | H | H | D64 |
| 4075 | A1 | D1 | H | H | D65 |
| 4076 | A1 | D1 | H | H | D76 |
| 4077 | A1 | D1 | Ph | H | D56 |
| 4078 | A1 | D1 | Ph | H | D57 |
| 4079 | A1 | D1 | Ph | H | D60 |
| 4080 | A1 | D1 | Ph | H | D64 |
| 4081 | A1 | D1 | Ph | H | D65 |
| 4082 | A1 | D1 | Ph | H | D76 |
| 4083 | A1 | D1 | H | Ph | D56 |
| 4084 | A1 | D1 | H | Ph | D57 |
| 4085 | A1 | D1 | H | Ph | D60 |
| 4086 | A1 | D1 | H | Ph | D64 |
| 4087 | A1 | D1 | H | Ph | D65 |
| 4088 | A1 | D1 | H | Ph | D76 |
| 4089 | A1 | D56 | H | H | D1 |
| 4090 | A1 | D57 | H | H | D1 |
| 4091 | A1 | D60 | H | H | D1 |
| 4092 | A1 | D64 | H | H | D1 |
| 4093 | A1 | D65 | H | H | D1 |
| 4094 | A1 | D76 | H | H | D1 |

TABLE 1-continued

| No. | $R^1$ | $R^2$ | $R^3$ | $R^4$ | $R^5$ |
|---|---|---|---|---|---|
| 4095 | A1 | D56 | Ph | H | D1 |
| 4096 | A1 | D57 | Ph | H | D1 |
| 4097 | A1 | D60 | Ph | H | D1 |
| 4098 | A1 | D64 | Ph | H | D1 |
| 4099 | A1 | D65 | Ph | H | D1 |
| 4100 | A1 | D76 | Ph | H | D1 |
| 4101 | A1 | D56 | H | Ph | D1 |
| 4102 | A1 | D57 | H | Ph | D1 |
| 4103 | A1 | D60 | H | Ph | D1 |
| 4104 | A1 | D64 | H | Ph | D1 |
| 4105 | A1 | D65 | H | Ph | D1 |
| 4106 | A1 | D76 | H | Ph | D1 |
| 4107 | A20 | D1 | H | H | D56 |
| 4108 | A20 | D1 | H | H | D57 |
| 4109 | A20 | D1 | H | H | D60 |
| 4110 | A20 | D1 | H | H | D64 |
| 4111 | A20 | D1 | H | H | D65 |
| 4112 | A20 | D2 | H | H | D76 |
| 4113 | A20 | D1 | Ph | H | D56 |
| 4114 | A20 | D1 | Ph | H | D57 |
| 4115 | A20 | D1 | Ph | H | D60 |
| 4116 | A20 | D1 | Ph | H | D64 |
| 4117 | A20 | D1 | Ph | H | D65 |
| 4118 | A20 | D1 | Ph | H | D76 |
| 4119 | A20 | D1 | H | Ph | D56 |
| 4120 | A20 | D1 | H | Ph | D57 |
| 4121 | A20 | D1 | H | Ph | D60 |
| 4122 | A20 | D1 | H | Ph | D64 |
| 4123 | A20 | D1 | H | Ph | D65 |
| 4124 | A20 | D1 | H | Ph | D76 |
| 4125 | A20 | D56 | H | H | D1 |
| 4126 | A20 | D57 | H | H | D1 |
| 4127 | A20 | D60 | H | H | D1 |
| 4128 | A20 | D64 | H | H | D1 |
| 4129 | A20 | D65 | H | H | D1 |
| 4130 | A20 | D76 | H | H | D1 |
| 4131 | A20 | D56 | Ph | H | D1 |
| 4132 | A20 | D57 | Ph | H | D1 |
| 4133 | A20 | D60 | Ph | H | D1 |
| 4134 | A20 | D64 | Ph | H | D1 |
| 4135 | A20 | D65 | Ph | H | D1 |
| 4136 | A20 | D76 | Ph | H | D1 |
| 4137 | A20 | D56 | H | Ph | D1 |
| 4138 | A20 | D57 | H | Ph | D1 |
| 4139 | A20 | D60 | H | Ph | D1 |
| 4140 | A20 | D64 | H | Ph | D1 |
| 4141 | A20 | D65 | H | Ph | D1 |
| 4142 | A20 | D76 | H | Ph | D1 |
| 4143 | A21 | D1 | H | H | D56 |
| 4144 | A21 | D1 | H | H | D57 |
| 4145 | A21 | D1 | H | H | D60 |
| 4146 | A21 | D1 | H | H | D64 |
| 4147 | A21 | D1 | H | H | D65 |
| 4148 | A21 | D1 | H | H | D76 |
| 4149 | A21 | D1 | Ph | H | D56 |
| 4150 | A21 | D1 | Ph | H | D57 |
| 4151 | A21 | D1 | Ph | H | D60 |
| 4152 | A21 | D1 | Ph | H | D64 |
| 4153 | A21 | D1 | Ph | H | D65 |
| 4154 | A21 | D1 | Ph | H | D76 |
| 4155 | A21 | D1 | H | Ph | D56 |
| 4156 | A21 | D1 | H | Ph | D57 |
| 4157 | A21 | D1 | H | Ph | D60 |
| 4158 | A21 | D1 | H | Ph | D64 |
| 4159 | A21 | D1 | H | Ph | D65 |
| 4160 | A21 | D1 | H | Ph | D76 |
| 4161 | A21 | D56 | H | H | D1 |
| 4162 | A21 | D57 | H | H | D1 |
| 4163 | A21 | D60 | H | H | D1 |
| 4164 | A21 | D64 | H | H | D1 |
| 4165 | A21 | D65 | H | H | D1 |
| 4166 | A21 | D76 | H | H | D1 |
| 4167 | A21 | D56 | Ph | H | D1 |
| 4168 | A21 | D57 | Ph | I | D1 |
| 4169 | A21 | D60 | Ph | H | D1 |
| 4170 | A21 | D64 | Ph | H | D1 |
| 4171 | A21 | D65 | Ph | H | D1 |
| 4172 | A21 | D76 | Ph | H | D1 |

TABLE 1-continued

| No. | $R^1$ | $R^2$ | $R^3$ | $R^4$ | $R^5$ |
|---|---|---|---|---|---|
| 4173 | A21 | D56 | H | Ph | D1 |
| 4174 | A21 | D57 | H | Ph | D1 |
| 4175 | A21 | D60 | H | Ph | D1 |
| 4176 | A21 | D64 | H | Ph | D1 |
| 4177 | A21 | D65 | H | Ph | D1 |
| 4178 | A21 | D76 | H | Ph | D1 |
| 4179 | A1 | D56 | D56 | H | D56 |
| 4180 | A1 | D57 | D57 | H | D57 |
| 4181 | A1 | D60 | D60 | H | D60 |
| 4182 | A1 | D64 | D64 | H | D64 |
| 4183 | A1 | D65 | D65 | H | D65 |
| 4184 | A1 | D76 | D76 | H | D76 |
| 4185 | A1 | D56 | D56 | Ph | D56 |
| 4186 | A1 | D57 | D57 | Ph | D57 |
| 4187 | A1 | D60 | D60 | Ph | D60 |
| 4188 | A1 | D64 | D84 | Ph | D64 |
| 4189 | A1 | D65 | D65 | Ph | D65 |
| 4190 | A1 | D76 | D76 | Ph | D76 |
| 4191 | A20 | D56 | D56 | H | D56 |
| 4192 | A20 | D57 | D57 | H | D57 |
| 4193 | A20 | D60 | D60 | H | D60 |
| 4194 | A20 | D64 | D84 | H | D64 |
| 4195 | A20 | D65 | D65 | H | D65 |
| 4196 | A20 | D76 | D76 | H | D76 |
| 4197 | A20 | D56 | D56 | Ph | D56 |
| 4198 | A20 | D57 | D57 | Ph | D57 |
| 4199 | A20 | D60 | D60 | Ph | D60 |
| 4200 | A20 | D64 | D64 | Ph | D64 |
| 4201 | A20 | D65 | D65 | Ph | D65 |
| 4202 | A20 | D76 | D76 | Ph | D76 |
| 4203 | A21 | D56 | D56 | H | D56 |
| 4204 | A21 | D57 | D57 | H | D57 |
| 4205 | A21 | D60 | D60 | H | D60 |
| 4206 | A21 | D64 | D64 | H | D64 |
| 4207 | A21 | D65 | D65 | H | D65 |
| 4208 | A21 | D76 | D76 | H | D76 |
| 4209 | A21 | D56 | D56 | Ph | D56 |
| 4210 | A21 | D57 | D57 | Ph | D57 |
| 4211 | A21 | D60 | D60 | Ph | D60 |
| 4212 | A21 | D64 | D64 | Ph | D64 |
| 4213 | A21 | D65 | D65 | Ph | D65 |
| 4214 | A21 | D76 | D76 | Ph | D76 |
| 4215 | A1 | D1 | D56 | H | D56 |
| 4216 | A1 | D1 | D57 | H | D57 |
| 4217 | A1 | D1 | D60 | H | D60 |
| 4218 | A1 | D1 | D64 | H | D64 |
| 4219 | A1 | D1 | D65 | H | D65 |
| 4220 | A1 | D1 | D76 | H | D76 |
| 4221 | A1 | D1 | D56 | Ph | D56 |
| 4222 | A1 | D1 | D57 | Ph | D57 |
| 4223 | A1 | 01 | D60 | Ph | D60 |
| 4224 | A1 | D1 | D64 | Ph | D64 |
| 4225 | A1 | D1 | D65 | Ph | D65 |
| 4226 | A1 | D1 | D76 | Ph | D76 |
| 4227 | A1 | D56 | D1 | H | D56 |
| 4228 | A1 | D57 | D1 | H | D57 |
| 4229 | A1 | D60 | D1 | H | D60 |
| 4230 | A1 | D64 | D1 | H | D64 |
| 4231 | A1 | D65 | D1 | H | D65 |
| 4232 | A1 | D76 | D1 | H | D76 |
| 4233 | A1 | D56 | D1 | Ph | D56 |
| 4234 | A1 | D57 | D1 | Ph | D57 |
| 4235 | A1 | D60 | D1 | Ph | D60 |
| 4236 | A1 | D64 | D1 | Ph | D64 |
| 4237 | A1 | D65 | D1 | Ph | D65 |
| 4238 | A1 | D76 | D1 | Ph | D76 |
| 4239 | A1 | D56 | D56 | H | D1 |
| 4240 | A1 | D57 | D57 | H | D1 |
| 4241 | A1 | D60 | D60 | H | D1 |
| 4242 | A1 | D64 | D64 | H | D1 |
| 4243 | A1 | D65 | D65 | H | D1 |
| 4244 | A1 | D76 | D76 | H | D1 |
| 4245 | A1 | D56 | D56 | Ph | D1 |
| 4246 | A1 | D57 | D57 | Ph | D1 |
| 4247 | A1 | D60 | D60 | Ph | D1 |
| 4248 | A1 | D64 | D64 | Ph | D1 |
| 4249 | A1 | D65 | D65 | Ph | D1 |
| 4250 | A1 | D76 | D76 | Ph | D1 |

TABLE 1-continued

| No. | $R^1$ | $R^2$ | $R^3$ | $R^4$ | $R^5$ |
|---|---|---|---|---|---|
| 4251 | A20 | D1 | D56 | H | D56 |
| 4252 | A20 | D1 | D57 | H | D57 |
| 4253 | A20 | D1 | D60 | H | D60 |
| 4254 | A20 | D1 | D64 | H | D64 |
| 4255 | A20 | D1 | D65 | H | D65 |
| 4256 | A20 | D1 | D76 | H | D76 |
| 4257 | A20 | D1 | D56 | Ph | D56 |
| 4258 | A20 | D1 | D57 | Ph | D57 |
| 4259 | A20 | D1 | D60 | Ph | D60 |
| 4260 | A20 | D1 | D64 | Ph | D64 |
| 4261 | A20 | D1 | D65 | Ph | D65 |
| 4262 | A20 | D1 | D76 | Ph | D76 |
| 4263 | A20 | D56 | D1 | H | D56 |
| 4264 | A20 | D57 | D1 | H | D57 |
| 4265 | A20 | D60 | D1 | H | D60 |
| 4266 | A20 | D64 | D1 | H | D64 |
| 4267 | A20 | D65 | D1 | H | D65 |
| 4268 | A20 | D76 | D1 | H | D76 |
| 4269 | A20 | D56 | D1 | Ph | D56 |
| 4270 | A20 | D57 | D1 | Ph | D57 |
| 4271 | A20 | D60 | D1 | Ph | D60 |
| 4272 | A20 | D64 | D1 | Ph | D64 |
| 4273 | A20 | D65 | D1 | Ph | D65 |
| 4274 | A20 | D76 | D1 | Ph | D76 |
| 4275 | A20 | D56 | D56 | H | D1 |
| 4276 | A20 | D57 | D57 | H | D1 |
| 4277 | A20 | D60 | D60 | H | D1 |
| 4278 | A20 | D64 | D64 | H | D1 |
| 4279 | A20 | D65 | D65 | H | D1 |
| 4280 | A20 | D76 | D76 | H | D1 |
| 4281 | A20 | D56 | D56 | Ph | D1 |
| 4282 | A20 | D57 | D57 | Ph | D1 |
| 4283 | A20 | D60 | D60 | Ph | D1 |
| 4284 | A20 | D64 | D64 | Ph | D1 |
| 4285 | A20 | D65 | D65 | Ph | D1 |
| 4286 | A20 | D76 | D76 | Ph | D1 |
| 4287 | A21 | D1 | D56 | H | D56 |
| 4288 | A21 | D1 | D57 | H | D57 |
| 4289 | A21 | D1 | D60 | H | D60 |
| 4290 | A21 | D1 | D64 | H | D64 |
| 4291 | A21 | D1 | D65 | H | D65 |
| 4292 | A21 | D1 | D76 | H | D76 |
| 4293 | A21 | D1 | D56 | Ph | D56 |
| 4294 | A21 | D1 | D57 | Ph | D57 |
| 4295 | A21 | D1 | D60 | Ph | D60 |
| 4296 | A21 | D1 | D64 | Ph | D64 |
| 4297 | A21 | D1 | D65 | Ph | D65 |
| 4298 | A21 | D1 | D76 | Ph | D76 |
| 4299 | A21 | D56 | D1 | H | D56 |
| 4300 | A21 | D57 | D1 | H | D57 |
| 4301 | A21 | D60 | D1 | H | D60 |
| 4302 | A21 | D64 | D1 | H | D64 |
| 4303 | A21 | D65 | D1 | H | D65 |
| 4304 | A21 | D76 | D1 | H | D76 |
| 4305 | A21 | D56 | D1 | Ph | D56 |
| 4306 | A21 | D57 | D1 | Ph | D57 |
| 4307 | A21 | D60 | D1 | Ph | D60 |
| 4308 | A21 | D64 | D1 | Ph | D64 |
| 4309 | A21 | D65 | D1 | Ph | D65 |
| 4310 | A21 | D76 | D1 | Ph | D76 |
| 4311 | A21 | D56 | D56 | H | D1 |
| 4312 | A21 | D57 | D57 | H | D1 |
| 4313 | A21 | D60 | D60 | H | D1 |
| 4314 | A21 | D64 | D64 | H | D1 |
| 4315 | A21 | D65 | D65 | H | D1 |
| 4316 | A21 | D76 | D76 | H | D1 |
| 4317 | A21 | D56 | D56 | Ph | D1 |
| 4318 | A21 | D57 | D57 | Ph | D1 |
| 4319 | A21 | D60 | D60 | Ph | D1 |
| 4320 | A21 | D64 | D64 | Ph | D1 |
| 4321 | A21 | D65 | D65 | Ph | D1 |
| 4322 | A21 | D76 | D76 | Ph | D1 |
| 4323 | A1 | D56 | H | D56 | D56 |
| 4324 | A1 | D57 | H | D57 | D57 |
| 4325 | A1 | D60 | H | D60 | D60 |
| 4326 | A1 | D64 | H | D64 | D64 |
| 4327 | A1 | D65 | H | D65 | D65 |
| 4328 | A1 | D76 | H | D76 | D76 |

TABLE 1-continued

| No. | $R^1$ | $R^2$ | $R^3$ | $R^4$ | $R^5$ |
|---|---|---|---|---|---|
| 4329 | A1 | D56 | Ph | D56 | D56 |
| 4330 | A1 | D57 | Ph | D57 | D57 |
| 4331 | A1 | D60 | Ph | D60 | D60 |
| 4332 | A1 | D64 | Ph | D64 | D64 |
| 4333 | A1 | D65 | Ph | D65 | D65 |
| 4334 | A1 | D76 | Ph | D76 | D76 |
| 4335 | A20 | D56 | H | D56 | D56 |
| 4336 | A20 | D57 | H | D57 | D57 |
| 4337 | A20 | D60 | H | D60 | D60 |
| 4338 | A20 | D64 | H | D64 | D64 |
| 4339 | A20 | D65 | H | D65 | D65 |
| 4340 | A20 | D76 | H | D76 | D76 |
| 4341 | A20 | D56 | Ph | D56 | D56 |
| 4342 | A20 | D57 | Ph | D57 | D57 |
| 4343 | A20 | D60 | Ph | D60 | D60 |
| 4344 | A20 | D64 | Ph | D64 | D64 |
| 4345 | A20 | D65 | Ph | D65 | D65 |
| 4346 | A20 | D76 | Ph | D76 | D76 |
| 4347 | A21 | D56 | H | D56 | D56 |
| 4348 | A21 | D57 | H | D57 | D57 |
| 4349 | A21 | D60 | H | D60 | D60 |
| 4350 | A21 | D64 | H | D64 | D64 |
| 4351 | A21 | D65 | H | D65 | D65 |
| 4352 | A21 | D76 | H | D76 | D76 |
| 4353 | A21 | D56 | Ph | D56 | D56 |
| 4354 | A21 | D57 | Ph | D57 | D57 |
| 4355 | A21 | D60 | Ph | D60 | D60 |
| 4356 | A21 | D64 | Ph | D64 | D64 |
| 4357 | A21 | D65 | Ph | D65 | D65 |
| 4358 | A21 | D76 | Ph | D76 | D76 |
| 4359 | A1 | D1 | H | D56 | D56 |
| 4360 | A1 | D1 | H | D57 | D57 |
| 4361 | A1 | D1 | H | D60 | D60 |
| 4362 | A1 | D1 | H | D64 | D64 |
| 4363 | A1 | D1 | H | D65 | D65 |
| 4364 | A1 | D1 | H | D76 | D76 |
| 4365 | A1 | D1 | Ph | D56 | D56 |
| 4366 | A1 | D1 | Ph | D57 | D57 |
| 4367 | A1 | D1 | Ph | D60 | D60 |
| 4368 | A1 | D1 | Ph | D64 | D64 |
| 4369 | A1 | D1 | Ph | D65 | D65 |
| 4370 | A1 | D1 | Ph | D76 | D76 |
| 4371 | A1 | D56 | H | D1 | D56 |
| 4372 | A1 | D57 | H | D1 | D57 |
| 4373 | A1 | D60 | H | D1 | D60 |
| 4374 | A1 | D64 | H | D1 | D84 |
| 4375 | A1 | D65 | H | D1 | D65 |
| 4376 | A1 | D76 | H | D1 | D76 |
| 4377 | A1 | D56 | Ph | D1 | D56 |
| 4378 | A1 | D57 | Ph | D1 | D57 |
| 4379 | A1 | D60 | Ph | D1 | D60 |
| 4380 | A1 | D64 | Ph | D1 | D64 |
| 4381 | A1 | D65 | Ph | D1 | D65 |
| 4382 | A1 | D76 | Ph | D1 | D76 |
| 4383 | A1 | D56 | H | D56 | D1 |
| 4384 | A1 | D57 | H | D57 | D1 |
| 4385 | A1 | D60 | H | D60 | D1 |
| 4386 | A1 | D64 | H | D64 | D1 |
| 4387 | A1 | D65 | H | D65 | D1 |
| 4388 | A1 | D76 | H | D76 | D1 |
| 4389 | A1 | D56 | Ph | D56 | D1 |
| 4390 | A1 | D57 | Ph | D57 | D1 |
| 4391 | A1 | D60 | Ph | D60 | D1 |
| 4392 | A1 | D64 | Ph | D64 | D1 |
| 4393 | A1 | D65 | Ph | D65 | D1 |
| 4394 | A1 | D76 | Ph | D76 | D1 |
| 4395 | A20 | D1 | H | D56 | D56 |
| 4396 | A20 | D1 | H | D57 | D57 |
| 4397 | A20 | D1 | H | D60 | D60 |
| 4398 | A20 | D1 | H | D64 | D64 |
| 4399 | A20 | D1 | H | D65 | D65 |
| 4400 | A20 | D1 | H | D76 | D76 |
| 4401 | A20 | D1 | Ph | D56 | D56 |
| 4402 | A20 | D1 | Ph | D57 | D57 |
| 4403 | A20 | D1 | Ph | D60 | D60 |
| 4404 | A20 | D1 | Ph | D64 | D64 |
| 4405 | A20 | D1 | Ph | D65 | D65 |
| 4406 | A20 | D1 | Ph | D76 | D76 |

TABLE 1-continued

| No. | $R^1$ | $R^2$ | $R^3$ | $R^4$ | $R^5$ |
|---|---|---|---|---|---|
| 4407 | A20 | D56 | H | D1 | D56 |
| 4408 | A20 | D57 | H | D1 | D57 |
| 4409 | A20 | D60 | H | D1 | D60 |
| 4410 | A20 | D64 | H | D1 | D64 |
| 4411 | A20 | D65 | H | D1 | D65 |
| 4412 | A20 | D76 | H | D1 | D76 |
| 4413 | A20 | D56 | Ph | D1 | D56 |
| 4414 | A20 | D57 | Ph | D1 | D57 |
| 4415 | A20 | D60 | Ph | D1 | D60 |
| 4416 | A20 | D64 | Ph | D1 | D64 |
| 4417 | A20 | D65 | Ph | D1 | D65 |
| 4418 | A20 | D76 | Ph | D1 | D76 |
| 4419 | A20 | D56 | H | D56 | D1 |
| 4420 | A20 | D57 | H | D57 | D1 |
| 4421 | A20 | D60 | H | D60 | D1 |
| 4422 | A20 | D64 | H | D64 | D1 |
| 4423 | A20 | D65 | H | D65 | D1 |
| 4424 | A20 | D76 | H | D76 | D1 |
| 4425 | A20 | D56 | Ph | D56 | D1 |
| 4426 | A20 | D57 | Ph | D57 | D1 |
| 4427 | A20 | D60 | Ph | D60 | D1 |
| 4428 | A20 | D64 | Ph | D64 | D1 |
| 4429 | A20 | D65 | Ph | D65 | D1 |
| 4430 | A20 | D76 | Ph | D76 | D1 |
| 4431 | A21 | D1 | H | D56 | D56 |
| 4432 | A21 | D1 | H | D57 | D57 |
| 4433 | A21 | D1 | H | D60 | D60 |
| 4434 | A21 | D1 | H | D64 | D64 |
| 4435 | A21 | D1 | H | D65 | D65 |
| 4436 | A21 | D1 | H | D76 | D76 |
| 4437 | A21 | D1 | Ph | D56 | D56 |
| 4438 | A21 | D1 | Ph | D57 | D57 |
| 4439 | A21 | D1 | Ph | D60 | D60 |
| 4440 | A21 | D1 | Ph | D64 | D64 |
| 4441 | A21 | D1 | Ph | D65 | D65 |
| 4442 | A21 | D1 | Ph | D76 | D76 |
| 4443 | A21 | D56 | H | D1 | D56 |
| 4444 | A21 | D57 | H | D1 | D57 |
| 4445 | A21 | D60 | H | D1 | D60 |
| 4446 | A21 | D64 | H | D1 | D64 |
| 4447 | A21 | D65 | H | D1 | D65 |
| 4448 | A21 | D76 | H | D1 | D76 |
| 4449 | A21 | D56 | Ph | D1 | D56 |
| 4450 | A21 | D57 | Ph | D1 | D57 |
| 4451 | A21 | D60 | Ph | D1 | D60 |
| 4452 | A21 | D64 | Ph | D1 | D64 |
| 4453 | A21 | D65 | Ph | D1 | D65 |
| 4454 | A21 | D76 | Ph | D1 | D76 |
| 4455 | A21 | D56 | H | D56 | D1 |
| 4456 | A21 | D57 | H | D57 | D1 |
| 4457 | A21 | D60 | H | D60 | D1 |
| 4458 | A21 | D64 | H | D64 | D1 |
| 4459 | A21 | D65 | H | D65 | D1 |
| 4460 | A21 | D76 | H | D76 | D1 |
| 4461 | A21 | D56 | Ph | D56 | D1 |
| 4462 | A21 | D57 | Ph | D57 | D1 |
| 4463 | A21 | D60 | Ph | D60 | D1 |
| 4464 | A21 | D64 | Ph | D64 | D1 |
| 4465 | A21 | D65 | Ph | D65 | D1 |
| 4466 | A21 | D76 | Ph | D76 | D1 |
| 4467 | D56 | A1 | H | D56 | D56 |
| 4468 | D57 | A1 | H | D57 | D57 |
| 4469 | D60 | A1 | H | D60 | D60 |
| 4470 | D64 | A1 | H | D64 | D64 |
| 4471 | D65 | A1 | H | D65 | D65 |
| 4472 | D76 | A1 | H | D76 | D76 |
| 4473 | D56 | A1 | Ph | D56 | D56 |
| 4474 | D57 | A1 | Ph | D57 | D57 |
| 4475 | D60 | A1 | Ph | D60 | D60 |
| 4476 | D64 | A1 | Ph | D64 | D64 |
| 4477 | D65 | A1 | Ph | D65 | D65 |
| 4478 | D76 | A1 | Ph | D76 | D76 |
| 4479 | D56 | A20 | H | D56 | D56 |
| 4480 | D57 | A20 | H | D57 | D57 |
| 4481 | D60 | A20 | H | D60 | D60 |
| 4482 | D64 | A20 | H | D64 | D64 |
| 4483 | D65 | A20 | H | D65 | D65 |
| 4484 | D76 | A20 | H | D76 | D76 |

TABLE 1-continued

| No. | $R^1$ | $R^2$ | $R^3$ | $R^4$ | $R^5$ |
|---|---|---|---|---|---|
| 4485 | D56 | A20 | Ph | D56 | D56 |
| 4486 | D57 | A20 | Ph | D57 | D57 |
| 4487 | D60 | A20 | Ph | D60 | D60 |
| 4488 | D64 | A20 | Ph | D64 | D64 |
| 4489 | D65 | A20 | Ph | D65 | D65 |
| 4490 | D76 | A20 | Ph | D76 | D76 |
| 4491 | D56 | A21 | H | D56 | D56 |
| 4492 | D57 | A21 | H | D57 | D57 |
| 4493 | D60 | A21 | H | D60 | D60 |
| 4494 | D64 | A21 | H | D64 | D64 |
| 4495 | D65 | A21 | H | D65 | D65 |
| 4496 | D76 | A21 | H | D76 | D76 |
| 4497 | D56 | A21 | Ph | D56 | D56 |
| 4498 | D57 | A21 | Ph | D57 | D57 |
| 4499 | D60 | A21 | Ph | D60 | D60 |
| 4500 | D64 | A21 | Ph | D64 | D64 |
| 4501 | D65 | A21 | Ph | D65 | D65 |
| 4502 | D76 | A21 | Ph | D76 | D76 |
| 4503 | D1 | A1 | H | D56 | D56 |
| 4504 | D1 | A1 | H | D57 | D57 |
| 4505 | D1 | A1 | H | D60 | D60 |
| 4506 | D1 | A1 | H | D64 | D64 |
| 4507 | D1 | A1 | H | D65 | D65 |
| 4508 | D1 | A1 | H | D76 | D76 |
| 4509 | D1 | A1 | Ph | D56 | D56 |
| 4510 | D1 | A1 | Ph | D57 | D57 |
| 4511 | D1 | A1 | Ph | D60 | D60 |
| 4512 | D1 | A1 | Ph | D64 | D64 |
| 4513 | D1 | A1 | Ph | D65 | D65 |
| 4514 | D1 | A1 | Ph | D76 | D76 |
| 4515 | D56 | A1 | H | D1 | D56 |
| 4516 | D57 | A1 | H | D1 | D57 |
| 4517 | D60 | A1 | H | D1 | D60 |
| 4518 | D64 | A1 | H | D1 | D64 |
| 4519 | D65 | A1 | H | D1 | D65 |
| 4520 | D76 | A1 | H | D1 | D76 |
| 4521 | D56 | A1 | Ph | D1 | D56 |
| 4522 | D57 | A1 | Ph | D1 | D57 |
| 4523 | D60 | A1 | Ph | D1 | D60 |
| 4524 | D64 | A1 | Ph | D1 | D64 |
| 4525 | D65 | A1 | Ph | D1 | D65 |
| 4526 | D76 | A1 | Ph | D1 | D76 |
| 4527 | D56 | A1 | H | D56 | D1 |
| 4528 | D57 | A1 | H | D57 | D1 |
| 4529 | D60 | A1 | H | D60 | D1 |
| 4530 | D64 | A1 | H | D64 | D1 |
| 4531 | D65 | A1 | H | D65 | D1 |
| 4532 | D76 | A1 | H | D76 | D1 |
| 4533 | D56 | A1 | Ph | D56 | D1 |
| 4534 | D57 | A1 | Ph | D57 | D1 |
| 4535 | D60 | A1 | Ph | D60 | D1 |
| 4536 | D64 | A1 | Ph | D64 | D1 |
| 4537 | D65 | A1 | Ph | D65 | D1 |
| 4538 | D76 | A1 | Ph | D76 | D1 |
| 4539 | D1 | A20 | H | D56 | D56 |
| 4540 | D1 | A20 | H | D57 | D57 |
| 4541 | D1 | A20 | H | D60 | D60 |
| 4542 | D1 | A20 | H | D64 | D64 |
| 4543 | D1 | A20 | H | D65 | D65 |
| 4544 | D1 | A20 | H | D76 | D76 |
| 4545 | D1 | A20 | Ph | D56 | D56 |
| 4546 | D1 | A20 | Ph | D57 | D57 |
| 4547 | D1 | A20 | Ph | D60 | D60 |
| 4548 | D1 | A20 | Ph | D64 | D64 |
| 4549 | D1 | A20 | Ph | D65 | D65 |
| 4550 | D1 | A20 | Ph | D76 | D76 |
| 4551 | D56 | A20 | H | D1 | D56 |
| 4552 | D57 | A20 | H | D1 | D57 |
| 4553 | D60 | A20 | H | D1 | D60 |
| 4554 | D64 | A20 | H | D1 | D64 |
| 4555 | D65 | A20 | H | D1 | D65 |
| 4556 | D76 | A20 | H | D1 | D76 |
| 4557 | D56 | A20 | Ph | D1 | D56 |
| 4558 | D57 | A20 | Ph | D1 | D57 |
| 4559 | D60 | A20 | Ph | D1 | D60 |
| 4560 | D64 | A20 | Ph | D1 | D64 |
| 4561 | D65 | A20 | Ph | D1 | D65 |
| 4562 | D76 | A20 | Ph | D1 | D76 |

TABLE 1-continued

| No. | $R^1$ | $R^2$ | $R^3$ | $R^4$ | $R^5$ |
|---|---|---|---|---|---|
| 4583 | D56 | A20 | H | D56 | D1 |
| 4564 | D57 | A20 | H | D57 | D1 |
| 4565 | D60 | A20 | H | D60 | D1 |
| 4568 | D64 | A20 | H | D64 | D1 |
| 4567 | D65 | A20 | H | D65 | D1 |
| 4568 | D76 | A20 | H | D76 | D1 |
| 4589 | D56 | A20 | Ph | D56 | D1 |
| 4570 | D57 | A20 | Ph | D57 | D1 |
| 4571 | D60 | A20 | Ph | D60 | D1 |
| 4572 | D64 | A20 | Ph | D64 | D1 |
| 4573 | D65 | A20 | Ph | D65 | D1 |
| 4574 | D76 | A20 | Ph | D76 | D1 |
| 4575 | D1 | A21 | H | D56 | D56 |
| 4576 | D1 | A21 | H | D57 | D57 |
| 4577 | D1 | A21 | H | D60 | D60 |
| 4578 | D1 | A21 | H | D64 | D64 |
| 4579 | D1 | A21 | H | D65 | D65 |
| 4580 | D1 | A21 | H | D76 | D76 |
| 4581 | D1 | A21 | Ph | D56 | D56 |
| 4582 | D1 | A21 | Ph | D57 | D57 |
| 4583 | D1 | A21 | Ph | D60 | D60 |
| 4584 | D1 | A21 | Ph | D64 | D64 |
| 4585 | D1 | A21 | Ph | D65 | D65 |
| 4586 | D1 | A21 | Ph | D76 | D76 |
| 4587 | D56 | A21 | H | D1 | D56 |
| 4588 | D57 | A21 | H | D1 | D57 |
| 4589 | D60 | A22 | H | D1 | D60 |
| 4590 | D64 | A21 | H | D1 | D64 |
| 4591 | D65 | A21 | H | D1 | D65 |
| 4592 | D76 | A21 | H | D1 | D76 |
| 4593 | D56 | A21 | Ph | D1 | D56 |
| 4594 | D57 | A21 | Ph | D1 | D57 |
| 4595 | D60 | A21 | Ph | D1 | D60 |
| 4596 | D64 | A21 | Ph | D1 | D64 |
| 4597 | D65 | A21 | Ph | D1 | D65 |
| 4598 | D76 | A21 | Ph | D1 | D76 |
| 4599 | D56 | A21 | H | D56 | D1 |
| 4600 | D57 | A21 | H | D57 | D1 |
| 4601 | D60 | A21 | H | D60 | D1 |
| 4602 | D64 | A21 | H | D64 | D1 |
| 4603 | D65 | A21 | H | D65 | D1 |
| 4604 | D76 | A21 | H | D76 | D1 |
| 4605 | D56 | A21 | Ph | D56 | D1 |
| 4606 | D57 | A21 | Ph | D57 | D1 |
| 4607 | D60 | A21 | Ph | D60 | D1 |
| 4608 | D64 | A21 | Ph | D64 | D1 |
| 4609 | D65 | A21 | Ph | D65 | D1 |
| 4610 | D76 | A21 | Ph | D76 | D1 |
| 4611 | D56 | A1 | H | H | D56 |
| 4612 | D57 | A1 | H | H | D57 |
| 4613 | D60 | A1 | H | H | D60 |
| 4614 | D64 | A1 | H | H | D64 |
| 4615 | D65 | A1 | H | H | D65 |
| 4616 | D76 | A1 | H | H | D76 |
| 4617 | D56 | A1 | Ph | H | D56 |
| 4618 | D57 | A1 | Ph | H | D57 |
| 4619 | D60 | A1 | Ph | H | D60 |
| 4620 | D64 | A1 | Ph | H | D64 |
| 4621 | D65 | A1 | Ph | H | D65 |
| 4622 | D76 | A1 | Ph | H | D76 |
| 4623 | D56 | A1 | H | Ph | D56 |
| 4624 | D57 | A1 | H | Ph | D57 |
| 4625 | D60 | A1 | H | Ph | D60 |
| 4626 | D64 | A1 | H | Ph | D64 |
| 4627 | D65 | A1 | H | Ph | D65 |
| 4628 | D76 | A1 | H | Ph | D76 |
| 4629 | D56 | A1 | Ph | Ph | D56 |
| 4630 | D57 | A1 | Ph | Ph | D57 |
| 4631 | D60 | A1 | Ph | Ph | D60 |
| 4632 | D64 | A1 | Ph | Ph | D64 |
| 4633 | D65 | A1 | Ph | Ph | D65 |
| 4634 | D76 | A1 | Ph | Ph | D76 |
| 4635 | D56 | A20 | H | H | D56 |
| 4636 | D57 | A20 | H | H | D57 |
| 4637 | D60 | A20 | H | H | D60 |
| 4638 | D64 | A20 | H | H | D64 |
| 4639 | D65 | A20 | H | H | D65 |
| 4640 | D76 | A20 | H | H | D76 |

TABLE 1-continued

| No. | $R^1$ | $R^2$ | $R^3$ | $R^4$ | $R^5$ |
|---|---|---|---|---|---|
| 4641 | D56 | A20 | Ph | H | D56 |
| 4642 | D57 | A20 | Ph | H | D57 |
| 4643 | D60 | A20 | Ph | H | D60 |
| 4644 | D64 | A20 | Ph | H | D64 |
| 4645 | D65 | A20 | Ph | H | D65 |
| 4646 | D76 | A20 | Ph | H | D76 |
| 4647 | D56 | A20 | H | Ph | D56 |
| 4648 | D57 | A20 | H | Ph | D57 |
| 4649 | D60 | A20 | H | Ph | D60 |
| 4650 | D64 | A20 | H | Ph | D64 |
| 4651 | D65 | A20 | H | Ph | D65 |
| 4652 | D76 | A20 | H | Ph | D76 |
| 4653 | D56 | A20 | Ph | Ph | D56 |
| 4654 | D57 | A20 | Ph | Ph | D57 |
| 4655 | D60 | A20 | Ph | Ph | D60 |
| 4656 | D64 | A20 | Ph | Ph | D64 |
| 4657 | D65 | A20 | Ph | Ph | D65 |
| 4658 | D76 | A20 | Ph | Ph | D76 |
| 4659 | D56 | A21 | H | H | D56 |
| 4660 | D57 | A21 | H | H | D57 |
| 4661 | D60 | A21 | H | H | D60 |
| 4662 | D64 | A21 | H | H | D64 |
| 4663 | D65 | A21 | H | H | D65 |
| 4664 | D76 | A21 | H | H | D76 |
| 4665 | D56 | A21 | Ph | H | D56 |
| 4666 | D57 | A21 | Ph | H | D57 |
| 4667 | D60 | A21 | Ph | H | D60 |
| 4668 | D64 | A21 | Ph | H | D64 |
| 4669 | D65 | A21 | Ph | H | D65 |
| 4670 | D76 | A21 | Ph | H | D76 |
| 4671 | D56 | A21 | H | Ph | D56 |
| 4672 | D57 | A21 | H | Ph | D57 |
| 4673 | D60 | A21 | H | Ph | D60 |
| 4674 | D64 | A21 | H | Ph | D64 |
| 4675 | D65 | A21 | H | Ph | D65 |
| 4676 | D76 | A21 | H | Ph | D76 |
| 4677 | D56 | A21 | Ph | Ph | D56 |
| 4678 | D57 | A21 | Ph | Ph | D57 |
| 4679 | D60 | A21 | Ph | Ph | D60 |
| 4680 | D64 | A21 | Ph | Ph | D64 |
| 4681 | D65 | A21 | Ph | Ph | D65 |
| 4682 | D76 | A21 | Ph | Ph | D76 |
| 4683 | D1 | A1 | H | H | D56 |
| 4684 | D1 | A1 | H | H | D57 |
| 4685 | D1 | A1 | H | H | D60 |
| 4686 | D1 | A1 | H | H | D64 |
| 4687 | D1 | A1 | H | H | D65 |
| 4688 | D1 | A1 | H | H | D76 |
| 4689 | D1 | A1 | Ph | H | D56 |
| 4690 | D1 | A1 | Ph | H | D57 |
| 4691 | D1 | A1 | Ph | H | D60 |
| 4692 | D1 | A1 | Ph | H | D64 |
| 4693 | D1 | A1 | Ph | H | D65 |
| 4694 | D1 | A1 | Ph | H | D76 |
| 4695 | D1 | A1 | H | Ph | D56 |
| 4696 | D1 | A1 | H | Ph | D57 |
| 4697 | D1 | A1 | H | Ph | D60 |
| 4698 | D1 | A1 | H | Ph | D64 |
| 4699 | D1 | A1 | H | Ph | D65 |
| 4700 | D1 | A1 | H | Ph | D76 |
| 4701 | D56 | A1 | H | H | D1 |
| 4702 | D57 | A1 | H | H | D1 |
| 4703 | D60 | A1 | H | H | D1 |
| 4704 | D64 | A1 | H | H | D1 |
| 4705 | D65 | A1 | H | H | D1 |
| 4706 | D76 | A1 | H | H | D1 |
| 4707 | D56 | A1 | Ph | H | D1 |
| 4708 | D57 | A1 | Ph | H | D1 |
| 4709 | D60 | A1 | Ph | H | D1 |
| 4710 | D64 | A1 | Ph | H | D1 |
| 4711 | D65 | A1 | Ph | H | D1 |
| 4712 | D76 | A1 | Ph | H | D1 |
| 4713 | D56 | A1 | H | Ph | D1 |
| 4714 | D57 | A1 | H | Ph | D1 |
| 4715 | D60 | A1 | H | Ph | D1 |
| 4716 | D64 | A1 | H | Ph | D1 |
| 4717 | D65 | A1 | H | Ph | D1 |
| 4718 | D76 | A1 | H | Ph | D1 |

TABLE 1-continued

| No. | $R^1$ | $R^2$ | $R^3$ | $R^4$ | $R^5$ |
|---|---|---|---|---|---|
| 4719 | D1 | A20 | H | H | D56 |
| 4720 | D1 | A20 | H | H | D57 |
| 4721 | D1 | A20 | H | H | D60 |
| 4722 | D1 | A20 | H | H | D64 |
| 4723 | D1 | A20 | H | H | D65 |
| 4724 | D1 | A20 | H | H | D76 |
| 4725 | D1 | A20 | Ph | H | D56 |
| 4726 | D1 | A20 | Ph | H | D57 |
| 4727 | D1 | A20 | Ph | H | D60 |
| 4728 | D1 | A20 | Ph | H | D64 |
| 4729 | D1 | A20 | Ph | H | D65 |
| 4730 | D1 | A20 | Ph | H | D76 |
| 4731 | D1 | A20 | H | Ph | D56 |
| 4732 | D1 | A20 | H | Ph | D57 |
| 4733 | D1 | A20 | H | Ph | D60 |
| 4734 | D1 | A20 | H | Ph | D64 |
| 4735 | D1 | A20 | H | Ph | D65 |
| 4736 | D1 | A20 | H | Ph | D76 |
| 4737 | D56 | A20 | H | H | D1 |
| 4738 | D57 | A20 | H | H | D1 |
| 4739 | D60 | A20 | H | H | D1 |
| 4740 | D64 | A20 | H | H | D1 |
| 4741 | D65 | A20 | H | H | D1 |
| 4742 | D76 | A20 | H | H | D1 |
| 4743 | D56 | A20 | Ph | H | D1 |
| 4744 | D57 | A20 | Ph | H | D1 |
| 4745 | D60 | A20 | Ph | H | D1 |
| 4746 | D64 | A20 | Ph | H | D1 |
| 4747 | D65 | A20 | Ph | H | D1 |
| 4748 | D76 | A20 | Ph | H | D1 |
| 4749 | D56 | A20 | H | Ph | D1 |
| 4750 | D57 | A20 | H | Ph | D1 |
| 4751 | D60 | A20 | H | Ph | D1 |
| 4752 | D64 | A20 | H | Ph | D1 |
| 4753 | D65 | A20 | H | Ph | D1 |
| 4754 | D76 | A20 | H | Ph | D1 |
| 4755 | D1 | A21 | H | H | D56 |
| 4756 | D1 | A21 | H | H | D57 |
| 4757 | D1 | A21 | H | H | D60 |
| 4758 | D1 | A21 | H | H | D64 |
| 4759 | D1 | A21 | H | H | D65 |
| 4760 | D1 | A21 | H | H | D76 |
| 4761 | D1 | A21 | Ph | H | D56 |
| 4762 | D1 | A21 | Ph | H | D57 |
| 4763 | D1 | A21 | Ph | H | D60 |
| 4764 | D1 | A21 | Ph | H | D64 |
| 4765 | D1 | A21 | Ph | H | D65 |
| 4766 | D1 | A21 | Ph | H | D76 |
| 4767 | D1 | A21 | H | Ph | D56 |
| 4768 | D1 | A21 | H | Ph | D57 |
| 4769 | D1 | A21 | H | Ph | D60 |
| 4770 | D1 | A21 | H | Ph | D64 |
| 4771 | D1 | A21 | H | Ph | D65 |
| 4772 | D1 | A21 | H | Ph | D76 |
| 4773 | D56 | A21 | H | H | D1 |
| 4774 | D57 | A21 | H | H | D1 |
| 4775 | D60 | A21 | H | H | D1 |
| 4776 | D64 | A21 | H | H | D1 |
| 4777 | D65 | A21 | H | H | D1 |
| 4778 | D76 | A21 | H | H | D1 |
| 4779 | D56 | A21 | Ph | H | D1 |
| 4780 | D57 | A21 | Ph | H | D1 |
| 4781 | D60 | A21 | Ph | H | D1 |
| 4782 | D64 | A21 | Ph | H | D1 |
| 4783 | D65 | A21 | Ph | H | D1 |
| 4784 | D76 | A21 | Ph | H | D1 |
| 4785 | D56 | A21 | H | Ph | D1 |
| 4786 | D57 | A21 | H | Ph | D1 |
| 4787 | D60 | A21 | H | Ph | D1 |
| 4788 | D64 | A21 | H | Ph | D1 |
| 4789 | D65 | A21 | H | Ph | D1 |
| 4790 | D76 | A21 | H | Ph | D1 |
| 4791 | D56 | A1 | H | D56 | H |
| 4792 | D57 | A1 | H | D57 | H |
| 4793 | D60 | A1 | H | D60 | H |
| 4794 | D64 | A1 | H | D64 | H |
| 4795 | D65 | A1 | H | D65 | H |
| 4796 | D76 | A1 | H | D76 | H |

TABLE 1-continued

| No. | $R^1$ | $R^2$ | $R^3$ | $R^4$ | $R^5$ |
|---|---|---|---|---|---|
| 4797 | D56 | A1 | Ph | D56 | H |
| 4798 | D57 | A1 | Ph | D57 | H |
| 4799 | D60 | A1 | Ph | D60 | H |
| 4800 | D64 | A1 | Ph | D64 | H |
| 4801 | D65 | A1 | Ph | D65 | H |
| 4802 | D76 | A1 | Ph | D76 | H |
| 4803 | D56 | A1 | H | D56 | Ph |
| 4804 | D57 | A1 | H | D57 | Ph |
| 4805 | D60 | A1 | H | D60 | Ph |
| 4806 | D64 | A1 | H | D64 | Ph |
| 4807 | D65 | A1 | H | D65 | Ph |
| 4808 | D76 | A1 | H | D76 | Ph |
| 4809 | D56 | A1 | Ph | D56 | Ph |
| 4810 | D57 | A1 | Ph | D57 | Ph |
| 4811 | D60 | A1 | Ph | D60 | Ph |
| 4812 | D64 | A1 | Ph | D64 | Ph |
| 4813 | D65 | A1 | Ph | D65 | Ph |
| 4814 | D76 | A1 | Ph | D76 | Ph |
| 4815 | D56 | A20 | H | D56 | H |
| 4816 | D57 | A20 | H | D57 | H |
| 4817 | D60 | A20 | H | D60 | H |
| 4818 | D64 | A20 | H | D64 | H |
| 4819 | D65 | A20 | H | D65 | H |
| 4820 | D76 | A20 | H | D76 | H |
| 4821 | D56 | A20 | Ph | D56 | H |
| 4822 | D57 | A20 | Ph | D57 | H |
| 4823 | D60 | A20 | Ph | D60 | H |
| 4824 | D64 | A20 | Ph | D64 | H |
| 4825 | D65 | A20 | Ph | D65 | H |
| 4826 | D76 | A20 | Ph | D76 | H |
| 4827 | D56 | A20 | H | D56 | Ph |
| 4828 | D57 | A20 | H | D57 | Ph |
| 4829 | D60 | A20 | H | D60 | Ph |
| 4830 | D64 | A20 | H | D64 | Ph |
| 4831 | D65 | A20 | H | D65 | Ph |
| 4832 | D76 | A20 | H | D76 | Ph |
| 4833 | D56 | A20 | Ph | D56 | Ph |
| 4834 | D57 | A20 | Ph | D57 | Ph |
| 4835 | D60 | A20 | Ph | D60 | Ph |
| 4836 | D64 | A20 | Ph | D64 | Ph |
| 4837 | D65 | A20 | Ph | D65 | Ph |
| 4838 | D76 | A20 | Ph | D76 | Ph |
| 4839 | D56 | A21 | H | D56 | H |
| 4840 | D57 | A21 | H | D57 | H |
| 4841 | D60 | A21 | H | D60 | H |
| 4842 | D64 | A21 | H | D64 | H |
| 4843 | D65 | A21 | H | D65 | H |
| 4844 | D76 | A21 | H | D76 | H |
| 4845 | D56 | A21 | Ph | D56 | H |
| 4846 | D57 | A21 | Ph | D57 | H |
| 4847 | D60 | A21 | Ph | D60 | H |
| 4848 | D64 | A21 | Ph | D64 | H |
| 4849 | D65 | A21 | Ph | D65 | H |
| 4850 | D76 | A21 | Ph | D76 | H |
| 4851 | D56 | A21 | H | D56 | Ph |
| 4852 | D57 | A21 | H | D57 | Ph |
| 4853 | D60 | A21 | H | D60 | Ph |
| 4854 | D64 | A21 | H | D64 | Ph |
| 4855 | D65 | A21 | H | D65 | Ph |
| 4856 | D76 | A21 | H | D76 | Ph |
| 4857 | D56 | A21 | Ph | D56 | Ph |
| 4858 | D57 | A21 | Ph | D57 | Ph |
| 4859 | D60 | A21 | Ph | D60 | Ph |
| 4860 | D64 | A21 | Ph | D64 | Ph |
| 4861 | D65 | A21 | Ph | D65 | Ph |
| 4862 | D76 | A21 | Ph | D76 | Ph |
| 4863 | D1 | A1 | H | D56 | H |
| 4884 | D1 | A1 | H | D57 | H |
| 4885 | D1 | A1 | H | D60 | H |
| 4866 | D1 | A1 | H | D64 | H |
| 4867 | D1 | A1 | H | D65 | H |
| 4868 | D1 | A1 | H | D76 | H |
| 4869 | D1 | A1 | Ph | D56 | H |
| 4870 | D1 | A1 | Ph | D57 | H |
| 4871 | D1 | A1 | Ph | D60 | H |
| 4872 | D1 | A1 | Ph | D64 | H |
| 4873 | D1 | A1 | Ph | D65 | H |
| 4874 | D1 | A1 | Ph | D76 | H |

TABLE 1-continued

| No. | $R^1$ | $R^2$ | $R^3$ | $R^4$ | $R^5$ |
|---|---|---|---|---|---|
| 4875 | D1 | A1 | H | D56 | Ph |
| 4876 | D1 | A1 | H | D57 | Ph |
| 4877 | D1 | A1 | H | D60 | Ph |
| 4878 | D1 | A1 | H | D64 | Ph |
| 4879 | D1 | A1 | H | D65 | Ph |
| 4880 | D1 | A1 | H | D76 | Ph |
| 4881 | D1 | A1 | Ph | D56 | Ph |
| 4882 | D1 | A1 | Ph | D57 | Ph |
| 4883 | D1 | A1 | Ph | D60 | Ph |
| 4884 | D1 | A1 | Ph | D64 | Ph |
| 4885 | D1 | A1 | Ph | D65 | Ph |
| 4886 | D1 | A1 | Ph | D76 | Ph |
| 4887 | D56 | A1 | H | D1 | H |
| 4888 | D57 | A1 | H | D1 | H |
| 4889 | D60 | A1 | H | D1 | H |
| 4890 | D64 | A1 | H | D1 | H |
| 4891 | D65 | A1 | H | D1 | H |
| 4892 | D76 | A1 | H | D1 | H |
| 4893 | D56 | A1 | Ph | D1 | H |
| 4894 | D57 | A1 | Ph | D1 | H |
| 4895 | D60 | A1 | Ph | D1 | H |
| 4896 | D64 | A1 | Ph | D1 | H |
| 4897 | D65 | A1 | Ph | D1 | H |
| 4898 | D76 | A1 | Ph | D1 | H |
| 4899 | D56 | A1 | H | D1 | Ph |
| 4900 | D57 | A1 | H | D1 | Ph |
| 4901 | D60 | A1 | H | D1 | Ph |
| 4902 | D64 | A1 | H | D1 | Ph |
| 4903 | D65 | A1 | H | D1 | Ph |
| 4904 | D76 | A1 | H | D1 | Ph |
| 4905 | D56 | A1 | Ph | D1 | Ph |
| 4906 | D57 | A1 | Ph | D1 | Ph |
| 4907 | D60 | A1 | Ph | D1 | Ph |
| 4908 | D64 | A1 | Ph | D1 | Ph |
| 4909 | D65 | A1 | Ph | D1 | Ph |
| 4910 | D76 | A1 | Ph | D1 | Ph |
| 4911 | D1 | A20 | H | D56 | H |
| 4912 | D1 | A20 | H | D57 | H |
| 4913 | D1 | A20 | H | D60 | H |
| 4914 | D1 | A20 | H | D64 | H |
| 4915 | D1 | A20 | H | D65 | H |
| 4916 | D1 | A20 | H | D76 | H |
| 4917 | D1 | A20 | Ph | D56 | H |
| 4918 | D1 | A20 | Ph | D57 | H |
| 4919 | D1 | A20 | Ph | D60 | H |
| 4920 | D1 | A20 | Ph | D64 | H |
| 4921 | D1 | A20 | Ph | D65 | H |
| 4922 | D1 | A20 | Ph | D76 | H |
| 4923 | D1 | A20 | H | D56 | Ph |
| 4924 | D1 | A20 | H | D57 | Ph |
| 4925 | D1 | A20 | H | D60 | Ph |
| 4926 | D1 | A20 | H | D64 | Ph |
| 4927 | D1 | A20 | H | D65 | Ph |
| 4928 | D1 | A20 | H | D76 | Ph |
| 4928 | D1 | A20 | Ph | D56 | Ph |
| 4930 | D1 | A20 | Ph | D57 | Ph |
| 4931 | D1 | A20 | Ph | D60 | Ph |
| 4932 | D1 | A20 | Ph | D64 | Ph |
| 4933 | D1 | A20 | Ph | D65 | Ph |
| 4934 | D1 | A20 | Ph | D76 | Ph |
| 4935 | D56 | A20 | H | D1 | H |
| 4936 | D57 | A20 | H | D1 | H |
| 4937 | D60 | A20 | H | D1 | H |
| 4938 | D64 | A20 | H | D1 | H |
| 4939 | D65 | A20 | H | D1 | H |
| 4940 | D76 | A20 | H | D1 | H |
| 4941 | D56 | A20 | Ph | D1 | H |
| 4942 | D57 | A20 | Ph | D1 | H |
| 4943 | D60 | A20 | Ph | D1 | H |
| 4944 | D64 | A20 | Ph | D1 | H |
| 4945 | D65 | A20 | Ph | D1 | H |
| 4946 | D76 | A20 | Ph | D1 | H |
| 4947 | D56 | A20 | H | D1 | Ph |
| 4948 | D57 | A20 | H | D1 | Ph |
| 4949 | D60 | A20 | H | D1 | Ph |
| 4950 | D64 | A20 | H | D1 | Ph |
| 4951 | D65 | A20 | H | D1 | Ph |
| 4952 | D76 | A20 | H | D1 | Ph |

TABLE 1-continued

| No. | $R^1$ | $R^2$ | $R^3$ | $R^4$ | $R^5$ |
|---|---|---|---|---|---|
| 4953 | D56 | A20 | Ph | D1 | Ph |
| 4954 | D57 | A20 | Ph | D1 | Ph |
| 4955 | D60 | A20 | Ph | D1 | Ph |
| 4956 | D64 | A20 | Ph | D1 | Ph |
| 4957 | D65 | A20 | Ph | D1 | Ph |
| 4958 | D76 | A20 | Ph | D1 | Ph |
| 4959 | D1 | A21 | H | D56 | H |
| 4960 | D1 | A21 | H | D57 | H |
| 4961 | D1 | A21 | H | D60 | H |
| 4962 | D1 | A21 | H | D64 | H |
| 4963 | D1 | A21 | H | D65 | H |
| 4964 | D1 | A21 | H | D76 | H |
| 4965 | D1 | A21 | Ph | D56 | H |
| 4966 | D1 | A21 | Ph | D57 | H |
| 4967 | D1 | A21 | Ph | D60 | H |
| 4968 | D1 | A21 | Ph | D64 | H |
| 4969 | D1 | A21 | Ph | D65 | H |
| 4970 | D1 | A21 | Ph | D76 | H |
| 4971 | D1 | A21 | H | D56 | Ph |
| 4972 | D1 | A21 | H | D57 | Ph |
| 4973 | D1 | A21 | H | D60 | Ph |
| 4974 | D1 | A21 | H | D64 | Ph |
| 4975 | D1 | A21 | H | D65 | Ph |
| 4976 | D1 | A21 | H | D76 | Ph |
| 4977 | D1 | A21 | Ph | D56 | Ph |
| 4978 | D1 | A21 | Ph | D57 | Ph |
| 4979 | D1 | A21 | Ph | D60 | Ph |
| 4980 | D1 | A21 | Ph | D64 | Ph |
| 4981 | D1 | A21 | Ph | D65 | Ph |
| 4982 | D1 | A21 | Ph | D76 | Ph |
| 4983 | D56 | A21 | H | D1 | H |
| 4984 | D57 | A21 | H | D1 | H |
| 4985 | D60 | A21 | H | D1 | H |
| 4986 | D64 | A21 | H | D1 | H |
| 4987 | D65 | A21 | H | D1 | H |
| 4988 | D76 | A21 | H | D1 | H |
| 4989 | D56 | A21 | Ph | D1 | H |
| 4990 | D57 | A21 | Ph | D1 | H |
| 4991 | D60 | A21 | Ph | D1 | H |
| 4992 | D64 | A21 | Ph | D1 | H |
| 4993 | D65 | A21 | Ph | D1 | H |
| 4994 | D76 | A21 | Ph | D1 | H |
| 4995 | D56 | A21 | H | D1 | Ph |
| 4996 | D57 | A21 | H | D1 | Ph |
| 4997 | D60 | A21 | H | D1 | Ph |
| 4998 | D64 | A21 | H | D1 | Ph |
| 4999 | D65 | A21 | H | D1 | Ph |
| 5000 | D76 | A21 | H | D1 | Ph |
| 5001 | D56 | A21 | Ph | D1 | Ph |
| 5002 | D57 | A21 | Ph | D1 | Ph |
| 5003 | D60 | A21 | Ph | D1 | Ph |
| 5004 | D64 | A21 | Ph | D1 | Ph |
| 5005 | D65 | A21 | Ph | D1 | Ph |
| 5006 | D76 | A21 | Ph | D1 | Ph |
| 5007 | H | A1 | D56 | H | D56 |
| 5008 | H | A1 | D57 | H | D57 |
| 5009 | H | A1 | D60 | H | D60 |
| 5010 | H | A1 | D64 | H | D64 |
| 5011 | H | A1 | D65 | H | D65 |
| 5012 | H | A1 | D76 | H | D76 |
| 5013 | Ph | A1 | D56 | H | D56 |
| 5014 | Ph | A1 | D57 | H | D57 |
| 5015 | Ph | A1 | D60 | H | D60 |
| 5016 | Ph | A1 | D64 | H | D64 |
| 5017 | Ph | A1 | D65 | H | D65 |
| 5018 | Ph | A1 | D76 | H | D76 |
| 5019 | H | A1 | D56 | Ph | D56 |
| 5020 | H | A1 | D57 | Ph | D57 |
| 5021 | H | A1 | D60 | Ph | D60 |
| 5022 | H | A1 | D64 | Ph | D64 |
| 5023 | H | A1 | D65 | Ph | D65 |
| 5024 | H | A1 | D76 | Ph | D76 |
| 5025 | Ph | A1 | D56 | Ph | D56 |
| 5026 | Ph | A1 | D57 | Ph | D57 |
| 5027 | Ph | A1 | D60 | Ph | D60 |
| 5028 | Ph | A1 | D64 | Ph | D64 |
| 5029 | Ph | A1 | D65 | Ph | D65 |
| 5030 | Ph | A1 | D76 | Ph | D76 |

TABLE 1-continued

| No. | $R^1$ | $R^2$ | $R^3$ | $R^4$ | $R^5$ |
|---|---|---|---|---|---|
| 5031 | H | A20 | D56 | H | D56 |
| 5032 | H | A20 | D57 | H | D57 |
| 5033 | H | A20 | D60 | H | D60 |
| 5034 | H | A20 | D64 | H | D64 |
| 5035 | H | A20 | D65 | H | D65 |
| 5036 | H | A20 | D76 | H | D76 |
| 5037 | Ph | A20 | D56 | H | D56 |
| 5038 | Ph | A20 | D57 | H | D57 |
| 5039 | Ph | A20 | D60 | H | D60 |
| 5040 | Ph | A20 | D64 | H | D64 |
| 5041 | Ph | A20 | D65 | H | D65 |
| 5042 | Ph | A20 | D76 | H | D76 |
| 5043 | H | A20 | D56 | Ph | D56 |
| 5044 | H | A20 | D57 | Ph | D57 |
| 5045 | H | A20 | D60 | Ph | D60 |
| 5046 | H | A20 | D64 | Ph | D64 |
| 5047 | H | A20 | D65 | Ph | D65 |
| 5048 | H | A20 | D76 | Ph | D76 |
| 5049 | Ph | A20 | D56 | Ph | D56 |
| 5050 | Ph | A20 | D57 | Ph | D57 |
| 5051 | Ph | A20 | D60 | Ph | D60 |
| 5052 | Ph | A20 | D64 | Ph | D64 |
| 5053 | Ph | A20 | D65 | Ph | D65 |
| 5054 | Ph | A20 | D76 | Ph | D76 |
| 5055 | H | A21 | D56 | H | D56 |
| 5056 | H | A21 | D57 | H | D57 |
| 5057 | H | A21 | D60 | H | D60 |
| 5058 | H | A21 | D64 | H | D64 |
| 5059 | H | A21 | D65 | H | D65 |
| 5060 | H | A21 | D76 | H | D76 |
| 5061 | Ph | A21 | D56 | H | D56 |
| 5062 | Ph | A21 | D57 | H | D57 |
| 5063 | Ph | A21 | D60 | H | D60 |
| 5064 | Ph | A21 | D64 | H | D64 |
| 5065 | Ph | A21 | D65 | H | D65 |
| 5066 | Ph | A21 | D76 | H | D76 |
| 5067 | H | A21 | D56 | Ph | D56 |
| 5068 | H | A21 | D57 | Ph | D57 |
| 5069 | H | A21 | D60 | Ph | D60 |
| 5070 | H | A21 | D64 | Ph | D64 |
| 5071 | H | A21 | D65 | Ph | D65 |
| 5072 | H | A21 | D76 | Ph | D76 |
| 5073 | Ph | A21 | D56 | Ph | D56 |
| 5074 | Ph | A21 | D57 | Ph | D57 |
| 5075 | Ph | A21 | D60 | Ph | D60 |
| 5076 | Ph | A21 | D64 | Ph | D64 |
| 5077 | Ph | A21 | D65 | Ph | D65 |
| 5078 | Ph | A21 | D76 | Ph | D76 |
| 5079 | H | A1 | D1 | H | D56 |
| 5080 | H | A1 | D1 | H | D57 |
| 5081 | H | A1 | D1 | H | D60 |
| 5082 | H | A1 | D1 | H | D64 |
| 5083 | H | A1 | D1 | H | D65 |
| 5084 | H | A1 | D1 | H | D76 |
| 5085 | Ph | A1 | D1 | H | D56 |
| 5086 | Ph | A1 | D1 | H | D57 |
| 5087 | Ph | A1 | D1 | H | D60 |
| 5088 | Ph | A1 | D1 | H | D64 |
| 5089 | Ph | A1 | D1 | H | D65 |
| 5090 | Ph | A1 | D1 | H | D76 |
| 5091 | H | A1 | D1 | Ph | D56 |
| 5092 | H | A1 | D1 | Ph | D57 |
| 5093 | H | A1 | D1 | Ph | D60 |
| 5094 | H | A1 | D1 | Ph | D64 |
| 5095 | H | A1 | D1 | Ph | D65 |
| 5096 | H | A1 | D1 | Ph | D76 |
| 5097 | Ph | A1 | D1 | Ph | D56 |
| 5098 | Ph | A1 | D1 | Ph | D57 |
| 5099 | Ph | A1 | D1 | Ph | D60 |
| 5100 | Ph | A1 | D1 | Ph | D64 |
| 5101 | Ph | A1 | D1 | Ph | D65 |
| 5102 | Ph | A1 | D1 | Ph | D76 |
| 5103 | H | A1 | D56 | H | D1 |
| 5104 | H | A1 | D57 | H | D1 |
| 5105 | H | A1 | D60 | H | D1 |
| 5106 | H | A1 | D64 | H | D1 |
| 5107 | H | A1 | D65 | H | D1 |
| 5108 | H | A1 | D76 | H | D1 |

TABLE 1-continued

| No. | $R^1$ | $R^2$ | $R^3$ | $R^4$ | $R^5$ |
|---|---|---|---|---|---|
| 5109 | Ph | A1 | D56 | H | D1 |
| 5110 | Ph | A1 | D57 | H | D1 |
| 5111 | Ph | A1 | D60 | H | D1 |
| 5112 | Ph | A1 | D64 | H | D1 |
| 5113 | Ph | A1 | D65 | H | D1 |
| 5114 | Ph | A1 | D76 | H | D1 |
| 5115 | H | A1 | D56 | Ph | D1 |
| 5116 | H | A1 | D57 | Ph | D1 |
| 5117 | H | A1 | D60 | Ph | D1 |
| 5118 | H | A1 | D64 | Ph | D1 |
| 5119 | H | A1 | D65 | Ph | D1 |
| 5120 | H | A1 | D76 | Ph | D1 |
| 5121 | Ph | A1 | D56 | Ph | D1 |
| 5122 | Ph | A1 | D57 | Ph | D1 |
| 5123 | Ph | A1 | D60 | Ph | D1 |
| 5124 | Ph | A1 | D64 | Ph | D1 |
| 5125 | Ph | A1 | D65 | Ph | D1 |
| 5126 | Ph | A1 | D76 | Ph | D1 |
| 5127 | H | A20 | D1 | H | D56 |
| 5128 | H | A20 | D1 | H | D57 |
| 5129 | H | A20 | D1 | H | D60 |
| 5130 | H | A20 | D1 | H | D64 |
| 5131 | H | A20 | D1 | H | D65 |
| 5132 | H | A20 | D1 | H | D76 |
| 5133 | Ph | A20 | D1 | H | D56 |
| 5134 | Ph | A20 | D1 | H | D57 |
| 5135 | Ph | A20 | D1 | H | D60 |
| 5136 | Ph | A20 | D1 | H | D64 |
| 5137 | Ph | A20 | D1 | H | D65 |
| 5138 | Ph | A20 | D1 | H | D76 |
| 5139 | H | A20 | D1 | Ph | D56 |
| 5140 | H | A20 | D1 | Ph | D57 |
| 5141 | H | A20 | D1 | Ph | D60 |
| 5142 | H | A20 | D1 | Ph | D64 |
| 5143 | H | A20 | D1 | Ph | D65 |
| 5144 | H | A20 | D1 | Ph | D76 |
| 5145 | Ph | A20 | D1 | Ph | D56 |
| 5146 | Ph | A20 | D1 | Ph | D57 |
| 5147 | Ph | A20 | D1 | Ph | D60 |
| 5148 | Ph | A20 | D1 | Ph | D64 |
| 5149 | Ph | A20 | D1 | Ph | D65 |
| 5150 | Ph | A20 | D1 | Ph | D76 |
| 5151 | H | A20 | D56 | H | D1 |
| 5152 | H | A20 | D57 | H | D1 |
| 5153 | H | A20 | D60 | H | D1 |
| 5154 | H | A20 | D64 | H | D1 |
| 5155 | H | A20 | D65 | H | D1 |
| 5156 | H | A20 | D76 | H | D1 |
| 5157 | Ph | A20 | D56 | H | D1 |
| 5158 | Ph | A20 | D57 | H | D1 |
| 5159 | Ph | A20 | D60 | H | D1 |
| 5160 | Ph | A20 | D64 | H | D1 |
| 5161 | Ph | A20 | D65 | H | D1 |
| 5162 | Ph | A20 | D76 | H | D1 |
| 5163 | H | A20 | D56 | Ph | D1 |
| 5164 | H | A20 | D57 | Ph | D1 |
| 5165 | H | A20 | D60 | Ph | D1 |
| 5166 | H | A20 | D64 | Ph | D1 |
| 5167 | H | A20 | D65 | Ph | D1 |
| 5168 | H | A20 | D76 | Ph | D1 |
| 5169 | Ph | A20 | D56 | Ph | D1 |
| 5170 | Ph | A20 | D57 | Ph | D1 |
| 5171 | Ph | A20 | D60 | Ph | D1 |
| 5172 | Ph | A20 | D64 | Ph | D1 |
| 5173 | Ph | A20 | D65 | Ph | D1 |
| 5174 | Ph | A20 | D76 | Ph | D1 |
| 5175 | H | A21 | D1 | H | D56 |
| 5176 | H | A21 | D1 | H | D57 |
| 5177 | H | A21 | D1 | H | D60 |
| 5178 | H | A21 | D1 | H | D64 |
| 5179 | H | A2 | D1 | H | D65 |
| 5180 | H | A21 | D1 | H | D76 |
| 5181 | Ph | A21 | D1 | H | D56 |
| 5182 | Ph | A21 | D1 | H | D57 |
| 5183 | Ph | A21 | D1 | H | D60 |
| 5184 | Ph | A21 | D1 | H | D64 |
| 5185 | Ph | A21 | D1 | H | D65 |
| 5186 | Ph | A21 | D1 | H | D76 |

TABLE 1-continued

| No. | $R^1$ | $R^2$ | $R^3$ | $R^4$ | $R^5$ |
|---|---|---|---|---|---|
| 5187 | H | A21 | D1 | Ph | D56 |
| 5188 | H | A21 | D1 | Ph | D57 |
| 5189 | H | A21 | D1 | Ph | D60 |
| 5190 | H | A21 | D1 | Ph | D64 |
| 5191 | H | A21 | D1 | Ph | D65 |
| 5192 | H | A21 | D1 | Ph | D76 |
| 5193 | Ph | A21 | D1 | Ph | D56 |
| 5194 | Ph | A21 | D1 | Ph | D57 |
| 5195 | Ph | A21 | D1 | Ph | D60 |
| 5196 | Ph | A21 | D1 | Ph | D64 |
| 5197 | Ph | A21 | D1 | Ph | D65 |
| 5198 | Ph | A21 | D1 | Ph | D76 |
| 5199 | H | A21 | D56 | H | D1 |
| 5200 | H | A21 | D57 | H | D1 |
| 5201 | H | A21 | D60 | H | D1 |
| 5202 | H | A21 | D64 | H | D1 |
| 5203 | H | A21 | D65 | H | D1 |
| 5204 | H | A21 | D76 | H | D1 |
| 5205 | Ph | A21 | D56 | H | D1 |
| 5206 | Ph | A21 | D57 | H | D1 |
| 5207 | Ph | A21 | D60 | H | D1 |
| 5208 | Ph | A21 | D64 | H | D1 |
| 5209 | Ph | A21 | D65 | H | D1 |
| 5210 | Ph | A21 | D76 | H | D1 |
| 5211 | H | A21 | D56 | Ph | D1 |
| 5212 | H | A21 | D57 | Ph | D1 |
| 5213 | H | A21 | D60 | Ph | D1 |
| 5214 | H | A21 | D64 | Ph | D1 |
| 5215 | H | A21 | D65 | Ph | D1 |
| 5216 | H | A21 | D76 | Ph | D1 |
| 5217 | Ph | A21 | D56 | Ph | D1 |
| 5218 | Ph | A21 | D57 | Ph | D1 |
| 5219 | Ph | A21 | D60 | Ph | D1 |
| 5220 | Ph | A21 | D64 | Ph | D1 |
| 5221 | Ph | A21 | D65 | Ph | D1 |
| 5222 | Ph | A21 | D76 | Ph | D1 |
| 5223 | D72 | A1 | H | H | D72 |
| 5224 | D1 | A1 | H | H | D72 |
| 5225 | D72 | A1 | H | H | D1 |
| 5226 | D72 | A20 | H | H | D72 |
| 5227 | D1 | A20 | H | H | D72 |
| 5228 | D72 | A20 | H | H | D1 |
| 5229 | D72 | A21 | H | H | D72 |
| 5230 | D1 | A21 | H | H | D72 |
| 5231 | D72 | A21 | H | H | D1 |

[Synthesis Method of Compound Represented by Formula (1)]

The compound represented by the formula (1) can be synthesized by combining existing reactions. For example, a compound of the formula (1), in which $R^1$, $R^4$ and $R^5$ are D1's, and $R^2$ is A1, can be synthesized via an intermediate through the following reaction scheme.

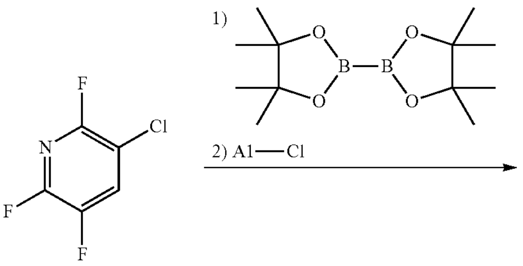

-continued

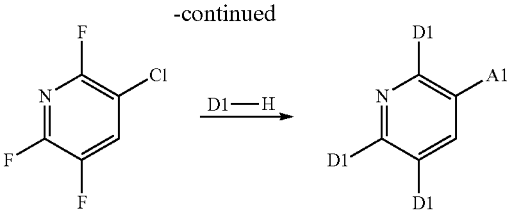

In this reaction scheme, halogenated pyridine is used as a starting material. Here, halogenated pyridine having a fluorine atom at a position where D1 is to be introduced and having a chlorine atom at a position where A1 is to be introduced is prepared. The halogenated pyridine is reacted with 4,4,4',5,5',5'-octamethyl-2,2'-bi(1,3,2-oxaborane) in the presence of a catalyst, and then is reacted with A1-Cl so as to obtain an intermediate in which the chlorine atom is substituted with A1. The intermediate is further reacted with D1-H in the presence of a catalyst so as to obtain a target compound in which the fluorine atom is substituted with D1. In this two-step reaction, the first reaction and the second reaction can be performed in reverse order.

The reaction is an application of a conventionally known reaction, and conventionally known reaction conditions can be appropriately selected and used. For the details of the reaction, synthesis examples to be described below can be referred to. Further, the compound represented by the formula (1) can also be synthesized by combining conventionally known other synthesis reactions.

A compound represented by the following formula (1'), which is a synthetic intermediate of the compound represented by the formula (1), includes a novel compound.

Formula (1')

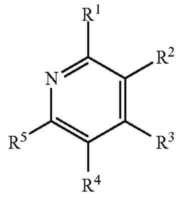

$R^1$ to $R^5$ in the formula (1') satisfy the following condition 1 or condition 2.

(Condition 1) Among $R^1$ to $R^5$, one of $R^1$ and $R^2$ is a halogen atom, among the rest of $R^1$ to $R^5$, p are D's, and the remaining 4-p are R's.

(Condition 2) Among $R^1$ to $R^5$, one of $R^1$ and $R^2$ is A, among the rest of $R^1$ to $R^5$, p are halogen atoms, and the remaining 4-p are R's.

Here,

A is a group represented by Het-$L^A$-* or CN-$L^A$-*, in which Het represents a substituted or unsubstituted heteroaryl group bonded via a carbon atom (meanwhile, at least one nitrogen atom is included as a ring skeleton-forming atom of the heteroaryl group), $L^A$ represents a single bond or a substituted or unsubstituted arylene group, and * represents a bond position.

D is a group represented by the following formula (IIa), (IIb), (IIc) or (IId).

Formula (IIa)

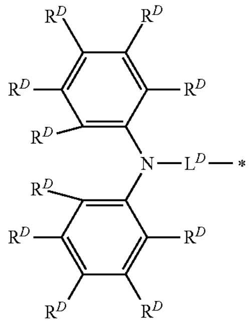

Formula (IIb)

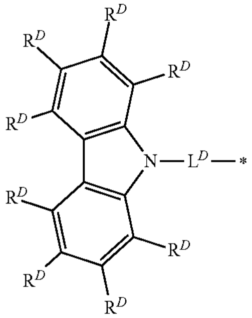

Formula (IIc)

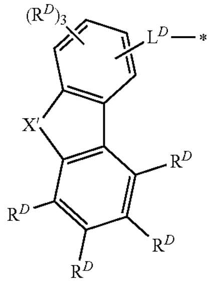

Formula (IId)

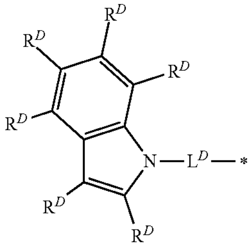

Here, X' represents N—$R^{D'}$, an oxygen atom, or a sulfur atom, each $R^D$ independently represents a hydrogen atom, a deuterium atom, a substituted or unsubstituted alkyl group, a substituted or unsubstituted alkoxy group, a substituted or unsubstituted amino group, a cyano group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure.

$R^{D'}$ represents a hydrogen atom, a deuterium atom, a substituted or unsubstituted alkyl group, a substituted or unsubstituted aryl group, or a substituted or unsubstituted heteroaryl group, and $R^D$, may be bonded to one or more $R^{D'}$s to form a cyclic structure, each $L^D$ independently represents a single bond, a substituted or unsubstituted arylene group, or a substituted or unsubstituted heteroarylene group, and

* represents a bond position.

R is a hydrogen atom, a deuterium atom, or a substituted or unsubstituted aryl group (but, other than a group that may be A or D).

p is any integer of 1 to 3. When p is 2 or 3, D's present in the molecule may be the same or different. When p is 1 or 2, R's present in the molecule may be the same or different.

The descriptions and preferable ranges of A, D, R, and p of the formula (1') can be made with reference to the corresponding descriptions of the formula (1).

In some embodiments, the condition 1 is satisfied. In some embodiments, p is 2. In some embodiments, D is a group represented by the formula (IIb). In some embodiments, the halogen atom is a chlorine atom. In some embodiments, the halogen atom is an iodine atom. In some embodiments, R is a substituted or unsubstituted aryl group. In some embodiments, R is an unsubstituted phenyl group.

In some embodiments, the condition 2 is satisfied. In some embodiments, p is 2 or 3. In some embodiments, A has a substituted or unsubstituted triazinyl group. In some embodiments, the halogen atom is a fluorine atom.

Synthetic intermediates of Synthesis Examples 1 to 3 to be described below can be mentioned as preferable examples.

All the definitions of terms described in [0039] to [0101] of US2020/0168814A1 are incorporated herein, as a part of the present specification, and are used as definitions of terms of the present invention.

In some embodiments, the compound represented by the formula (I) is a light-emitting material.

In some embodiments, the compound represented by the formula (I) is a compound capable of emitting delayed fluorescence.

In some embodiments of the present disclosure, the compound represented by the formula (1) is, when excited thermally or by an electronic means, able to emit light in a UV region, light of blue, green, yellow or orange in a visible region, in a red region (e.g., about 420 nm to about 500 nm, about 500 nm to about 600 nm, or about 600 nm to about 700 nm) or in a near IR region.

In some embodiments of the present disclosure, the compound represented by the formula (1) is, when excited thermally or by an electronic means, able to emit light of red or orange in a visible region (e.g., about 620 nm to about 780 nm, about 650 nm).

In some embodiments of the present disclosure, the compound represented by the formula (1) is, when excited thermally or by an electronic means, able to emit light of orange or yellow in a visible region (e.g., about 570 nm to about 620 nm, about 590 nm, about 570 nm).

In some embodiments of the present disclosure, the compound represented by the formula (1) is, when excited thermally or by an electronic means, able to emit light of green in a visible region (e.g., about 490 nm to about 575 nm, about 510 nm).

In some embodiments of the present disclosure, the compound represented by the formula (1) is, when excited thermally or by an electronic means, able to emit light of blue in a visible region (e.g., about 400 nm to about 490 nm, about 475 nm).

In some embodiments of the present disclosure, the compound represented by the formula (1) is, when excited thermally or by an electronic means, able to emit light in a UV region (e.g., about 280 to 400 nm).

In some embodiments of the present disclosure, the compound represented by the formula (1) is, when excited thermally or by an electronic means, able to emit light in an IR region (e.g., about 780 nm to 2 μm). In some embodiments of the present disclosure, the compound represented by the formula (I) is a charge transport material. In some embodiments of the present disclosure, the compound represented by the formula (I) is used for a charge transport layer. In some embodiments of the present disclosure, the compound represented by the formula (I), as a charge transport material, has high mobility, and is excellent in durability.

In some embodiments of the present disclosure, an organic semiconductor device using the compound represented by the formula (I), such as CMOS (complementary metal oxide semiconductor), can be manufactured. In some embodiments of the present disclosure, it is possible to manufacture an organic optical device such as an organic electroluminescence device or a solid-state image sensing device (for example, a CMOS image sensor) by using the compound represented by the formula (I).

Electronic characteristics of small-molecule chemical substance libraries can be calculated by known ab initio quantum chemistry calculation. For example, according to time-dependent density functional theory calculation using 6-31G* as a basis, and a functional group known as Becke's three parameters, Lee-Yang-Parr hybrid functionals, the Hartree-Fock equation (TD-DFT/B3LYP/6-31G*) is analyzed and molecular fractions (parts) having HOMO not lower than a specific threshold value and LUMO not higher than a specific threshold value can be screened, and the calculated triplet state of the parts is more than 2.75 eV.

With that, for example, in the presence of a HOMO energy (for example, ionizing potential) of −6.5 eV or more, a donor part ("D") can be selected. On the other hand, for example, in the presence of a LUMO energy (for example, electron affinity) of −0.5 eV or less, an acceptor part ("A") can be selected. A bridge part ("B") is a strong conjugated system, for example, capable of strictly limiting the acceptor part and the donor part in a specific three-dimensional configuration, and therefore prevents the donor part and the acceptor part from overlapping in the pai-conjugated system.

In some embodiments, a compound library is screened using at least one of the following characteristics.

1. Light emission around a specific wavelength.
2. A triplet state over a calculated specific energy level.
3. $\Delta E_{ST}$ value lower than a specific value.
4. Quantum yield more than a specific value.
5. HOMO level.
6. LUMO level.

In some embodiments, the difference ($\Delta E_{ST}$) between the lowest singlet excited state and the lowest triplet excited state at 77 K is less than about 0.5 eV, less than about 0.4 eV, less than about 0.3 eV, less than about 0.2 eV, or less than about 0.1 eV. In some embodiments, $\Delta E_{ST}$ value is less than about 0.09 eV, less than about 0.08 eV, less than about 0.07 eV, less than about 0.06 eV, less than about 0.05 eV, less than about 0.04 eV, less than about 0.03 eV, less than about 0.02 eV, or less than about 0.01 eV.

In some embodiments, the compound represented by the formula (1) shows a quantum yield of more than 25%, for example, about 30%, about 35%, about 40%, about 45%, about 50%, about 55%, about 60%, about 65%, about 70%, about 75%, about 80%, about 85%, about 90%, about 95% or more.

[Components Using Compound of the Present Disclosure]

In some embodiments, a solid-state film or layer is formed through combining with the compound represented by the formula (I), dispersing of the compound, covalent bonding with the compound, coating of the compound, carrying of the compound, or the co-use of one or more materials that associate with the compound (for example, small molecules, polymers, metals, metal complexes, etc.). For example, the compound represented by the formula (I) can be combined with an electrically active material to form a film. In some cases, the compound represented by the formula (I) may be combined with a hole transport polymer. In some cases, the compound represented by the formula (I) may be combined with an electron transport polymer. In some cases, the compound represented by the formula (I) may be combined with a hole transport polymer and an electron transport polymer. In some cases, the compound represented by the formula (I) may be combined with a copolymer having both a hole transport part and an electron transport part. According to the above embodiments, electrons and/or holes formed within the solid-state film or layer can interact with the compound represented by the formula (I).

[Film Formation]

In some embodiments, a film containing the compound represented by the formula (1) can be formed in a wet process. In a wet process, a solution prepared by dissolving a composition containing the compound of the present invention is applied onto a surface, and then the solvent is removed to form a film. The wet process includes a spin coating method, a slit coating method, an ink jet method (a spraying method), a gravure printing method, an offset printing method and flexographic printing method, which, however, are not limitative. In the wet process, an appropriate organic solvent capable of dissolving a composition containing the compound of the present invention is selected and used. In some embodiments, a substituent (for example, an alkyl group) capable of increasing the solubility in an organic solvent can be introduced into the compound to be contained in the composition.

In some embodiments, a film containing the compound of the present invention can be formed in a dry process. In some embodiments, a vacuum evaporation method is employable as a dry process, which, however, is not limitative. In the case where a vacuum evaporation method is employed, compounds to constitute a film can be co-evaporated from individual evaporation sources, or can be co-evaporated from a single evaporation source formed by mixing the compounds. In the case where a single evaporation source is used, a mixed powder prepared by mixing compound powders can be used, or a compression molded body prepared by compression-molding the mixed powder can be used, or a mixture prepared by heating and melting the constituent compounds and cooling the resulting melt can be used. In some embodiments, by co-evaporation under the condition where the evaporation rate (weight reduction rate) of the plural compounds contained in a single evaporation source is the same or is nearly the same, a film having a compositional ratio corresponding to the compositional ratio of the plural compounds contained in the evaporation source can be formed. When plural compounds are mixed in the same compositional ratio as the compositional ratio of the film to be formed to prepare an evaporation source, a film having a desired compositional ratio can be formed in a simplified manner. In some embodiments, the temperature at which the compounds to be co-evaporated has the same weight reduction ratio is specifically defined, and the temperature can be employed as the temperature of co-evaporation.

All the descriptions on use examples, a device, a display, a screen, etc., which are described in [0141] to [0169] and [0192] to [0242] of US2020/0168814A1, are incorporated herein as a part of the present specification, and are used as descriptions of the present invention.

In some embodiments of the present invention, the following compounds can be preferably used as host materials.

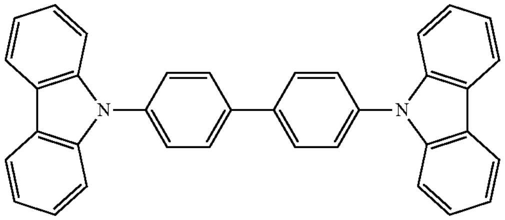

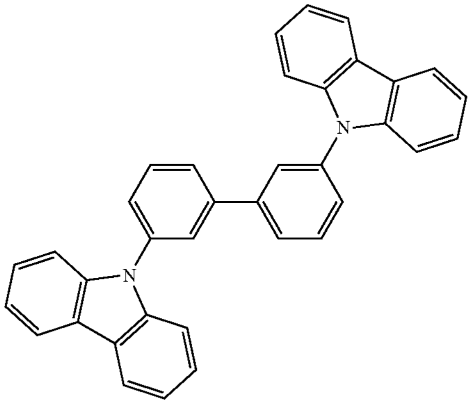

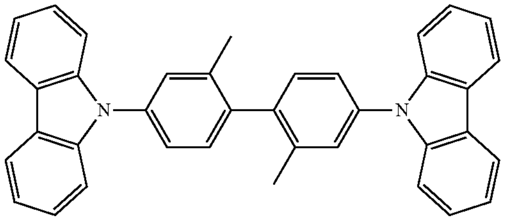

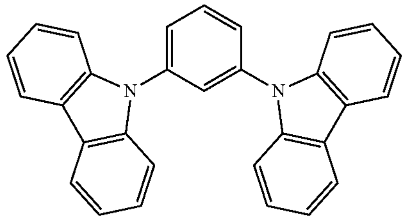

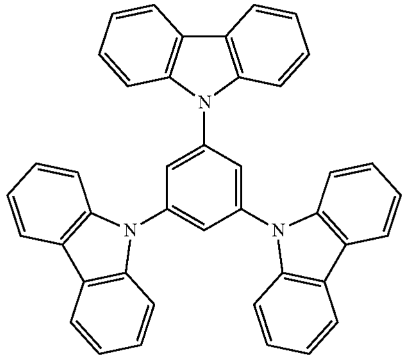

-continued
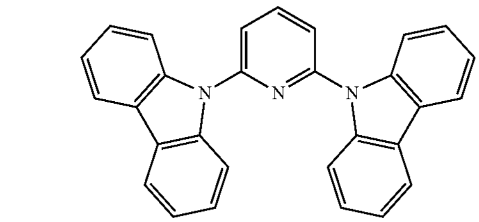
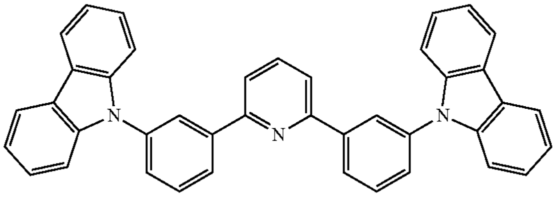
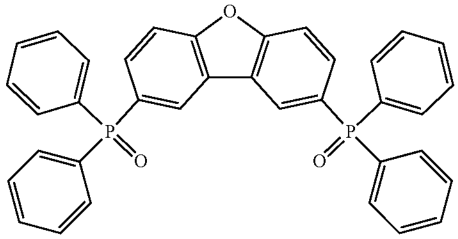
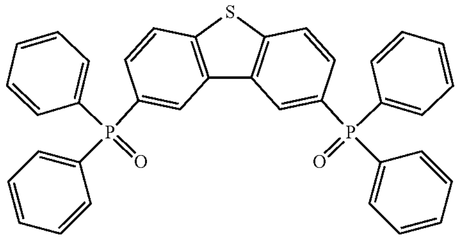
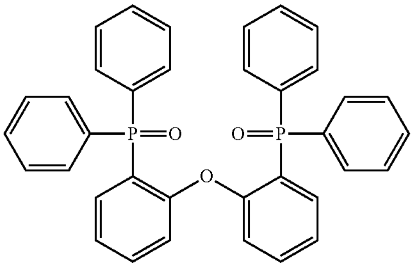
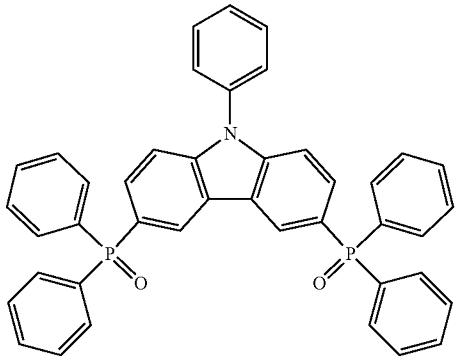
-continued
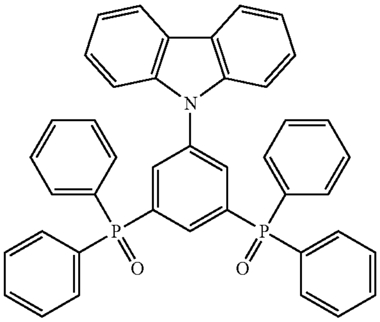
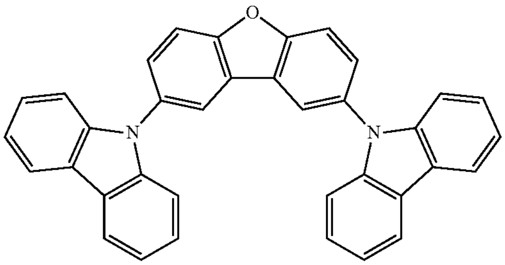
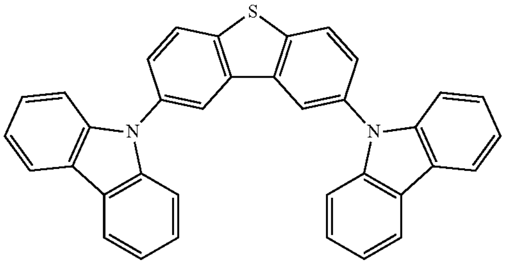
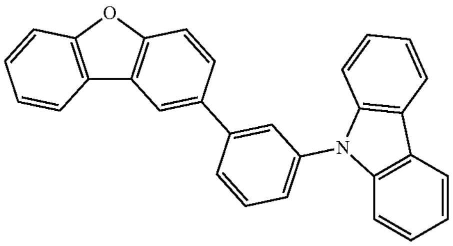
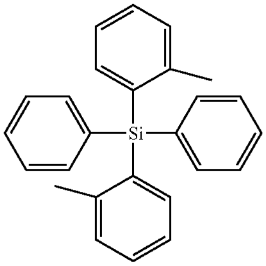
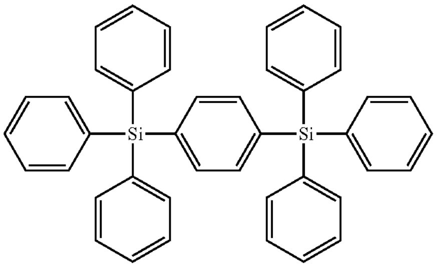

-continued
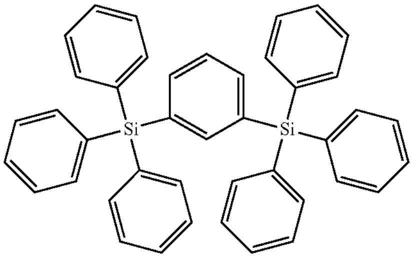
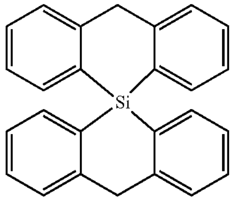
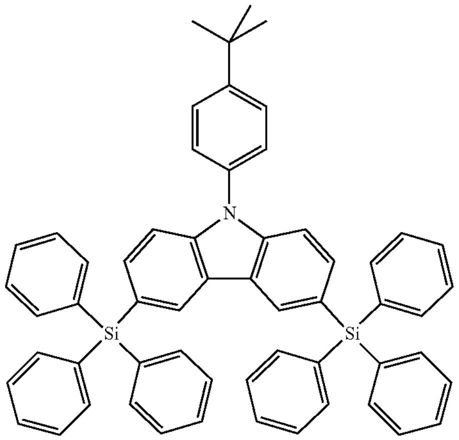
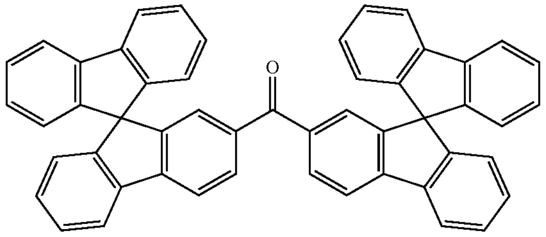
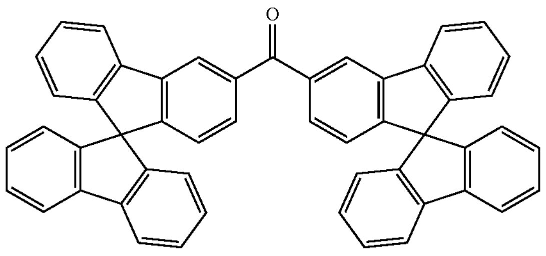
-continued
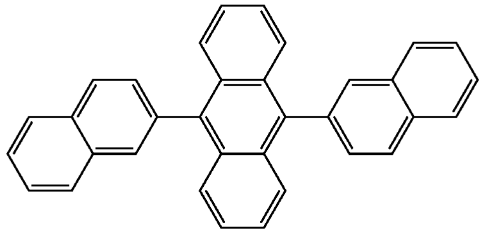
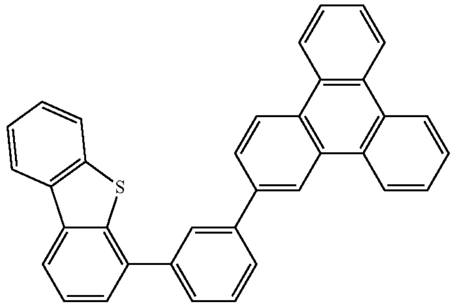
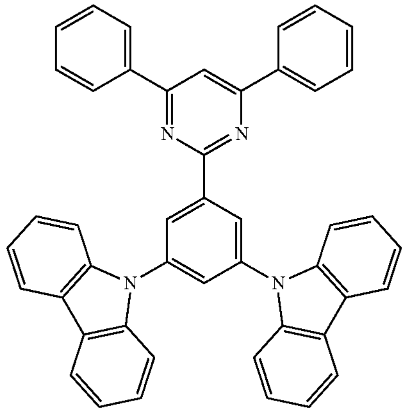
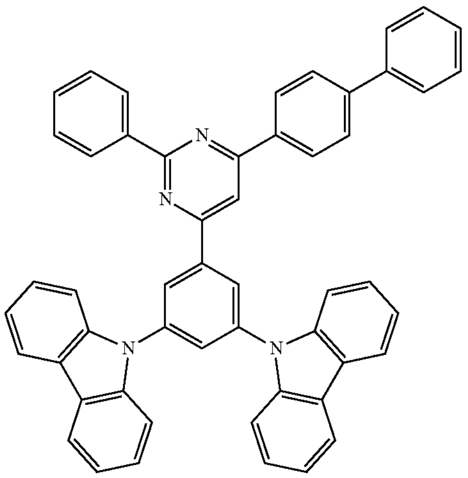

-continued
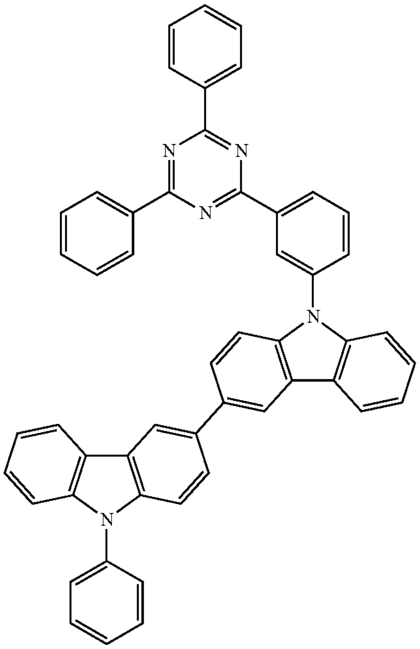
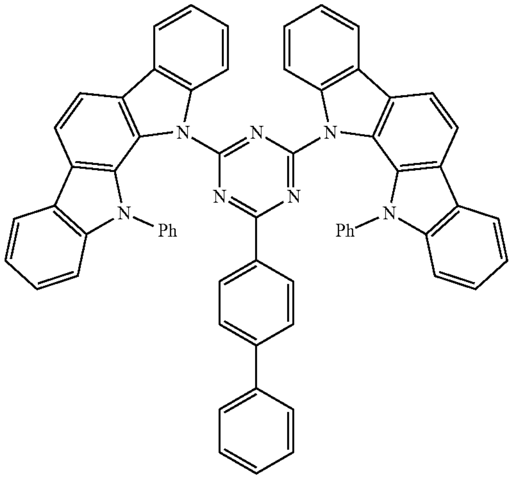
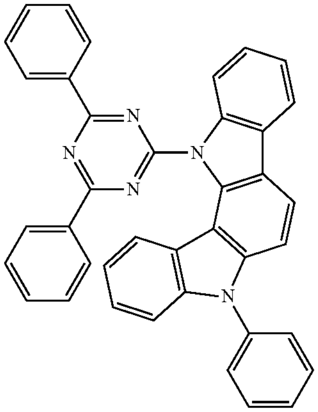
In some embodiments of the present invention, the following compounds can be preferably used as electron blocking materials.
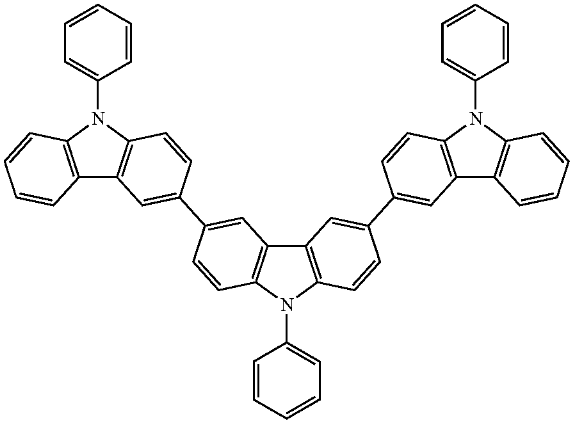
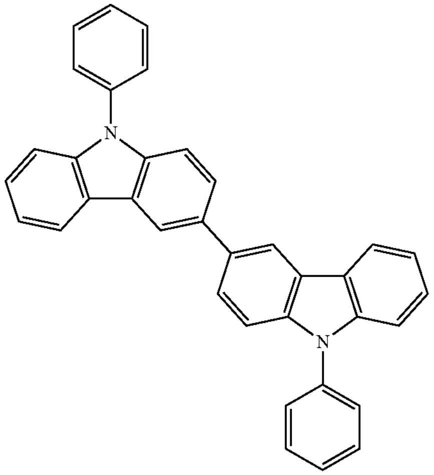
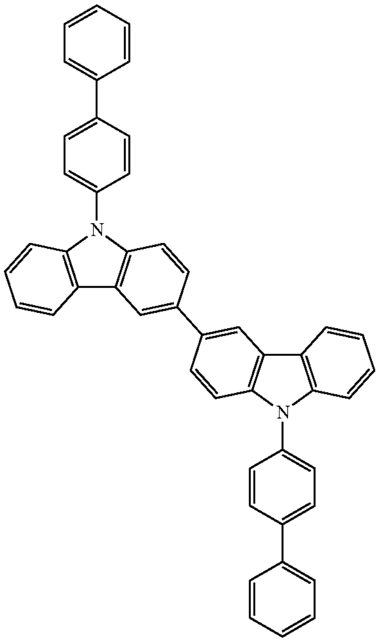

-continued
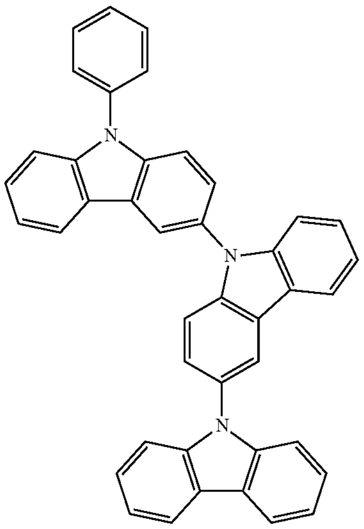
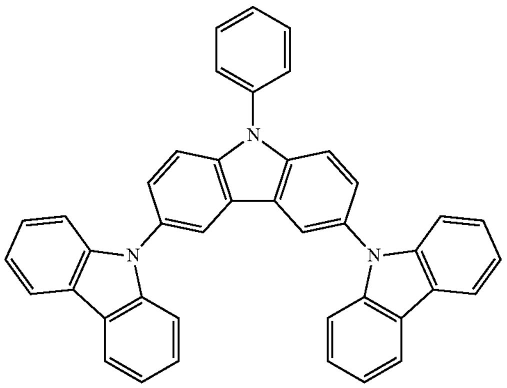
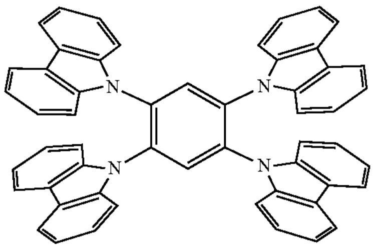
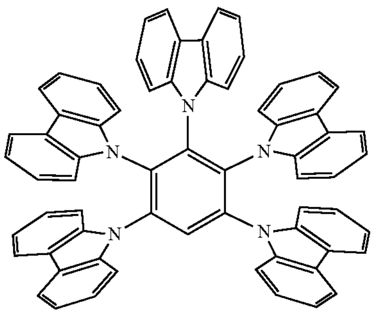
In some embodiments of the present invention, the following compounds can be preferably used as hole blocking materials.
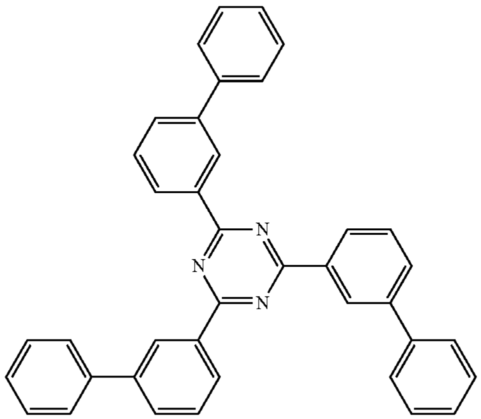
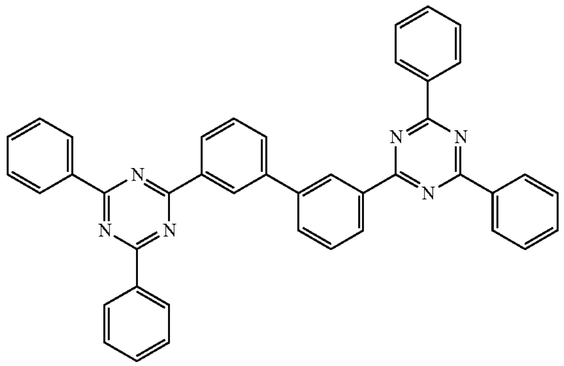
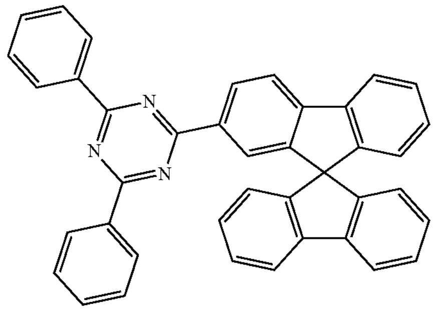
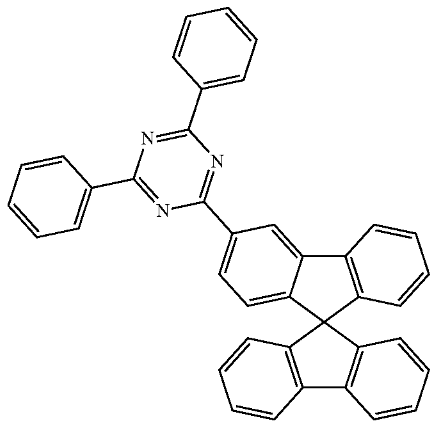

-continued
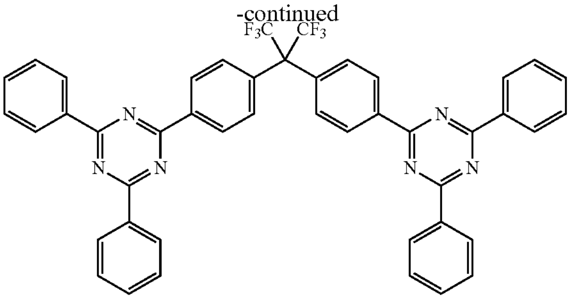
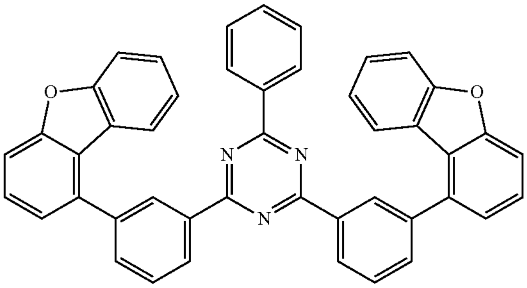
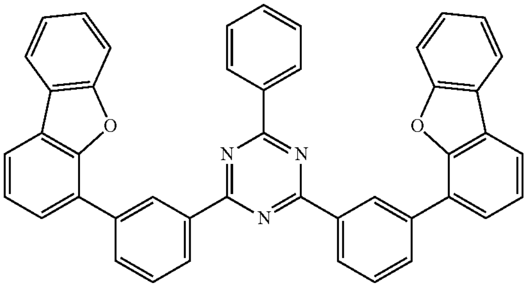
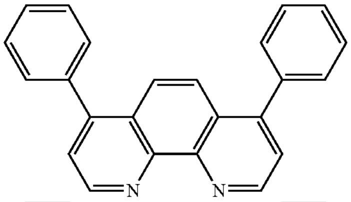
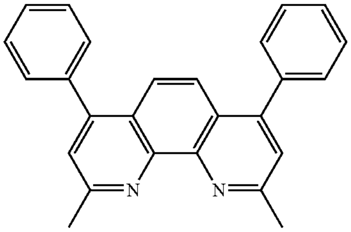
Hereinafter, preferable compounds that can be used as a hole injection material of an organic electroluminescence device will be exemplified. $MoO_3$,
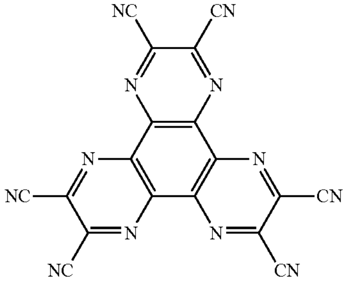
-continued
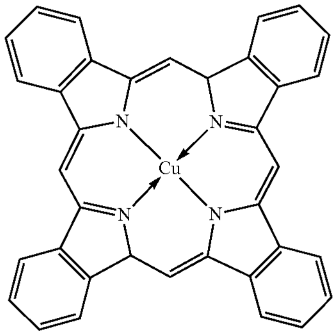
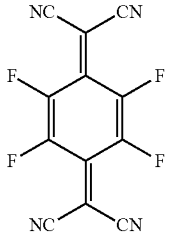
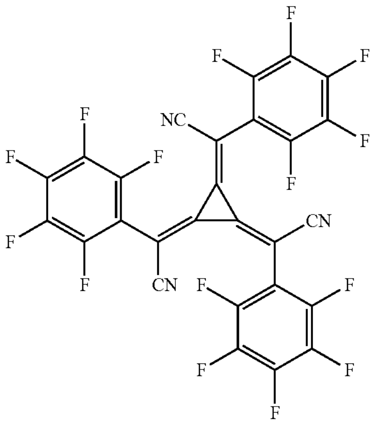
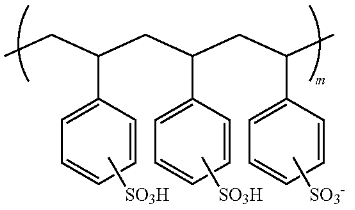
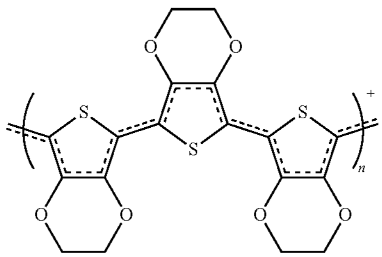
Next, preferable compounds that can be used as an electron injection material of an organic electroluminescence device will be exemplified.

LiF, CsF, 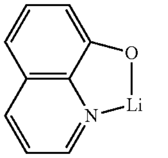

Further, preferable compounds as materials that can be added to each organic layer of an organic electroluminescence device will be exemplified. For example, addition as a stabilizing material, or the like may be taken into consideration.

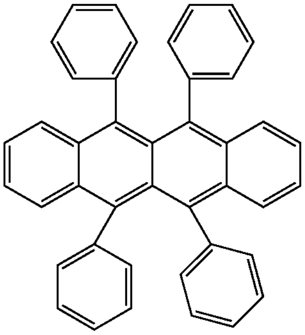

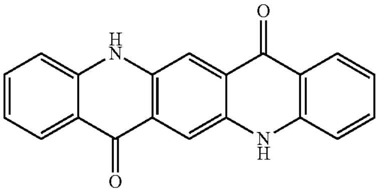

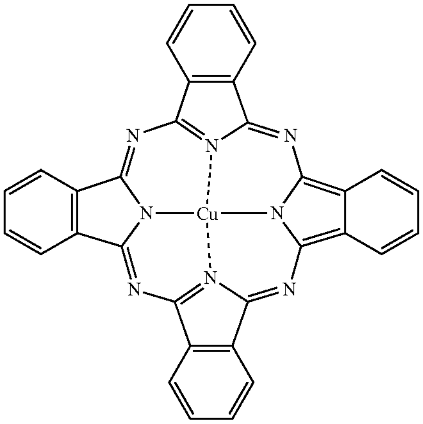

-continued

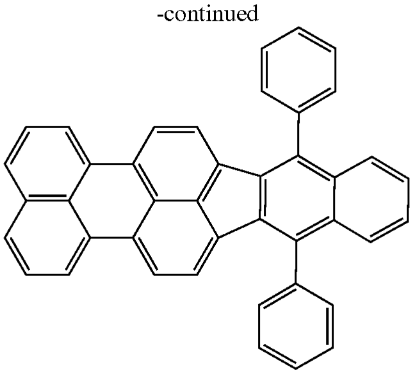

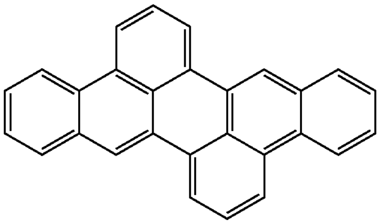

EXAMPLES

Hereinafter, the features of the present invention will be described in more detail with reference to Synthesis examples and Examples. The materials, the processing contents, the processing procedures, etc. illustrated below can be appropriately changed as long as they do not deviate from the gist of the present invention. Therefore, the scope of the present invention should not be construed as limiting to specific examples illustrated below. Further, the features of the following samples were evaluated by using NMR (manufactured by Bruker, nuclear magnetic resonance 500 MHz), LC/MS (manufactured by Waters, liquid chromatography mass spectrometer), AC3 (manufactured by RIKEN KEIKI), a high-performance UV/Vis/NIR spectrophotometer (manufactured by PerkinElmer, Lambda950), a fluorescence spectrophotometer (manufactured by Horiba, FluoroMax-4), a photonic multi-channel analyzer (manufactured by Hamamatsu Photonics, PMA-12 C10027-01), an absolute PL quantum yield measuring system (manufactured by Hamamatsu Photonics, C11347), an automatic current voltage luminance measuring system (manufactured by System GIKEN, ETS-170), a lifetime measuring system (manufactured by System GIKEN, EAS-26C) and a streak camera (manufactured by Hamamatsu Photonics, model C4334). As a host material, PYD-2Cz was employed in Examples, and mCBP was employed in Comparative Compound A. Further, the compounds of Examples of the present application were used for manufacturing a device and the like after sublimation purification.

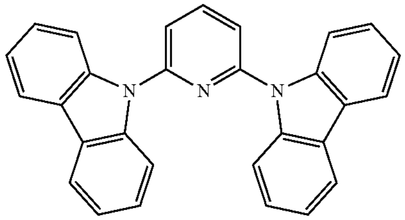

PYD-2Cz

-continued

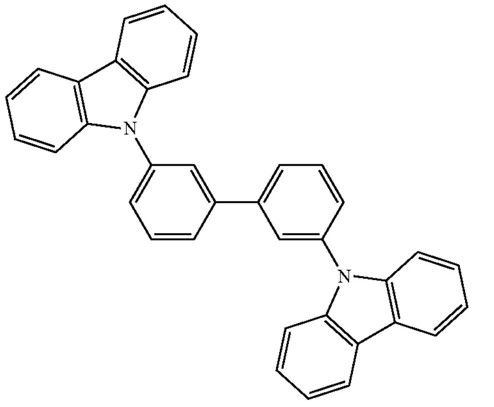

mCBP (Synthesis Example 1) Synthesis of Compound 939

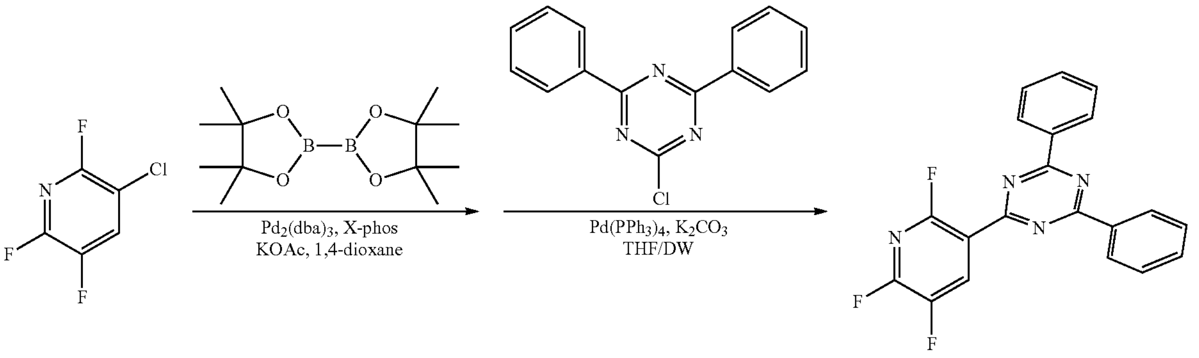

1-1

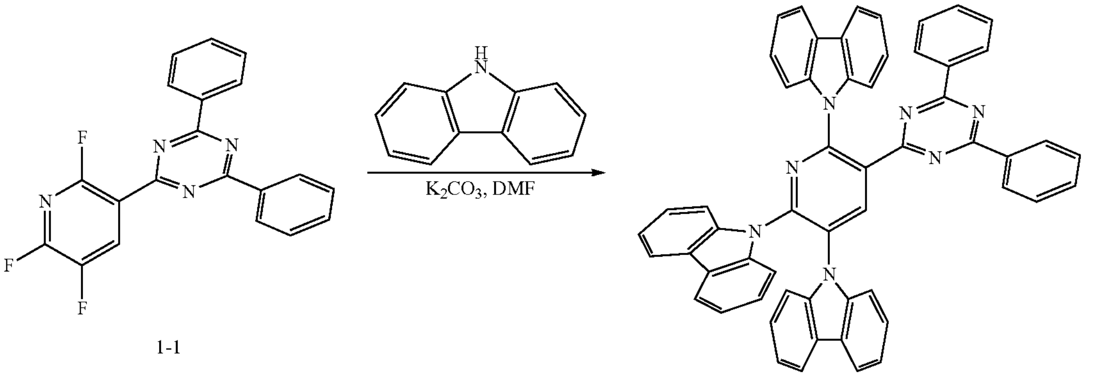

1-1

939

Synthesis of Intermediate 1-1

Potassium acetate (2.93 g, 29.85 mmol), 4,4',4',5,5',5'-octamethyl-2,2'-bi(1,3,2-oxaborane) (3.34 g, 13.13 mmol), tris(dibenzylideneacetone)dipalladium(0) (0.22 g, 2 mol %), 2-dicyclohexylphosphino-2',4',6'-triisopropylbiphenyl (0.34 g, 6 mol %) and 3-chloro-2,5,6-trifluoropyridine (2.00 g, 11.94 mmol) were dissolved in 1,4-dioxane under a nitrogen atmosphere. The mixture was heated to 110° C., and was stirred overnight. After the starting compounds were no longer detected through thin-layer chromatography, the temperature of the mixture was lowered to a room temperature.

To a flask containing the mixture, 2-chloro-4,6-diphenyl-1,3,5-triazine (3.97 g, 14.82 mmol), tetrakis(triphenylphosphine)palladium(0) (0.43 g, 3 mol %) and potassium carbonate (2.56 g, 18.53 mmol, 2M aqueous solution) were added while a nitrogen atmosphere was maintained. The mixture was heated to 100° C. and was stirred overnight under a nitrogen atmosphere. The reaction was stopped with a brine solution at a room temperature, and the mixture was extracted with chloroform and dried over $MgSO_4$, and then was concentrated by a vacuum evaporator system. This mixture was purified through silica gel column chromatography using n-hexane/chloroform as an eluent to obtain 2,4-diphenyl-6-(2,5,6-trifluoropyridine-3-yl)-1,3,5-triazine (Intermediate 1-1) as a powdery product (yield 2.30 g, yield 51.1%).

$^1$H NMR (500 MHz, $CDCl_3$) S 7.59 (t, J=8.0 Hz, 4H), 7.65 (t, J=7.5 Hz, 2H), 8.73 (d, J=8.0 Hz, 4H), 8.91 (q, J=8.0 Hz, 1H), $^{19}$F NMR (470 MHz, $CDCl_3$) δ −144.64 (t, $J_F$=29.1 Hz, 1F), −81.56 (t, $J_F$=13.63 Hz, 1F), −65.22 (t, $J_F$=19.74 Hz, 1F). MS (APCI) m/z 365.24 [$(M+H)^+$].

Synthesis of Compound 939

Potassium carbonate (1.90 g, 13.72 mmol), 2,4-diphenyl-6-(2,5,6-trifluoropyridine-3-yl)-1,3,5-triazine (Intermediate 1-1) (1.00 g, 2.74 mmol) and 9H-carbazole (1.84 g, 10.98 mmol) were placed in a three-necked round-bottom flask. The mixture was dried in a vacuum system, and then DMF (dimethylformamide), as a solvent, was added thereto under a nitrogen atmosphere. The reaction mixture was stirred overnight while being kept at 160° C. The reaction was stopped with a $NH_4Cl$ aqueous solution, and extraction with chloroform was performed. An organic layer separated after extraction was dried over $MgSO_4$, and the solvent was concentrated by a vacuum evaporator system. Through column chromatography using a mixture of toluene and hexane (1:4) as an eluent, the reaction product, 9,9',9"-((2r,3r,6r)-5-(4,6-diphenyl-1,3,5-triazine-2,3,6-triyl)pyridine-2,3,6-triyl)tris(9H-carbazole) (compound 939), was separated (yield 2.20 g, yield 99.5%).

$^1H$ NMR (500 MHz, $CDCl_3$) δ 6.99 (t, J=6.5 Hz, 2H), 7.08 (t, J=7.5 Hz, 2H), 7.13 (t, J=7.0 Hz, 4H) 7.22-7.35 (m, 10H), 7.47-7.51 (m, 4H), 7.62 (d, J=9.0 Hz, 2H), 7.78 (d, J=8.5 Hz, 2H), 7.89 (d, J=8.0 Hz, 2H), 8.01 (d, J=7.5 Hz, 2H), 8.07 (d, J=8.0 Hz, 2H), 9.42 (s, 1H), MS (APCI) m/z 806.50 [$(M+H)^+$]

(Synthesis Example 2) Synthesis of Compound 962

Synthesis of Intermediate 2-1

Potassium carbonate (1.51 g, 10.89 mmol), 5-chloro-2,3-difluoro-4-iodopyridine (1.00 g, 3.63 mmol) and 9H-carbazole (1.82 g, 10.89 mmol) were placed in a three-necked round-bottom flask. The mixture was dried under vacuum, and then DMF, as a solvent, was added thereto under a nitrogen atmosphere. After the reaction mixture was stirred overnight while being kept at 160° C., the reaction was stopped with a $NH_4Cl$ aqueous solution, and the mixture was extracted with chloroform. An organic layer separated after extraction was dried over $MgSO_4$, and was concentrated by a vacuum evaporator system. Through column chromatography using a mixture of toluene and hexane (1:4) as an eluent, the reaction product, 9,9'-(((2r,3s)-5-chloro-4-iodopyridine-2,3-diyl)bis(9H-carbazole)(intermediate 2-1), was separated (yield 2.00 g, yield 96.7%).

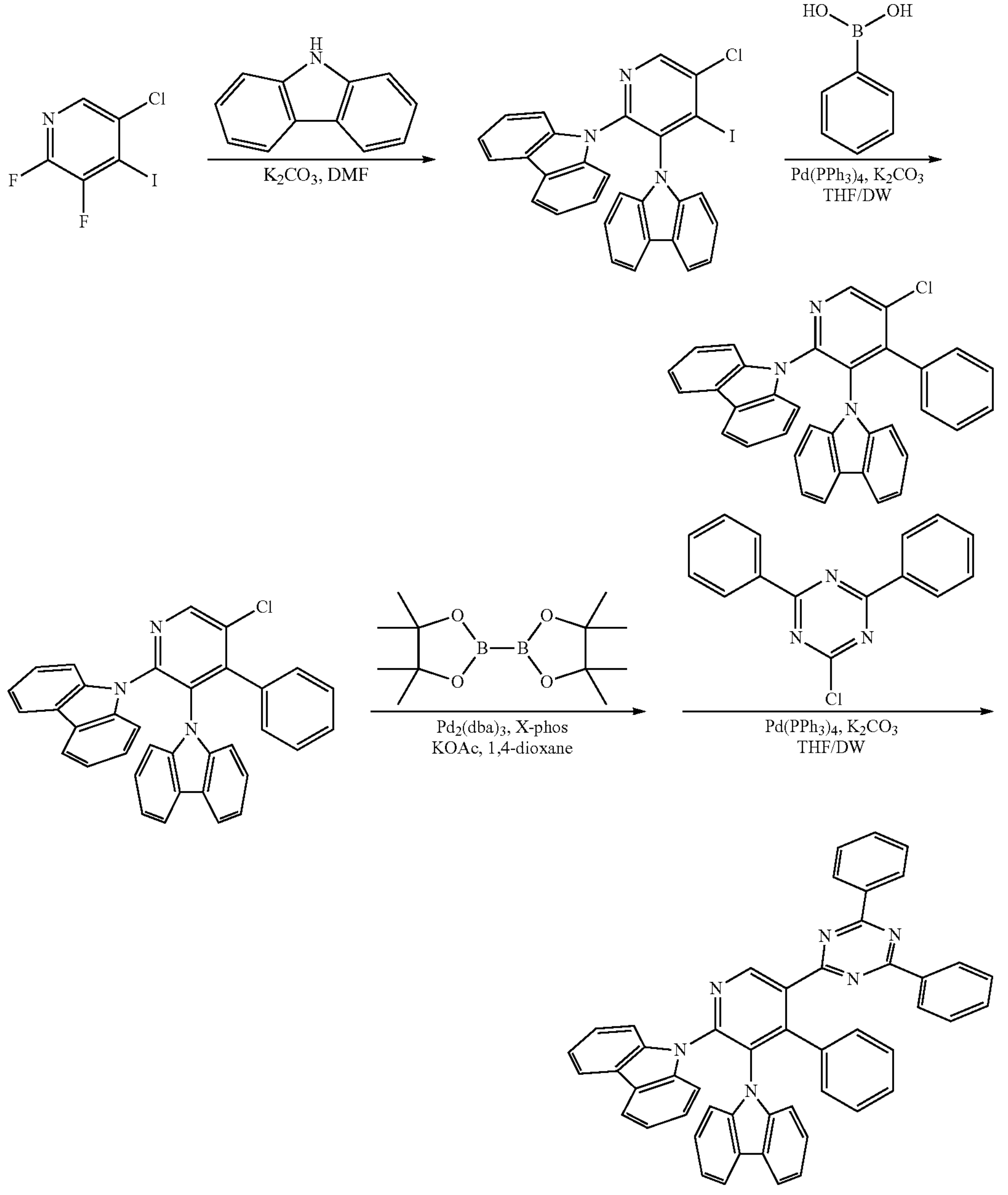

$^1$H NMR (500 MHz, $CDCl_3$) δ 6.77-7.18 (m, 12H), 7.68 (d, J=7.5 Hz, 2H), 7.75-7.77 (m, 2H) 8.83 (s, 1H), MS (APCI) m/z 570.28 [$(M+H)^+$]

Synthesis of Intermediate 2-2

9'-((2r,3s)-5-chloro-4-iodopyridine-2,3-diyl)bis(9H-carbazole) (intermediate 2-1) (2.50 g, 4.39 mmol), phenylboronic acid (0.64 g, 5.26 mmol), potassium carbonate (1.82 g in an aqueous solution, 13.16 mmol, 2M) and tetrakis (triphenylphosphine)palladium (0.15 g, 3 mol %) were dissolved in THF and distilled water (depending on the amount of $K_2CO_3$). The resultant solution was refluxed under a nitrogen atmosphere for 12 h, and then was cooled to a room temperature. After extraction using ethyl acetate and distilled water, the solvent of an organic layer was evaporated under vacuum. Through purification with column chromatography using toluene:hexane (1:1) as an eluent, 9,9'-(((2r, 3r)-5-chloro-4-phenylpyridine-2,3-diyl)bis(9H-carbazole) (Intermediate 2-2) was obtained as a white powdery product (yield 2.19 g, yield 96.1%).

$^1$H NMR (500 MHz, $CDCl_3$) δ 6.59-7.05 (m, 15H), 7.21 (d, J=8.5 Hz, 2H), 7.58-7.59 (m, 2H) 7.72 (d, J=7.5 Hz, 2H), 9.00 (s, 1H), MS (APCI) m/z 520.42 [$(M+H)^+$]

Synthesis of Compound 962

Potassium acetate (1.13 g, 4,4',5',5'-octamethyl-2,2'-bi(1, 3,2-dioxaborane) (2.93 g, 11.54 mmol), tris(dibenzylideneacetone)dipalladium (0.11 g, 3 mol %), and 2-dicyclohexylphosphino-2',4'-triisopropylbiphenyl (0.11 g) ((2r,3r)-5-chloro-4-phenylpyridine-2,3-diyl)bis(9H-carbazole) (Intermediate 2-2) (2.00 g, 3.85 mmol) were dissolved in 1,4-dioxane under a nitrogen atmosphere. The mixture was heated to 110° C. and was stirred overnight. After the starting compounds were no longer detected through thin-layer chromatography, the temperature of the mixture was lowered to a room temperature. To the mixture in a flask, 2-chloro-4,6-diphenyl-1,3,5-triazine (1.58 g, 5.89 mmol), tetrakis(triphenylphosphine)palladium(0) (0.14 g, 3 mol %) and potassium carbonate (1.63 g, 11.77 mmol, 2M aqueous solution) were added while a nitrogen atmosphere was maintained. The mixture was heated to 100° C. and was stirred overnight under a nitrogen atmosphere. The reaction was stopped with a brine solution at a room temperature, and the mixture was extracted with chloroform and dried over $MgSO_4$, and then was concentrated by a vacuum evaporator system. This mixture was purified through silica gel column chromatography using n-hexane/methylene chloride as an eluent to obtain 9,9'-((2r,3r)-5-(4,6-diphenyl-1,3,5-triazine-2-yl)-4-phenylpyridine-2,3-diyl)bis(9H-carbazole)(Compound 962) as a powdery product (yield 0.37 g, yield 13.0%).

$^1$H NMR (500 MHz, $CDCl_3$) δ 6.84-7.05 (m, 16H), 7.26 (d, J=8.0 Hz, 1H), 7.46 (t, J=7.5 Hz, 4H), 7.57 (t, J=7.0 Hz, 2H), 7.62-7.64 (m, 2H), 7.74 (d, J=7.5 Hz, 2H), 8.35 (d, J=8.0 Hz, 4H), 9.61 (s, 1H), MS (APCI) m/z 717.42 [$(M+H)^+$]

(Synthesis Example 3) Synthesis of Compound 950

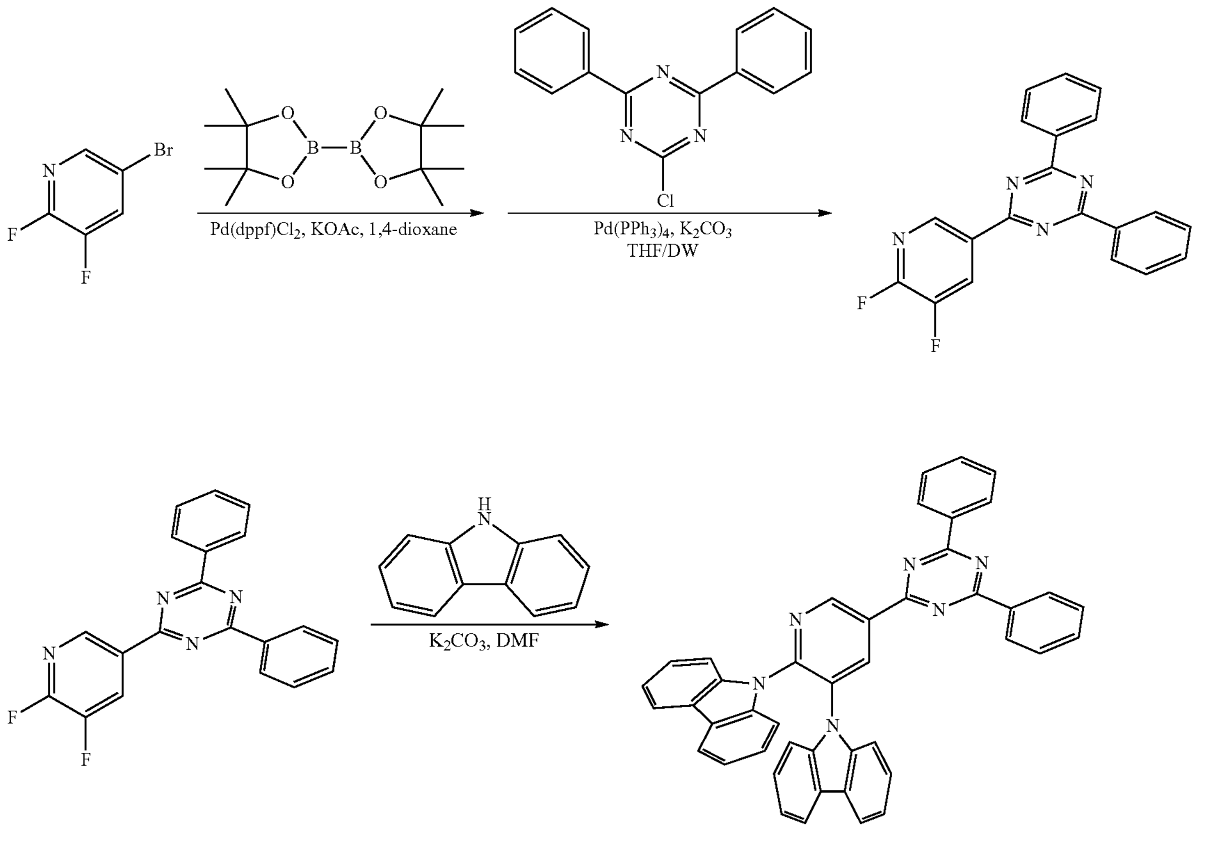

Synthesis of Intermediate 3-1

Potassium acetate (5.06 g, 51.55 mmol), 4,4',4'4',5,5',5', 5'-octamethyl-2,2'-bi(1,3,2-dioxaborane) (7.20 g, 28.35 mmol), [1,1'-bis(diphenylphosphino)ferrocene]dichloropalladium(II) (0.57 g, 3 mol %) and 5-bromo-2,3-difluoropyridine (5.00 g, 25.78 mmol) were dissolved in 1,4-dioxane under a nitrogen atmosphere. The mixture was heated to 100° C. and was stirred overnight. After the starting compounds were no longer detected through thin-layer chromatography, the temperature of the mixture was lowered to a room temperature. To a flask containing the mixture, 2-chloro-4,6-diphenyl-1,3,5-triazine (8.66 g, 32.36 mmol), tetrakis(triphenylphosphine)palladium(0) (0.93 g, 3 mol %) and potassium carbonate (5.59 g, 40.45 mmol, 2M aqueous solution) were added while a nitrogen atmosphere was maintained. The mixture was heated to 100° C. and was stirred overnight under a nitrogen atmosphere. The reaction was stopped with a brine solution at a room temperature, and the mixture was extracted with chloroform and dried over $MgSO_4$, and then was concentrated by a vacuum evaporator system. This mixture was purified through silica gel column chromatography using n-hexane/toluene as an eluent to obtain 2-(5,6-difluoropyridine-3-yl)-4,6-diphenyl-1,3,5-triazine (Intermediate 3-1) as a powdery product (yield 8.80 g, yield 94.2%).

$^1H$ NMR (500 MHz, $CDCl_3$) δ 7.60 (t, J=7.5 Hz, 4H), 7.66 (t, J=7.5 Hz, 2H), 8.74 (d, J=8.0 Hz, 4H), 8.86 (t, J=9.0 Hz, 1H), 9.36 (s, 1H), MS (APCI) m/z 347.23 $[(M+H)^+]$

Synthesis of Compound 950

Potassium carbonate (1.20 g, 8.66 mmol), 2-(5,6-difluoropyridine-3-yl)-4,6-diphenyl-1,3,5-triazine (Intermediate 3-1) (1.00 g, 2.89 mmol) and 9H-carbazole (1.45 g, 8.66 mmol) were placed in a three-necked round-bottom flask. The mixture was dried in a vacuum system, and then DMF, as a solvent, was added thereto under a nitrogen atmosphere. The reaction mixture was stirred overnight while being kept at 160° C. The reaction was stopped with a $NH_4Cl$ aqueous solution, and the mixture was extracted with chloroform. An organic layer separated after extraction was dried over $MgSO_4$, and the solvent was concentrated by a vacuum evaporator system. Through column chromatography using a mixture of toluene and hexane (1:4) as an eluent, the reaction product, 9,9'-(((2r,3r)-5-(4,6-diphenyl-1,3,5-triazine-2,3-diyl)pyridine-2,3-diyl)bis(9H-carbazole) (Compound 950), was separated (yield 1.50 g, yield 81.1%).

$^1H$ NMR (500 MHz, $CDCl_3$) δ 7.03 (t, J=7.5 Hz, 2H), 7.07-7.15 (m, 6H), 7.19 (d, J=7.5 Hz, 2H), 7.36 (d, J=8.0 Hz, 2H), 7.59 (t, J=8.0 Hz, 4H), 7.65 (t, J=7.5 Hz, 2H), 7.78 (d, J=7.5 Hz, 2H), 7.87 (d, J=7.5 Hz, 2H), 8.78 (d, J=7.5 Hz, 4H), 9.48 (s, 1H), 10.19 (s, 1H), MS (APCI) m/z 641.52 $[(M+H)^+]$

The synthesized compound 950 is superior to 9,9'-(((2r, 3r)-5-(4,6-di-p-tolyl-1,3,5-triazine-2,3-diyl)pyridine-2,3-diyl)bis(9H-carbazole), which is a substituent of 4,6-di-p-tolyl, in the luminescence characteristics. A substituent of unsubstituted diphenyl-1,3,5-triazinyl is superior to a substituent of dialkylphenyl-1,3,5-triazinyl, in the luminescence characteristics.

(Synthesis Example 4) Synthesis of Compound 947

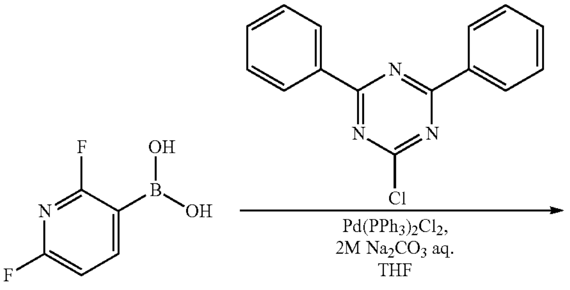

-continued

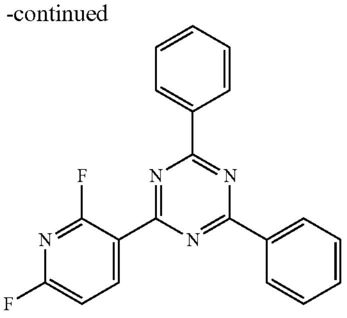

4-1

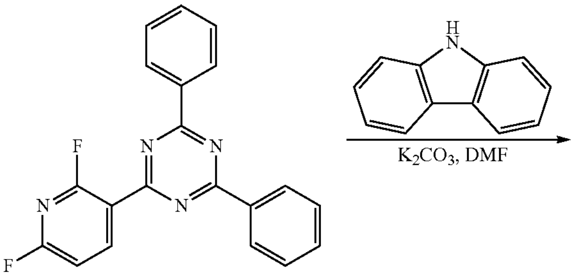

4-1

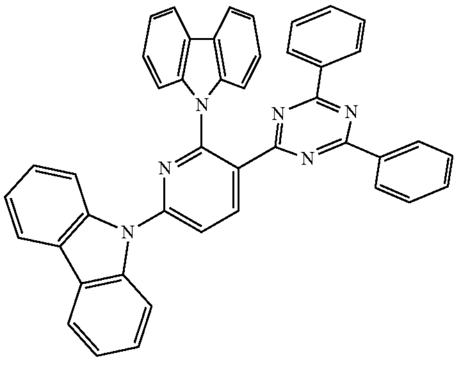

947

Synthesis of Intermediate 4-1

Under a nitrogen stream, dichlorobis(triphenylphosphine) palladium (II) (0.13 g, 0.19 mmol) was added to a THF solution (20 mL) of 2,6-difluoro-3-pyridineboronic acid (1.00 g, 6.29 mmol), 2-chloro-4,6-diphenyl-1,3,5-triazine (1.77 g, 6.61 mmol), and a 2M sodium carbonate aqueous solution (6.3 mL, 12.6 mmol), followed by heat-reflux for 12 h. The reaction solution was returned to a room temperature, and then was quenched through addition of water and was extracted with dichloromethane. The solvent was distilled off with an evaporator, and then through purification with silica gel column chromatography (hexane:toluene=1:1), Intermediate 4-1 (2.00 g, 5.77 mmol, yield 91.7%) was obtained as a white solid.

$^1H$ NMR (400 MHz, $CDCl_3$) δ 7.05-7.07 (m, 1H), 7.57-7.64 (m, 6H), 8.74 (d, J=6.8 Hz, 1H), 9.11 (dd, J=9.2 Hz, J=8.4 Hz, 1H)

ASAP MS spectral analysis: $C_{20}H_{12}F_2N_4$: theoretical value 346, observed value 347.

Synthesis of Compound 947

Under a nitrogen stream, a dimethylformamide solution (10 mL) of 9H-carbazole (0.87 g, 5.20 mmol), potassium carbonate (0.72 g, 5.20 mmol), and intermediate 4-1 (0.60 g, 1.73 mmol) was stirred at 120° C. overnight. This mixture was returned to a room temperature, and then was quenched through addition of a saturated ammonium chloride solution and was extracted with chloroform. The solvent was distilled off with an evaporator, and then through purification with silica gel column chromatography (toluene:hexane), Compound 947 (1.10 g, 1.72 mmol, yield 99.1%) was obtained.

$^1$H NMR (400 MHz, $CDCl_3$) δ 7.21 (t, J=6.8 Hz, 2H), 7.27-7.38 (m, 13H), 8.00 (d, J=8.4 Hz, 3H), 8.08 (d, J=6.8 Hz, 3H), 8.12 (d, J=6.8 Hz, 2H), 8.19 (d, J=8.0 Hz, 2H), 9.13 (d, J=8.8 Hz, 1H).

ASAP MS spectral analysis: $C_{44}H_{28}N_5$: theoretical value 640, observed value 640.

(Synthesis Example 5) Synthesis of Compound 5225

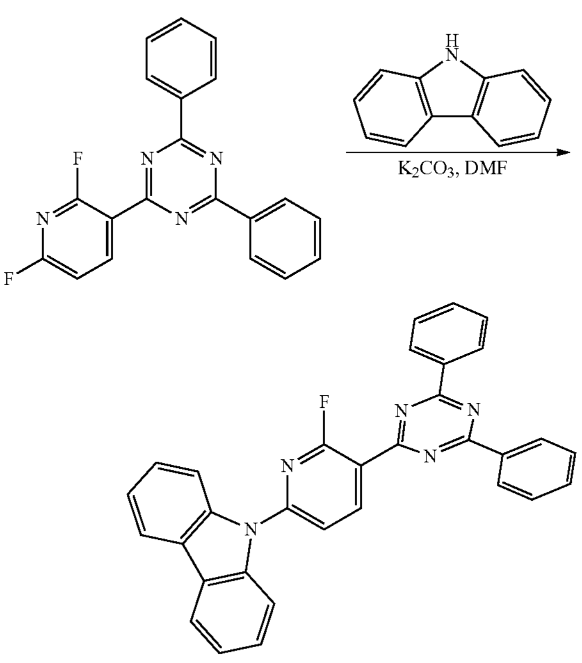

5-1

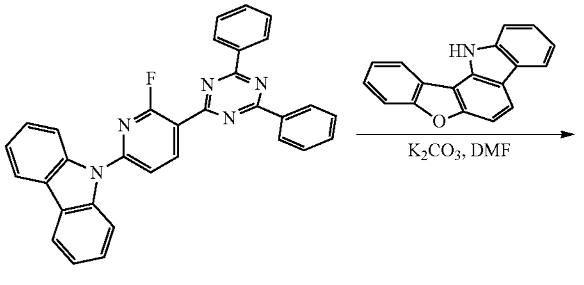

5-1

-continued

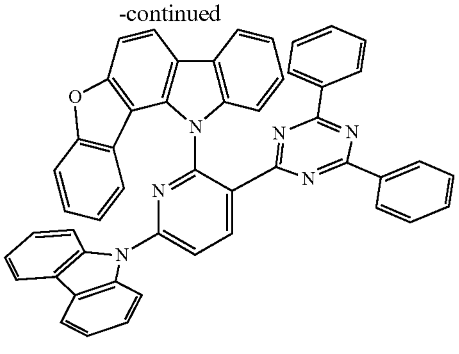

5225

Synthesis of Intermediate 5-1

Under a nitrogen stream, a dimethylformamide solution (20 mL) of 9H-carbazole (0.48 g, 2.89 mmol), potassium carbonate (0.51 g, 3.76 mmol), and Compound 1 (1.0 g, 2.89 mmol) was stirred at 70° C. overnight. This mixture was returned to a room temperature, and then was quenched through addition of a saturated ammonium chloride solution, and was extracted with chloroform. The solvent was distilled off with an evaporator, and then through purification with silica gel column chromatography (toluene:hexane), Intermediate 5-1 (1.08 g, 2.19 mmol, yield 75.7%) was obtained.

$^1$H NMR (400 MHz, $CDCl_3$) δ 7.38 (t, J=7.2 Hz, 2H), 7.51 (t, J=8.4 Hz, 2H), 7.58-7.66 (m, 6H), 7.79 (d, J=8.0 Hz, 1H), 8.12 (t, J=8.0 Hz, 4H), 8.78 (d, J=6.4 Hz, 4H), 9.20 (t, J=9.6 Hz, 1H).

ASAP MS spectral analysis: $C_{32}H_{20}FN_5$: theoretical value 493, observed value 494.

Synthesis of Compound 5225

Under a nitrogen stream, a dimethylformamide solution (30 mL) of 12H-[3,2-a]-benzofurocarbazole (0.76 g, 2.96 mmol), potassium carbonate (0.41 g, 2.96 mmol), and Intermediate 5-1 (0.73 g, 1.48 mmol) was stirred at 110° C. overnight. This mixture was returned to a room temperature, and then was quenched through addition of a saturated ammonium chloride solution, and was extracted with chloroform. The solvent was distilled off with an evaporator, and then through purification with silica gel column chromatography (toluene:hexane), Compound 5225 (0.91 g, 1.25 mmol, yield 84.1%) was obtained.

$^1$H NMR (400 MHz, $CDCl_3$) δ 6.21 (d, J=7.6 Hz, 1H), 6.94 (t, J=6.8 Hz, 1H), 7.23-7.47 (m, 15H), 7.55 (d, J=7.6 Hz, 1H), 7.87 (d, J=7.6 Hz, 4H), 8.02 (d, J=8.8 Hz, 2H), 8.08 (t, J=6.8 Hz, 4H), 8.22 (d, J=8.4 Hz, 1H), 9.14 (d, J=8.8 Hz, 1H).

ASAP MS spectral analysis: $C_{50}H_{30}N_{60}$: theoretical value 730, observed value 731.

(Synthesis Example 6) Synthesis of Compound 5223

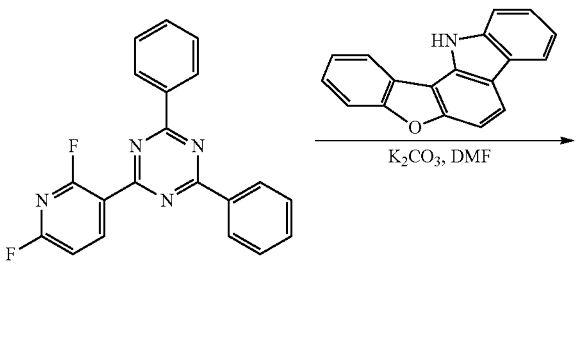

-continued

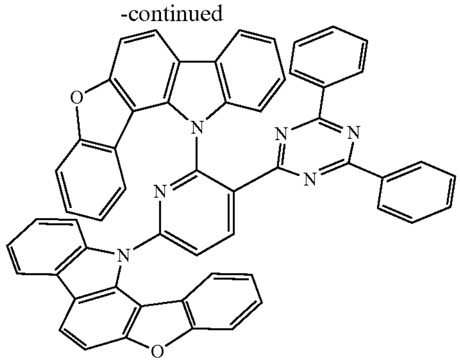

Under a nitrogen stream, a dimethylformamide solution (30 mL) of 12H-[3,2-a]-benzofurocarbazole (0.93 g, 3.61 mmol), potassium carbonate (0.60 g, 4.33 mmol), and Compound 1 (0.50 g, 1.44 mmol) was stirred at 100° C. overnight. This mixture was returned to a room temperature, and then was quenched through addition of a saturated ammonium chloride solution and was extracted with chloroform. The solvent was distilled off with an evaporator, and then through purification with silica gel column chromatography (toluene:hexane), Compound 5223 (0.70 g, 0.85 mmol, yield 59.2%) was obtained.

$^1$H NMR (400 MHz, $CDCl_3$) δ 6.34 (d, J=8.0 Hz, 1H), 6.72 (d, J=7.6 Hz, 1H), 6.90 (t, J=6.8 Hz, 1H), 7.10 (t, J=7.6 Hz, 1H), 7.18 (t, J=6.8 Hz, 1H), 7.24-7.35 (m, 8H), 7.41-7.47 (m, 5H), 7.54-7.56 (m, 1H), 7.67-7.73 (m, 3H), 7.88-7.91 (m, 4H), 7.95 (d, J=8.4 Hz, 1H) 8.01 (d, J=8.4 Hz, 1H), 8.05-8.11 (m, 2H), 8.24 (d, J=8.0 Hz, 1H), 9.04 (d, J=8.0 Hz, 1H).

ASAP MS spectral analysis: $C_{56}H_{32}N_6O_2$: theoretical value 820, observed value 821.

(Synthesis Example 7) Synthesis of Compound 90

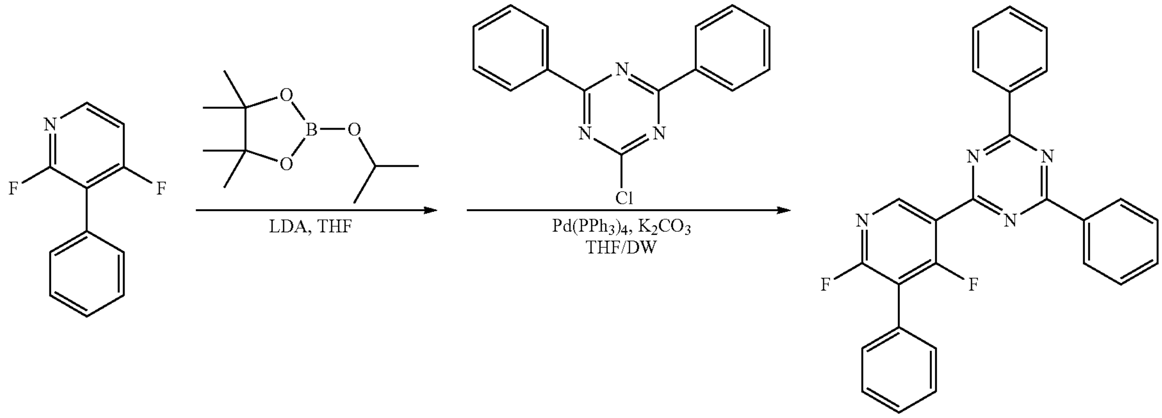

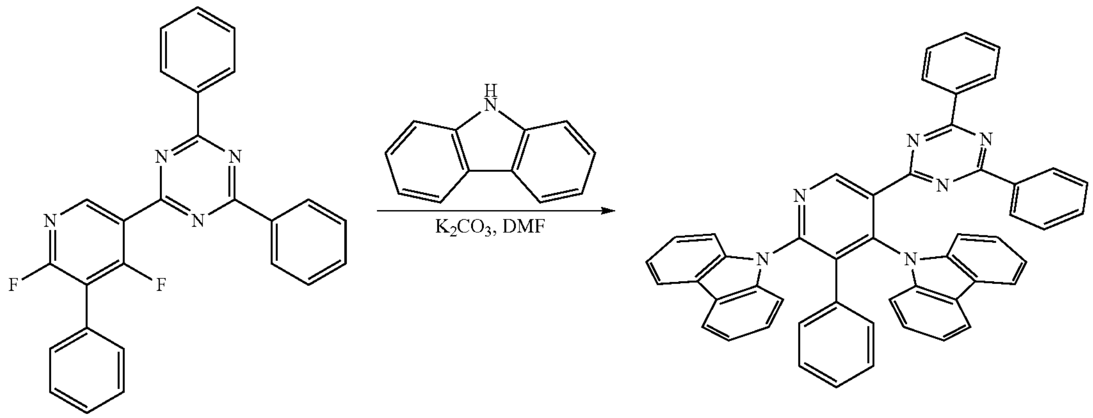

Synthesis of Intermediate 7-1

Under a nitrogen stream, a 1M diisopropylamide lithium solution (5.23 mL, 5.23 mmol) was added little by little to a tetrahydrofuran solution (15 mL) of 2,4-difluoro-3-phenylpyridine (1.0 g, 5.23 mmol), and 2-isopropoxy-4,4,5,5-tetramethyl-1,3,2-dioxaborolane bromobenzene (0.97 g, 5.23 mmol), which was cooled to −85° C. After 10 min, the temperature was raised to −75° C., and stirring was performed for 1 h. This mixture was slowly returned to a room temperature, and then 2-chloro-4,6-diphenyl-1,3,5-triazine (1.68 g, 6.28 mmol), a 2M sodium carbonate aqueous solution (3.9 mL, 7.85 mmol), tetrahydrofuran (20 mL), and tetrakis(triphenylphosphine)palladium(0) (0.3 g, 0.26 mmol) were added thereto, followed by heat-reflux for 12 h. The reaction solution was returned to a room temperature, and then was quenched through addition of water and was extracted with chloroform. The solvent was distilled off with an evaporator, and then through purification with silica gel column chromatography (hexane:toluene=1:1), Intermediate 7-1 (1.77 g, 4.19 mmol, yield 80.1%) was obtained as a white solid.

$^1$H NMR (400 MHz, $CDCl_3$) δ 7.50-7.65 (m, 11H), 8.77-8.76 (m, 4H), 9.32 (d, J=9.6 Hz, 1H).

ASAP MS spectral analysis: $C_{26}H_{16}F_2N_4$: theoretical value 422, observed value 423.

Synthesis of Compound 960

Under a nitrogen stream, a dimethylformamide solution (10 mL) of 9H-carbazole (1.19 g, 7.10 mmol), potassium carbonate (1.31 g, 9.47 mmol), and Compound 7-1 (1.0 g, 2.37 mmol) was stirred at 120° C. overnight. This mixture was returned to a room temperature, and then was quenched through addition of a saturated ammonium chloride solution, and was extracted with chloroform. The solvent was distilled off with an evaporator, and then through purification with silica gel column chromatography (toluene:hexane), Compound 960 (1.60 g, 2.23 mmol, yield 94.2%) was obtained.

$^1$H NMR (400 MHz, $CDCl_3$) δ 6.56 (t, J=7.6 Hz, 2H), 6.64 (t, J=7.2 Hz, 1H), 6.74 (d, J=7.2 Hz, 2H), 7.13 (t, J=7.6 Hz, 4H), 7.19-7.24 (m, 4H), 7.30-7.35 (m, 8H), 7.48 (d, J=7.2 Hz, 2H), 7.86 (d, J=7.2 Hz, 2H), 8.00 (t, J=8.4 Hz, 6H), 9.71 (s, 1H).

ASAP MS spectral analysis: $C_{50}H_{32}N_6$: theoretical value 716, observed value 717.

Compounds 1 to 5231, excluding the compounds synthesized in Synthesis Examples 1 to 7, can also be similarly synthesized.

Examples and Comparative Examples

Compound 939 and a host material were vapor-deposited on a quartz substrate by a vacuum deposition method under a condition of a vacuum degree of $5\times10^{-5}$ Pa or less from different vapor deposition sources to form a thin film having a thickness of 100 nm in which the content of the compound 939 was 20 mass %. This was used as a doped thin film in Example 1. Further, thin films were formed only with a change in a point that Compound 947, Compound 5225, Compound 5223, Compound 960, and the following Comparative Compound A were used instead of the Compound 939. These were used as doped thin films in Examples 2 to 5, and Comparative Example 1. Each prepared doped thin film was irradiated with excitation light of 360 nm, and an emission spectrum and a transient decay curve of light emission were measured. Delayed fluorescence was observed from all thin films. Table 2 illustrates the emission maximum wavelength λmax, the emission quantum yield PLQY, and the lifetime $\tau_d$ of delayed fluorescence (unit: milliseconds).

Further, Compound 939 was vapor-deposited alone on a quartz substrate by a vacuum deposition method under a condition of a vacuum degree of $5\times10^{-5}$ Pa or less to form a neat thin film of Example 1. Under the same conditions, Compound 947, Compound 5225, Compound 5223, Compound 960, and Comparative compound A were vapor-deposited alone to form neat thin films of Examples 2 to 5, and Comparative Example 1. Energy levels of HOMO and LUMO of each compound were measured by using each neat thin film, and Table 2 illustrates the results.

Comparative compound A

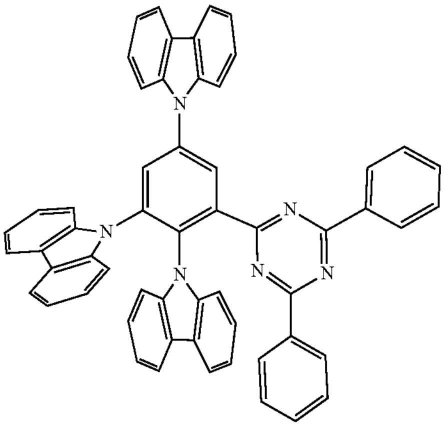

TABLE 2

| | Compound No. | PLQY (%) | λmax (nm) | $\tau_d$ (μs) | HOMO (eV) | LUMO (eV) |
|---|---|---|---|---|---|---|
| Example 1 | Compound 939 | 77 | 493 | 9.3 | 6.13 | 3.25 |
| Example 2 | Compound 947 | 70 | 492 | 4.0 | 5.92 | 3.10 |
| Example 3 | Compound 5225 | 82 | 472 | — | 6.04 | 3.20 |
| Example 4 | Compound 5223 | 77 | 489 | 8.5 | 6.00 | 3.08 |
| Example 5 | Compound 960 | 80 | 473 | 3.9 | 5.97 | 3.07 |
| Comparative Example 1 | Comparative Compound A | 50 | 534 | 19.0 | 6.00 | 3.51 |

The results of Table 2 indicate that the compound represented by the formula (1) has a better luminous efficiency, and a shorter delayed fluorescence lifetime than Comparative compound A. Further, these also indicate that the compound represented by the formula (1) is useful as a blue light-emitting material. Like in the compound 939, in other compounds synthesized in Synthesis Examples as well, excellent luminescence characteristics are recognized.

INDUSTRIAL APPLICABILITY

The compound of the present invention has excellent luminescence characteristics, and is also useful as a delayed fluorescence material. Thus, the light-emitting material of the present invention is effectively used for an organic optical device such as an organic electroluminescence device. Therefore, the present invention has high industrial applicability.

The invention claimed is:

1. A compound represented by the following formula (1),

Formula (1)

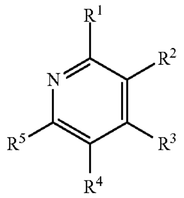

wherein, $R^1$ is a hydrogen atom or a deuterium atom, $R^2$ is A, each of $R^3$ and $R^5$ is independently D, and $R^4$ is R, where, A is a group represented by the following formula (IIIa), Formula (IIIa)

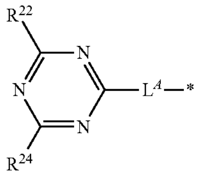

where, each of R22 and $R^{24}$ independently represents a substituted or unsubstituted aryl group or a substituted or unsubstituted heteroaryl group, $L^A$ represents a single bond, and * represents a bond position, D is a group represented by the following formula Formula (IIb)

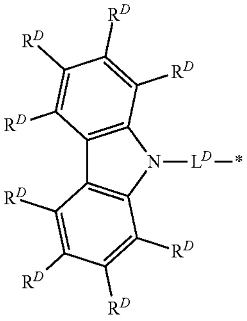

where, each $R^D$ independently represents a hydrogen atom, a deuterium atom, a substituted or unsubstituted alkyl group, a substituted or unsubstituted alkoxy group, a substituted or unsubstituted amino group, a cyano group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $L^D$ represents a single bond, and

* represents a bond position,

R is a substituted or unsubstituted aryl group.

2. An organic optical device comprising the compound according to claim 1.

3. The organic optical device according to claim 2, which is an organic light emitting diode (OLED).

* * * * *